United States Patent [19]

Glamkowski et al.

[11] Patent Number: 5,652,241
[45] Date of Patent: Jul. 29, 1997

[54] 4-(HETEROARYL)-1-[(2,3-DIHYDRO-1-INDOL-1-YL)ALKYL]PIPERADINES AND RELATED COMPOUNDS AND THEIR THERAPEUTIC UTILITY

[75] Inventors: Edward J. Glamkowski, Warren; Yulin Chiang, Covent Station, both of N.J.

[73] Assignee: Hoechst Marion Roussel, Inc., Kansas City, Mo.

[21] Appl. No.: 468,344

[22] Filed: Jun. 6, 1995

Related U.S. Application Data

[60] Division of Ser. No. 329,000, Oct. 25, 1994, which is a continuation-in-part of Ser. No. 144,265, Oct. 28, 1993, abandoned, which is a continuation-in-part of Ser. No. 969,383, Oct. 30, 1992, Pat. No. 5,364,866, which is a continuation-in-part of Ser. No. 788,269, Nov. 5, 1991, abandoned, which is a continuation-in-part of Ser. No. 944,705, Sep. 5, 1991, abandoned, which is a continuation of Ser. No. 619,825, Nov. 29, 1990, abandoned, which is a continuation of Ser. No. 456,790, Dec. 29, 1989, abandoned, which is a continuation-in-part of Ser. No. 354,411, May 19, 1989, abandoned.

[51] Int. Cl.$^6$ .............. C07D 403/14; C07D 417/14; C07D 413/14; A61K 31/495
[52] U.S. Cl. .............. 514/254; 514/63; 544/229; 544/366; 544/368
[58] Field of Search .............. 544/366, 368, 544/229; 514/254, 63

[56] References Cited

U.S. PATENT DOCUMENTS

| | | | |
|---|---|---|---|
| 3,950,527 | 4/1976 | Derible et al. | 514/323 |
| 4,355,037 | 10/1982 | Strupczewski et al. | 546/198 |
| 4,411,901 | 10/1983 | Temple, Jr. et al. | 424/250 |
| 4,458,076 | 7/1984 | Strupczewski et al. | 546/199 |
| 4,590,196 | 5/1986 | Smith et al. | 514/253 |
| 4,670,447 | 6/1987 | Strupczewski et al. | 514/322 |
| 4,780,466 | 10/1988 | Hrib et al. | 514/254 |
| 4,937,249 | 6/1990 | Antoku et al. | 514/321 |
| 4,954,503 | 9/1990 | Strupczewski et al. | 514/254 |
| 4,968,792 | 11/1990 | Stack et al. | 540/524 |
| 4,999,356 | 3/1991 | Strupczewski et al. | 514/254 |
| 5,001,134 | 3/1991 | Ferrand et al. | 514/321 |
| 5,364,866 | 11/1994 | Strupczewski et al. | 514/321 |

FOREIGN PATENT DOCUMENTS

| | | |
|---|---|---|
| 2503816 | 7/1975 | Denmark . |
| 0013612 | 7/1980 | European Pat. Off. . |
| 0135781 | 4/1985 | European Pat. Off. . |
| 0196096 | 10/1986 | European Pat. Off. . |
| 0261688 | 3/1988 | European Pat. Off. . |
| 0302423 | 2/1989 | European Pat. Off. . |
| 0314098 | 5/1989 | European Pat. Off. . |
| 0329168 | 8/1989 | European Pat. Off. . |
| 0353821 | 2/1990 | European Pat. Off. . |
| 0398425 | 11/1990 | European Pat. Off. . |
| 0402644 | 12/1990 | European Pat. Off. . |
| 0464846 | 1/1992 | European Pat. Off. . |
| 3530089 | 3/1986 | Germany . |
| 233710 | 5/1990 | New Zealand . |
| 233503 | 6/1991 | New Zealand . |
| 233525 | 9/1991 | New Zealand . |
| 2163432 | 2/1986 | United Kingdom . |
| WO93/16703 | 8/1985 | WIPO . |

*Primary Examiner*—Philip I. Datlow
*Assistant Examiner*—Sabiha N. Qazi
*Attorney, Agent, or Firm*—Finnegan, Henderson, Farabow, Garrett & Dunner, L.L.P.

[57] ABSTRACT

Heteroarylpiperidines, pyrrolidines, and piperazines are useful as antipsychotic and analgesic agents, the compounds are especially useful for treating psychoses by administering to a mammal a psychoses-treating effective amount of one of the compounds. Depot derivatives of the compounds are useful for providing long acting effects of the compounds. The compounds are also useful as analgesics by administering a pain-relieving effective amount of one of the compounds to a mammal.

16 Claims, No Drawings

4-(HETEROARYL)-1-[(2,3-DIHYDRO-1-INDOL-1-YL)ALKYL]PIPERADINES AND RELATED COMPOUNDS AND THEIR THERAPEUTIC UTILITY

This a division of pending application Ser. No. 08/329,000 filed Oct. 25, 1994 of Joseph T. Strupczewski, Grover C. Helsley, Edward J. Glamkowski, Yulin Chiang, Kenneth J. Bordeau, Peter A. Nemoto and John J. Tegeler for HETEROARYLPIPERIDINES, PYRROLIDINES AND PIPERAZINES AND THEIR USE AS ANTIPSYCHOTICS AND ANALGETICS, which is a CIP application of Ser. No. 08/144,265, filed Oct. 28, 1993, abandoned which is a CIP application of Ser. No. 07/969,383, filed Oct. 30, 1992, U.S. Pat. No. 5,364,866, which is a CIP application of Ser. No. 07/788,269, filed Nov. 5, 1991, now abandoned, which is a CIP application of Ser. No. 07/944,705, filed Sep. 5, 1991, now abandoned, which is a continuation application of Ser. No. 07/619,825, filed Nov. 29, 1990, now abandoned, which is a continuation application of Ser. No. 07/456,790, filed Dec. 29, 1989, now abandoned, which is a CIP application of Ser. No. 07/354,411, filed May 19, 1989, now abandoned.

BACKGROUND OF THE INVENTION

This invention relates to heteroarylpiperidines, pyrrolidines and piperazines. More particularly, this invention relates to heteroarylpiperidines, pyrrolidines and piperazines having antipsychotic activity and to their use as antipsychotic drugs.

The therapeutic treatment of schizophrenic patients by administration of neuroleptic drugs, such as chlorpromazine, haloperidol, sulpiride, and chemically closely related compounds, is widespread. While control of schizophrenic symptoms has been successful, treatment with these drugs does not cure the psychotic patient, who will almost certainly relapse if medication is discontinued. There exists a continuing need in the art for antipsychotic drugs for the treatment of psychoses.

Moreover, some of the known neuroleptics produce unwanted side effects. For example, the side effects of many antipsychotic drugs include the so-called extrapyramidal symptoms, such as rigidity and tremor, continuous restless walking, and tardive dyskinesia which causes facial grimacing, and involuntary movements of the face and extremities. Orthostatic hypotension is also common. Thus, there also exists a need in the art for antipsychotic drugs that produce fewer or less severe manifestations of these common side effects.

In addition, because of the frequent long term administration of neuroleptics and the problems with patient compliance, there is a further need in the art for long lasting neuroleptics, which can be formulated into sustained release depot preparations, without the side effects previously mentioned.

Moreover, there has been a need for drugs that can produce other biological effects. For example, relief from pain has been an age-old aspiration which has led to the discovery of natural and synthetic analgetics. Nevertheless, the need for safe and effective analgetics has continued to the present day.

SUMMARY OF THE INVENTION

This invention aids in fulfilling these needs in the art by providing a compound of the formula:

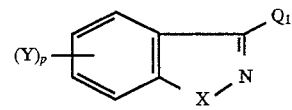

wherein

X is —O—, —S—, —NH—, or —N(R$_2$)—

R$_2$ is selected from the group consisting of lower alkyl, aryl lower alkyl, aryl, cycloalkyl, aroyl, alkanoyl, alkoxycarbonyl and phenylsulfonyl groups;

p is 1 or 2;

Y is hydrogen, lower alkyl, hydroxy, chlorine, fluorine, bromine, iodine, lower alkoxy, trifluoromethyl, nitro, or amino;

Q$_1$ is selected from the group consisting of:

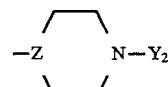

and

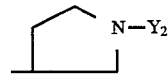

where Z is

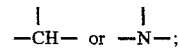

and

Y$_2$ is selected from the group consisting of:

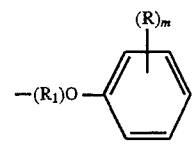

in which (R$_1$) is —CR$_{24}$R$_{27}$—(CR$_{23}$R$_{24}$)$_n$—CR$_{24}$R$_{27}$— where n is 0,1,2, or 3; or
—CHR$_{24}$—CH=CH—CHR$_{24}$—,
—CHR$_{24}$—C≡C—CHR$_{24}$—,
—CHR$_{24}$—CH=CH—CR$_{23}$R$_{24}$—CHR$_{24}$—,
—CHR$_{24}$—CR$_{23}$R$_{24}$—CH=CH—CHR$_{24}$—,
—CHR$_{24}$—C≡C—CR$_{23}$R$_{24}$—CHR$_{24}$—, or
—CHR$_{24}$—CR$_{23}$R$_{24}$—C≡C—CHR$_{24}$—,
the —CH=CH— bond being cis or trans;

R and m are as defined hereinafter;

R$_{23}$ hydrogen, alkyl, aryl, hydroxy, alkoxy, aryloxy, arylalkyloxy, alkanoyloxy, hydroxy lower alkyl, alkoxy lower alkyl, aryloxy lower alkyl, arylalkyl oxy lower alkyl, alkanoyloxy lower alkyl or

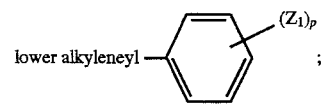

where Z$_1$ is lower alkyl, —OH, lower alkoxy, —CF$_3$, —NO$_2$, —NH$_2$ or halogen; and R$_{24}$, is hydrogen, alkyl, aryl, hydroxy lower alkyl, alkoxy lower alkyl, aryloxy lower alkyl, arylalkoxy lower alkyl, alkanoyloxy lower alkyl or

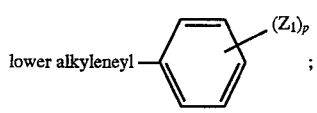

where $Z_1$ is as previously defined;

$R_{27}$ is hydrogen or $R_{24}$ and $R_{27}$ taken together with the carbon to which they are attached form C=O or C=S; and R and m are as defined hereinafter;

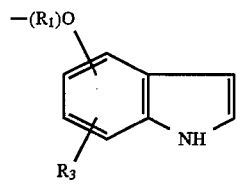
(2)

where $R_1$ is as previously defined, and $R_3$ is hydrogen or —OCH$_3$;

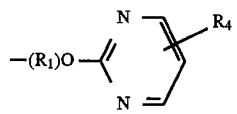
(3)

where $R_1$ is as previously defined; and $R_4$ is hydrogen, lower alkyl, lower alkoxy, hydroxy, tri(C$_1$-C$_6$)alkylsilyloxy, hydroxy lower alkyl, alkanoyloxy lower alkyl, amino, mono- or dialkylamino, (C$_1$-C$_{18}$)acyl amino, (C$_1$-C$_{18}$)alkanoyl, trifluoromethyl, chlorine, fluorine, bromine, nitro, —O—C(=O)—(C$_1$-C$_{18}$ straight or branched chain) alkyl or —C(=O)-aryl;

in which aryl is phenyl or

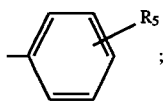
;

where $R_5$ is hydrogen, lower alkyl, lower alkoxy, hydroxy, chlorine, fluorine, bromine, iodine, lower monoalkylamino, lower dialkylamino, nitro, cyano, trifluoromethyl, trifluoromethoxy;

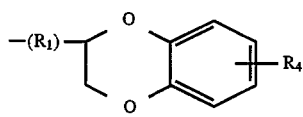
(4)

where $R_1$ and $R_4$ are as previously defined;

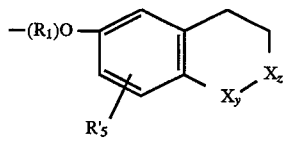
(5)

where either one of $X_y$ or $X_z$ is —C(=O)— and the other is —CH$_2$—; and $R_5'$ is hydrogen, lower alkyl, lower alkoxy, chlorine, fluorine, or bromine; and $R_1$ is as previously defined;

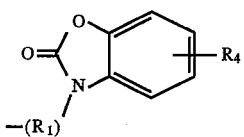
(6)

where $R_1$ and $R_4$ are as previously defined;

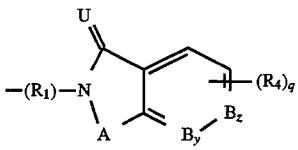
(7)

where A is —C(=O)—, —C(=S)—, —C(=CH$_2$)—, —C(=O)CH$_2$—, —CH$_2$CH$_2$—, —CR$_{26}$=N—, or —CR$_{25}$R$_{26}$—;

$R_{25}$ is hydrogen, lower alkyl, hydroxy or alkanoyloxy;

$R_{26}$ is hydrogen or lower alkyl;

either one of $B_y$ and $B_z$ is CH or N and the other is CH;

U is O or S;

q is 1,2,3 or 4, and $R_1$ and $R_4$ are as previously defined;

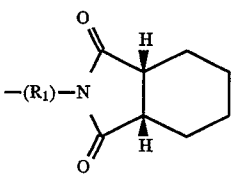
(8)

where $R_1$ is as previously defined;

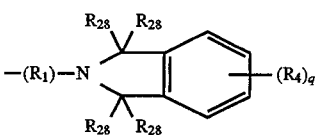
(9)

wherein $R_1$, $R_4$ and q are as defined above; and $R_{28}$ is hydrogen, (C$_1$-C$_6$)alkyl, aryl(C$_1$-C$_6$)alkyl, phenyl or substituted phenyl;

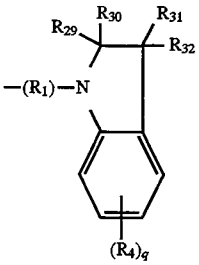
(10)

wherein $R_1$, $R_4$ and q are as defined above;

$R_{29}$ and $R_{30}$ are hydrogen, (C$_1$-C$_6$)alkyl, aryl(C$_1$-C$_6$) alkyl, phenyl or substituted phenyl;

$R_{31}$ and $R_{32}$ are hydrogen, hydroxy, (C$_1$-C$_6$)alkyl, aryl (C$_1$-C$_6$)alkyl, phenyl, substituted phenyl, hydroxymethyl, or CHOR$_{33}$ where $R_{33}$ is (C$_1$-C$_{18}$) alkanoyl; or either $R_{29}$ and $R_{30}$ taken together or $R_{31}$ and $R_{32}$ taken together with the carbon group to which they are attached form a C=O or C=S group;

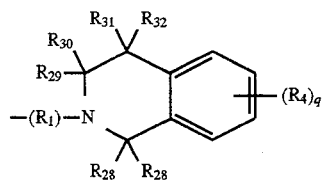
(11)

where $R_1$, $R_4$, $R_{28}$, $R_{29}$, $R_{30}$, $R_{31}$, $R_{32}$ and q are as defined above;

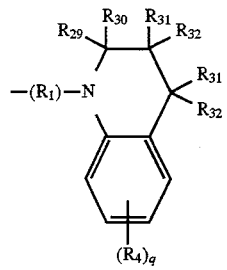
(12)

where $R_1$, $R_4$, $R_{28}$, $R_{29}$, $R_{30}$, $R_{31}$, $R_{32}$ and q are as defined above;

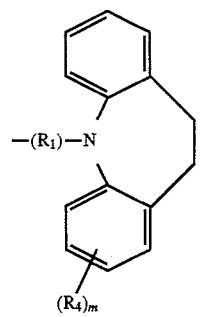
(13)

wherein $R_1$ and $R_4$ are previously defined and m is defined hereinafter;

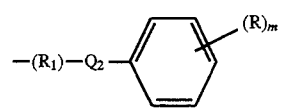
(14)

where $R_1$ is as previously defined;
$Q_2$ is S, NH, or —$CH_2$—; and
R and m are as defined hereinafter;

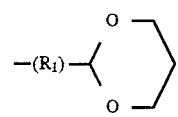
(15)

where $R_1$ is as previously defined;

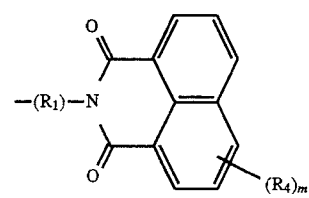
(16)

where $R_1$, and $R_4$ are as previously defined and m is as defined hereinafter;

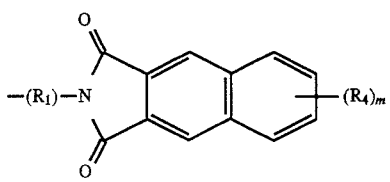
(17)

where $R_1$, $R_4$ are as previously defined and m is as defined hereinafter;

$$-R_1-O-R_{12} \qquad (18)$$

where $R_{12}$ is selected from the group consisting of:
hydrogen,
alkyl,
—C(=O)—($C_1$-$C_{18}$ straight chain or branched)alkyl,
—C(=O)—$NR_{13}R_{14}$,
—C(=O)—$NR_{15}R_{16}$,
—S(=O)2—$R_{17}$, and

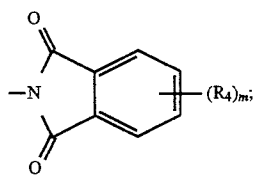

where $R_{13}$ is selected from the group consisting of hydrogen and ($C_1$-$C_{18}$)alkyl groups;
where $R_{14}$ is selected from the group consisting of hydrogen and ($C_1$-$C_{18}$)alkyl groups;
where $NR_{15}R_{16}$ taken together form a ring structure selected from the group consisting of piperidinyl, morpholinyl and piperazinyl;
where $R_{17}$ is selected from the group consisting of lower alkyl and aryl groups;
where $R_4$ is previously defined and m is defined hereinafter;

$$-R_1-NR_{18}R_{19} \qquad (19)$$

where $R_{18}$ and $R_{19}$ are independently selected from the group consisting of:
hydrogen,
($C_1$-$C_{12}$ straight or branched chain)alkyl,
—C(=O)—O—($C_1$-$C_{18}$)alkyl,
—C(=O)—($C_1$-$C_{18}$)alkyl;
—C(=O)-pyridyl or

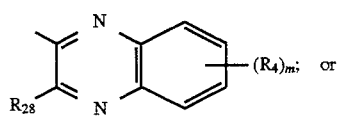

where $NR_{18}R_{19}$ taken together form a ring structure selected from the group consisting of piperidinyl, morpholinyl and piperazinyl; where the piperidinyl or piperazinyl ring is optionally substituted by

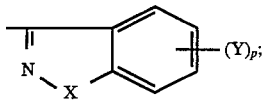

where $R_1$, X, Y, p, $R_4$ and $R_{28}$ are as previously defined and m is defined hereinafter;

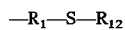  (20)

where $R_1$ and $R_{12}$ are as previously defined;

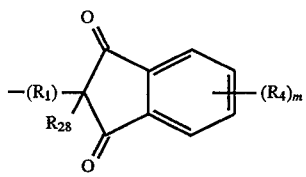  (21)

where $R_1$, $R_4$ and $R_{28}$ are as previously defined; and where

R is hydrogen, lower alkyl, lower alkoxy, hydroxyl, carboxyl, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, monoalkylaminocarbonyl, dialkylaminocarbonyl, formyl,
—C(=O)-alkyl,
—C(=O)—O-alkyl,
—C(=O)-aryl,
—C(=O)-heteroaryl,
—CH(OR$_7$)-alkyl,
—C(=W)-alkyl,
—C(=W)-aryl, and
—C(=W)-heteroaryl;
alkyl is (C$_1$–C$_{18}$)alkyl;
aryl is as previously defined;
heteroaryl is

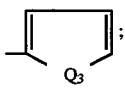

$Q_3$ is —O—, —S—, —NH—, —CH=N—;
W is CH$_2$ or CHR$_8$ or N—R$_9$;
R$_7$ is hydrogen, alkyl, or alkanoyl;
R$_8$ is lower alkyl;
R$_9$ is hydroxy, alkoxy, or —NHR$_{10}$; and
R$_{10}$ is hydrogen, alkyl, (C$_1$–C$_3$)acyl, aryl, —C(=O)aryl or —C(=O)heteroaryl, where aryl and heteroaryl are as defined above; and
m is 1,2, or 3;
with the proviso that in formula (14) Z is not

when X is —S—, Q$_2$ is —CH$_2$—, Y is hydrogen, lower alkyl, lower alkoxy, halogen, hydroxy or trifluoromethyl, and p is 1 or 2;
with the proviso that in formula (4) R$_4$ is not H when R$_1$ is —(CH$_2$)$_{2-5}$—, Z is not

X is —S—, Y is hydrogen, halogen, lower alkyl, lower alkoxy, hydroxy or trifluoromethyl, and p is 1 or 2;

with the proviso that in formula (14) Z is not

when X is —NH— or —N(R$_2$)—, Y is hydrogen, halogen, lower alkyl, lower alkoxy, hydroxy or trifluoromethyl and Q$_2$ is —CH$_2$—;

with the proviso that in formula (14) Z is not

when X is —O—, Q$_2$ is —CH$_2$—, Y is hydrogen, lower alkyl, lower alkoxy, hydroxy or halogen, and p is 1 or 2;

with the proviso that in formula (14) Z is not

when X is —S—, Q$_2$ is —CH$_2$—, Y is hydrogen, halogen, lower alkyl, lower alkoxy or hydroxy, p is 1 or 2, R is hydrogen, and m is 1;

with the proviso that in formula (14) Z is not

when X is —N(R$_2$)—, Q$_2$ is —CH$_2$—, R is chlorine, fluorine, bromine, iodine, lower alkyl, lower alkoxy, lower alkyl thio, lower mono- or dialkylamino, amino, cyano, hydroxy, trifluoromethyl; R$_2$ is aryl; Y is hydrogen, halogen, lower alkyl, lower alkoxy or hydroxy, p is 1 or 2;

with the proviso that in formula (14) Z is not

when X is —NH— or —N(R$_2$)—, where R$_2$ is lower alkyl, aryl lower alkyl, or phenylsulfonyl, Y is hydrogen, halogen, lower alkyl, lower alkoxy or hydroxy, p is 1 or 2 and Q$_2$ is —CH$_2$—;

with the proviso that Y$_2$ is not the moiety of formula (8) when Z is

X is O, p is 1, and Y is hydrogen, lower alkyl, lower alkoxy, chlorine, fluorine, bromine, iodine or a hydroxyl group;

with the proviso that in formula (1) Z is not

when X is O or S, Y is hydrogen, R is hydrogen, ($C_1$-$C_4$)alkyl, chlorine, fluorine, bromine, iodine, cyano, ($C_1$-$C_4$)alkoxy, aryl, —COOR$_{25}$ where R$_{25}$ is ($C_1$-$C_4$)alkyl;

with the proviso that in formula (1) Z is not

when X is —S—, $R_1$ is —(CH$_2$)$_{2-5}$—, R is H, and m=1;

with the proviso that in formula (7) $R_4$ is not hydrogen when Y is 6-F, X is —O—, Z is

and n is 2, 3 or 4;

with the proviso that in formula (18) $R_{12}$ is not H when Z is

X is —NH— or —N($R_2$)— where $R_2$ is lower alkyl, aryl lower alkyl, or phenylsulfonyl, Y is hydrogen, lower alkyl, lower alkoxy, chlorine, fluorine, bromine, iodine or a hydroxyl group and p is 1 or 2;

with the proviso that in formula (18), $R_{12}$ is not H when X is —N($R_2$)—, where $R_2$ is phenyl, Z is

and Y is hydrogen, lower alkyl, lower alkoxy, chlorine, fluorine, bromine, iodine or a hydroxyl group;

with the proviso that in formula (19), $R_{18}$ and $R_{19}$ are not lower alkyl when Z is

X is —N($R_2$)— and $R_2$ is aryl and Y is hydrogen, lower alkyl, lower alkoxy, chlorine, fluorine, bromine, iodine or a hydroxyl group;

with the proviso that in formula (19), when X is —O—, Z is

and Y is hydrogen, lower alkyl, lower alkoxy, chlorine, fluorine, bromine, iodine or a hydroxyl group, $R_{18}$ and $R_{19}$ are not lower alkyl;

with the proviso that in formula (19), $R_{18}$ and $R_{19}$ are not hydrogen when $R_1$ is —(CH$_2$)$_{2-5}$—, Z is

X is —O—, and Y is 6-F;

all geometric, optical and stereoisomers thereof, or a pharmaceutically acceptable acid addition salt thereof.

This invention also provides compounds selected from formula I which are suitable for acylation with ($C_4$-$C_{18}$) carboxylic acids or reactive functional derivatives thereof to form highly lipophilic esters, amides and carbamates, which compounds are also compounds of this invention. Such selected compounds possess a hydroxyl group attached to either an aliphatic or aromatic carbon atom capable of forming the highly lipophilic esters of the invention, a primary or secondary nitrogen atom including the nitrogen at the 1-position of an indazole ring system capable of forming the highly lipophilic amides of the invention. The primary or secondary nitrogen atom may alternatively be acylated with a ($C_4$-$C_{18}$)alkoxycarbonyl chloride to form a highly lipophilic carbamate derivative of the invention.

The invention also provides for the highly lipophilic compounds which provide long acting pharmaceutical effects when administered in the form of depot preparations.

This invention also provides a pharmaceutical composition, which comprises a compound of the invention and a pharmaceutically acceptable carrier therefor. In one embodiment of the invention, the pharmaceutical composition is an antipsychotic composition comprising a compound of the invention in an amount sufficient to produce an antipsychotic effect.

In addition, this invention provides a method of treating psychoses, which comprises administering to a patient a pharmaceutically effective amount of a compound of the invention.

Further, this invention provides a method of sustained release of a pharmaceutically effective amount of a lipophilic compound of the invention in the form of a depot preparation.

Finally, this invention provides a method of alleviating pain by administering to a patient a pain-relieving amount of a compound of the invention.

DETAILED DESCRIPTION OF THE PREFERRED EMBODIMENT

The compounds of this invention are useful as antipsychotic drugs and as analgesic agents. The compounds of the invention can contain a variety of different substituents and chemical groups. As used herein, when the term "lower" is mentioned in connection with the description of a particular group, the term means that the group it is describing contains from 1 to 6 carbon atoms.

The term "alkyl" as used herein refers to a straight or branched chain hydrocarbon group having up to 18 carbon atoms and containing no unsaturation, for example, methyl, ethyl, isopropyl, 2-butyl, neopentyl, n-hexyl or pentadecyl.

The term "alkoxy" as used herein refers to a monovalent substituent comprising an alkyl group linked through an ether oxygen having its free valence bond from the ether oxygen, e.g. methoxy, ethoxy, propoxy, butoxy, or pentoxy.

The term "alkylene" as used herein refers to a bivalent radical of a lower branched or unbranched alkyl group having valence bonds on two terminal carbons thereof, for example, ethylene (—CH$_2$CH$_2$—), propylene (—CH$_2$CH$_2$CH$_2$—), or isopropylene (—CH(CH$_3$)CH$_2$—).

The term "cycloalkyl" refers to a saturated hydrocarbon group possessing at least one carbocyclic ring, the ring containing from 3 to 10 carbon atoms such as cyclopropyl, cyclobutyl, cyclopentyl, cyclohexyl, cycloheptyl, cyclodecyl and the like.

The term "alkanoyl" refers to the radical formed by removal of the hydroxyl function from an alkanoic acid. More particularly, the term "alkanoyl" as used herein refers to an alkyl carbonyl moiety containing from 2 to 18 carbon atoms, e.g.

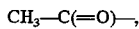

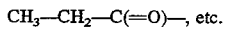, etc.

Examples of alkanoyl groups are formyl, acetyl, propionyl, 2,2-dimethylacetyl, hexanoyl, octanoyl, decanoyl, and the like.

The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid, decanoic acid, and the like.

The term "aryl lower alkyl" refers to compounds wherein "aryl" and "loweralkyl" are as defined above.

The term "lower alkylthio" refers to a monovalent substituent having the formula lower alkyl—S—.

The term "phenylsulfonyl" refers to a monovalent substituent having the formula phenyl—SO—.

The term "acyl" refers to a substituent having the formula lower alkyl—C(=O)— or $CF_3$—C(=O)— or aryl—C(=O)— or heteroaryl—C(=O)—.

The term "lower monoalkylamino" refers to a monosubstituted derivative of ammonia, wherein a hydrogen of ammonia is replaced by a lower alkyl group.

The term "lower dialkylamino" refers to a disubstituted derivative of ammonia, wherein two hydrogens of ammonia are replaced by lower alkyl groups.

The term "acylamino" refers to a primary or secondary amine, wherein a hydrogen of the amine is replaced by an acyl group, where acyl is as previously defined.

The term "dialkylaminocarbonyl" refers to a derivative of an acid, wherein the hydroxyl group of the acid is replaced by a lower dialkylamino group.

The term "aroyl" refers to a disubstituted carbonyl, wherein at least one substituent is an aryl group, where "aryl" is as previously defined.

Unless otherwise indicated, the term "halogen" as used herein refers to a member of the halogen family selected from the group consisting of fluorine, chlorine, bromine, and iodine.

Throughout the specification and appended claims, a given chemical formula or name shall encompass all geometric, optical and stereoisomers thereof where such isomers exist.

A. Compounds of the Invention

The compounds of this invention can be represented by the following formula:

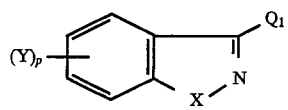 (I)

wherein

X is —O—, —S—, —NH—, or —N($R_2$)—;

$R_2$ is selected from the group consisting of lower alkyl, aryl lower alkyl, aryl, cycloalkyl, aroyl, alkanoyl, alkoxycarbonyl and phenylsulfonyl groups;

p is 1 or 2;

Y is hydrogen, lower alkyl, hydroxy, chlorine, fluorine, bromine, iodine, lower alkoxy, trifluoromethyl, nitro, or amino;

$Q_1$ is selected from the group consisting of:

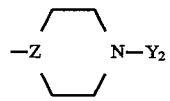 (a)

and

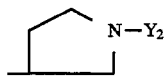 (b)

where Z is

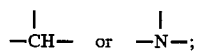

and $Y_2$ is selected from the group consisting of:

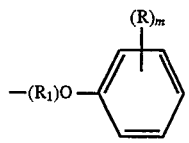 (1)

in which ($R_1$) is —$CR_{24}R_{27}$—$(CR_{23}R_{24})_n$—$CR_{24}R_{27}$— where n is 0,1,2, or 3; or
—$CHR_{24}$—CH=CH—$CHR_{24}$—,
—$CHR_{24}$—C≡C—$CHR_{24}$—,
—$CHR_{24}$—CH=CH—$CR_{23}R_{24}$—$CHR_{24}$—,
—$CHR_{24}$—$CR_{23}R_{24}$—CH=CH—$CHR_{24}$—,
—$CHR_{24}$C≡C—$CR_{23}R_{24}$—$CHR_{24}$—, or
—$CHR_{24}$—$CR_{23}R_{24}$—C≡C—$CHR_{24}$—,
the —CH=CH— bond being cis or trans;

$R_{23}$ is hydrogen, ($C_1$-$C_{18}$) linear alkyl, phenyl, hydroxy, ($C_1$-$C_{18}$)alkoxy, aryloxy, aryl($C_1$-$C_{18}$)alkyloxy, ($C_1$-$C_{18}$)alkanoyloxy, hydroxy($C_1$-$C_6$)alkyl, ($C_1$-$C_{18}$) alkoxy($C_1$-$C_6$)alkyl, phenyl($C_1$-$C_6$)alkyloxy, aryl ($C_1$-$C_6$)alkyloxy($C_1$-$C_6$)alkyl or ($C_1$-$C_{18}$)alkanoyloxy ($C_1$-$C_6$)alkyl or

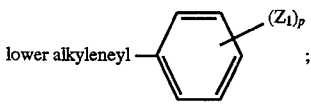

where $Z_1$ is lower alkyl, —OH, lower alkoxy, —$CF_3$, —$NO_2$, —$NH_2$ or halogen; and $R_{24}$ is hydrogen, ($C_1$-$C_{18}$) linear alkyl, phenyl, hydroxy ($C_1$-$C_6$)alkyl, ($C_1$-$C_{18}$)alkoxy($C_1$-$C_6$)alkyl, phenyl ($C_1$-$C_6$)alkyloxy, aryl($C_1$-$C_6$)alkyloxy($C_1$-$C_6$)alkyl or ($C_1$-$C_{18}$)alkanoyloxy($C_1$-$C_6$)alkyl or

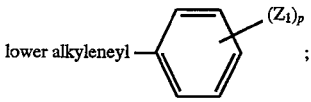

where $Z_1$ is as previously defined;

$R_{27}$ is hydrogen or $R_{24}$ and $R_{27}$ taken together with the carbon to which they are attached form C=O or C=S; and R and m are as defined hereinafter;

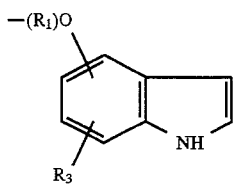 (2)

where $R_1$ is as previously defined, and $R_3$ is hydrogen or —$OCH_3$;

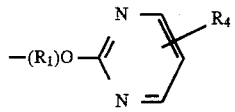 (3)

where $R_1$ is as previously defined; and $R_4$ is hydrogen, lower alkyl, lower alkoxy, hydroxy, tri($C_1$–$C_6$)alkylsilyloxy, hydroxy lower alkyl, alkanoyloxy lower alkyl, amino, mono- or dialkylamino, ($C_1$–$C_{18}$)acyl amino, ($C_1$–$C_{18}$)alkanoyl, trifluoromethyl, chlorine, fluorine, bromine, —O—C(=O)—($C_1$–$C_{18}$ straight or branched chain)alkyl or —C(=O)-aryl;

in which aryl is phenyl or

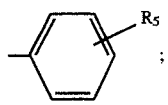

where $R_5$ is hydrogen, lower alkyl, lower alkoxy, hydroxy, chlorine, fluorine, bromine, iodine, lower monoalkylamino, lower dialkylamino, nitro, cyano, trifluoromethyl, trifluoromethoxy;

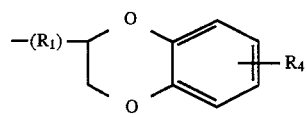 (4)

where $R_1$ and $R_4$ are as previously defined;

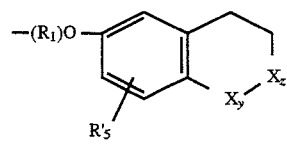 (5)

where either one of $X_y$ or $X_z$ is —C(=O)— and the other is —$CH_2$—; and $R_5'$ is hydrogen, lower alkyl, lower alkoxy, chlorine, fluorine, or bromine; and $R_1$ is as previously defined;

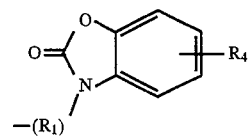 (6)

where $R_1$ and $R_4$ are as previously defined;

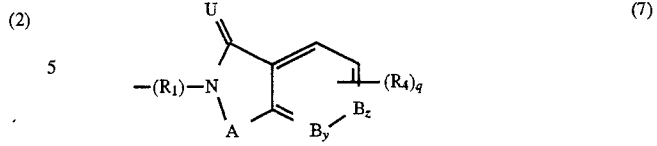 (7)

where A is —C(=O)—, —C(=S)—, —C(=$CH_2$)—, —C(=O)$CH_2$—, —$CH_2CH_2$—, —$CR_{26}$=N— or —$CR_{25}R_{26}$;

$R_{25}$ is hydrogen, ($C_1$–$C_6$)alkyl, hydroxy or ($C_1$–$C_{18}$) alkanoyloxy;

$R_{26}$ is hydrogen or ($C_1$–$C_6$)alkyl;

either one of $B_y$ and $B_z$ is CH or N and the other is CH;

U is O or S;

q is 1,2,3 or 4, and $R_1$ and $R_4$ are as previously defined;

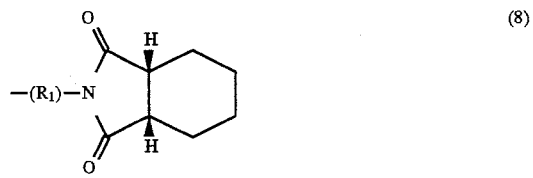 (8)

where $R_1$ is as previously defined;

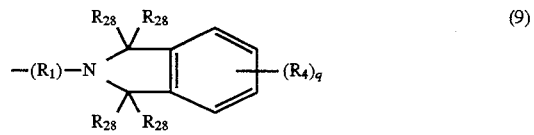 (9)

wherein $R_1$, $R_4$ and q are as defined above; and $R_{25}$ is hydrogen, ($C_1$–$C_6$)alkyl, aryl($C_1$–$C_6$)alkyl, phenyl or substituted phenyl;

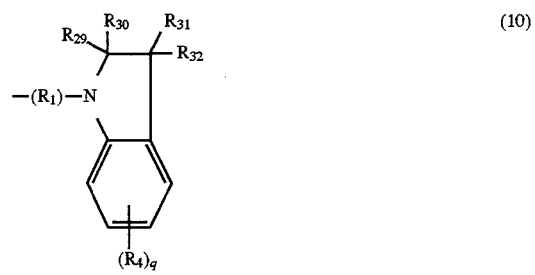 (10)

wherein $R_1$, $R_4$ and q are as defined above;

$R_{29}$ and $R_{30}$ are hydrogen, ($C_1$–$C_6$)alkyl, aryl($C_1$–$C_6$) alkyl, phenyl or substituted phenyl;

$R_{31}$ and $R_{32}$ are hydrogen, hydroxy, ($C_1$–$C_6$)alkyl, aryl($C_1$–$C_{18}$)alkyl, phenyl, substituted phenyl, hydroxymethyl, or $CHOR_{33}$ where $R_{33}$ is ($C_1$–$C_{18}$) alkanoyl; or either $R_{29}$ and $R_{30}$ taken together or $R_{31}$ and $R_{32}$ taken together with the carbon group to which they are attached form a C=O or C=S group;

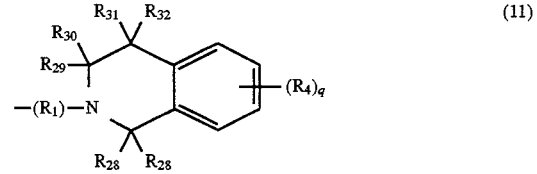 (11)

where $R_1, R_4, R_{28}, R_{29}, R_{30}, R_{31}, R_{32}$ and q are as defined above;

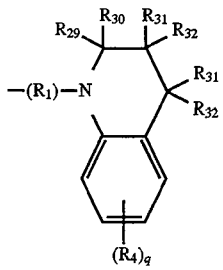 (12)

where $R_1, R_4, R_{28}, R_{29}, R_{30}, R_{31}, R_{32}$ and q are as defined above;

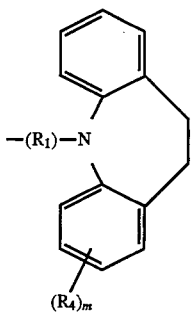 (13)

wherein $R_1$ and $R_4$ are previously defined and m is defined hereinafter;

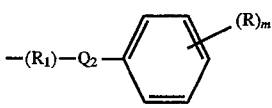 (14)

where $R_1$ is as previously defined;
$Q_2$ is S, NH, or —$CH_2$—; and
R and m are as defined hereinafter;

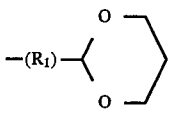 (15)

where $R_1$ is as previously defined;

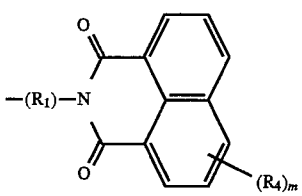 (16)

where $R_1$ and $R_4$ are as previously defined and m is defined hereinafter;

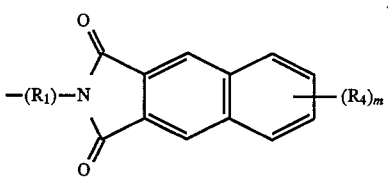 (17)

where $R_1$ and $R_4$ are as previously defined and m is defined hereinafter;

$$—R_1—O—R_{12} \quad (18)$$

where $R_{12}$ is selected from the group consisting of:
hydrogen,
alkyl,
—C(=O)—($C_1$-$C_{18}$ straight chain or branched)alkyl,
—C(=O)—$NR_{13}R_{14}$,
—C(=O)—$NR_{15}R_{16}$,
—S(=O)$_2$—$R_{17}$, and

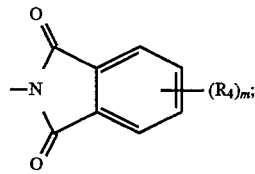

where $R_{13}$ is selected from the group consisting of hydrogen and ($C_1$-$C_{18}$)alkyl groups;

where $R_{14}$ is selected from the group consisting of hydrogen and ($C_1$-$C_{18}$)alkyl groups;

where $NR_{15}R_{16}$ taken together form a ring structure selected from the group consisting of piperidinyl, morpholinyl and piperazinyl;

where $R_{17}$ is selected from the group consisting of ($C_1$-$C_{18}$)alkyl and aryl groups;

where $R_4$ is previously defined and m is defined hereinafter;

$$—R_1—NR_{18}R_{19} \quad (19)$$

where $R_{18}$, and $R_{19}$ are independently selected from the group consisting of:
hydrogen,
($C_1$-$C_{18}$ straight or branched chain)alkyl,
—C(=O)—O—($C_1$-$C_{18}$)alkyl,
—C(=O)—($C_1$-$C_{18}$)alkyl; —C(=O)-pyridyl;

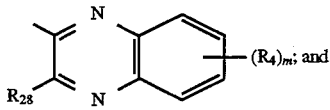

where $NR_{18}R_{19}$ taken together form a ring structure selected from the group consisting of piperidinyl, morpholinyl and piperazinyl;

where the piperidinyl or piperazinyl ring is optionally substituted by

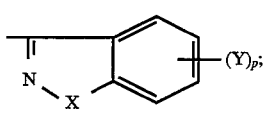

where X, Y, p, $R_1$, $R_4$ and $R_{28}$ are as previously defined and m is defined hereinafter;

$$—R_1—S—R_{12} \quad (20)$$

where $R_1$ and $R_{12}$ are as previously defined;

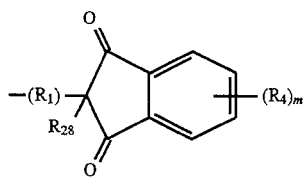
(21)

where $R_1$, $R_4$ and $R_{28}$ are as previously defined; and where

R is hydrogen, lower alkyl, lower alkoxy, hydroxyl, carboxyl, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, monoalkylaminocarbonyl, dialkylaminocarbonyl, formyl,
—C(=O)—alkyl,
—C(=O)—O—alkyl,
—C(=O)—aryl,
—C(=O)-heteroaryl,
—CH(OR$_7$)—alkyl,
—C(=W)—alkyl,
—C(=W)—aryl, and
—C(=W)—heteroaryl;

alkyl is $(C_1-C_{18})$alkyl;
aryl is as previously defined;
heteroaryl is

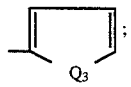;

$Q_3$ is —O—, —S—, —NH—, —CH=N—;
W is $CH_2$ or $CHR_8$ or N—$R_9$;
$R_7$ is hydrogen, alkyl, or alkanoyl;
$R_8$ is lower alkyl;
$R_9$ is hydroxy, alkoxy, or —NHR$_{10}$; and
$R_{10}$ is hydrogen, lower alkyl, $(C_1-C_{18})$acyl, aryl, —C(=O)-aryl or —C(=O)-heteroaryl, where aryl and heteroaryl are as defined above; and
m is 1,2, or 3;

with the proviso that in formula (14) Z is not

when X is —S—, $Q_2$ is —CH$_2$—, Y is hydrogen, lower alkyl, lower alkoxy, halogen, hydroxy or trifluoromethyl, and p is 1 or 2;

with the proviso that in formula (4) $R_4$ is not H when $R_1$ is —(CH$_2$)$_{2-5}$—, Z is not

X is —S—, Y is hydrogen, halogen, lower alkyl, lower alkoxy, hydroxy or trifluoromethyl, and p is 1 or 2;

with the proviso that in formula (14) Z is not

when X is —NH— or —N(R$_2$)—, Y is hydrogen, halogen, lower alkyl, lower alkoxy, hydroxy or trifluoromethyl and $Q_2$ is —CH$_2$—;

with the proviso that in formula (14) Z is not

when X is —O—, $Q_2$ is —CH$_2$—, Y is hydrogen, lower alkyl, lower alkoxy, hydroxy or halogen, and p is 1 or 2;

with the proviso that in formula (14) Z is not

when X is —S—, $Q_2$ is —CH$_2$—, Y is hydrogen, halogen, lower alkyl, lower alkoxy or hydroxy, p is 1 or 2, R is hydrogen, and m is 1;

with the proviso that in formula (14) Z is not

when X is —N(R$_2$)—, $Q_2$ is —CH$_2$—, R is chlorine, fluorine, bromine, iodine, lower alkyl, lower alkoxy, lower alkyl thio, lower mono- or dialkylamino, amino, cyano, hydroxy, trifluoromethyl; $R_2$ is aryl; Y is hydrogen, halogen, lower alkyl, lower alkoxy or hydroxy, p is 1 or 2;

with the proviso that in formula (14) Z is not

when X is —NH— or —N(R$_2$)—, where $R_2$ is lower alkyl, aryl lower alkyl, or phenylsulfonyl, Y is hydrogen, halogen, lower alkyl, lower alkoxy or hydroxy, p is 1 or 2 and $Q_2$ is —CH$_2$—;

with the proviso that $Y_2$ is not the moiety of formula (8) when Z is

is O, p is 1, and Y is hydrogen, lower alkyl, lower alkoxy, chlorine, fluorine, bromine, iodine or a hydroxyl group;

with the proviso that in formula (1) Z is not

when X is O or S, Y is hydrogen, R is hydrogen, $(C_1-C_4)$alkyl, chlorine, fluorine, bromine, iodine, cyano, $(C_1-C_4)$alkoxy, aryl, —COOR$_{25}$ where $R_{25}$ is $(C_1-C_4)$alkyl;

with the proviso that in formula (1) Z is not

when X is —S—, R, is —(CH$_2$)$_{2-5}$—, R is H, and m=1;

with the proviso that in formula (7) R$_4$ is not hydrogen when Y is 6-F, X is —O—, Z is

and n is 2, 3 or 4;

with that the proviso that in formula (18) R$_{12}$ is not H when Z is

X is —NH— or ——N(R$_2$)— where R$_2$ is lower alkyl, aryl lower alkyl, or phenylsulfonyl, Y is hydrogen, lower alkyl, lower alkoxy, chlorine, fluorine, bromine, iodine or a hydroxyl group and p is 1 or 2;

with the proviso that in formula (18), R$_{12}$ is not H when X is —N(R$_2$)—, where R$_2$ is phenyl, Z is

and Y is hydrogen, lower alkyl, lower alkoxy, chlorine, fluorine, bromine, iodine or a hydroxyl group;

with the proviso that in formula (19), R$_{18}$ and R$_{19}$ are not lower alkyl when Z is

X is —N(R$_2$)— and R$_2$ is aryl and Y is hydrogen, lower alkyl, lower alkoxy, chlorine, fluorine, bromine, iodine or a hydroxyl group;

with the proviso that in formula (19), when X is —O—, Z is

and Y is hydrogen, lower alkyl, lower alkoxy, chlorine, fluorine, bromine, iodine or a hydroxyl group, R$_{18}$ and R$_{19}$ are not lower alkyl;

with the proviso that in formula (19), R$_{18}$ and R$_{19}$ are not hydrogen when R$_1$ is —(CH$_2$)$_{2-5}$—, Z is

X is —O—, and Y is 6-F;

all geometric, optical and stereoisomers thereof, or a pharmaceutically acceptable acid addition salt thereof.

When the compounds of the invention are represented by the following formula:

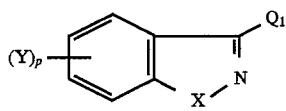

where Q$_1$ is selected from the group consisting of:

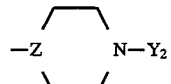

and

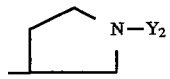

the substituent X in formula (I) is selected from the group consisting of —O—, —S—, —NH—, or —N(R$_2$)—. When the substituent X is —O—, the compounds of the invention contain a 1,2-benzisoxazole nucleus, and when X is —S—, the compounds of the invention contain a 1,2-benzisothiazole nucleus. When X is —NH— or —N(R$_2$)—, the compounds of the invention contain the indazole nucleus.

When p in formula (I) is 1, the substituent Y is selected from the group consisting of hydrogen, lower alkyl, hydroxyl, halogen, lower alkoxy, —CF$_3$, —NO$_2$, and —NH$_2$. The substituent Y is preferably in the 5- or 6-position of the ring. Moreover, in the preferred embodiments of the invention, the substituent Y is hydrogen, hydroxy, chlorine, bromine, or fluorine, and in the particularly preferred compounds of the invention, Y is fluorine, especially in the 6-position of the ring.

When p in formula (I) is 2 and X is —O—, each Y substituent can be independently selected from lower alkoxy, hydroxy or halogen groups, preferably methoxy groups.

When the substituent Y$_2$ has the formula (b)(1):

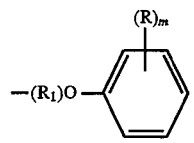

and R$_1$ contains unsaturation, R$_1$ preferably has the formula

—CH$_2$—CH=CH—CH$_2$—.

When the substituent Y$_2$ has the formula (b)(3):

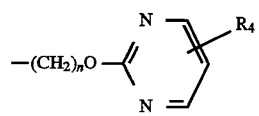

the substituent R$_4$ is preferably hydrogen or (C$_1$–C$_6$)alkyl carbonyl and n is 3.

When the substitutent Y$_2$ has the formula (b)(4):

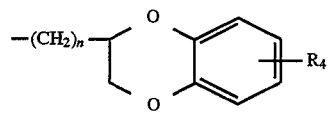

the substitutent R$_4$ is preferably hydrogen or —C(=O)CH$_3$ and n is preferably 1 or 2.

When the substituent $Y_2$ has the formula (b)(5):

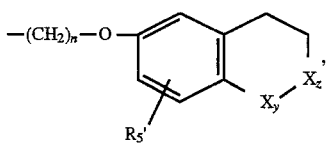

the substituent $R_5'$ is preferably —$OCH_3$ and n is preferably 3.

When the substituent $R_4$ has the formula (b)(6):

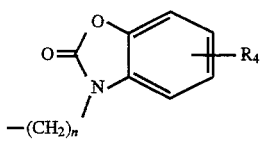

the substituent $R_4$ is preferably —C(=O)$CH_3$ and n is preferably 3.

When the substituent $Y_2$ has the formula (b)(7):

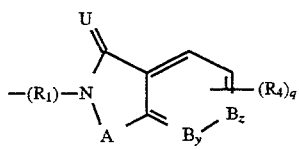

the substituent $R_4$ is preferably hydrogen or methyl and n is preferably 2.

When the substituent $Y_2$ has the formula (b)(8):

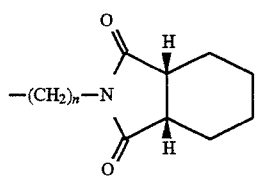

the value of n is preferably 3 or 4.

When the substituent $Y_2$ has the formula (b)(9):

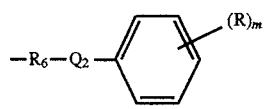

the substituent $R_6$ is preferably —$CH_2$—CH=$CH_2$—$CH_2$— when $R_6$ contains unsaturation.

When the substituent R is

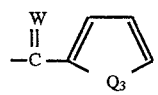

the substituent $Q_3$ is preferably —CH=N; and the substituent W is preferably $CH_2$, the substituent $R_8$ in $CHR_8$ is preferably $CH_3$, the substituent $R_9$ in N—$R_9$ is preferably hydroxy, lower alkoxy, or $NH_2$, and the substituent $R_{10}$ in $NHR_{10}$ is preferably hydrogen.

The value of n in the foregoing formulas can be 2, 3, 4, or 5, and preferably is 2, 3, or 4. In the particularly preferred compounds of the invention n is 2 or 3.

When X in the compounds of the invention is —N($R_2$)—, the substituent $R_2$ is selected from the group consisting of lower alkyl, aryl lower alkyl, aryl, cycloalkyl, aroyl, alkanoyl, alkanoyloxy and phenylsulfonyl groups.

The substituent Z can be

in which case the compounds of the invention are heteroarylpiperidine derivatives, or

in which case the compounds are heteroaryl-piperazine derivatives. When the substituent $Q_1$ has the formula

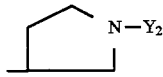

the compounds of the invention are heteroarylpyrrolidines. The preferred compounds of the invention are the heteroarylpiperidines, i.e. compounds in which Z is

The compounds of the invention can contain one, two, or three R-substituents. The substituent R can be hydrogen, lower alkyl, ($C_1$-$C_{18}$)alkoxy, hydroxyl, carboxyl, Cl, F, Br, I, amino, ($C_1$-$C_{18}$)mono or dialkyl amino, —$NO_2$, lower alkyl thio, —$OCF_3$, cyano, acylamino, —$CF_3$, trifluoroacetyl (i.e. —C(=O)—$CF_3$), aminocarbonyl (i.e. —C(=O)—$NH_2$), dialkylaminocarbonyl,
formyl,
  —C(=O)-alkyl,
  —C(=O)—O-alkyl,
  —C(=O)-aryl,
  —C(=O)-heteroaryl, or
  —CH($OR_7$)-alkyl,
  —C(=W)-alkyl,
  —C(=W)-aryl, or
  —C(=W)-heteroaryl;
alkyl is ($C_1$-$C_{18}$)alkyl;
aryl is phenyl or

where $R_5$ is hydrogen, lower alkyl, ($C_1$-$C_6$)alkoxy, hydroxy, Cl, F, Br, I, ($C_1$-$C_{18}$)alkylamino, —$NO_2$, —CN, —$CF_3$, —$OCF_3$;
heteroaryl is

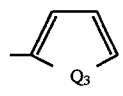

$Q_3$ is —O—, —S—, —NH—, —CH=N—;
W is $CH_2$ or $CHR_8$ or N-$R_9$;
$R_7$ is hydrogen, alkyl, or alkanoyl;
$R_8$ is lower alkyl;
$R_9$ is hydroxy, alkoxy, or —$NHR_{10}$; and $R_{10}$ is hydrogen, lower alkyl, $(C_1-C_{18})$acyl, aryl, —C(=O)-aryl or —C(=O)-heteroaryl, where aryl and heteroaryl are as defined above; and m is 1,2, or 3.

When the compounds of the invention contain two or three R-substituents, each of the R-substituents can be independently selected from the above substituents. Preferably, each of the R-substituents is selected from the group consisting of hydrogen, $(C_1-C_{18})$alkyl, $(C_1-C_{18})$ alkoxy, hydroxyl, —COCF$_3$, $(C_1-C_{18})$alkanoyl, Cl, F, Br, I, $(C_1-C_3)$alkylamino, —NO$_2$, —CF$_3$, —OCF$_3$, —C(=O)-lower alkyl, and —CH(OR$_7$)-lower alkyl.

The compounds of the present invention are prepared in the following manner. The substituents R, $R_1$, $R_2$, $R_3$, etc., X, Y, and Z and the integers m, n, and p are as defined above unless indicated otherwise.

B. Preparation of Compounds of the Invention

The compounds of the invention can generally be prepared by reacting a piperidine or a piperazine of the formula:

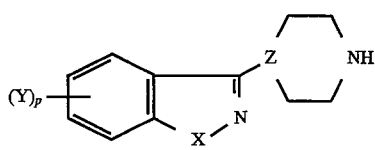
(3)

or a pyrrolidine of the formula:

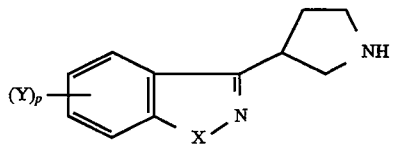
(3A)

under alkylating conditions with a compound of the formula:

HAL—Y$_2$ (4)

where HAL is Cl, Br, or I. The procedures that can be employed for preparing the piperidines, the piperazines, and the pyrrolidines and the alkylating agents identified by the above formulas will now be described in detail.

1. Preparation of 3-(1-unsubstituted-4-piperazinyl)-1H-indazoles

Compounds of the formulae:

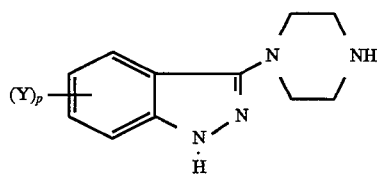
(5)

and

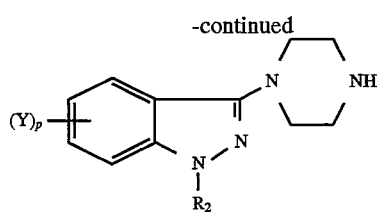
(6)

for use in synthesizing the indazoyl-substituted piperazines of the invention can be prepared as follows.

A substituted aryl ester of formula (7) is selected,

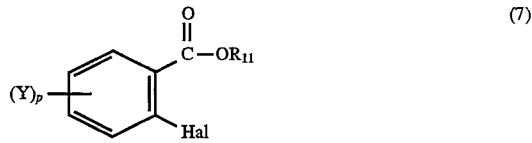
(7)

where $R_{11}$ is lower alkyl and Hal is a halogen selected from the group consisting of Cl, Br, and I. The ester of formula (7) is reacted with hydrazine, H$_2$NNH$_2$, under standard hydrazide formation conditions. Typically, the reaction is carried out in a nonreactive solvent, e.g. ethanol, methanol, or toluene, at a temperature of ambient temperature to the reflux temperature of the solvent for 4 to 16 hours to form a hydrazide of formula (8):

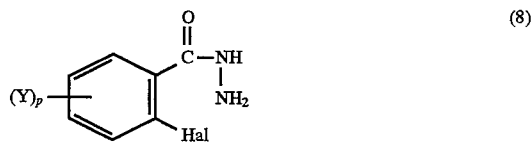
(8)

The hydrazide of formula (8) is reacted with a phenyl sulfonyl halide of the formula

(9)

where Hal is a halogen selected from the group consisting of Cl and Br, to form a compound of the formula

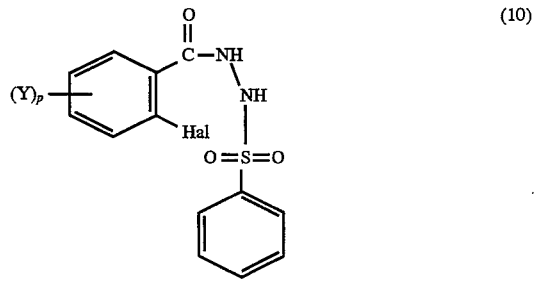
(10)

Typically this reaction is carried out in a basic solvent, such as pyridine or collidine, at a temperature of 0° to 30° C. for 2 to 16 hours.

The compound of formula (10) in turn is reacted neat with thionyl chloride at a temperature of 50° to 79° C. (reflux temperature) for 2 to 16 hours to form a compound of formula (11)

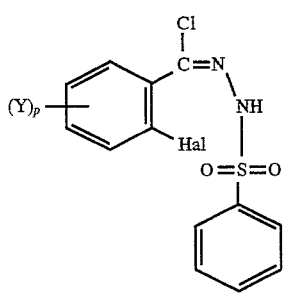

(11)

Compound (11) is reacted with a compound of formula (12),

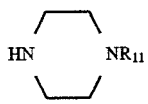

(12)

where $R_{11}$ is lower alkyl, under conventional nucleophilic reaction conditions, for example in an inert solvent, such as tetrahydrofuran (THF), toluene, or diethylether, at a temperature of 5° to 50° C. for 1 to 16 hours to form a compound having the formula

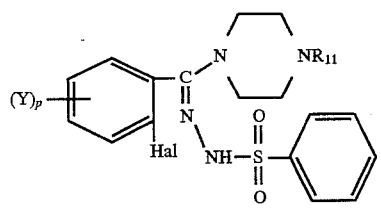

(13)

The compound of formula (13) is then reacted with a condensation agent, such as copper, copper-bronze, or cuprous oxide, in a solvent such as dimethylformamide, dimethylacetamide, or tetramethylurea, at a temperature of 120° to 177° C. for 1 to 16 hours to form a piperazine-substituted phenylsulfonyl indazole of the formula

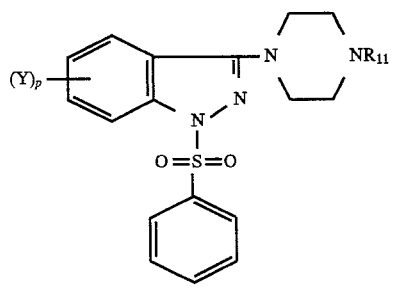

(14)

A cyano-substituted piperazine phenylsulfonyl indazole is then formed by reacting the compound of formula (14) with a conventional cyanation source, such as a halo-cyanide, e.g. BrCN or ClCN, under conventional cyanation conditions, typically in an inert solvent, e.g. dimethylsulfoxide (DMSO) or $CHCl_3$, at ambient temperature for 2 to 16 hours to form a compound of formula

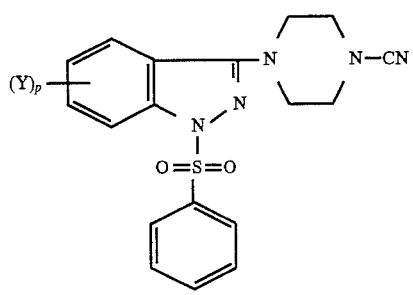

(15)

The compound of formula (15) is then subjected to reduction by means of a metal hydride, e.g. lithium aluminum hydride ($LiAlH_4$). Typically the reduction is carried out under standard reduction conditions in a solvent, such as tetrahydrofuran or diethyl ether, at a temperature of 35° to 67° C. for 6 to 16 hours to form a compound of formula (16):

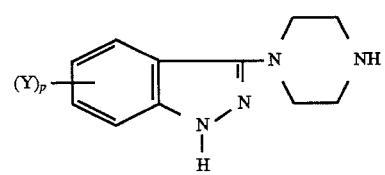

(16)

A compound of formula (16) can be formed in an alternative manner by first reacting a compound of formula (14) with a strong base, such as a metal alcoholate, e.g. sodium methoxide, sodium ethoxide, or sodium butoxide, or with KOH in tetrahydrofuran to form a compound of formula (17):

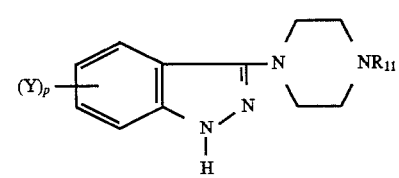

(17)

This reaction is typically carried out in a polar solvent, such as for example $CH_3OH$ or $C_2H_5OH$, at a temperature of ambient to 50° C. for 1 to 16 hours.

Alternatively, the compound of formula (17) can be formed by reducing compound (14) with $LiAlH_4$ under conditions as previously described.

The compound of formula (17) in turn can be reacted with a cyanation reagent, as previously described, to form a cyano substituted piperazine indazole of the formula

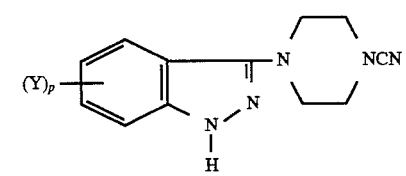

(18)

which in turn can be reduced with a metal hydride, as previously described, to form a compound of formula (16).

In an alternative embodiment, a compound of formula (18) can be reacted with an aqueous mineral acid, e.g. $H_2SO_4$ or HCl, at a temperature of 50° to 120° C. for 2 to 16 hours to form a compound of formula (16).

2. Preparation of 3-(1-unsubstituted-4-piperazinyl)-1,2-benzisoxazoles

A compound of the formula:

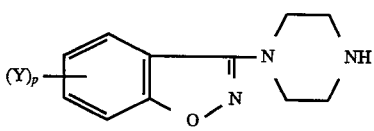 (19)

can be prepared according to conventional techniques. Suitable procedures are described in J. Med. Chem. 1986, 29:359. Compounds of formula (19) are useful for synthesizing the benzisoxazole substituted piperazines of the invention.

3. Preparation of 3-(1-unsubstituted-4-piperazinyl)-1,2-benzisothiazoles

A compound of the formula:

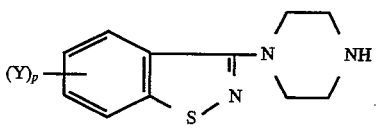 (20)

for use in synthesizing the benzisothiazole substituted piperazines of the invention can be prepared according to the techniques described in J. Med. Chem. 1986, 29:359, United Kingdom Patent (GB) 2 163 432 A and Tetrahedron Letters, Vol 34, No. 41, pp 6525–6528, 1993.

4. Preparation of 3-(1-unsubstituted-4-piperidinyl)-1H-indazoles

A compound of the formula:

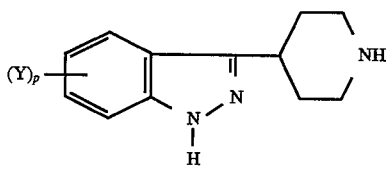 (21)

or

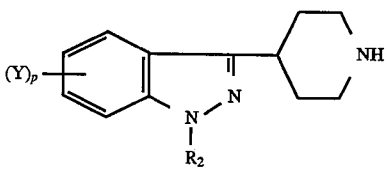 (22)

for use in synthesizing the indazole-substituted piperidines of the invention can be prepared using known techniques. For example, suitable techniques are described in substantial detail in U.S. Pat. No. 4,710,573.

5. Preparation of 3-(1-unsubstituted-4-piperidinyl)-1,2-benzisoxazoles

A compound of the formula:

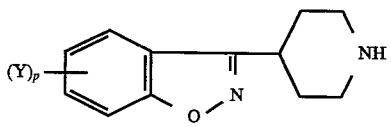 (23)

can be prepared by following the teachings from several sources. For example, U.S. Pat. No. 4,355,037 contains a detailed description of compounds of formula (23) and of methods for preparing the compounds. Additional disclosure of methods for preparing the compounds of formula (23) can be found in U.S. Pat. No. 4,327,103 and in Strupczewski et al., J. Med. Chem., 28:761–769 (1985). The compounds of formula (23) can be employed in the synthesis of the benzisoxazole substituted piperidines of the invention.

6. Preparation of 3-(1-unsubstituted-4-piperidinyl)-1,2-benzisothiazoles

Certain 3-(4-piperidinyl)-1,2-benzisothiazoles can be employed in the synthesis of the N-(aryloxyalkyl)heteroaryl piperidines of the invention. Specifically, a benzisothiazole of the formula:

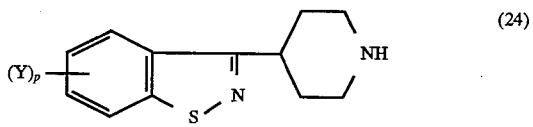 (24)

can be reacted with the alkylating agent previously described to form the N-(aryloxyalkyl)heteroarylpiperidines of the invention. Compounds of formula (24) and their methods of preparation are described in detail in U.S. Pat. No. 4,458,076.

7. Preparation of alkylating agents

The compounds described in Sections 1–6 above can be reacted with alkylating agents as is known in the art. For example, when $Y_2$ is as described in formula (1), an alkylating agent of the formula:

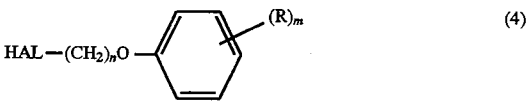 (4)

is reacted to form the N-(aryloxyalkyl) heteroarylpiperidines, piperazines, and pyrrolidines of the invention. The alkylating agents of formula (4) and methods for preparing the alkylating agents are described in U.S. Pat. No. 4,366,162. Additional disclosure can be found in South African publication EA 86 14522. In addition, procedures for making alkylating agents are described in the following Examples. These procedures can be employed to make other alkylating agents for use in this invention.

8. Alkylation of heteroarylpiperidines, piperazines, and pyrrolidines

The heteroarylpiperidines, piperazines, and pyrrolidines described in Sections 1–6 above can be reacted under alkylating conditions with the alkylating agents described in Section 7 to form selected compounds of this invention. The reaction can be carried out by dissolving the reagents in an inert solvent, such as dimethylformamide, acetonitrile, or butanol, and allowing the reagents to react from a temperature of 50° C. to refluxing of the solvent in the presence of an acid receptor, such as a base. Examples of suitable bases are alkali metal carbonates, such as potassium carbonate, sodium carbonate, or sodium bicarbonate. The reaction can be carried out with or without a catalytic amount of an alkaline iodide, such as potassium iodide or sodium iodide, for a time sufficient to form a compound of formula (I) of the invention. Generally, the alkylation reaction is carried out for about 4 to about 16 hours, depending on reactivity of the reagents. The reaction temperature can vary from about 50° to about 120° C. The products can be isolated by treating the reaction product with water, extracting the product into an organic solvent that is immiscible in water, washing, drying, and concentrating the organic solvent to yield the free base, and then, if indicated, converting the resulting compound to an acid addition salt in a conventional manner.

In addition, the compounds of formula 19 where $R_{18}R_{19}$ are both hydrogen may be prepared from the phthalimido compound of formula 7 by treatment with base such as, for example, hydrazine as is known in the art.

More specifically, certain of the compounds of the invention can be synthesized by the folowing methods:

A. Synthesis of Phthalimides

The phthalimido compounds of the invention of formula (25) can be synthesized

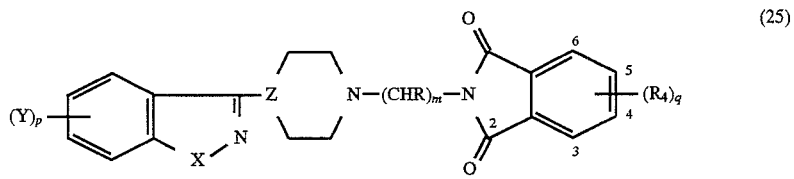

in several ways.

1. Alkylation with an N-haloalkylphthalimide

The heteroarylpiperidines, piperazines and pyrrolidines described in Sections 1–6 above are alkylated under known conditions using the appropriate haloalkylphthalimide, preferably an N-bromoalkylphthalimide (26), in a nonprotic

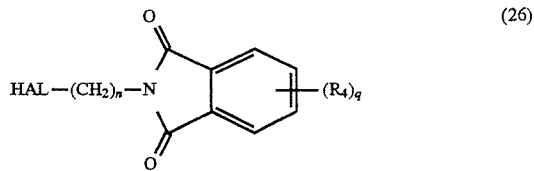

organic solvent such as acetonitrile in the presence of a base such as potassium carbonate at a temperature of from about room temperature to about 120° C., preferably from about 80° C. to about 100° C.

2. Reaction with a phthalic anhydride

The heteroarylpiperidines, piperazines and pyrrolidines described in Sections 1–6 above are first reacted with a haloalkylnitrile to form the corresponding substituted nitrile (27) wherein R is a substitutent as defined for $R_1$ above. The reaction is carried out in a polar, nonprotic organic solvent such as

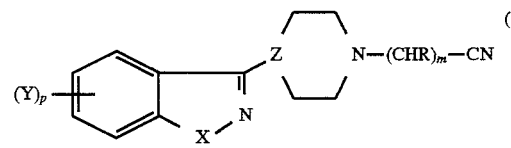

acetonitrile in the presence of a base such as potassium carbonate at a temperature of from about room temperature to about 120° C., preferably from about 80° C. to about 100° C.

The nitrile is then reduced, for example with lithium aluminum hydride in an organic solvent such as tetrahydrofuran at a temperature of from about 0° C. to about 80° C. preferably at about room temperature to yield the corresponding primary amine (28).

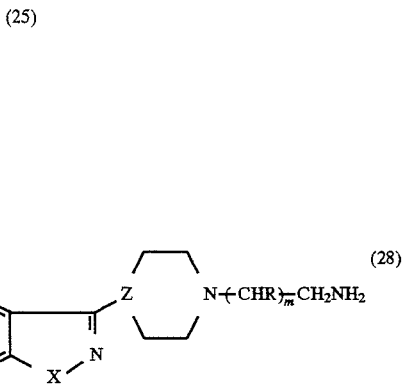

The amine(28) is reacted with phthalic anhydride or a substitued phthalic anhydride or the corresponding phthalic acid under known conditions, for example in dichloromethane or dimethylformamide at temperatures of from about 10° C. to about 150° C. to yield the corresponding phthalimido compound. Preferred conditions for the reaction include dichloromethane at room temperature or dimethylformamide at 135° C.

B. Synthesis of isoindolines

The isoindolines of Formula (29) can be prepared by the following routes.

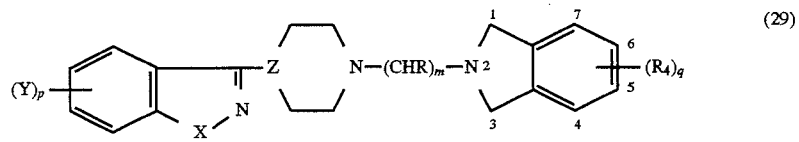

1. Condensation with an α,α'-dibromo-ortho-xylene

The amine (28) is reacted with an α,α'-dibromo-ortho-xylene to obtain the isoindoline. The reaction is carried out in an organic solvent such as acetonitrile in the presence of a base such as potassium carbonate at temperatures of from about room temperature to about 150° C., preferably from about 75° C. to about 100° C.

2. Reduction of a phthalimide

Alternatively, a phthalimido compound of the invention is reduced, for example with lithium aluminun hydride in an organic solvent such as tetrahydrofuran at a temperature of from about 0° C. to about 100° C., preferably from about 70° C. to about 90° C.

C. Synthesis of Tetrahydroquinolines and Tetrahydroisoquinolines

The tetrahydroquinolines and tetrahydroisoquinolines of the invention can be prepared by alkylating the heteroarylpiperidine, piperazine and pyrrolidines (3,3A) with the appropriate 2-bromoacetyltetrahydroquinoline or 2-bromoacetyltetrahydroisoquinoline in the presence of a polar organic solvent such as acetonitrile in the presence of a base such as potassium carbonate at temperatures of from about room temperature to about 150° C., preferably from about 75° C. to about 100° C. to form the corresponding amide (30,30a).

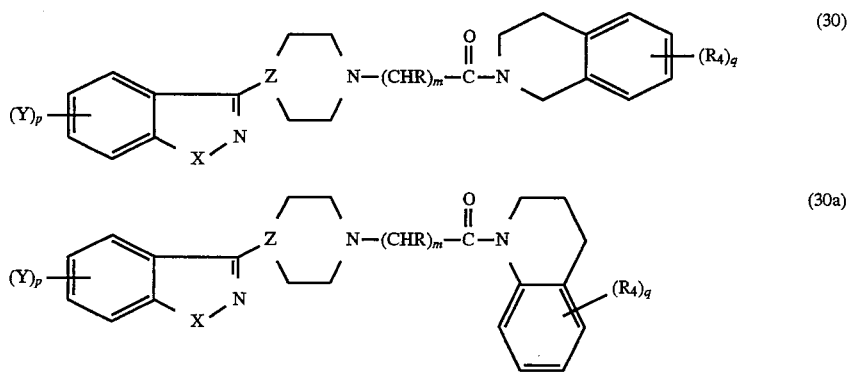

(30)

(30a)

The amide (30,30a) is reduced, for example with lithium aluminum hydride in an organic solvent such as tetrahydrofuran at a temperature of from about 0° C. to about 80° C. preferably at about room temperature to yield the alkyl compound.

9. Preparation of the "depot" Compounds of the Invention

Selected compounds of the invention possess a hydroxyl group attached to either an aliphatic or aromatic carbon capable of forming the highly lipophilic esters of this invention or possess a primary or secondary nitrogen atom including the nitrogen at the 1-position of an indazole ring system capable of forming the highly lipophilic amides of this invention. The primary or secondary nitrogen atom may alternatively be acylated with a $C_4$–$C_{18}$ alkoxycarbonyl chloride to form a highly lipophilic carbamate derivative. Representatives of such alcohols and amines and their highly lipophilic derivatives are found in the Examples of this invention.

It is known in the art that long acting derivatives of drugs may be obtained by such transformation. European Patent Publication No. 260,070 discloses the prolonged action of haloperidol decanoate ester. International Publication No. WO 92/06089 discloses sustained release amide derivatives of sertindole.

Following are typical examples of compounds of the invention that can be prepared by following the techniques described above:

1-[4-[3-[4-(1H-indazol-3-yl)-1-piperazinyl]propoxyl]-3-methoxyphenyl]ethanone;
1-[4-[3-[4-(1,2-benzisoxazol-3-yl)-1-piperidinyl]propoxy]-3-methoxyphenyl]ethanone;
1-[4-[3-[4-(6-fluoro-1,2-benzisoxazol-3-yl)-1-piperidinyl]propoxy]-3-methoxyphenyl]ethanone;
1-[4-[4-[4-(1,2-benzisoxazol-3-yl)-1-piperidinyl]butoxy]-3-methoxyphenyl]ethanone;
1-[4-[4-[4-(6-fluoro-1,2-benzisoxazol-3-yl)-1-piperidinyl]butoxy]-3-methoxyphenyl]ethanone;
1-[4-[2-[4-(1,2-benzisoxazol-3-yl)-1-piperidinyl]ethoxy]-3-methoxyphenyl]ethanone fumarate;
1-[4-[4-[4-(1H-indazol-3-yl)-1-piperazinyl]butoxyl]-3-methoxyphenyl]ethanone fumarate;
1-[4-[2-[4-(6-fluoro-1,2-benzisoxazol-3-yl)-1-piperidinyl]ethoxy]-3-methoxyphenyl]ethanone;
4-[3-[4-(6-fluoro-1,2-benzisoxazol-3-yl)-1-piperidinyl]propoxy]-3-methoxy-α-methylbenzenemethanol;
1-[4-[3-[4-(1,2-benzisothiazol-3-yl)-1-piperidinyl]propoxy]-3-methoxyphenyl]ethanone;
1-[4-[3-[4-(6-fluoro-1,2-benzisoxazol-3-yl)-1-piperidinyl]propoxy]- 3-hydroxyphenyl]ethanone;
1-[4-[3-[4-(6-fluoro-1H-indazol-3-yl)-1-piperazinyl]propoxy]-3-methoxyphenyl]ethanone;

1-[4-[4-[4-(6-fluoro-1H-indazol-3-yl)-1-piperazinyl]butoxy]-3-methoxyphenyl]ethanone;
1-[4-[3-[4-(1H-indazol-3-yl)-1-piperidinyl]propoxy-3-methoxyphenyl]ethanone;
1-[4-[3-[4-(6-chloro-1,2-benzisoxazol-3-yl)-1-piperidinyl]propoxy]-3-methoxyphenyl]ethanone;
1-[4-[4-[4-(6-chloro-1,2-benzisoxazol-3-yl)-1-piperidinyl]butoxy]-3-methoxyphenyl]ethanone fumarate;
1-[4-[3-[4-(5-fluoro-1,2-benzisoxazol-3-yl)-1-piperidinyl]propoxy]-3-methoxyphenyl]ethanone;
6-fluoro-3-[1-[3-(2-methoxyphenoxy)propyl]-4-piperidinyl]-1,2-benzisoxazole fumarate;
4-[3-[4-(6-fluoro-1,2-benzoisoxazol-3-yl)-1-piperidinyl]propoxy]-3-methoxyphenyl]phenylmethane;
1-[4-[4-[4-(1H-indazol-3-yl)-1-piperidinyl]butoxy]-3-methoxyphenyl]ethanone;
1-[4-[2-[4-(6-chloro-1,2-benzisoxazol-3-yl)-1-piperdinyl]ethoxy]-3-methoxyphenyl]ethanone;
1-[3-[3-[4-(6-fluoro-1,2-benzisoxazol-3-yl)-1piperidinyl]propoxy]phenyl]ethanane fumarate;
1-[4-[3-[4-(6-fluoro-1,2-benzisoxazol-3-yl)-1-piperidinyl]propoxy]-3-methylphenyl]ethanone;
1-[2-[3-[4-(6-fluoro-1,2-benzisoxazol-3-yl)-1-piperidinyl]propoxy]-3-methylphenyl]ethanone;
N-[4-[3-[4-(6-fluoro-1,2-benzisoxazol-3-yl)-1-piperidinyl]propoxy]-3-methoxyphenyl]acetamide hemifumarate;
6-chloro-3-(1-piperazinyl)-1H-indazole;
1-[4-[3-[4-(6-fluoro-1H-indazol-3-yl)-1-piperidinyl]propoxyl-3-methoxyphenyl]ethanone;
1-[4-[3-[4-(6-fluoro-1,2-benzisoxazol-3-yl)-1-piperidinyl]propoxy]-3-methylphenyl]ethanone hemifumarate;
1-[4-[3-[4-(6-fluoro-1,2-benzisoxazol-3-yl)-1-piperidinyl]propoxy]phenyl]ethanone;
1-[4-[3-[4-(6-chloro-1H-indazol-3-yl)-1-piperazinyl]propoxy]-3-methoxyphenyl]ethanone;
1-[4-[4-[4-(1,2-benzisothiazol-3-yl)-1-piperazinyl]butoxy]-3-methoxyphenyl]ethanone;
4-[3-[4-(6-fluoro-1,2-benzisoxazol-3-yl)-1-piperidinyl]propoxy]-3-methoxybenzonitrile;
1-[4-[4-[4-(6-fluoro-1H-indazol-3-yl)-1-piperidinyl]butoxy]-3-methoxyphenyl]ethanone;
1-[4-[3-[4-(1-benzoyl-6-fluoro-1H-indazol-3-yl)-1-piperazinyl]propoxy]- 3-methoxyphenyl]ethanone sesquifumarate;
1-[4-[4-[4-(6-chloro-1H-indazol-3-yl)-1-piperazinyl]butoxy]-3-methoxyphenyl]ethanone;
1-[4-[3-[4-(1,2-benzisothiazol-3-yl)-1-piperazinyl]propoxy]-3-methoxyphenyl]ethanone hemifumarate;
1-[3,5-dibromo-4-[3-[4-(6-fluoro-1,2-benzisoxazol-3-yl)-1-piperidinyl]propoxy]phenyl]ethanone;
1-[4-[2-[4-(1,2-benzisothiazol-3-yl)-1-piperazinyl]ethoxy]-3-methoxyphenyl]ethanone;

6-fluoro-3-[1-(3-phenoxypropyl)-4-piperidinyl]-1,2-benzisoxazole;

1-[4-[2-[4-(6-chloro-1H-indazol-3-yl)-1-piperazinyl]ethoxyl-3-methoxyphenyl]ethanone;

1-[4-[3-[4-(6-fluoro-1,2-benzoisoxazol-3-yl)-1-piperidinyl]propoxy]-3-methylmercaptophenyl]ethanone;

1-[4-[4-[4-(1,2-benzisothiazol-3-yl)-1-piperidinyl]butoxy]-3-methoxyphenyl]ethanone;

1-[4-[3-[4-(6-fluoro-1,2-benzisoxazol-3-yl)-1-piperidinyl]propoxy]3-methoxyphenyl]phenylmethanone;

1-[3-bromo-4-[3-[4-(6-fluoro-1,2-benzisoxazol-3-yl)-1-piperidinyl]propoxy]phenyl]ethanone;

3-[-1-[3-[4-(1-ethoxyethyl)-2-methoxyphenoxy]propyl]-4-piperidinyl]-6-fluoro-1,2-benzisoxazole hydrochloride;

3-[1-[3-[4-(1-acetoxyethyl)-2-methoxyphenoxy]propyl]-4-piperidinyl]-6-fluoro-1,2-benzisoxazole fumarate;

1-[4-[3-[4-(6-fluoro-1,2-benzisoxazol-3-yl)-1-piperidinyl]propoxy-3-methoxyphenyl]pentanone;

2-[3-[4-(6-fluoro-1,2-benzisoxazol-3-yl)-1-piperdinyl]propoxy]-N-methylbenzenamine hemifumarate;

3-[1-[3-(4-bromo-2-methoxphenoxy)propyl]-4-piperidinyl]-6-fluoro-1,2-benzisoxazole;

1-[4-[3-[4-(6-fluoro-1,2-benzisoxazol-3-yl)-1-piperidinyl]propoxy]-3-methoxyphenyl]propanone;

4-[3-[4-(6-fluoro-1,2-benzisoxazol-3-yl)-1-piperidinyl]propoxy]-3-methoxybenzamide;

1-[4-[3-[4-(6-fluoro-1,2-benzisoxazol-3-yl)-1-piperidinyl]propoxy]-3-(methylamino)phenyl]ethanone;

1-[4-[3-[4-(6-fluoro-1,2-benzisoxazol-3-yl)-1-piperidinyl]propoxy]-3-ethoxyphenyl]ethanone;

N-[2-[3-[4-(6-fluoro-1,2-benzisoxazol-3-yl)-1-piperidinyl]propoxy]phenyl]acetamide;

1-[4-[3-[4-(6-fluoro-1,2-benzisoxazol-3-yl)-1-piperidinyl]propoxy]-3-dimethylaminophenyl]ethanone;

1-[4-[3-[4-(6-fluoro-1,2-benzisoxazol-3-yl)-1-piperidinyl]propoxy]-2-methoxyphenyl]ethanone hydrochloride;

1-[4-[3-[4-(6-fluoro-1,2-benzisoxazol-3-yl)-1-piperidinyl]propoxy]-3-methoxyphenyl]-2,2,2-trifluoroethanone;

4-[3-[4-(6-fluoro-1,2-benzisoxazol-3-yl)-1-piperidinyl]propoxy]-3-hydroxy-α-methylbenzenemethanol;

2-[3-[4-(6-fluoro-1,2-benzisoxazol-3-yl)-1-piperidinyl]propoxy]aniline dihydrochloride;

N-[5-acetyl-2-[3-[4-(6-fluoro-1,2-benzisoxazol-3-yl)-1-piperidinyl]propoxy]phenyl]acetamide;

3-[1-[3-(4-ethyl-3-methoxyphenoxy)propyl]-4-piperidinyl]-6-fluoro-1,2-benzisoxazole hydrochloride;

1-[3,5-dimethoxy-4-[3-[4-(6-fluoro-1,2-benzisoxazol-3-yl)-1-piperidinyl]propoxy]phenyl]ethanone;

N-[3-[3-[4-(6-fluoro-1,2-benzoisoxazol-3-yl)-1-piperidinyl]propoxy]phenyl]acetamidehemifumarate;

3-[3-[4-(6-fluoro-1,2-benzisoxazol-3-yl)-1-piperidinyl]propoxy]aniline;

3-[3-[4-(6-fluoro-1,2-benzisoxazol-3-yl)-1-piperidinyl]propoxy]-4-methoxyaniline;

1-[4-[3-[4-(6-fluoro-1,2-benzisothiazol-3-yl)-1-piperidinyl]propoxy-3-methylaminophenyl]ethanone fumarate;

N-[3-[3-[4-(6-fluoro-1,2-benzisothiazol-3-yl)-1-piperidinyl]propoxy]-4-methoxyphenyl]acetamide;

1-[4-[3-[4-(6-fluoro-1,2-benzisothiazol-3-yl)-1-piperidinyl]propoxy]-3-methoxyphenyl]ethanone hydrochloride;

N,N-dimethyl-4-[3-[4-(6-fluoro-1,2-benzisoxazol-3-yl)-1-piperidinyl]propoxy]-3-methoxybenzamide;

1-[4-[3-[4-(6-fluoro-1,2-benzisoxazol-3-yl)-1-piperidinyl]propoxy]-3-methoxyphenyl]ethanone oxime;

1-[4-[3-[4-(6-fluoro-1,2-benzisoxazol-3-yl)-1-piperidinyl]propoxy]methoxyphenyl]-ethanone oxime O-methyl ether;

1-[4-[3-[4-(6-fluoro-1,2-benzisoxazol-3-yl)-1-piperidinyl]propoxy]-3-methoxyphenyl]ethanone hydrazone;

6-fluoro-3-[1-[3-[2-methoxy-4-(1-methylethenyl)phenoxy]propyl]-4-piperidinyl]-1,2-benzisoxazole hydrochloride;

(Z)-1-[4-[(4-chloro-2-butenyl)oxy]-3-methoxyphenyl]ethanone;

(Z)-1-[4-[[4-[4-(6-fluoro-1,2-benzisoxazol-3-yl)-1-piperidinyl]-2-butenyl]oxy]-3-methoxyphenyl]ethanone;

(E)-1-[3-[[4-[4-(6-fluoro-1,2-benzisoxazol-3-yl)-1-piperidinyl]-2-butenyl]oxy]-4-hydroxyphenyl]ethanone hydrochloride;

(E)-1-[3-[[4-[4-(6-fluoro-1,2-benzisoxazol-3-yl)-1-piperidinyl]-2-butenyl]oxy]- 4-benzyloxyphenyl]ethanone;

6-(3-chloropropoxy)-5-methoxyindole;

6-fluoro-3-[1-[3-[(5-methoxy-1H-indol-6-yl)oxy]propyl]-4-piperidinyl]-1,2-benzisoxazole;

6-fluoro-3-[1-[3-[(1H-indol-7-yl)oxy]propyl]-4-piperidinyl]-1,2-benzisoxazole hemifumarate;

6-fluoro-3-[1-(3-hydroxypropyl)-4-piperidinyl]-1,2-benzisoxazole;

6-fluoro-3-[1-(2-pyrimidinoxy)propyl]-4-piperidinyl]-1,2-benzisoxazole fumarate;

6-aceto-2-[4-(6-fluoro-1,2-benzisoxazol-3-yl)-1-piperidinyl]methyl]-1,4-benzodioxan;

2-[4-(6-fluoro-1,2-benzisoxazol-3-yl)-1-piperidinyl]methyl-1,4-benzodioxan;

2-[4-(6-fluoro-1,2-benzisoxazol-3-yl)-1-piperidinyl]ethyl-1,4-benzodioxan;

6-(3-chloropropoxy)-7-methoxy-1-tetralone;

6-[3-[4-(6-fluoro-1,2-benzisoxazol-3-yl)-1-piperidinyl]propoxy]-7-methoxy-1-tetralone;

N-(3-chloropropyl)-2-benzoxazolinone;

N-(3-chloropropyl)-6-acetyl-2-benzoxazolinone;

N-[3-[4-(6-fluoro-1,2-benzisoxazol-3-yl)-1-piperidinyl]propyl]-6-acetyl-2-benzoxazolinone;

N-[3-[4-(6-fluoro-1,2-benzisoxazol-3-yl)-1-piperidinyl]propyl]phthalimide;

1-(3-aminopropyl)-4-(6-fluoro-1,2-benzisoxazol-3-yl)piperidine dihydrochloride;

cis-2-(3-(4-(6-fluoro-1,2-benzisoxazol-3-yl)-1-piperidinyl)propyl)hexahydro-1H-isoindole-1,3-dione hydrochloride;

N-[4-[4-(6-fluoro-1,2-benzisoxazol-3-yl)-1-piperidinyl]-butyl]phthalimide;

1-(4-aminobutyl)-4-(6-fluoro-1,2-benzisoxazol-3-yl)piperidine dihydrochloride;

cis-2-(4-(4-(6-fluoro-1,2-benzisoxazol-3-yl)-1-piperidinyl)butyl)hexahydro-1H-isoindole-1,3-dione hydrochloride;

1-[4-[[3-[4-(6-fluoro-1,2-benzisoxazol-3-yl)-1-piperidinyl]propyl]thio]-3-methoxyphenyl]ethanone;

4-(6-fluoro-1,2-benzisoxazol-3-yl)-1-(2'-methoxyphenyl)butylpiperidine maleate;

4-(4-bromobutyl)-1-(1,3-dithian-2-yl)ethylbenzene;

1-[4-(1,3-dithian-2-yl)ethyl]phenyl-4-(6-fluoro-1,2-benzisoxazol-3-yl)butylpiperidine;

1-[4-(4'-acetophenyl)butyl]-4-(6-fluoro-1,2-benzisoxazol-3-yl)piperidine;

1-[4-[3-[4-(6-fluoro-1,2-benzisoxazol-3-yl)-1-piperidinyl]propylamino]-3-methoxyphenyl]ethanone;

(2,4-difluorophenyl)-[1-(phenylmethyl)-3-pyrrolidinyl]methanone oxalate;

6-fluoro-3-[1-phenylmethyl)-3-pyrrolidinyl]-1,2-benzisoxazole fumarate;

(E)-1-[4-[(4-bromo-2-butenyl)oxy]-3-methoxyphenyl]ethanone;

4-(3-chloropropoxy)-3-methoxybenzaldehyde;

6-fluoro-3-(3-pyrrolidinyl)-1,2-benzisoxazole hydrochloride;

1-[4-[3-[4-(6-fluoro-1,2-benzisoxazol-3-yl)-1-piperidinyl]propylamino]-3-hydroxyphenyl]ethanone;

1-[3-acetylamino-4-(3-chloropropoxy)phenyl]ethanone;

N-[2-(3-hydroxypropoxy)phenyl]acetamide;

4-(3-chloropropoxy)-3-methoxybenzaldehyde;

(±)-1-[4-[3-[4-(6-fluoro-1,2-benzisoxazol-3-yl)-1-piperidinyl]-2-methylpropoxy]-3-methoxyphenyl]ethanone;

(S)-(+)-1-[4-[3-[4-(6-fluoro-1,2-benzisoxazol-3-yl)-1-piperidinyl]-2-methylpropoxy]-3-methoxyphenyl]ethanone;

(R)-(−)-1-[4-[3-[4-(6-fluoro-1,2-benzisoxazol-3-yl)-1-piperidinyl]-2-methylpropoxy]-3-methoxyphenyl]ethanone;

1-[4-[3-[4-[(6-fluoro-1,2-benzisoxazol-3-yl)-1-piperidinyl]-2,2-dimethylpropoxy]-3-methoxyphenyl]ethanone;

(±)-1-[4-[3-[4-(6-fluoro-1,2-benzisoxazol-3-yl)-1-piperidinyl]-2-phenylpropoxy]-3-methoxyphenyl]ethanone;

(±)-1-[4-[3-[4-(6-fluoro-1,2-benzisoxazol-3-yl)-1-piperidinyl]-2-(3-chloropheyl)propoxy]-3-methoxyphenyl]ethanone;

(±)-1-[4-[3-[4-(6-fluoro-1,2-benzisoxazol-3-yl)-1-piperidinyl]-2-(phenylmethyl)propoxy]]-3-methoxyphenyl]ethanone;

(±)-1-[4-[3-[4-(6-fluoro-1,2-benzisoxazol-3-yl)-1-piperidinyl]-1-methylpropoxy]-3-methoxyphenyl]ethanone;

(±)-1-[4-[3-[4-(6fluoro-1,2-benzisoxazol-3-yl)-1-piperidinyl]-3-methylpropoxy]-3-methoxyphenyl]ethanone;

(±)-1-[4-[4-[4-(1,2-benzisoxazol-3-yl)-1-piperidinyl]-3-methylbutoxy]-3-methoxyphenyl]ethanone;

(±)-1-[4-[4-[4-(1,2-benzisoxazol-3-yl)-1-piperidinyl]-3-phenylbutoxy]-3-methoxyphenyl]ethanone;

(±)-[1-[4-[4-[4(1,2-benzisoxazol-3-yl)-benzisoxazol-3-yl)-1-piperidinyl]-2-(2-phenylethyl)butoxy]-3-methoxyphenyl]ethanone;

(±)-[4-[2-[4-(6-fluoro-1,2-benzisoxazol-3-yl)-1-piperidinyl]-1-methylethoxyl-3methoxyphenyl]ethanone;

(E)-1-[4-[[4-[4-(6-fluoro-1,2-benzisoxazol-3-yl)-1-piperidinyl]-1-methyl-2-butenyl]oxy]-3-methoxyphenyl]ethanone;

(Z)-1-[4-[[4-[4-(6-fluoro-1,2-benzisoxazol-3-yl)-1-piperidinyl]-3-methyl]-2-butenyl]oxy]-3-methoxyphenyl]ethanone;

(±)-1-[4-[[4-[4-(6-fluoro-1,2-benzisoxazol-3-yl)-1-piperidinyl]-1-propyl]-2-butynyl]oxy]3-methoxyphenyl]ethanone;

(S)-(+)-1-[4-[3-[4-(6-fluoro-1H-indazol-3-yl)-1-piperazinyl]-2-methylpropoxy]-3-methoxyphenyl]ethanone;

(R)-(−)-1-[4-[3-[4-(6-fluoro-1H-indazol-3-yl)-1-piperazinyl]-2-methylpropoxy]-3-methoxyphenyl]ethanone;

(±)-1-[4-[4-[4-(1,2-benzisothiazol-3-yl)-1-piperazinyl]-3-methylbutoxy]-3-methoxyphenyl]ethanone;

(±)-1-[4-[3-[4-(6-fluoro-1,2-benzisoxazol-3-yl)-1-piperidinyl]-2-phenylpropoxy]-3-methoxyphenyl]ethanone; and (±)-6-fluoro-3-[1-[3-(2-methyl-(2-methoxyphenoxy)propyl]-4-piperidinyl]-1,2-benzisoxazole.

The compounds of the present invention are useful for treating psychoses by virtue of their ability to elicit an antipsychotic response in mammals. Antipsychotic activity is determined in the climbing mice assay by a method similar to those described by P. Protais, et al., Psychopharmacol., 50:1 (1976) and B. Costall, Eur. J. Pharmacol., 50:39 (1978).

Subject CK-1 male mice (23–27 grams) are group-housed under standard laboratory conditions. The mice are individually placed in wire mesh stick cages (4"×10") and are allowed one hour for adaption and exploration of the new environment. Then apomorphine is injected subcutaneously at 1.5 mg/kg, a dose causing climbing in all subjects for 30 minutes. Compounds to be tested for antipsychotic activity are injected intraperitoneally or given oral doses at various time intervals, e.g. 30 minutes, 60 minutes, etc. prior to the apomorphine challenge at a screening dose of 10–60 mg/kg.

For evaluation of climbing, 3 readings are taken at 10, 20, and 30 minutes after apomorphine administration according to the following scale:

| Climbing Behavior Mice with: | Score |
| --- | --- |
| 4 paws on bottom (no climbing) | 0 |
| 2 paws on the wall (rearing) | 1 |
| 4 paws on the wall (full climb) | 2 |

Mice consistently climbing before the injection of apomorphine are discarded.

With full-developed apomorphine climbing, the animals are hanging on to the cage walls, rather motionless, over long periods of time. By contrast, climbs due to mere motor stimulation usually only last a few seconds.

The climbing scores are individually totaled (maximal score: 6 per mouse over 3 readings) and the total score of the control group (vehicle intraperitoneally-apomorphine subcutaneously) is set to 100%. $ED_{50}$ values with 95% confidence limits, calculated by a linear regression analysis, of some of the compounds of the present invention as well as a standard antipsychotic agent are presented in Table 1.

TABLE 1

| COMPOUND | CLIMBING MOUSE ASSAY ($ED_{50}$ mg/kg, ip) |
| --- | --- |
| 1-[4-[3-[4-(1H-indazol-3-yl)-1-piperazinyl]propoxy]-3-methoxyphenyl]ethanone | 0.98 |
| 1-[4-[3-[4-(1,2-benzisoxazol-3-yl)-1-piperidinyl]propoxy]-3-methoxyphenyl]ethanone | 0.67 |
| 1-[4-[3-[4-(6-fluoro-1,2-benzisoxazol-3-yl)-1-piperidinyl]propoxy]-3-methoxyphenyl]ethanone | 0.095 |
| 1-[4-[4-[4-(1,2-benzisoxazol-3-yl)-1-piperidinyl]butoxy]-3-methoxyphenyl]ethanone | 1.6 |
| 1-[4-[4-[4-(6-fluoro-1,2-benzisoxazol-3-yl)-1-piperidinyl]butoxy]-3-methoxyphenyl]ethanone | 0.68 |
| 1-[4-[3-[4-(6-fluoro-1,2-benzisothiazol-3-yl)-1-piperidinyl]propoxy]-3-methoxyphenyl]ethanone hydrochloride | 0.16 |
| 2-[4-(6-fluoro-1,2-benzisoxazol-3-yl)-1-piperidinyl]ethyl]-1,4-benzodioxan | 0.29 |
| (Z)-1-[4-[[4-[4-(6-fluoro-1,2-benzisoxazol-3-yl)-1-piperidinyl]-2-butenyl]oxy]-3-methoxyphenyl]ethanone | 0.61 |
| 1-[4-(4'-acetophenyl)butyl]-4-(6-fluoro-1,2-benzisoxazol-3-yl)piperidine | 0.34 |
| 6-fluoro-3-[1-(3-hydroxypropyl)-4-piperidinyl]-1,2-benzisoxazole | 4.1 |

TABLE 1-continued

| COMPOUND | CLIMBING MOUSE ASSAY (ED$_{50}$ mg/kg, ip) |
|---|---|
| 4-[4-(6-fluoro-1,2-benzisoxazol-3-yl)-1-piperidinyl]butyl decanoate fumarate | 3.31 |
| 1-(3-aminopropyl)-4-(6-fluoro-1,2-benzisoxazol-3-yl)-piperidine dihydrochloride | 22.6 |
| N-[2-[4-(6-fluoro-1,2-benzisoxazol-3-yl)-1-piperidinyl]ethyl]phthalimide | 5.0 |
| N-[2-[4-(6-fluoro-1,2-benzisoxazol-3-yl)-1-piperidinyl]ethyl]phthalimide hydrochloride | 0.48 |
| 6-fluoro-3-[1-[3-[(isoquinol-5-yl)oxy]propyl]-4-piperidinyl]-1,2-benzisoxazole sesquifumarate | 0.172 |
| N-[2-[4-(6-fluoro-1,2-benzisothiazol-3-yl)-1-piperidinyl]ethyl]phthalimide hydrochloride | 0.38 |
| N-[2-[4-(6-fluoro-1,2-benzisoxazol-3-yl)-1-piperidinyl]ethyl]-3,6-difluorophthalimide | 2.9 |
| N-[2-[4-(6-fluoro-1H-indazol-3-yl)-1-piperazinyl]ethyl]phthalimide | 1.2 |
| N-[2-[4-(6-fluoro-1H-indazol-3-yl)-1-piperidinyl]ethyl]phthalimide hydrochloride | 0.8 |
| 2,3-dihydro-2-[2-[4-(6-fluoro-1,2-benzisoxazol-3-yl)-1-piperidinyl]ethyl]-3-methylene-1H-isoindol-1-one hydrochloride | 0.64 |
| 2,3-dihydro-2-[2-[4-(6-fluoro-1,2-benzisoxazol-3-yl)-1-piperidinyl]ethyl]-3-methyl-1H-isoindol-1-one hydrochloride | 1.17 |
| N-[2-[4-[(6-fluoro-1,2-benzoxazol-3-yl)-1-piperidinyl]ethyl]-4-aminophthalimide fumarate | 0.097 |
| N-[2-[4-(6-fluoro-1,2-benzisoxazol-3-yl)-1-piperidinyl]ethyl]4-hydroxyphthalimide hydrochloride | 1.6 |
| 2-[2-[4-(6-fluoro-1H-indazol-3-yl)-1-piperazinyl]ethyl]-2,3-dihydro-3-hydroxy-1H-isoindol-1-one hemifumarate | 2.2 |
| 2-[2-[4-[(6-fluoro-1,2-benzisoxazol-3-yl)-1-piperidinyl]ethyl]-2,3-dihydro-1H-isoindol-1-one | 1.9 |
| N-[2-[4-(6-fluoro-1H-indazol-3-yl)-1-piperazinyl]ethyl]-4-methylphthalimide dihydrochloride | 0.37 |
| N-[2-[4-(6-fluoro-1,2-benzisoxazol-3-yl)-1-piperidinyl]ethyl]-3-methoxyphthalimide | 0.16 |
| 4-(6-fluoro-1,2-benzisoxazol-3-yl)-1-[2-(2,3-dihydro-1H-isoindol-2-yl)ethyl]piperidine dihydrochloride | 0.36 |
| 3-[2-[4-(6-fluoro-1,2-benzisoxazol-3-yl)-1-piperidinyl]ethyl]-2-methyl-3H-quinazolin-4-one | 0.61 |
| 4-(6-fluoro-1H-indazol-3-yl)-1-[2-(2,3-dihydro-1H-isoindol-2-yl)-ethyl]piperazine dimaleate | 0.25 |
| N-[3-[4-(6-fluoro-1,2-benzisoxazol-3-yl)-1-piperidinyl]-butyl]phthalmide hydrochloride | 0.7 |
| 1-(1,2,3,4-tetrahydro-1H-isoquinolin-2-yl)-2-[4-(6-fluoro-1,2-benzisoxazol-3-yl)-1-piperidinyl]-ethanone hydrochloride ethanolate | 6.25 |
| 4-(6-fluoro-1H-indazol-3-yl)-1-[2-(5-fluoro-2,3-dihydro-1H-isoindol-2-yl)ethyl]piperazine dimaleate | 0.16 |
| 4-(6-fluoro-1H-indazol-3-yl)-1-[3-(2,3-dihydro-1H-isoindol-2-yl)propyl]piperazine dimaleate | 0.46 |
| N-[2-[4-(6-fluoro-1,2-benzisoxazol-3-yl)-1-piperidinyl]ethyl-1,2,3,4-tetrahydroisoquinoline difumarate | 0.23 |
| 2-[4-(6-fluoro-1,2-benzisoxazol-3-yl)-1-piperidinyl]-1-(2,3-dihydro-1H-isoindol-2-yl)ethanone fumarate | 2.33 |
| 4-(6-fluoro-1H-indazol-3-yl)-1-[2-(5-fluoro-2,3-dihydro-1H-isoindol-2-yl)ethyl]piperidine dimaleate | 0.27 |
| N-[2-[4-(6-fluoro-1,2-benzisoxazol-3-yl)-1-piperidinyl]ethyl]-1,2,3,4-tetrahydroquinoline fumarate | 1.19 |
| 4-(6-fluoro-1H-indazol-3-yl)-1-[2-(2,3-dihydro-5-methyl-1H-isoindol-2-yl)ethyl]piperazine difumarate | 0.17 |
| 4-(6-fluoro-1H-indazol-3-yl)-1-[2-(2,3-dihydro-4-methyl-1H-isoindol-2-yl)ethyl]piperazine difumarate | 0.35 |
| 4-(1H-indazol-3-yl)-1-[2-(2,3-dihydro-5-fluoro-1H-isoindol-2-yl)ethyl]piperazine dimaleate | 1.32 |

TABLE 1-continued

| COMPOUND | CLIMBING MOUSE ASSAY (ED$_{50}$ mg/kg, ip) |
|---|---|
| N-[2-[4-(6-fluoro-1H-indazol-3-yl)-1-piperidinyl]ethyl]-1,2,3,4-tetrahydroisoquinoline dimaleate | 0.44 |
| Clozapine (standard) | 8.1 |

Antipsychotic response is achieved when the compounds of the present invention are administered to a subject requiring such treatment as an effective oral, parenteral, or intravenous dose of from 0.01 to 50 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

Some of the compounds of the present invention are also useful as analgetics due to their ability to alleviate pain in mammals. The analgetic utility is demonstrated in the phenyl p-quinone writhing assay in mice, a standard assay for analgesia: Proc. Soc. Exptl. Biol. Med., 95:729 (1957). Thus, for instance, the subcutaneous dose effecting an approximately 50% inhibition of writhing (ED$_{50}$) in mice produced in this assay is as shown in Table 2.

TABLE 2

| COMPOUND | INHIBITION OF PHENYLQUINONE INDUCED WRITHING ED$_{50}$ mg/kg, sc |
|---|---|
| 1-[4-[3-[4-(1H-indazol-3-yl)-1-piperazinyl]propoxy]-3-methoxy-phenyl]ethanone | 0.06 |
| 1-[4-[3-[4-(1,2-benzisoxazol-3-yl)-1-piperidinyl]propoxy]-3-methoxyphenyl]ethanone | 0.17 |
| 1-[4-[3-[4-(6-fluoro-1,2-benzisoxazol-3-yl)-1-piperidinylpropoxy]-3-methoxyphenyl]ethanone | 0.03 |
| Propoxyphene (standard) | 3.9 |
| Pentazocine (standard) | 1.3 |

Analgesia is achieved when the compounds of the present invention are administered to a subject requiring such treatment as an effective oral, parenteral, or intravenous dose of from 0.01 to 100 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Effective amounts of the compounds of the present invention can be administered to a subject by any one of several methods, for example, orally as in capsules or tablets, parenterally in the form of sterile solutions or suspensions, and in some cases intravenously in the form of sterile solutions.

The compounds of the present invention, while effective themselves, can be formulated and administered in the form of their pharmaceutically acceptable addition salts for purposes of stability, convenience of crystallization, increased solubility, and the like. Preferred pharmaceutically acceptable addition salts include salts of mineral acids, for example, hydrochloric acid, sulfuric acid, nitric acid, and the like; salts of monobasic carboxylic acids, for example, acetic acid, propionic acid, and the like; salts of dibasic carboxylic acids, for example, maleic acid, fumaric acid, and the like; and salts of tribasic carboxylic acids, such as carboxysuccinic acid, citric acid, and the like.

Effective quantities of the compounds of the invention can be administered orally, for example, with an inert diluent or with an edible carrier. They can be enclosed in gelatin capsules or compressed into tablets. For the purposes of oral therapeutic administration, compounds of the invention can be incorporated with an excipient and used in the form of tablets, troches, capsules, elixirs, suspensions, syrups, wafers, chewing gums, and the like. These preparations should contain at least 0.5% of active compound of the invention, but can be varied depending upon the particular form and can conveniently be between 4% to about 70% of the weight of the unit. The amount of active compound in such a composition is such that a suitable dosage will be obtained. Preferred compositions and preparations according to the present invention are prepared so that an oral dosage unit form contains between 1.0–300 milligrams of the active compound of the invention.

Tablets, pills, capsules, troches, and the like can also contain the following ingredients: a binder, such as microcrystalline cellulose, gum tragacanth, or gelatin; an excipient, such as starch or lactose; a disintegrating agent such as alginic acid, Primogel, corn starch, and the like; a lubricant such as magnesium stearate or Sterotes; a glidant such as colloidal silicon dioxide; and a sweetening agent such as sucrose; or saccharin, or a flavoring agent, such as peppermint, methyl salicylate, or orange flavoring. When the dosage unit form is a capsule, it can contain, in addition to materials of the above type, a liquid carrier such as a fatty oil Other dosage unit forms can contain various materials that modify the physical form of the dosage unit, for example, as coatings. Thus, tablets or pills can be coated with sugar, shellac, or other enteric coating agents. A syrup can contain, in addition to the active compounds, sucrose as a sweetening agent and certain preservatives, dyes, colorings, and flavors. Materials used in preparing these various compositions should be pharmaceutically pure and non-toxic in the amounts used.

For the purpose of parenteral therapeutic administration, the active compound of the invention can be incorporated into a solution or suspension. These preparations should contain at least 0.1% of active compound, but can be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

Solutions or suspensions can also include the following components: a sterile diluent, such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates, and agents for the adjustment of tonicity such as sodium chloride or dextrose. The parenteral preparation can be enclosed in ampules, disposable syringes, or multiple dose vials made of glass or plastic.

The highly lipophilic esters, amides and carbamates of the present invention are capable of sustained release in mammals for a period of several days or from about one to four weeks when formulated and administered as depot preparations, as for example, when injected in a properly selected pharmaceutically acceptable oil. The preferred oils are of vegetable origin such as sesame oil, cottonseed oil, corn oil, coconut oil, soybean oil, olive oil and the like, or they are synthetic esters of fatty acids and polyfunctional alcohols such as glycerol or propyleneglycol.

The depot compositions of the present invention are prepared by dissolving a highly lipophilic ester, amide or carbamate of the instant invention in a pharmaceutically acceptable oil under sterile conditions. The oil is selected so as to obtain a release of the active ingredient over a desired period of time. The appropriate oil may easily be determined by consulting the prior art, or without undue experimentation by one skilled in the art.

An appropriate dose of a compound in accordance with this embodiment of the invention is from about 0.01 to 10 mg/kg of body weight per injection. Preferably, the depot formulations of this invention are administered as unit dose preparations comprising about 0.5 to 5.0 ml of a 0.1 to 20% weight/weight solution of compound in the oil. It is to be understood that the doses set forth herein are exemplary only and that they do not, to any extent, limit the scope or practice of the invention.

The following examples are for illustrative purposes only and are not to be construed as limiting the invention. All temperatures are given in degrees Centigrade (°C.) unless indicated otherwise.

EXAMPLE 1

1-[4-[3-[4-(1H-Indazol-3-yl)-1-piperazinyl] propoxyl]-3-methoxyphenyl]ethanone.

(A) 2-Bromobenzoic acid 2-phenylsulfonylhydrazide

To a solution of 2-bromobenzoic acid hydrazide (132 g) in pyridine (1.2 L) cooled to about 10° C. with an ice hath, was added benzensulfonyl chloride (78.3 ml). After complete addition, the reaction was stirred at ambient temperature for four hours, and then poured into ice-hydrochloric acid to precipitate a yellow solid, 135 g. The material was recrystallized from isopropanol to yield 125 g of 2-bromobenzoic acid 2-phenylsulfonylhydrazide, m.p.= 154°–156° C.

(B) α-Chloro-2-bromobenzaldehyde phenylsulfonylhydrazone

A mixture of 2-bromobenzoic acid phenylsulfonylhydrazide (125 g, 350 mmol) and thionyl chloride (265 ml) was stirred and refluxed for 2 hours. After about 15 minutes of reflux, the solid went into solution. The reaction was permitted to cool, and then it was poured into hexane. The resultant white solid was collected to afford 124 g of α-chloro-2-bromobenzaldehyde phenylsulfonylhydrazone, m.p.=120°–122° C.

(C) 1-[[(Phenylsulfonyl)hydrazono]-(2-bromophenyl) methyl]-4-methylpiperazine

To a stirred solution, under nitrogen, of α-chloro-2-bromobenzaldehyde phenylsulfonylhydrazone (271.1 g; 720 mmol) in tetrahydrofuran (THF; 2 L), was added dropwise N-methylpiperazine (159.7 g; 1600 mmol). The reaction was stirred at ambient temperature for three hours, and then permitted to stand at ambient temperature for 16 hours. The reaction was chilled in an ice bath, and then filtered to remove the piperazine hydrochloride that was formed. The filtrate was concentrated to yield a brown gum. The gum was triturated with hot acetonitrile, the mixture was cooled in an ice hath, and when cold, was filtered to remove unwanted side product. The filtrate was then concentrated to afford 392.9 g of a brown gum of crude 1-[[(phenylsulfon-yl) hydrazono]-(2-bromophenyl)methyl]-4-methylpiperazine.

(D) 3-(4-Methyl-1-piperazinyl)-1-phenylsulfonyl-1H-indazole

A mixture of 1-[[(phenylsulfonyl)hydrazono]-(2-bromo phenyl)methyl]- 4-methylpiperazine (31.0 g, 80 mmol), copper bronze (3.1 g), $K_2CO_3$ (11.5 g), and dimethylformamide (500 ml), was stirred and refluxed for 1.5 hours. The reaction was poured into water and the aqueous suspension was stirred vigorously with ethyl acetate. The biphasic mixture was filtered through Celite, and subsequently the layers were separated. The aqueous portion was extracted with another portion of ethyl acetate, and the combined extracts were washed ($H_2O$) and dried ($MgSO_4$). Concentration of the extract afforded a solid, which upon trituration with ether gave 19.7 g of solid. The solid was recrystallized from isopropanol to afford 17.7 g (60%) of product, m.p.= 158°–161° C. An analytical sample was obtained by another recrystallization from isopropanol (with charcoal treatment) to afford colorless crystals of the indazole, 3-(4-methyl-1-piperazinyl)-1-phenylsulfonyl-1H-indazole, m.p.= 160°–161° C.

Analysis: Calculated for $C_{18}H_{20}N_4O_2S$: 60.66%C, 5.66%H, 15.72%N; Found: 60.45%C, 5.62%H; 15.61%N.

(E) 4-[1-(Phenylsulfonyl)-1H-indazol-3-yl]-1-piperazinecarbonitrile

To a stirred mixture of 3-(4-methyl-1-piperazinyl)-1-phenylsulfonyl-1H-indazole (237 g, 0.67 mole), $K_2CO_3$ (102 g, 0.74 mole) and dimethylsulfoxide (DMSO, 2000 ml), under nitrogen, was added cyanogen bromide (72 g, 0.68 mmol) dissolved in DMSO (525 ml). The reaction was stirred at ambient temperature for 5.5 hours and was then poured into $H_2O$ (7 1). The solid, which precipitated from solution, was collected by filtration and was washed well with $H_2O$ affording 168 g (68%) of product. A 5.2 g sample was recrystallized twice from ethanol-$H_2O$ yielding 4.0 g of 4-[1-(phenylsulfonyl)-1H-indazol-3-yl]-1-piperazinecarbonitrile, m.p.=178°–180° C.

Analysis: Calculated for $C_{18}H_{17}N_5O_2S$: 58.85%C, 4.66%H, 19.06%N; Found: 59.01%C, 4.63%H; 19.09%N.

(F) 3-(1-Piperazinyl)-1H-indazole

To a stirred mixture of 4-[1-(phenylsulfonyl)-1H-indazol-3-yl]-1-piperazinecarbonitrile (163 g, 0.44 mol) in tetrahydrofuran (2.0 l) was added, dropwise, lithium aluminum hydride (880 ml; 0.88 mol of a 1M lithium aluminum hydride solution in tetrahydrofuran). After complete addition, the reaction was heated to reflux and stirred for 6 hours, stirred at ambient temperature for one hour and allowed to sit at room temperature overnight. The reaction was quenched by the careful dropwise addition of water. After no more hydrogen could be observed to evolve, the reaction was filtered and the lithium salt filter cake was washed well with tetrahydrofuran. The filtrate was combined with the filtrate of another run (all together the starting material totaled 300 g, i.e. 820 mmol) and the combined filtrates were concentrated to afford 372 g of a yellow solid suspended in water. An attempt was made to partition the product between water and dichloromethane, but the product proved to be only slightly soluble in dichloromethane. Therefore, the biphasic product suspension was filtered through a course sintered funnel and the white product which was collected was dried to afford 121 g. The two phases of the filtrate were separated and the water was extracted again with dichloromethane. All of the dichloromethane phases were combined, washed twice with water, dried with magnesium sulfate, and concentrated to afford 41 g of a brown residue. The residue was triturated with diethyl ether and filtered to afford 10 g of a beige solid, m.p.= 139°–150° C. The NMR and MS spectra were consistent with the structure. Recrystallization of 10 g from toluene afforded 7.5 g of 3-(1-piperazinyl)-1H-indazole, m.p.153°–155° C.

(G) 3-(4-Methyl-1-piperazinyl)-1H-indazole

A stirred mixture of 3-(4-methyl-1-piperazinyl)-1-phenylsulfonyl-1H-indazole (13.5 g, 38 mmol), methanol (150 ml) and 25% $CH_3ONa$ in methanol (15.3 ml) was stirred and refluxed for 2.5 hours. The reaction was concentrated to about one-tenth its volume, and water was added to the mixture, resulting in a red solution. The solution was extracted with dichloromethane, the extract washed ($H_2O$), dried ($MgSO_4$), and the solvent was concentrated to afford 6.6 g of a rose-colored solid. Two recrystallizations from toluene-hexane afforded 4.3 g (52%) of 3-(4-methyl-1-piperazinyl)-1H-indazole as an off-white solid, m.p.= 111°–113° C.

Analysis: Calculated for $C_{12}H_{16}N_4$: 66.64%C, 7.46%H, 25.91%N; Found: 66.83%C, 7.42%H; 25.69%N.

(H) 4-(1H-indazol-3-yl)-1-piperazinecarbonitrile

To a stirred mixture of cyanogen bromide (5.3 g, 0.05 mol), $K_2CO_3$ (7.1 g) and dimethylsulfoxide (40 ml) was added, dropwise, 3-(4-methyl-1-piperazinyl)- 1H-indazole (11.0 g, 0.051 mol) dissolved in dimethylsulfoxide (60 ml). The reaction was stirred at ambient temperature for 1 hour, and then it was poured into water. The aqueous suspension was extracted with ethyl acetate, the ethyl acetate was washed ($H_2O$), dried ($MgSO_4$), and concentrated to afford 7.8 g (67%) of a yellow solid. This sample was combined with another and recrystallized twice from toluene to afford analytically pure 4-(1H-indazol-3-yl)-1-piperazinecarbonitrile as a white solid, m.p.=120°–122° C.

Analysis: Calculated for $C_{12}H_{13}N_5$: 63.42%C, 5.76%H; Found: 63.04%C, 5.84%H.

(I) 3-(1-Piperazinyl)-1H-indazole

A mixture of 4-(1H-indazol-3-yl)-1-piperazinecarbonitrile (8.0 g, 40 mmol) and 25% $H_2SO_4$ (100 ml) was stirred at reflux for 4.5 hours. The reaction was cooled in an ice bath and made basic by the dropwise addition of 50% NaOH. The basic solution was extracted with ethyl acetate. The ethyl acetate was washed with $H_2O$, dried with $MgSO_4$, and concentrated to afford 5.2 g (73% of the desired compound, as a solid. The solid was recrystallized twice from toluene to afford 3.0 g of 3-(1-piperazinyl) -1H-indazole, m.p.=153°–155° C.

Analysis: Calculated for $C_{11}H_{14}N_4$: 65.32%C, 6.98%H, 27.70%N; Found: 65.21%C, 6.99%H; 27.80%N.

(J) 1-[4-[3-[4-(1H-indazol-3-yl)-1-piperazinyl]propoxy]-3-methoxyphenyl]ethanone A mixture of 3-(1-piperazinyl)-1H-indazole (4.0 g, 20 mmol), $K_2CO_3$ (3.0 g, 22 mmol), 1-[4-(3-chloropropoxy)-3-methoxyphenyl]ethanone (5.3 g, 22 mmol), a few crystals of KI, and dimethylformamide (60 ml) was stirred at 90° C. for 5 hours. The reaction was poured into water, and the aqueous mixture was extracted with ethyl acetate. The extract was washed (brine), dried ($MgSO_4$), and the solvent was concentrated to afford a white solid, which was triturated with diethyl ether and collected to yield 7.0 g of product. Two recrystallizations from absolute ethyl alcohol yielded 5.3 g (64%) of analytically pure 1-[4-[3-[4-(1H-indazol-3-yl)-1-piperazinyl]propoxy]-3-methoxyphenyl]ethanone, m.p.=155°–157° C.

Analysis: Calculated for $C_{23}H_{28}N_4O_3$: 67.62%C, 6.91%H, 13.72%N; Found: 67.45%C, 6.74%H; 13.56%N.

EXAMPLE 2

1-[4-[3-[4-(1,2-Benzisoxazol-3-yl)-1-piperidinyl]propoxy]-3-methoxyphenyl]-ethanone A mixture of 3-(4-piperidinyl)-1,2-benzisoxazole hydrochloride (4.8 g, 20 mmol), $K_2CO_3$ (5.2 g, 40 mmol), 1-[4-(3-chloropropoxy)-3-methoxyphenyl]ethanone (5.3 g, 22 mmol), a few crystals of KI and dimethylformamide (60 ml) was stirred at 90° C. for 16 hours. The reaction was poured into water and the aqueous mixture was extracted with ethyl acetate. The extract was washed (water), dried ($MgSO_4$) and concentrated to afford a brown oil. The oil was chromatographed on a Waters Prep 500 utilizing silica gel columns and ethyl acetate-diethylamine (2%), as eluent. Concentration of the appropriate fractions afforded 3.9 g of product as an off-white solid. Recrystallization from absolute ethyl alcohol afforded 2.6 g (33%) of 1-[4-[3-[4-(1,2-benzisoxazol-3-yl)-1-piperidinyl]propoxy]-3-methoxyphenyl]ethanone, m.p.=102°–104° C., as colorless needles.

Analysis: Calculated for $C_{24}H_{28}N_2O_4$: 70.56%C, 6.91%H, 6.86%N; Found: 70.73%C, 6.93%H; 6.85%N.

EXAMPLE 3

1-[4-[3-[4-(6-Fluoro-1,2-benzisoxazol-3-yl)-1-piperidinyl]propoxy]-3-methoxy-phenyl]ethanone A stirred mixture of 6-fluoro-3-(4-piperidinyl)-1,2 benzisoxazole hydrochloride (5.1 g, 20 mmol), $K_2CO_3$ (5.2 g, 40 mmol), 1-[4-(3-chloropropoxy)-3-methoxyphenyl]ethanone (5.3 g, 22 mmol), and dimethylformamide (60 ml) was heated at 90° C. for 16 hours. The reaction was poured into water, and the aqueous mixture was extracted with ethyl acetate. The ethyl acetate was washed (water), dried ($MgSO_4$) and concentrated to afford a moist solid. Recrystallization (twice) from ethyl alcohol afforded 5.0 g (58%) of 1-[4-[3-[4-(6-fluoro-1,2-benzisoxazol-3-yl)-1-piperidinyl]propoxy]-3-methoxyphenyl]-ethanone as a beige solid, m.p.=118°–120° C.

Analysis: Calculated for $C_{24}H_{27}FN_2O_4$: 67.60%C, 6.38%H, 6.57%N; Found: 67.47%C, 6.40%H; 6.53%N.

EXAMPLE 4

1-[4-[4-[4-(1,2-Benzisoxazol-3-yl)-1-piperidinyl]butoxy]3-methoxyphenyl]ethanone A mixture of 3-(4-piperidinyl)-1,2-benzisoxazole hydrochloride (4.3 g, 18 mmol), $K_2CO_3$ (5.5 g, 40 mmol), and 1-[4-(4-bromobutoxy)-3-methoxyphenyl]ethanone (5.5 g, 18 mmol), and dimethylformamide (60 ml) was stirred and heated at 75° C. for 16 hours. The reaction was poured into water and was extracted with ethyl acetate. The ethyl acetate was washed (water), dried ($MgSO_4$), and the solvent concentrated to afford 7.2 g of a beige solid. Recrystallization (twice) from ethyl alcohol yielded 3.3 g (43%) of 1-[4-[4-[4-(1,2-benzisoxazol-3-yl)-1-piperidinyl]butoxy]-3-methoxyphenyl]ethanone, m.p.=99°–101° C.

Analysis: Calculated for $C_{25}H_{30}N_2O_4$: 71.11%C, 7.16%H, 6.63%N; Found: 70.76%C, 7.24%H; 6.58%N.

EXAMPLE 5

1-[4-[4-[4-(6-Fluoro-1,2-benzisoxazol-3-yl)-1-piperidinyl]butoxy]-3-methoxyphenyl]ethanone A stirred mixture of 6-fluoro-3-(4-piperidinyl)-1,2-benzisoxazole hydrochloride (5.1 g, 0.02 mol), $K_2CO_3$ (5.2 g, 0.04 mol), 1-[4-(4-bromobutoxy)-3-methoxyphenyl]methanone (6.6 g, 22 mmol), and dimethylformamide (60 ml) was heated at 75° C. for 5 hours. The reaction was poured into water, and the aqueous mixture was extracted with ethyl acetate. The ethyl acetate was washed (water), dried ($MgSO_4$), and the solvent was concentrated to yield initially an oil, which solidified upon standing. The solid was triturated with hexane and collected to afford 7.7 g of the product as a waxy solid. The compound was chromatographed on a Waters Prep 500 utilizing silica gel columns and eluting with dichloromethane/methanol (5%). Concentration of the appropriate fractions yielded 5.1 g of off-white solid 1-[4-[4-[4-(6-fluoro-1,2-benzisoxazol-3-yl)-1-piperidinyl]-butoxy]-3-methoxyphenyl]ethanone, which when recrystallized from ethyl alcohol yielded 3.2 g (36%) of feathery-white needles, m.p.=88°–90° C.

Analysis: Calculated for $C_{25}H_{29}FN_2O_4$: 68.16%C, 6.64%H, 6.36%N; Found: 67.96%C, 6.49%H; 6.29%N.

EXAMPLE 6

1-[4-[2-[4-(1,2-Benzisoxazol-3-yl)-1-piperidinyl]ethoxyl-3-methoxyphenyl-]ethanone fumarate A mixture of 3-(4-piperidinyl)-1,2-benzisoxazole hydrochloride (4.8 g, 20 mmol), $K_2CO_3$ (5.2 g, 40 mmol), 1-[4-(2-chloroethoxy)-3-methoxyphenyl]ethanone (5.0 g, 22 mmol), and dimethylformamide (90 ml) was heated at 90° C. for 16 hours. The reaction was poured into water and the aqueous mixture was extracted with ethyl acetate. The ethyl acetate was washed (water), dried ($MgSO_4$), and the solvent was concentrated to afford an oil. Upon standing, the oil solidified to afford a beige solid. The crude solid was recrystallized twice from ethyl alcohol to afford 5.9 g of an off-white solid. The solid was dissolved in ethyl acetate, and fumaric acid (1.2 g, 1.1 equiv.) was added. The mixture was heated briefly on a steam bath, and then stirred at ambient temperature for 2 hours. An initial green oil settled out and the supernatant solution was decanted. Ether was added to the decantate and 4.0 g of a white fumarate salt was collected. The salt was recrystallized twice from ethanol-ether to yield 1.7 g (17%) of 1-[4-[2-[4-(1,2-benzisoxazol-3-yl)-1-piperidinyl]ethoxy]-3-methoxyphenyl]ethanone fumarate, m.p.=127°–129° C.

Analysis: Calculated for $C_{23}H_{26}N_2O_4 \cdot C_4H_4O_4$: 63.52%C, 5.92%H, 5.49%N; Found: 63.00%C, 5.87%H; 5.42%N.

EXAMPLE 7

1-[4-[4-[4-(1H-Indazol-3-yl)-1-piperazinyl]butoxyl-3-methoxyphenyl]ethanone fumarate A stirred mixture of 3-(1-piperazinyl)-1H-indazole (4.0 g, 20 mmol), $K_2CO_3$ (5.3 g, 40 mmol), 1-[4-(4-bromobutoxy)-3-methoxyphenyl]ethanone (6.6 g, 22 mmol), and dimethylformamide (60 ml) was heated at 75° C. for 6 hours. The reaction was poured into water, and a white solid precipitated from solution. The solid was collected and dried to afford 7.2 g of the crude product. The crude solid was recrystallized twice from ethyl alcohol to yield 4.1 g of the free base, which was converted to its fumarate salt by the addition of fumaric acid (1.1 g) to the compound dissolved in refluxing acetone. The resulting fumarate salt (5.0 g) was recrystallized from ethyl alcohol to afford 3.8 g (35%) of 1-[4-[4-[4-(1H-indazol-3-yl)-1-piperazinyl]butoxy]-3-methoxyphenyl]ethanone fumarate, as a white solid, m.p.= 163°–165° C.

Analysis: Calculated for $C_{24}H_{30}N_4O_3 \cdot C_4H_4O_4$: 62.44%C, 6.36%H, 10.40%N; Found: 62.28%C, 6.62%H; 10.34%N.

EXAMPLE 8

1-[4-[2-[4-(6-Fluoro-1,2-benzisoxazol-3-yl)-1-piperidinyl]ethoxy]-3-methoxyphenyl]-ethanone A stirred mixture of 6-fluoro-3-(4-piperidinyl)-1,2-benzisoxazole hydrochloride (5.1 g, 20 mmol), $K_2CO_3$ (5.2 g), 1-[4-(2-chloroethoxy)-3-methoxyphenyl]ethanone (5.0 g, 1022 mmol), and dimethylformamide (90 ml) was heated at 90° C. for 16 hours. The reaction was poured into water, and the aqueous mixture was extracted with ethyl acetate. The ethyl acetate was washed (water), dried ($MgSO_4$), and concentrated to afford 7.4 g of a yellow solid. The solid was chromatographed on a Waters Prep LC 500 utilizing dichloromethane/methanol (4%) as eluent, and subsequent concentration of the appropriate fraction afforded 4.0 g of a yellow solid. The solid was recrystallized from ethyl alcohol to yield 3.1 g (38%) of 1-[4-[2-[4-(6-fluoro-1,2-benzisoxazol-3-yl)-1-piperidinyl]ethoxy]-3-methoxyphenyl]ethanone, as slightly yellow flakes, m.p.= 132°–134° C.

Analysis: Calculated for $C_{23}H_{25}FN_2O_4$: 66.98%C, 6.11%H, 6.79%N; Found: 66.90%C, 6.20%H; 6.74%N.

EXAMPLE 9

4-[3-[4-(6-Fluoro-1,2-benzisoxazol-3-yl)-1-piperidinyl]propoxy]-3-methoxy-α-methylbenzenemethanol To a stirred mixture of 1-[4-[3-[4-(6-fluoro-1,2-benzisoxazol-3-yl)-1-piperidinyl]-propoxy-3-methoxyphenyl]ethanone (4.0 g, 9.4 mmol) in methanol/tetrahydrofuran (60 ml, 1:1), was added sodium borohydride (0.4 g, 10 mmol). After an initial evolution of gas, all insolubles went into solution. The reaction was stirred at ambient temperature for 3 hours and TLC at this time showed a very slight amount of starting ketone. Therefore, another 0.1 g of sodium borohydride was added, and stirring was continued for an additional 0.5 hour. TLC now showed complete disappearance of starting material. The reaction was concentrated to an off-white residue, which was diluted with water and collected to yield 3.4 g of alcohol. This was recrystallized from toluene (twice, with a charcoal treatment) to yield 2.7 g (67%) of 4-[3-[4-(6-fluoro-1,2-benzisoxazol-3-yl)-1-piperidinyl]-3-methoxy-α-methylbenzenemethanol as a white solid, m.p.=136°–138° C.

Analysis: Calculated for $C_{24}H_{29}FN_2O_4$: 67.27%C, 6.82%H, 6.54%N; Found: 67.59%C, 6.89%H; 6.47%N.

EXAMPLE 10

1-[4-[3-[4-(1,2-Benzisothiazol-3-yl)-1-piperidinyl] propoxy]-3-methoxyphenyl]-ethanone A mixture of 3-(4-piperidinyl)-1,2-benzisothiazole (3.0 g, 13.7 mmol), potassium carbonate (2.3 g, 16.5 mmol), 1-[4-(3-chloropropoxy)-3-methoxyphenyl]ethanone (4.0 g, 16.5 mmol), potassium iodide (200 mg) and acetonitrile (100 ml) was stirred at reflux under $N_2$ for 24 hours. The cooled reaction was filtered and the cake was washed well with acetonitrile. The filtrate was concentrated to an oily residue, which was partitioned between water and ethyl acetate. The ethyl acetate extract was washed well with water, dried with $MgSO_4$ and concentrated to yield 6.1 g of a beige oil which solidified upon standing. The product was triturated with diethyl ether and filtered to give 4.2 g of a beige solid. The compound was recrystallized from ethyl alcohol to afford 3.5 g, and another recrystallization from ethyl alcohol (utilizing decolonizing carbon) provided 2.4 g (41%) of 1-[4-[3-[4-(1,2-benzisothiazol-3-yl)-1-piperidinyl]propoxy] -3-methoxyphenyl]ethanone, m.p.93°–95° C.

Analysis: Calculated for $C_{24}H_{28}N_2O_3S$: 67.90%C, 6.65%H, 6.60%N; Found: 67.89%C, 6.61%H; 6.59%N.

EXAMPLE 11

1-[4-[3-[4-(6-Fluoro-1,2-benzisoxazol-3-yl)-1-piperidinyl]propoxy]-3-hydroxyphenyl]ethanone (A) 1-[4-(3-chloropropoxy)-3-hydroxyphenyl]ethanone To a stirred solution of 1-[4-(3-chloropropoxy)-3-methoxyphenyl]ethanone (10.0 g, 41 mmol) in methylene chloride (120 ml) cooled to −50° C. (dry ice-methanol) was added, dropwise, 1M boron tribromide in methylene chloride (123 ml, 120 mmol). The temperature was kept between −40° C. and −50° C. After complete addition, the reaction was permitted to reach −30° C., and the TLC checked (ca. 15 min. after final boron tribromide was added). Saturated $NaHCO_3$ was added, dropwise, never allowing the temperature to go above 0° C. during most of the addition. When sufficient $NaHCO_3$ had been added to make the solution basic, the organic layer was collected. The layer was washed with brine, dried ($MgSO_4$), and concentrated to yield 8.1 g of dark brown oil, which solidified on standing. This was chromatographed on a Waters Prep 500 LC (2 silica columns, 2% methanol-methylene chloride as eluent). Upon concentration of the appropriate fractions, 5.8 g of a brown tacky solid were obtained. This was recrystallized from isopropyl ether (with decanting of the yellow isopropyl ether supernatant from the dark brown oily residue) to give initially 2.5 g of a yellow solid. Concentration of the mother liquor gave an additional 0.5 g, m.p.=110°–113° C.

(B) 1-[4-[3-[4-(6-Fluoro-1,2-benzisoxazol-3-yl)-1-piperidinyl]propoxy]-3-hydroxyphenyl]ethanone A stirred mixture of 6-fluoro-3-(4-piperidinyl)-1,2-benzisoxazole (2.8 g, 13 mmol ), $NaHCO_3$ (1.1 g), several crystals of KI, 1-[4-(3-chloropropoxy)-3-hydroxyphenyl] ethanone, and acetonitrile (100 ml) was refluxed for 16 hours. The reaction was poured into water, and the aqueous mixture was extracted with ethyl acetate. The organic extract was washed (water), dried ($MgSO_4$), and the solvent was concentrated to afford 5.7 g of a thick yellow oil. The oil was chromatographed on a Waters Prep 500 LC on silica gel, eluting with 7% methanol/methylene chloride. Concentration of the appropriate fraction afforded a yellow oil, which upon standing yielded 3.5 g of the compound as a pale, yellow solid. The solid was recrystallized from ethyl alcohol to afford 2.7 g (50%) of 1-[4-[3-[4-(6-fluoro-1,2-benzisoxazol-3-yl)-1-piperidinyl]-propoxy]-3-hydroxyphenyl]ethanone as a pale yellow solid, m.p.= 122°–124° C.

Analysis: Calculated for $C_{23}H_{25}FN_2O_4$: 66.98%C, 6.11%H, 6.79%N; Found: 66.97%C, 6.20%H; 6.69%N.

EXAMPLE 12

1-[4-[3-[4-(6-Fluoro-1H-indazol-3-yl)-1-piperazinyl] propoxy]-3-methoxyphenyl]-ethanone A stirred mixture of 6-fluoro-3-(1-piperazinyl)-1H-indazole (2.3 g, 100 mmol), $K_2CO_3$ (1.5 g), 1-[4-(3- chloropropoxy)-3-methoxyphenyl]ethanone (2.8 g, 11 mmol), several crystals of KI and dimethylformamide (60 ml) was heated at 90° C. for 16 hours. The reaction was poured into $H_2O$, and the aqueous suspension was extracted with ethyl acetate. The ethyl acetate was washed ($H_2O$), dried ($MgSO_4$) and concentrated to afford 5.0 g of a yellow oil. The oil was chromatographed on a Waters Prep 500 utilizing silica gel columns and eluting with methylene chloride/methanol (7%). Concentration of the desired fractions yielded 2.0 g (46%) of an off-white solid. This sample was combined with 1.0 g of a previous sample, and this was recrystallized from toluene to afford 2.6 g of 1-[4-[3-[4-(6-fluoro-1H-indazol-3-yl)-1-piperazinyl]-propoxy]-3-methoxyphenyl]ethanone as a white solid, m.p.=135°–137° C.

Analysis: Calculated for $C_{23}H_{27}FN_4O_3$: 64.77%C, 6.38%H, 13.14%N; Found: 64.66%C, 6.21%H; 13.02%N.

EXAMPLE 13

1-[4-[4-[4-(6-Fluoro-1H-indazol-3-yl)-1-piperazinyl]butoxy]-3-methoxyphenyl]-ethanone A stirred mixture of 6-fluoro-3-(1-piperazinyl)-1H-indazole hydrochloride (5.0 g, 19 mmol), $K_2CO_3$ (5.8 g) and 1-[4-(4-bromobutoxy)-3-methoxyphenyl]ethanone (6.3 g, 21 mmol) and dimethylformamide (80 ml) was heated at 75° C. for 6 hours. The reaction was poured into water, and an off-white solid formed from solution. The solid was collected and dried to yield 4.5 g of crude product. The compound was recrystallized from ethanol (3 times) to afford 3.0 g of an off-white solid. The solid was chromatographed on a Waters Prep 500 utilizing silica gel columns and eluting with methylene chloride/methanol (7%). Concentration of the appropriate fractions afford 2.3 g of an off-white solid, which when recrystallized from ethanol yielded 1.9 g (26%) of analytically pure 1-[4-[4-[4-(6-fluoro-1H-indazol-3-yl)-1-piperazinyl]butoxy]-3-methoxyphenyl]ethanone, m.p.=156°–158° C.

Analysis: Calculated for $C_{24}H_{29}FN_4O_3$: 65.44%C, 6.64%H, 12.72%N; Found: 65.38%C, 6.49%H; 12.60%N.

EXAMPLE 14

1-[4-[3-[4-(1H-Indazol-3-yl)-1-piperidinyl]propoxyl]-3-methoxyphenyl]ethanone

A mixture of 3-(4-piperidinyl)-1H-indazole (3.0 g, 15 mmol), $K_2CO_3$ (1.6 g), 1-[4-(3-chloropropoxy)-3-methoxyphenyl]ethanone (5.3 g, 22 mmol), a few crystals of KI and acetonitrile (100 ml) was stirred and refluxed for 16 hours. The reaction was poured into water and a white solid separated from solution. The solid was collected, dried and afforded 5.1 g of product. Recrystallization from ethanol yielded 3.6 g of the compound, which upon chromatography (preparative HPLC on silica gel, eluting with methylene chloride/methanol-9:1) gave 3.0 g (49%) of an off-white solid. Recrystallization from ethanol afforded the analytically pure 1-[4-[3-[4-(1H-indazol-3-yl)-1-piperidinyl]-propoxy]-3-methoxyphenyl]ethanone as a white solid, m.p.=171°–173° C.

Analysis: Calculated for $C_{24}H_{29}N_3O_3$: 70.74%C, 7.17%H, 10.31%N; Found: 70.52%C, 7.27%H; 10.42%N.

EXAMPLE 15

1-[4-[3-[4-(6-Chloro-1,2-benzisoxazol-3-yl)-1-piperidinyl]propoxyl]-3-methoxyphenyl]ethanone A stirred mixture of 6-chloro-3-(4-piperidinyl)-1,2-benzisoxazole (4.7 g, 20 mmol), 1-[4-(3-chloropropoxy)-3-methoxyphenyl]ethanone (4.8 g, 20 mmol), $K_2CO_3$ (2.8 g), several crystals of KI and acetonitrile (120 ml) was refluxed for 16 hours. The reaction was filtered and the filtrate was concentrated to yield a solid-oil mixture. The residue was chromatographed on a Waters Prep 500 utilizing silica columns and eluting with methylene chloride/methanol (5%). Concentration of the desired fractions yielded 3.2 g of a beige solid, which upon recrystallization from ethanol afforded 2.7 g (31%) of 1-[4-[3-[4-(6-chloro-1,2-benzisoxazol-3-yl)-1-piperidinyl]propoxy]-3-methoxyphenyl]-ethanone as a beige solid, m.p.=116°–118° C.

Analysis: Calculated for $C_{24}H_{27}ClN_2O_4$: 65.08%C, 6.14%H, 6.32%N; Found: 65.35%C, 6.22%H; 6.28%N.

EXAMPLE 16

1-[4-[4-[4-(6-Chloro-1,2-benzisoxazol-3-yl)-1-piperidinyl]butoxyl]-3-methoxyphenyl]ethanone fumarate A stirred mixture of 6-chloro-3-(4-piperidinyl)-1,2-benzisoxazole (4.7 g, 20 mmol), 1-[4-(4-bromobutoxy)-3-methoxyphenyl]ethanone (6.0 g, 20 mmol), $K_2CO_3$ (2.8 g) and acetonitrile (120 ml) was refluxed for 16 hours. The reaction was allowed to cool, filtered, and the filtrate was concentrated to 9.9 g of a brown oil. The oil was chromatographed on a Waters Prep 500 utilizing silica gel columns and eluting with methylene chloride/methanol (5%). Concentration of the appropriate fractions afforded 2.3 g of an off-white solid. The solid was dissolved in ethanol and fumaric acid (0.62 g, 1.1 eq.) was added. Upon concentration of the ethanol, a crude, brown solid was collected, which was taken up in refluxing acetone. Upon cooling, a white solid crystallized from solution yielding 2.2 g (19%) of 1-[4-[4-[4-(6-chloro-1,2-benzisoxazol-3-yl)-1-piperidinyl]-butoxy]-3-methoxyphenyl]ethanone fumarate as a white solid, m.p.=139°–141° C.

Analysis: Calculated for $C_{25}H_{29}ClN_2O_4 \cdot C_4H_4O_4$: 60.78%C, 5.80%H, 4.89%N; Found: 60.69%C, 5.74%H; 4.85%N.

EXAMPLE 17

1-[4-[3-[4-(5-Fluoro-1,2-benzisoxazol-3-yl)-1-piperidinyl]propoxyl]-3-methoxyphenyl]ethanone A mixture of 5-fluoro-3-(4-piperidinyl)-1,2-benzisoxazole (2.2 g, 10 mmol), 1-[4-(3-chloropropoxy)-3-methoxyphenyl]ethanone (2.4 g, 10 mmol), $K_2CO_3$ (1.4 g), a few crystals of KI and acetonitrile (100 ml) was stirred and refluxed for 8 hours. The reaction was poured into water and the aqueous mixture was extracted with ethyl acetate. The ethyl acetate extract was washed (brine), dried ($MgSO_4$), and concentrated to afford 4.0 g of a white solid. The solid was chromatographed on a Waters Prep 500 HPLC utilizing silica gel columns and eluting with methylene chloride/methanol (5%). Concentration of the appropriate fractions afforded 2.0 g (47%) of 1-[4-[3-[4-(5-fluoro-1,2-benzisoxazol-3-yl)-1-piperidinyl]propoxy]-3-methoxyphenyl]-ethanone as a white crystalline solid, m.p.=103°–105° C.

Analysis: Calculated for $C_{24}H_{27}FN_2O_4$: 67.59%C, 6.38%H, 6.57%N; Found: 67.50%C, 6.47%H; 6.53%N.

EXAMPLE 18

6-Fluoro-3-[1-[3-(2-methoxyphenoxy)propyl]-4-piperidinyl]-1,2-benzisoxazole fumarate A stirred mixture of 6-fluoro-3-(4-piperidinyl)-1,2-benzisoxazole (2.45 g; 11.1 mmol), $K_2CO_3$ (2.0 g), and 3-(2-methoxyphenoxy)propyl chloride (3.5 g, 17.4 mmol) in acetonitrile (40 ml) was heated at 90° C. for 4 hours. At the end of the reaction, the solvent was removed, and the solids were dissolved into dichloromethane (100 ml). The solution was washed with water and brine, then dried over $MgSO_4$. The crude material from the solution was combined with 1.2 g of crude material prepared in the same fashion (using 0.5 g of starting material). The combined material was purified by flash chromatography on a silica gel column (49 g, eluted with 0.5% diethylamine: 1% methanol:98.5% dichloromethane, 1L). The fractions containing the pure product were pooled and concentrated down to a light oil (3.68 g). This oil was treated with fumaric acid (1.14 g, 9.8 mmol) in ethanol (13 ml). The 6-fluoro-3-[1-[3-(2-methoxyphenoxy)-propyl]-4-piperidinyl]-1,2-benzisoxazole fumarate crystals obtained weighed 4.01 g (60%), m.p.=169°–170° C.

Analysis: Calculated for $C_{22}H_{25}FN_2O_3 \cdot C_4H_4O_4$: 62.39%C, 5.84%H, 5.60%N; Found: 62.37%C, 5.88%H; 5.60%N.

EXAMPLE 19

1-[3-[3-[4-(6-Fluoro-1,2-benzisoxazol-3-yl)-1-piperidinyl]propoxy]-4-methoxyphenyl]phenylmethanone A stirred mixture of 6-fluoro-3-(4-piperidinyl)-1,2-benzisoxazole (2.01 g; 9.13 mmol), $K_2CO_3$ (2.0 g), and 1-[3-(3-chloropropoxy)-4-methoxy-phenyl]phenylmethanone (3.93 g; 11.3 mmol) and acetonitrile (50 ml) was heated at reflux for 4 hours. At the end of the reaction, the solvent was evaporated and the residue was partitioned between water (150 ml) and dichloromethane (400 ml). The dichloromethane solution was washed with water and brine (100 ml), dried over $MgSO_4$, then concentrated to an oil. The purification was done by flash chromatography over a silica gel column ($SiO_2$, 40 g; eluted with dichloromethane, 300 ml; 1% methanol in dichloromethane, 850 ml). The material thus obtained as a colorless oil solidified on standing. Recrystallization from ethanol (150 ml) gave 1-[3-[3-[4-(6-fluoro-1,2-benzisoxazol-3-yl)-1-piperidinyl]propoxy]-4-methoxyphenyl]phenylmethanone as white crystals, 3.07 g (63%), m.p.=140°–141° C.

Analysis: Calculated for $C_{29}H_{29}FN_2O_4$: 71.30%C, 5.98%H, 5.73%N; Found: 71.09%C, 5.98%H; 5.73%N.

EXAMPLE 20

1-[4-[4-[4-(1H-indazol-3-yl)-1-piperidinyl]-butoxy]-3-methoxyphenyl]ethanone

A mixture of 3-(4-piperidinyl)-1H-indazole (3.2 g, 16 mmol), 1-[4-(4-bromo-butoxy)-3-methoxyphenyl]ethanone (5.0 g, 16 mmol), $K_2CO_3$ (2.2 g) and acetonitrile (100 ml) was stirred and refluxed for 6 hours. The reaction was poured into water and the resulting yellow solid that formed was collected to afford 5.3 g of product. The compound was recrystallized from acetonitrile and then from ethyl acetate to yield 3.0 g (45%) of a slightly yellow solid of 1-[4-[4-[4-(1H-indazol-3-yl)-1-piperidinyl]-butoxy]-3-methoxyphenyl]ethanone, m.p.=133°–135° C.

Analysis: Calculated for $C_{25}H_{31}N_3O_3$: 71.23%C, 7.41%H, 9.97%N; Found: 70.85%C, 7.61%H; 9.81%N.

EXAMPLE 21

1-[4-[2-[4-(6-Chloro-1,2-benzisoxazol-3-yl)-1-piperidinyl]ethoxy]-3-methoxyphenyl]-ethanone A stirred mixture of 6-chloro-3-(4-piperidinyl)-1,2-benzisoxazole (4.6 g, 19 mmol),1-[4-(2-chloroethoxy)-3-methoxyphenyl]ethanone (4.3 g, 19 mmol), $K_2CO_3$ (2.8 g), a few crystals of KI and acetonitrile (120 ml) was refluxed for 16 hours. The reaction was filtered and the filtrate was concentrated to yield 8.0 g of yellow solid. The solid was chromatographed on a Waters Prep 500 LC (silica columns, eluting with methylene chloride/methanol, 5%). Concentration of the appropriate fractions yielded 3.2 g of a light yellow solid, which upon recrystallization from ethyl acetate afforded 2.3 g (28%) of 1-[4-[2-[4-(6-chloro-1,2-benzisoxazol-3-yl)-1-piperidinyl]ethoxy]-3-methoxyphenyl]ethanone as a pale yellow solid, m.p.= 133°–135° C.

Analysis: Calculated for $C_{23}H_{25}ClN_2O_4$: 64.41%C, 5.88%H, 6.53%N; Found: 64.35%C, 5.87%H; 6.41%N.

EXAMPLE 22

3-(3-Bromopropoxy-4-methoxyphenyl) phenylmethanone

A solution of 3-hydroxy-4-methoxybenzophenone (4.6 g, 20 mmol) in dimethylformamide (35 ml) was treated with sodium hydride (600 mg, 25 mmol) at 0° C. for 20 minutes, then 1,3-dibromopropane (5 g, 24.7 mmol) was added in one portion. The mixture was heated at 90° C. for 1 hour, and then stirred at room temperature for 2 hours. At the end of the reaction, the mixture was poured into water (500 ml) and extracted with ethyl acetate (400 ml). The ethyl acetate solution was washed with water, brine and dried over anhydrous $MgSO_4$. The solvent was removed and the crude oil was purified by flash chromatography over a silica gel column ($SiO_2$, 85 g; eluted with 3:1 hexane:dichloromethane, 1.6 l; 3:7 hexane: dichloromethane, 1.4 l). The pure product thus obtained weighed 4.67 g, (66%) as an oil. Recrystallization twice from isopropyl ether (500 ml) gave analytically pure 3-(3-bromopropoxy-4-methoxyphenyl)phenylmethanone (2.42 g), m.p.=81°–83° C.

Analysis: Calculated for $C_{17}H_{17}BrO_3$: 58.47%C, 4.91%H; Found: 58.63%C, 4.82%H.

EXAMPLE 23

1-[3-[3-[4-(6-Fluoro-1,2-benzisoxazol-3-yl)-1-piperidinyl]propoxy]-phenyl]ethanone fumarate A mixture of 6-fluoro-3-(4-piperidinyl)-1,2-benzisoxazole hydrochloride (4.53 g, 20.5 mmol), $K_2CO_3$ (4.5 g), 1-[3-(3-chloropropoxy)phenyl]ethanone (6.4 g, 29 mmol) in acetonitrile (60 ml) was heated at reflux for 5 hours. At the end of the reaction, the solvent was removed and the residue was extracted into dichloromethane (300 ml). The inorganic insolubles were filtered off. The dichloromethane solution was concentrated to a small volume (10 ml) and purified on a flash chromatographic column ($SiO_2$, 75 g, eluted with dichloromethane, 900 ml; and 2% methanol in dichloromethane, 800 ml). The fractions containing the pure product were combined and concentrated to an oil (2.87 g, 35%). The oil was dissolved into ethanol and treated with a solution of fumaric acid (841 mg). Recrystallization (twice) from ethanol afforded 2.53 g of 1-[3-[3-[4-(6-fluoro-1,2-benzisoxazol-3-yl)-1-piperidinyl]propoxy]phenyl]ethanone fumarate as white crystals, m.p.=172°–174° C.

Analysis: Calculated for $C_{22}H_{25}FN_2O_3 \cdot C_4H_4O_4$: 63.27%C, 5.70%H, 5.47%N; Found: 63.00%C, 5.63%H; 5.43%N.

EXAMPLE 24

1-[4-[3-[4-(6-Fluoro-1,2-benzisoxazol-3-yl)-1-piperidinyl]propoxy]-2-methylphenyl]-ethanone A stirred mixture of 6-fluoro-3-(4-piperidinyl)-1,2-benzisoxazole hydrochloride (5.5 g, 21.6 mmol), $K_2CO_3$ (3.5 g), 1-[4-(3-bromopropoxy)-2-methylphenyl]-ethanone (4.83 g, 17.8 mmol) in dimethylformamide (25 ml) and acetonitrile (75 ml) was heated at 120° C. for 5 hours. At the end of the reaction, the solvent was removed and the residue was extracted into dichloromethane (300 ml) and the solution was washed with water and brine. The organic solution was dried and evaporated to a crude oil. The purification was done by flash chromatography over a silica gel column (80 g, eluted with dichloromethane, 11 l; 1% methanol:dichloromethane, 1.2 l; 2% methanol:dichloromethane, 1.2 l). The purest fractions were combined and afforded 2.91 g of solid. Recrystallization from dichloromethane and ethanol gave 1-[4-[3-[4-(6-fluoro-1,2-benzisoxazol-3-yl)-1-piperidinyl]propoxy]-2-methylphenyl]ethanone as off-white crystals: 2.42 g, m.p.=113°–114° C.

Analysis: Calculated for $C_{24}H_{27}FN_2O_3$: 70.22%C, 6.63%H, 6.82%N; Found: 70.13%C, 6.63%H; 6.77%N.

EXAMPLE 25

1-[2-[3-[4-(6-Fluoro-1,2-benzisoxazol-3-yl)-1-piperidinyl]propoxy]5-methylphenyl]-ethanone A mixture of 6-fluoro-3-(4-piperidinyl)-1,2-benzisoxazole hydrochloride (2.87 g, 11.23 mmol), $K_2CO_3$ (2.5 g), 1-[2-(3-bromopropoxy)-5-methylphenyl]ethanone (3.74 g, 13.8 mmol) in dimethylformamide (10 ml) and acetonitrile (50 ml) was heated at 95° C. for 6 hours. At the end of the reaction, the solvent was concentrated and the mixture was extracted into dichloromethane (300 ml). The organic solution was washed with water and brine, dried over $MgSO_4$, then concentrated down to a crude oil. The purification was done by flash chromatography over a silica gel column ($SiO_2$, 60 g, eluted with 1% $CH_3OH$:dichloromethane: 1.2 l; 3% $CH_3OH$:dichloromethane: 600 ml). The material thus obtained was crystallized from a small volume of ether and hexane to provide 2.13 g (46%) of off-white 1-[2-[3-[4-(6-fluoro-1,2-benzisoxazol-3-yl)-1-iperidinyl]propoxy]-5-methylphenyl]ethanone, m.p.=92°–93° C.

Analysis: Calculated for $C_{24}H_{27}FN_2O_3$: 70.22%C, 6.63%H, 6.82%N; Found: 70.21%C, 6.69%H; 6.81%N.

EXAMPLE 26

N-[3-[3-[4-(6-Fluoro-1,2-benzisoxazol-3-yl)-1-piperidinyl]propoxy]-4-methoxyphenyl]acetamide hemifumarate A mixture of 6-fluoro-3-(4-piperidinyl)-1,2-benzisoxazole hydrochloride (3.94 g, 15.4 mmol), $K_2CO_3$ (3.67 g, 26.6 mmole), N-[3-(3-bromopropoxy)-4-methoxyphenyl]acetamide (5.56 g, 18.6 mmol) in dimethylformamide (75 ml) and acetonitrile (100 ml) was heated at 100° C. for 3 hours. At the end of the reaction, the solvent was concentrated and the mixture was extracted into dichloromethane (500 ml). The organic solution was washed with water (500 ml) and brine (400 ml), dried, then concentrated to a crude oil. The purification was effected by flash chromatography over a silica gel column ($SiO_2$, 65 g, eluted with 1% $CH_3OH$:dichloromethane, 1,2 l; and 3% $CH_3OH$:dichloromethane, 500 ml). The material thus obtained weighed 2.33 g (34.3%) as an oil. This material was dissolved in ethanol and treated with a solution of fumaric acid (661 mg) in ethanol. The N-[3-[3-[4-(6-fluoro-1,2 benzisoxazol-3-yl)-1-piperidinyl]propoxy]-4-methoxyphenyl]acetamide hemifumarate was obtained as off-white crystals weighing 2.17 g, m.p.=205°–206° C.

Analysis: Calculated for $C_{24}H_{28}FN_3O_4 \cdot 0.5\ C_4H_4O_4$: 62.50%C, 6.05%H, 8.41%N; Found: 62.30%C, 6.05%H; 8.32%N.

EXAMPLE 27

6-Chloro-3-(1-piperazinyl)-1H-indazole

To a stirred suspension of 4-(6-chloro-1-phenylsulfonyl-1H-indazol-3-yl)-1-piperazinecarbonitrile (192.5 g, 479 mmol) in dry tetrahydrofuran (3.5 l) under $N_2$ was added, dropwise, $LiAlH_4$ (958 ml of a 1.0M solution of lithium aluminum hydride in tetrahydrofuran; 958 mmol). After complete addition, the reaction was heated to reflux and stirred under $N_2$ for 4 hours. The reaction was cooled to 4° in an ice-salt bath and the excess lithium aluminum hydride was destroyed by the careful, dropwise addition of $H_2O$. The mixture was stirred vigorously for an additional 30 minutes and was then filtered through a coarse sintered glass funnel. The filter cake was washed well with tetrahydrofuran (3×500 ml) and then with methanol (2×500 ml) and the filtrate was concentrated to yield 151.0 g of a beige gum. Trituration with diethyl ether afforded a solid, which was collected and dried to give 75.0 g (66%) of the desired indazole. A 4.0 g sample was recrystallized from toluene to yield 3.2 g, which was recrystallized again from toluene (utilizing decolonizing carbon) to provide 2.1 g (35%) of a beige, 6-chloro-3-(1-piperazinyl)-1H-indazole solid, m.p.= 135°–137° C.

Analysis: Calculated for $C_{11}H_{13}ClN_2$: 55.82%C, 5.54%H, 23.67%N; Found: 55.91%C, 5.54%H; 23.41%N.

EXAMPLE 28

1-[4-[3-[4-(6-Fluoro-1H-indazol-3-yl)-1-piperidinyl] propoxy]-3-methoxyphenyl]-ethanone A stirred mixture of 6-fluoro-3-(4-piperidinyl)-1H-indazole (3.5 g, 16 mmol), $K_2CO_3$ (2.2 g), 1-[4-(3-chloropropoxy)-3-methoxyphenyl]ethanone (3.8 g, 16 mmol) and acetonitrile (90 ml) was refluxed for 16 hours. The reaction was poured into water and the resulting white solid, which precipitated from solution, was collected to afford 5.5 g of the desired product. The compound was recrystallized from dimethylformamide (twice) to afford 3.0 g (44%) of 1-[4-[3-[4-(6-fluoro-1H-indazol-3-yl)-1-piperidinyl]propoxy]-methoxyphenyl]ethanone as a white solid, m.p.=202°–204° C.

Analysis: Calculated for $C_{24}H_{28}FN_3O_3$: 67.75%C, 6.63%H, 9.88%N; Found: 67.59%C, 6.61%H; 9.96%N.

EXAMPLE 29

1-[4-[3-[4-(6-Fluoro-1,2-benzisoxazol-3-yl)-1-piperidinyl]propoxy]-3-methylphenyl]-ethanone hemifumarate A stirred mixture of 6-fluoro-3-(4-piperidinyl)-1,2-benzisoxazole hydrochloride (3.0 g; 11.7 mmol), $K_2CO_3$ (3.0 g), and 1-[4-(3-bromopropoxy)-3-methylphenyl] ethanone (3.19 g) in dimethylformamide (20 ml) and acetonitrile (50 ml) was heated at 95° C. for 4 hours. At the end of the reaction, the solvent was concentrated down to about 30 ml, then partitioned between water (200 ml) and dichloromethane (300 ml). The dichloromethane solution was separated and washed with water and brine, then dried over $MgSO_4$. The crude product from the evaporated solution was purified by flash chromatography over a silica gel column ($SiO_2$, 60 g, eluted with 1% methanol in dichloromethane, 600 ml; 2% methanol in dichloromethane, 600 ml). The material thus obtained was a light yellow oil, weight: 2.07 g (43%). This oil was dissolved in ethanol and treated with a solution of fumaric acid (585 mg) in ethanol. The 1-[4-[3-[4-(6-fluoro-1,2-benzisoxazol-3-yl)-1-piperidinyl]propoxy]-3-methylphenyl]-ethanone hemifumarate crystals formed on cooling at 0° C. This was collected and weighed 1.5 g, m.p.=185°–187° C.

Analysis: Calculated for $C_{24}H_{27}FN_2O_3 \cdot C_4H_4O_4$: 66.65%C, 6.24%H, 5.98%N; Found: 66.69%C, 6.23%H; 6.95%N.

EXAMPLE 30

1-[4-[3-[4-(6-Fluoro-1,2-benzisoxazol-3-yl)-1-piperidinyl]propoxy]phenyl]ethanone A mixture of 6-fluoro-3-(4-piperidinyl)-1,2-benzisoxazole (3.27 g, 14.8 mmol), $K_2CO_3$ (3 g), 1-[4-(3-bromopropoxy)phenyl]ethanone (4.5 g, 17.5 mmol) in acetonitrile (60 ml) was heated at reflux for 4 hours. The solvent was removed. The residue was dissolved in dichloromethane (300 ml) and washed with water and brine, then dried over $MgSO_4$. The crude product from the evaporated solution was purified by flash chromatography ($SiO_2$, 60 g; eluted with 1% methanol in dichloromethane, 1 liter). The purest fractions were combined and gave 2.8 g, 48%, of 1-[4-[3-[4-(6-fluoro-1,2-benzisoxazol-3-yl)-1-piperidinyl]propoxy)phenyl]ethanone, m.p.=111°–112° C.

Analysis: Calculated for $C_{23}H_{25}FN_2O_3$: 69.68%C, 6.36%H, 7.07%N; Found: 69.80%C, 6.38%H; 7.07%N.

EXAMPLE 31

1-[4-[3-[4-(6-Chloro-1H-indazol-3-yl)-1-piperazinyl]propoxy]-3-methoxyphenyl]-ethanone A mixture of 6-chloro-3-(1-piperazinyl)-1H-indazole (3.4 g, 14 mmol), $K_2CO_3$ (2.5 g, 18 mmol), 1-[4-(3-chloropropoxy)-3-methoxyphenyl]ethanone (3.8 g, 16 mmol), KI (200 mg), and acetonitrile (125 ml) was stirred at reflux under $N_2$ for 30 hours. After standing at room temperature for 40 hours, the reaction was filtered and the filter cake was washed well with acetonitrile. The filtrate was concentrated to an oily solid, which was partitioned between water and ethyl acetate. The ethyl acetate extract was washed with water, dried with $MgSO_4$ and concentrated to yield 6.9 g of a dark oil, which solidified after 2 days under vacuum. The product was purified by preparative HPLC (Waters Associates Prep LC/system 500 utilizing 2 silica gel columns and 6% methanol/methylene chloride as eluent) to yield 4.2 g. The material was recrystallized from ethanol to yield 3.4 g of glistening, beige, 1-[4-[3-[4-(6-chloro-1H-indazol-3-yl)-1-piperazinyl]propoxy]-3-methoxyphenyl]ethanone crystals, m.p.=132°–134° C.

Analysis: Calculated for $C_{23}H_{27}ClN_4O_3$: 62.37%C, 6.14%H, 12.65%N; Found: 62.49%C, 6.16%H; 12.60%N.

EXAMPLE 32

1-[4-[4-[4-(1,2-Benzisothiazol-3-yl)-1-piperazinyl]butoxy]-3-methoxyphenyl]ethanone A mixture of 3-(1-piperazinyl)-1,2-benzisothiazole (4.0 g, 18.2 mmol), 1-[4-(4-bromobutoxy)-3-methoxyphenyl]ethanone (6.0 g, 20.0 mmol), $K_2CO_3$ (3.0 g, 21.8 mmol), KI (200 mg), and acetonitrile (125 ml) was stirred at reflux under $N_2$ for 5 hours. Most of the solvent was removed in vacuo and the resultant gummy residue was partitioned between ethyl acetate and water. The organic extract was washed with water, dried with $MgSO_4$, and concentrated to yield 7.8 g. Purification by preparative HPLC (Waters Associates Prep LC/System 500, utilizing 2 silica gel columns and 4% methanol-methylene chloride as eluent) afforded 6.5 g of a damp, off-white solid. The product was recrystallized twice from toluene to provide 3.1 g (39%) of 1-[4-[4-[4-(1,2-benzisothiazol-3-yl)-1-piperazinyl]butoxy]-3-methoxyphenyl]ethanone as a white solid, m.p.=114°–116° C.

Analysis: Calculated for $C_{24}H_{29}N_3O_3S$: 65.58%C, 6.65%H, 9.56%N; Found: 65.74%C, 6.66%H; 9.54%N.

EXAMPLE 33

4-[3-[4-(6-Fluoro-1,2-benzisoxazol-3-yl)-1-piperidinyl]propoxy]-3-methoxy-benzonitrile A mixture of 6-fluoro-3-(4-piperidinyl)-1,2-benzisoxazole (3.0 g, 13.6 mmol), $K_2CO_3$ (2.8 g), 4-(3-bromopropoxy)-3-methoxybenzonitrile (4.0 g, 14.8 mmol) in acetonitrile (70 ml) was heated at reflux for 3 hours. At the end of the reaction, the solvent was removed on a rotary evaporator. The organic material was extracted into dichloromethane (250 ml) and the inorganics were filtered off. The dichloromethane solution was concentrated to a crude oil. The purification was done by flash chromatography over a silica gel column ($SiO_2$, 55 g; eluted with dichloromethane, 600 ml; 1% methanol in dichloromethane, 600 ml). The material thus obtained was crystallized from a small amount of dichloromethane. Recrystallization from ethanol (25 ml) provided 3.8 g (68%) of 4-[3-[4-(6-fluoro-1,2-benzisoxazol-3-yl)-1-piperidinyl]propoxy]-3-methoxybenzonitrile as white crystals, m.p.=107°–108° C.

Analysis: Calculated for $C_{23}H_{24}FN_3O_3$: 67.47%C, 5.91%H, 10.26%N; Found: 67.32%C, 5.90%H; 10.24%N.

EXAMPLE 34

1-[4-[4-[4-(6-Fluoro-1H-indazol-3-yl)-1-piperidinyl]butoxy]-3-methoxyphenyl]-ethanone A stirred mixture of 6-fluoro-3-(4-piperidinyl)-1H-indazole (1.9 g, 8.6 mmol), 1-[4-(4-bromobutoxy)-3-methoxyphenyl]ethanone (2.6 g, 8.6 mmol), $K_2CO_3$ (1.2 g), and acetonitrile (75 ml) was refluxed for 6 hours. The reaction was poured into water and a white solid settled from solution. This was collected, dried and afforded 3.2 g of product. The product was recrystallized from ethanol to yield 2.7 g (71%) of 1-[4-[4-[4-(6-fluoro-1H-indazol-3-yl)-1-piperidinyl]butoxy]-3-methoxy-phenyl]ethanone as glistening white flakes, m.p.=158°–160° C.

Analysis: Calculated for $C_{25}H_{30}FN_3O_3$: 68.32%C, 6.88%H, 9.56%N; Found: 68.00%C, 6.93%H; 9.51%N.

EXAMPLE 35

1-[4-[3-[4-(1-Benzoyl-6-fluoro-1H-indazol-3-yl)-1-piperazinyl]propoxy]-3-methoxy-phenyl]ethanone sesguifumarate A mixture of 1-[4-[3-[4-(6-fluoro-1H-indazol-3-yl)-1-piperazinyl]propoxy]-3-methoxyphenyl]ethanone (3.2 g, 7.5 mmol) and benzoyl chloride (15 ml) was heated on a steam bath for 15 minutes. The reaction was allowed to cool and ether was added. The insoluble off-white compound was harvested to yield 4.4 g of the product as a hydrochloride salt. The salt was converted to free base with aqueous ammonium hydroxide, and after extractive workup with methylene chloride, 3.0 g of the free base was isolated as a white solid. The free base was dissolved in ethyl acetate and fumaric acid (0.72 g, 1.1 eq.) was added and the mixture heated on the steam bath for 15 min. After standing at ambient temperature for 4 days, 2.0 g of an off-white fumarate salt was collected, while concentration of the filtrate afforded an additional 1.0 g of the salt. Recrystallization, first from ethyl acetate, and then from ethanol yielded 1.4 g (26%) of 1-[4-[3-[4-(1-benzoyl-6-fluoro-1H-indazol-3-yl)-1-piperazinyl]propoxy]-3-methoxyphenyl]ethanone sesquifumarate, m.p.=138°–140° C.

Analysis: Calculated for $C_{30}H_{31}FN_4O_4 \cdot 1.5\ C_4H_4O_4$: 61.35%C, 5.29%H, 7.95%N; Found: 61.68%C, 5.31%H; 8.25%N.

EXAMPLE 36

1-[4-[4-[4-(6-Chloro-1H-indazol-3-yl)-1-piperazinyl]butoxy]-3-methoxyphenyl]-ethanone A mixture of 6-chloro-[3-(1-piperazinyl)]-1H-indazole (4.0 g, 17 mmol), $K_2CO_3$ (2.8 g, 20 mmol), 1-[4-(4-bromobutoxy)-3-methoxyphenyl]ethanone (5.7 g, 19 mmol), KI (100 mg) and acetonitrile (125 ml) was stirred at reflux under nitrogen for 18 hours. The cooled reaction was poured into water and the resultant off-white solid was collected by filtration and dried to yield 7.0 g. The compound was recrystallized twice from toluene to yield 6.2 g. Further purification by preparative HPLC (Waters Associates Prep LC/System 500, utilizing 5% methanol/methylene chloride as eluent and 2 silica gel columns) afforded 5.3 g of glistening, beige crystals, which were recrystallized four times from toluene to yield 3.1 g of a white solid. Analytically pure material was obtained by a subsequent recrystallization from dimethylformamide to afford 2.5 g (32%) of 1-[4-[4-[4-(6-chloro-1H-indazol-3-yl)-1-piperazinyl]butoxy]-3-methoxyphenyl]ethanone as an off-white powder, m.p.=189°–191° C.

Analysis: Calculated for $C_{24}H_{29}ClN_4O_3$: 63.08%C, 6.40%H, 12.26%N; Found: 62.86%C, 6.57%H; 12.49%N.

EXAMPLE 37

1-[4-[3-[4-(1,2-Benzisothiazol-3-yl)-1-piperazinyl]propoxy]-3-methoxyphenyl]-ethanone hemifumarate A mixture of 3-(1-piperazinyl)-1,2-benzisothiazole (4.0 g, 18.2 mmol), $K_2CO_3$ (3.0 g, 21.8 mmol), KI (200 mg), 1-[4-(3-chloropropoxy)-3-methoxyphenyl]ethanone (5.3 g, 20.0 mmol), and acetonitrile (125 ml) was stirred at reflux under $N_2$ for 26 hours. The cooled reaction was filtered and the filter cake was washed well with acetonitrile. The filtrate was concentrated to afford 10.7 g of an oily residue, which was extracted with ethyl acetate. The ethyl acetate extract was washed with water, dried with $MgSO_4$ and concentrated to yield 8.0 g of a dark oil. The oil was purified by preparative HPLC (Waters Associates Prep LC/System 500, utilizing 2 silica gel columns and 3% methanol/methylene chloride as eluent). Concentration of appropriate fractions provided 4.6 g of a red off, which solidified upon standing. A 3.4 g sample was taken up in ethyl acetate (100 ml) and fumaric acid (0.95 g) was added. The mixture was stirred at a mild reflux for 1 hour and then at ambient for 1.5 hours. The resultant beige solid was collected by filtration and dried to yield 4.0 g. The product was recrystallized twice from ethanol to provide 2.7 g (27%) of 1-[4-[3-[4-(1,2-benzisothiazol-3-yl)-1-piperazinyl]propoxy]-3-methoxyphenyl]ethanone hemifumarate as a beige powder, m.p.=186°–188° C.

Analysis: Calculated for $C_{23}H_{27}N_3O_3S \cdot 0.5\ C_4H_4O_4$: 62.09%C, 6.06%H, 8.69%N; Found: 62.01%C, 6.06%H; 8.68%N.

EXAMPLE 38

1-[3,5-Dibromo-4-[3-[4-(6-fluoro-1,2-benzisoxazol-3-yl)-1-piperidinyl]propoxy]-phenyl]ethanone A stirred mixture of 6-fluoro-3-(4-piperidinyl)-1,2-benzisoxazole (2.0 g, 9.0 mmol), $K_2CO_3$ (1.3 g), and 1-[4-(3-bromopropoxy)-3,5-dibromophenyl]ethanone (2.65 g, 9.0 mmol) and acetonitrile (50 ml) was heated at reflux for 3 hours. At the end of the reaction, the solvent was evaporated and the residue was extracted into dichloromethane (150 ml). The insolubles were filtered off. The dichloromethane solution was concentrated down to an oil. The purification was done by flash chromatography on a silica gel column ($SiO_2$, 47 g; eluted with dichloromethane, 300 ml; 1% methanol in dichloromethane, 600 ml). The material thus purified as a colorless oil, solidified on standing. Recrystallization from ethanol gave 1-[3,5-dibromo-4-[3-[4-(6-fluoro-1,2-benzisoxazol-3-yl)-1-piperidinyl]propoxy]phenyl]ethanone as white crystals (2.93 g, 57%), m.p.= 102°–103° C.

Analysis: Calculated for $C_{23}H_{23}Br_2FN_2O_3$: 49.84%C, 4.18%H, 5.05%N; Found: 49.91%C, 4.11%H; 4.98%N.

EXAMPLE 39

1-[4-[2-[4-(1,2-Benzisothiazol-3-yl)-1-piperazinyl]ethoxy]-3-methoxyphenyl]-ethanone A mixture of 3-(1-piperazinyl)-1,2-benzisothiazole (4.0 g, 18.2 mmol), 1-[4-(2-chloroethoxy)-3-methoxyphenyl]-ethanone (4.3 g, 20.0 mmol), $K_2CO_3$ (3.0 g, 21.8 mmol), acetonitrile (125 ml) and a catalytic amount of KI was heated to reflux and stirred under nitrogen for 24 hours. At this point, an additional amount of $K_2CO_3$ (1.0 g, 7.2 mmol) and alkylating agent (0.4 g, 1.7 mmol) was added to the reaction mixture and heating at reflux was resumed for 24 hours. The reaction was cooled to ambient temperature and filtered. The filter cake was washed with acetonitrile and the filtrate was concentrated to afford a dark oil. The oil was extracted with methylene chloride, and the organic extract was washed with water, dried with $MgSO_4$ and concentrated to yield 9.2 g of an oil. Purification by preparative HPLC (Waters Associates Prep LC/System 500 utilizing 2 silica gel columns and 3% methanol/methylene chloride as eluent) provided 3.8 g of a soft, beige gum, which readily solidified. The compound was recrystallized twice from ethanol to give 2.1 g (28%) of 1-[4-[2-[4-(1,2-benzisothiazol-3-yl)-1-piperazinyl]ethoxy]-3-methoxyphenyl]ethanone as a beige solid, m.p.=98°–100° C.

Analysis: Calculated for $C_{22}H_{25}N_3O_3S$: 64.21%C, 6.21%H, 10.21%N; Found: 64.05%C, 6.09%H; 10.12%N.

EXAMPLE 40

6-Fluoro-3-[1-(3-phenoxypropyl)-4-piperidinyl]-1,2-benzisoxazole

A mixture of 6-fluoro-3-(4-piperidinyl)-1,2-benzisoxazole (4.0 g, 18.2 mmol), $K_2CO_3$ (3.0 g, 21.8 mmol), KI (100 mg), 3-chloropropoxybenzene (3.4 g, 20.0 mmol), and acetonitrile was stirred at reflux under nitrogen for 30 hours. The reaction was poured into water and the aqueous mixture was extracted with ethyl acetate. The ethyl acetate extract was washed with brine, dried with MgSO$_4$ and concentrated to afford 6.2 g of a damp, beige solid. The compound was recrystallized twice from ethanol to yield (47%) of 6-fluoro-3-[1-(3-phenoxypropyl)-4-piperidinyl]-1, 2-benzisoxazole as a light beige solid, m.p.=78°–80° C.

Analysis: Calculated for C$_{21}$H$_{23}$FN$_2$O$_2$: 71.17%C, 6.54%H, 7.90%N; Found: 71.00%C, 6.52%H; 7.81%N.

EXAMPLE 41

1-[4-[2-[4-(6-Chloro-1H-indazol-3-yl)-1-piperazinyl]ethoxy]-3-methoxyphenyl]-ethanone A mixture of 6-chloro-[3-(1-piperazinyl)]-1H-indazole (2.1 g, 8.9 mmol), K$_2$CO$_3$ (1.5 g, 10.7 mmol), KI (100 mg), 1-[4-(2-chloroethoxy)-3-methoxyphenyl]ethanone (2.2 g, 9.8 mml) and acetonitrile (70 ml) was stirred at reflux for 48 hours under N$_2$ The cooled reaction was poured into water and the aqueous mixture was extracted with ethyl acetate. The organic extract was washed with water, dried with MgSO$_4$ and concentrated to yield 6.0 g of a light yellow oil. The oil was purified by preparative HPLC (Waters Associates prep LC/System 500, employing 2 silica gel columns and 5.5% methanol/methylene chloride as eluent). Concentration of later fractions provided 1.6 g of an off-white solid. This was combined with an additional sample (3.4 g total) and two consecutive recrystallizations from ethanol yielded 2.1 g (23%) of 1-[4-[2-[4-(6-chloro-1H-indazol-3-yl)-1-piperazinyl]ethoxy]-3-methoxyphenyl]ethanone as an off-white solid, m.p.=154°–156° C.

Analysis: Calculated for C$_{22}$H$_{25}$ClN$_4$O$_3$: 61.61%C, 5.58%H, 13.06%N; Found: 61.66%C, 5.87%H; 13.06%N.

EXAMPLE 42

1-[4-[3-[4-(6-Fluoro-1,2-benzisoxazol-3-yl)-1-piperidinyl]propoxy]3-methoxy-phenyl]-2,2,2-trifluoroethanone A mixture of 6-fluoro-3-(4-piperidinyl)-1,2-benzisoxazole (1.5 g, 6.7 mmol), 1-[4-(3-chloropropoxy)-3-methoxyphenyl]-2,2,2-trifluoroethanone (2.0 g, 6.7 mmol), K$_2$CO$_3$ (0.88 g), KI (0.1 g) and acetonitrile (50 ml) was stirred and refluxed for 16 hours. After cooling, the reaction was poured into water and the aqueous mixture extracted with ethyl acetate. The extract was washed (H$_2$O), dried (MgSO$_4$), and the solvent was concentrated to an oil, which upon evacuation at high vacuum afforded 3.2 g of a waxy solid. The solid was chromatographed on a Waters preparative LC (silica columns, eluting with 3% methanol-dichloromethane). Concentration of the appropriate fractions gave 1.8 g (56%) of 1-[4-[3-[4-(6-fluoro-1,2-benzisoxazol-3-yl)-1-piperidinyl]-propoxy]-3-methoxyphenyl]-2,2,2-trifluoro-ethanone solid, m.p.= 94°–96° C.

Analysis: Calculated for C$_{24}$H$_{24}$F$_4$N$_2$O$_4$: 60.00%C, 5.03%H, 5.83%N; Found: 60.01%C, 5.06%H; 5.68%N.

EXAMPLE 43

1-[4-[3-[4-(6-Fluoro-1,2-benzisoxazol-3-yl)-1-piperidinyl]propoxy]-3-methyl-mercaptophenyl] ethanone A stirred mixture of 6-fluoro-3-(4-piperidinyl)-1,2-benzisoxazole (1.88 g, 8.5 mmol), K$_2$CO$_3$ (1.8 g) and 1-[4-(3-bromopropoxy)-3-methylmercaptophenyl]ethanone (2.3 g, 7.6 mmol) in acetonitrile (100 ml) was heated at reflux for 4 hours. At the end of the reaction, the solvent was concentrated, then diluted with dichloromethane (250 ml). The insolubles were filtered off. The dichloromethane solution was concentrated to dryness as an oil. Purification was effected by flash chromatography on a silica gel column (SiO$_2$, 54 g, eluted with dichloromethane, 500 ml; 1% methanol-dichloromethane, 1.1 l). The purest fractions were combined to give a colorless oil which solidified to an off-white solid (2.4 g). Recrystallization from ethanol (100 ml) yielded 1-[4-[3-[4-(6-fluoro-1,2-benzoisoxazol-3-yl]-1-piperidinyl]propoxy]-3-methylmercaptophenyl]ethanone as off-white needle crystals, 215 g, m.p.=150°–152° C.

Analysis: Calculated for C$_{24}$H$_{27}$FN$_2$O$_3$S: 65.14%C, 6.15%H, 6.33%N; Found: 65.09%C, 6.10%H; 6.25%N.

EXAMPLE 44

1-[4-(3-Bromopropoxy)-3-bromophenyl]ethanone

A stirred mixture of 3-bromo-4-hydroxyacetophenone (4.5 g, 21.2 mmol), K$_2$CO$_3$ (4 g) and 1,3-dibromopropane (7.6 g) in acetonitrile (200 ml) was heated at reflux for 2 hours. At the end of the reaction, the solvent was removed and the residue was dissolved in dichloromethane (400 ml) and filtered. The dichloromethane solution was concentrated to an oil. The oil was added to isopropyl ether and stirred to cause crystallization (4.1 g; 58%). The solid was recrystallized from isopropyl ether to give 3.5 g of 1-[4-(3-bromopropoxy)-3-bromophenyl]ethanone as glistening crystals, m.p.=83°–84° C.

Analysis: Calculated for C$_{11}$H$_{12}$Br$_2$O$_2$: 39.31%C, 3.60%H; Found: 39.80%C, 3.55%H.

EXAMPLE 45

1-[4-(3-Bromopropoxy)-3,5-dibromophenyl] ethanone

A stirred mixture of 3,5-dibromo-4-hydroxyacetophenone (3.0 g, 10.1 mmol), K$_2$CO$_3$ (2.8 g, 20.3 mmol), 1,3-dibromo-propane (4.0 g, 19.8 mmol) in acetonitrile (100 ml) was heated at reflux for 5 hours. The solvent was removed. The crude product was extracted into dichloromethane (150 ml) and the insoluble inorganics were filtered off. The solution was concentrated to dryness again. Purification was carried out by flash chromatography on silica gel (45 g, SiO$_2$; eluted with 1:1 hexane:dichloromethane). The material thus obtained (2.8 g) was recrystallized twice from isopropyl ether to give analytically pure 1-[4-(3-bromopropoxy)-3,5-dibromophenyl]ethanone, m.p.=87°–88° C.

Analysis: Calculated for C$_{11}$H$_{11}$Br$_3$O$_2$: 31.84%C, 2.67%H; Found: 31.97%C, 2.63%H.

EXAMPLE 46

1-[4-[4-[4-(1,2-Benzisothiazol-3-yl)-1-piperidinyl] butoxyl]-3-methoxyphenyl]-ethanone A stirred mixture of 3-(4-piperidinyl)-1,2-benzisothiazole (2.6 g, 11.9 mmol), 1-[4-(4-bromobutoxy)-3-methoxyphenyl]ethanone (3.9 g, 13.1 mmol), K$_2$CO$_3$ (2.0 g, 14.3 mmol), KI (200 mg) and acetonitrile (125 ml) was stirred at reflux under nitrogen for 18 hours. The reaction was cooled to ambient temperature and filtered. The filter cake was washed well with fresh acetonitrile and the filtrate was concentrated to yield a wet, brown solid. The residue was diluted with water and the aqueous suspension was extracted with methylene chloride. The organic extract was washed with water, dried with MgSO$_4$ and concentrated to afford 6.5 g of a dark oil. The oil was purified by preparative HPLC (Waters Associates prep LC/System 500, utilizing 2 silica gel columns and 5% methanol/methylene chloride) to give 4.5 g of a beige solid. A 3.1 g (7.1 mmol) sample was taken up in absolute ethanol (80 ml) and oxalic acid (0.67 g, 7.4 mmol) was added. The solution was refluxed mildly on a steam bath for 45 minutes and was then stirred at ambient temperature for 1 hour. The resultant suspension was diluted with anhydrous ether (150 ml) and stirred for 5 minutes. The solid was collected and dried to afford 3.1 g of a light, beige solid. The salt was recrystallized from ethanol to yield 2.8 g. The compound was converted back to the free base with 50% NaOH to give 2.4 g, which was immediately recrystallized from ethanol to provide 1.5 g (29%) of 1-[4-[4-[4-(1,2-benzisothiazol-3-yl)-1-piperidinyl]butoxy]-3-methoxyphenyl]ethanone as a beige powder, m.p.=78°–80° C.

Analysis: Calculated for $C_{25}H_{30}N_2O_3S$: 68.46%C, 6.91%H, 6.39%N; Found: 68.34%C, 6.85%H, 6.33%N.

EXAMPLE 47

1-[4-[3-[4-(6-Fluoro-1,2-benzisoxazol-3-yl)-1-piperidinyl]propoxy]-3-methoxyphenyl]-phenylmethanone A mixture of 6-fluoro-3-(4-piperidinyl)-1,2-benzisoxazole (2.2 g, 10 mmol), $K_2CO_3$ (2.3 g) and 1-[4-(3-bromopropoxy)-3-methoxyphenyl]phenylmethanone (3.47 g, 10 mmol) in acetonitrile (100 ml) was heated at reflux for 3 hours. At the end of reaction, the acetonitrile was concentrated and the mixture was extracted into dichloromethane (200 ml). The insolubles were filtered off and the solvent was evaporated to an oil. Purification was carried out by flash chromatography over a silica gel column ($SiO_2$, 50 g; eluted with dichloromethane, 600 ml; 1% methanol:dichloromethane, 600 ml; 2% methanol: 98% dichloromethane, 600 ml). The fractions containing the pure product were combined and concentrated to give 4.24 g (87%) of an off-white solid. Recrystallization from ethanol (75 ml) gave 3.9 g of 1-[4-[3-[4-(6-fluoro-1,2-benziosoxazol-3-yl)-1-piperidinyl]-propoxy]-3-methoxyphenyl]phenylmethanone as off-white crystals, m.p.=128°–130° C.

Analysis: Calculated for $C_{29}H_{29}FN_2O_4$: 71.30%C, 5.98%H, 5.73%N; Found: 71.31%C, 5.99%H, 5.75%N.

EXAMPLE 48

1-[4-[3-[4-(6-Fluoro-1,2-benziosoxazol-3-yl)-1-piperidinyl]propoxy]-3-bromophenyl]ethanone A mixture of 6-fluoro-3-(4-piperidinyl)-1,2-benzisoxazole (2.1 g, 9.5 mmol), $K_2CO_3$ (2.0 g) 1-[3-bromo-4-(3-bromopropoxy)phenyl]ethanone (3.1 g, 9.2 mmol) in acetonitrile (100 ml) was heated at reflux for 3 hours. At the end of reaction, the solvent was concentrated and the mixture was extracted into dichloromethane (200 ml). The insolubles were filtered off. The dichloromethane was concentrated again. The crude residue was purified by flash chromatography over a silica gel column ($SiO_2$, 49 g; eluted with dichloromethane, 500 ml; 1% methanoo:dichloromethane, 600 ml; 3% methanol: 97% dichloromethane, 600 ml). The material thus obtained (3.26 g, 72%) was recrystallized from ethanol (40 ml) to give 1-[4-[3-[4-(6-fluoro-1,2-benzisoxazol-3-yl)-1-piperidinyl]-propoxy]-3-bromophenyl]ethanone as light yellow crystals (3.0 g), m.p.=126°–128° C.

Analysis: Calculated for $C_{23}H_{24}BrFN_2O_3$: 58.12%C, 5.09%H, 5.89%N; Found: 57.64%C, 5.35%H, 5.55%N.

EXAMPLE 49

3-[1-[3-[4-(1-Ethoxyethyl)-2-methoxyphenoxy]propyl]-4piperidinyl]-6-fluoro-1,2-benzisoxazole hydrochloride To a mixture of 4-[3-[4-(6-fluoro-1,2-benzisoxazol-3-yl)-1-piperidinyl]propoxy]-3-methoxy-α-methylbenzenemethanol (3.8 g, 89 mmol) in pyridine (25 ml) was added acetic anhydride (5 ml). The mixture was warmed briefly on the steam bath to effect solution, and then the reaction was allowed to stand at ambient temperature for 16 hours. Most of the pyridine was evaporated under reduced pressure and the resultant oil was diluted with water. The aqueous solution was made basic with dilute NaOH, and subsequently extracted with ethyl acetate. The organic extract was washed (water), dried ($MgSO_4$), and the solvent concentrated to give 3.7 g of the O-acetyl derivative as a colorless oil. The compound was dissolved in diethyl ether and ethereal HCl was added to precipitate a gum-like hydrochloride salt, which upon treatment with refluxing ethyl acetate afforded 3.4 g of a crystalline salt, m.p.=143°–145° C. Attempting to recrystallize the salt from ethanol:diethyl ether resulted in displacement of the acetate to afford the ethyl ether. The salt of this product (2.8 g) was recrystallized from ethanol:diethyl ether to yield 2.1 g (48%) of 3-[1-[3-[4-(1-ethoxyethyl)-2-methoxyphenoxy]propyl]-4-piperidinyl]-6-fluoro-1,2-benzisoxazole hydrochloride, m.p.=139°–141° C.

Analysis: Calculated for $C_{26}H_{33}FN_2O_4 \cdot HCl$: 63.34%C, 6.95%H, 5.68%N; Found: 63.06%C, 6.80%H, 5.63%N.

EXAMPLE 50

3-[1-[3-[4-(1-Acetoxyethyl)-2-methoxphenoxy]propyl]-4-piperidinyl]-6-fluoro-1,2-benzisoxazole fumarate A mixture of 4-[3-[4-(6-fluoro-1,2-benzisoxazol-3-yl)-1-piperidinyl]-3-methoxy-α-methylbenzenemethanol (4.8 g, 11 mmol) in pyridine (45 ml) was warmed briefly to effect solution and then acetic anhydride (6.3 ml) was added. The reaction stood at ambient temperature for 16 hours, was concentrated in vacuo, and the colorless oil that remained was dissolved in water. The aqueous solution was made basic with saturated $K_2CO_3$ solution, and the mixture was extracted with diethyl ether. The extract was washed (water), dried ($MgSO_4$) and concentrated to afford 5.2 g of a thick, colorless oil. The oil (4.8 g) was dissolved in anhydrous diethyl ether and fumaric acid (1.2 g, 0.01 mol) was added. The mixture was stirred at ambient temperature for 4 hours, and then was permitted to stand at ambient temperature for 16 hours. The resultant white, 3-[1-[3-[4-(1-acetoxyethyl)-2-methoxyphenoxy]propyl]-4-piperidinyl]-6-fluoro-1,2-benzisoxazole fumarate was collected and afforded 3.0 g of material. The filtrate was treated with an additional amount of fumaric acid (0.3 g) and 0.9 g more of 3-[1-[3-[4-(1-acetoxyethyl)-2-methoxyphenoxy]propyl]-4-piperidinyl]-6-fluoro-1,2-benzisoxazole fumarate was harvested. The two batches were combined and recrystallized from acetonitrile (twice) to yield 2.3 g (43%) of the acetate, m.p.=150°–152° C.

Analysis: Calculated for $C_{26}H_{31}FN_2O_3 \cdot C_4H_4O_4$: 61.43%C, 6.01%H, 4.78%N; Found: 61.06%C, 5.87%H, 4.73%N.

EXAMPLE 51

1-[4-[3-[4-(6-Fluoro-1,2-benzisoxazol-3-yl)-1-piperidinyl]propoxy]-3-methoxy-phenyl]pentanone A mixture of 6-fluoro-3-(4-piperidinyl)-1,2-benzisoxazole (2.2 g, 10 mmol), $K_2CO_3$ (3 g), 1-[4-(3-bromopropoxy)-3-methoxyphenyl]pentanone (3.7 g, 11.3 mmol) in acetonitrile (140 ml) was heated at reflux for 4 hours. At the end of the reaction, the mixture was cooled and filtered. The filtrate was concentrated to an oil. Purification was performed by flash chromatography over a silica gel column ($SiO_2$, 55 g; eluted with 1% methanol in dichloromethane, 600 ml; 3% methanol: 97% dichloromethane, 400 ml). The fractions containing pure product were pooled and concentrated to a solid (4.3 g, 91%). Recrystallization from ethanol (10 ml) gave a powdery solid of 1-[4-[3-[4-(6-fluoro-1,2-benzisoxazol-3-yl)-1-piperidinyl]propoxy]-3-methoxyphenyl]pentanone (3.22 g), m.p.=79°–80° C.

Analysis: Calculated for $C_{27}H_{33}FN_2O_4$: 69.21%C, 7.10%H, 5.98%N; Found: 69.00%C, 6.94%H, 6.39%N.

EXAMPLE 52

2-[3-[4-(6-Fluoro-1,2-benzisoxazol-3-yl)-1-piperidinyl]propoxy]N-methyl-benzenamine hemifumarate A mixture of 6-fluoro-3-(4-piperdinyl)-1,2-benzisoxazole (2.5 g, 11.4 mmol), $K_2CO_3$ (1.8 g, 13.0 mmol), 4-(3-chloropropoxy)-2-methylaminobenzene (2.4 g, 12.0 mmol) and acetonitrile (100 ml) was stirred at reflux for 18 hours. The reaction was cooled to ambient temperature and was poured into water. The aqueous mixture was extracted with ethyl acetate and the ethyl acetate extract was washed with water, dried with $MgSO_4$, and concentrated to yield 4.1 g of a brown oil. The oil was purified by preparative HPLC (Waters Associates prep LC/System 500, utilizing 2 silica gel columns and eluting with 4% methanol-methylene chloride). Concentration of appropriate fractions yielded 2.45 g of a beige oil. The product was taken up in ethyl acetate (50 ml) and fumaric acid (0.78 g) was added. The mixture was stirred at mild reflux for 45 minutes and then at ambient temperature for 1.5 hours. The product was isolated by vacuum filtration to provide 2.5 g of a pale yellow solid. Recrystallization from ethanol afforded 2.0 g (40%) of 2-[3-[4-(6-fluoro-1,2-benzisoxazol-3-yl)-1-piperidinyl]propoxy]-N-methylbenzenamine hemifumarate as beige crystals, m.p.=180°–182° C.

Analysis: Calculated for $C_{23}H_{26}FN_3O_2 \cdot 0.5\ C_4H_4O_4$: 65.28%C, 6.40%H, 9.52%N; Found: 65.08%C, 6.35%H, 9.45%N.

EXAMPLE 53

1-[4-[3-[4-(6-Fluoro-1,2-benzisoxazol-3-yl)-1-piperidinyl]propoxy]-3-methoxy-phenyl]propanone A mixture of 6-fluoro-3-(4-piperidinyl)-1,2-benzisoxazole (2.8 g, 15.2 mmol), $K_2CO_3$ (3 g), 1-[4-(3-bromopropoxy)-3-methoxyphenyl]propanone (4.6 g, 18.2 mmol) in acetonitrile (100 ml) was heated at reflux for 2 hours. At the end of the reaction, the mixture was filtered and the solvent was concentrated and the residue was extracted into dichloromethane (300 ml). The dichloromethane was filtered and concentrated again. The crude material (6.4 g) was purified by flash chromatography over a silica gel column ($SiO_2$, 50 g; eluted with dichloromethane, 700 ml; 1% methanol in dichloromethane, 1.4 l). The material thus purified (weight: 2.87 g, 51%) was recrystallized from ethanol (25 ml) to give 2.13 g of 1-[4-[3-[4-(6-fluoro-1,2-benzisoxazol-3-yl)-1-piperidinyl]propoxy]-3-methoxyphenyl]propanone as beige colored crystals, m.p.=118°–119° C.

Analysis: Calculated for $C_{25}H_{29}FN_2O_4$: 68.16%C, 6.64%H, 6.36%N; Found: 68.32%C, 6.63%H, 6.29%N.

EXAMPLE 54

4-[3-[4-(6-Fluoro-1,2-benzisoxazol-3-yl)-1-piperidinyl]propoxy]-3-methoxybenzamide A mixture of 6-fluoro-3-(4-piperidinyl)-1,2-benzisoxazole (2.2 g, 10.0 mmol), $K_2CO_3$ (2.0 g) and 4-(3-bromopropoxy)-3-methoxybenzamide (2.32 g, 8.0 mmol) in acetonitrile (80 ml) was heated at reflux for 5 hours. At the end of the reaction the solvent was evaporated. The residue was extracted into dichloromethane. The inorganic insolubles were filtered off. The dichloromethane was concentrated again. The crude residue was purified by flash chromatography over a silica gel column (55 g, $SiO_2$; eluted with 1% methanol in dichloromethane, 1 l; 2% methanol in dichloromethane, 1 l). The material thus obtained weighed 2.93 g (84%) as white crystals. Recrystallization from hot ethanol (60 ml) gave 2.2 g of 4-[3-[4-(6-fluoro-1,2-benzisoxazol-3-yl)-1-piperidinyl]propoxy]-3-methoxybenzamide as white crystals, m.p.=163°–164° C.

Analysis: Calculated for $C_{23}H_{26}FN_3O_4$: 64.62%C, 6.13%H, 9.83%N; Found: 64.20%C, 6.06%H, 9.71%N.

EXAMPLE 55

1-[4-[3-[4-(6-Fluoro-1,2-benzisoxazol-3-yl)-1-piperidinyl]propoxy]-3-(methylamino)-phenyl] ethanone A mixture of 6-fluoro-3-(4-piperidinyl)-1,2-benzisoxazole (2.3 g, 10.3 mmol), $K_2CO_3$ (1.4 g, 10.3 mmol), 1-[4-(3-chloropropoxy)-3-(methylamino)phenyl] ethanone (2.5 g, 10.3 mmol), KI (0.10 g), and acetonitrile (100 ml) was stirred at reflux under nitrogen for 23 hours. The reaction was cooled to ambient temperature, poured into water, and the aqueous mixture was extracted with ethyl acetate. The ethyl acetate extract was washed twice with water, dried with $MgSO_4$ and was concentrated to yield 4.8 g of a damp, brown solid. The compound was isolated by preparative HPLC (Waters Associates prep LC/System 500, utilizing 2 silica gel columns and 4% methanol-methylene chloride as eluent). Concentration of appropriate fractions afforded 2.4 g. Recrystallization from ethanol gave 2.1 g of 1-[4-[3-[4-(6-fluoro-1,2-benzisoxazol-3-yl)-1-piperidinyl]propoxy]-3-(methylamino)phenyl]ethanone as a beige solid, m.p.=151°–153° C.

Analysis: Calculated for $C_{24}H_{28}FN_3O_3$: 67.75%C, 6.63%H, 9.88%N; Found: 67.83%C, 6.76%H, 9.90%N.

EXAMPLE 56

1-[4-[3-[4-(6-Fluoro-1,2-benzisoxazol-3-yl)-1-piperidinyl]propoxy]-3-ethoxyphenyl]-ethanone A suspension of NaH (0.28 g of a 50% oil dispersion, 5.9 mmol) in dimethylformamide (20 ml) was cooled to 4° C. in an ice bath. To this was added, dropwise, 1-[4-[3-[4-(6-fluoro-1,2-benzisoxazol-3-yl)-1-piperidinyl]propoxy]-3-hydroxyphenyl]ethanone (2.3 g, 0.0056 mol) dissolved in dimethylformamide (40 ml). After total addition, the mixture was stirred under nitrogen for 1 hour, keeping the temperature below 10° C. A solution of bromoethane (1.3 g, 11.8 mmol) dissolved in dimethylformamide (15 ml) was then added, dropwise, to the reaction mixture. Stirring under nitrogen was continued for 3 hours allowing the temperature to slowly rise to ambient temperature. The reaction was cooled in an ice bath, water was added and the aqueous mixture was extracted with ethyl acetate. The ethyl acetate extract was washed with water, dried with $MgSO_4$, and was concentrated to yield 3.9 g of a damp, beige solid. The solid was triturated with diethyl ether and filtered to yield 1.5 g. This was combined with an additional sample (3.5 g total), and recrystallization from ethanol provided 3.0 g (57%) of glistening, beige crystals of 1-[4-[3-[4-(6-fluoro-1,2-benzisoxazol-3-yl)-1-piperidinyl]-propoxy]-3-ethoxyphenyl]ethanone, m.p.=112°–114° C.

Analysis: Calculated for $C_{25}H_{29}FN_2O_4$: 68.16%C, 6.64%H, 6.36%N; Found: 68.10%C, 7.03%H, 6.35%N.

EXAMPLE 57

1-[4-(3-Bromopropoxy)-3-(methylmercapto)phenyl] ethanone

A mixture of 1-[4-hydroxy-3-(methylmercapto)phenyl]-ethanone (5.4 g; 30 mmol), $K_2CO_3$ (4.2 g), 1,3-dibromopropane (8 g, 39 mmol) in acetonitrile (150 ml) was heated at reflux for 3 hours and stirred at room temperature overnight. Acetonitrile was removed at reduced pressure and the residue was extracted into dichloromethane (250 ml). Insolubles were filtered off. The dichloromethane solution was concentrated. The crude product was purified on a silica gel column ($SiO_2$, 100 g; eluted with 3:2 hexane:dichloromethane, 1.6 l). The compound crystallized upon concentration, and the product (3.5 g, 39%) was recrystallized from ethanol (40 ml) to yield 1-[4-(3-bromopropoxy)-3-(methylmercapto)phenyl]ethanone as white needles, 2.0 g; m.p.=120°–122° C.

Analysis: Calculated for $C_{12}H_{15}BrO_2S$: 47.53%C, 4.99%H; Found: 47.74%C, 4.91%H.

EXAMPLE 58

4-(3-Bromopropoxy)-3-methoxybenzonitrile

A mixture of 4-hydroxy-3-methoxybenzonitrile (7.5 g, 50 mmol), $K_2CO_3$ (12.5 g), and 1,3-dibromopropane (15 g, 75 mmol) in acetonitrile (100 ml) was heated at reflux for 3 hours and left standing at room temperature overnight. The solvent of the reaction was removed on a rotary evaporator, and the crude solid was extracted into methylene chloride (500 ml). The insolubles were filtered off. The dichloromethane solution was concentrated and the material was purified on a flash chromatography column ($SiO_2$, 105 g; eluted with 2:3 dichloromethane:hexane, and then with dichloromethane). The desired product thus purified weighed 7.74 g (52%). Recrystallization twice from ethanol gave analytically pure 4-(3-bromopropoxy)-3-methoxybenzonitrile, m.p.=99°–101° C.

Analysis: Calculated for $C_{11}H_{12}BrNO_2$: 48.91%C, 4.48%H, 5.19%N; Found: 49.49%C, 4.47%H, 5.21%N.

EXAMPLE 59

1-[4-(3-Bromopropoxy)-3-methylphenyl]ethanone

A mixture of 4-hydroxy-3-methylacetophenone (14.5 g, 96 mmol), $K_2CO_3$ (17.5 g, 144 mmol), and 1,3-dibromopropane (30 g, 144 mmol) in acetonitrile (400 ml) was heated at reflux for 6 hours. At the end of the reaction, the solvent was removed on a rotary evaporator, and the crude solid was extracted into dichloromethane (750 ml). The insoluble inorganics were filtered off. The dichloromethane solution was concentrated again to a crude oil (34.5 g). Purification was effected by flash chromatography over a silica gel column ($SiO_2$, 150 g; eluted with 7:3 hexane:dichloromethane, 2 l; and dichloromethane 2 l). The material thus purified weighed 14.6 g (56%) and was recrystallized from ethanol. Recrystallization again from ethanol gave analytically pure 1-[4-(3-bromopropoxy)-3-methylphenyl]ethanone, m.p.=59°–61° C.

Analysis: Calculated for $C_{12}H_{15}BrO_2$: 53.15%C, 5.58%H; Found: 53.35%C, 5.52%H.

EXAMPLE 60

1-[4-(3-Bromopropoxy)-3-methoxyphenyl] phenylmethanone

A mixture of 1-(4-hydroxy-3-methoxyphenyl)phenylmethanone (14 g, 61.4 mmol), $K_2CO_3$ (13 g, 92.1 mmol), and 1,3-dibromopropane (28 g, 86 mmol) in acetonitrile (400 ml) was heated at reflux for 4 hours. The reaction was followed by thin layer chromatography. At the end of the reaction, the inorganics were filtered off and the solvent was removed on a rotary evaporator. The residue was purified on a flash chromatographic column ($SiO_2$, 140 g, eluted with 4:1 hexane:dichloromethane, 1.2 l) to give a partially solidified material: 15.44 g (72%). Recrystallization twice from ethanol gave 2.84 g of 1-[4-(3-bromopropoxy)-3-methoxyphenyl]phenylmethanone as white crystals, m.p.= 88°–89° C.

Analysis: Calculated for $C_{17}H_{17}BrO_3$: 58.47%C, 4.91%H; Found: 59.03%C, 4.87%H.

EXAMPLE 61

N-[2-[3-[4-(6-fluoro-1,2-benzisoxazol-3-yl)-1-piperidinyl]propoxy]phenyl]acetamide (A) N-[2-(3-phenylsulfonyloxypropoxy)phenyl]acetamide To a solution of N-[2-(3-hydroxypropoxy)phenyl]-acetamide (Example 113) (7.5 g, 36 mmol) in pyridine (90 ml), cooled to 0° C, was added p-toluenesulfonyl chloride (13.6 g, 56 mmol). After the tosyl chloride went into solution, the reaction was then allowed to stand at 5° C. for 16 hours. The reaction was poured onto ice, and a brown oil settled. The aqueous supernatant was decanted from the oil, and the residual oil taken up in diethyl ether. The diethyl ether was washed with cold (5° C.) 3N HCl and then with brine. The organic layer was dried ($MgSO_4$), and concentrated to afford a thick, brown oil, 5.3 g.

(B) N-[2-[3-[4-(6-fluoro-1,2-benzisoxazol-3-yl)-1-piperidinyl]propoxy]-phenyl]acetamide A mixture of 6-fluoro-3-(4-piperidinyl)-1,2-benzisoxazole (3.4 g, 16 mmol), N-[2-(3-phenylsulfonyloxypropoxy)phenyl]acetamide (5.3 g, 16 mmol), $K_2CO_3$ (2.2 g), and acetonitrile (50 ml) was stirred and refluxed for 5 hours. The reaction was poured into water, and the aqueous suspension was extracted with ethyl acetate. The ethyl acetate was washed (water and brine), dried ($MgSO_4$) and the solvent was concentrated to afford 6.0 g of a thick, brown oil. The oil was chromatographed on a Waters Prep 500 LC on silica gel. Concentration of the appropriate fractions afforded 3.0 g of a beige solid. This was recrystallized from ethyl acetate to yield (with concentration of the mother liquors) 2.2 g (33%) of N-[2-[3-[4-(6-fluoro-1,2-benzisoxazol-3-yl)-1-piperidinyl]propoxy]phenyl] acetamide as a beige solid, m.p.=118°–120° C.

Analysis: Calculated for $C_{23}H_{26}FN_3O_3$: 67.14%C, 6.37%H, 10.21%N; Found: 67.06%C, 6.43%H, 10.23%N.

EXAMPLE 62

1-[4-[3-[4-(6-Fluoro-1,2-benzisoxazol-3-yl)-1-piperidinyl]propoxy]-3-dimethyl-aminophenyl] ethanone (A) 1-[4-(3-Chloropropoxy)-3-dimethylaminophenyl] ethanone To a suspension of sodium hydride (2.3 g, 48.5 mmol of 50% oil dispersion) with dimethylformamide (75 ml), and cooled to 3° C. in an ice-salt bath and under a stream of nitrogen was added, dropwise, 1-(4-hydroxy-3-dimethylaminophenyl)ethanone (8.7 g, 48.5 mmol) dissolved in dimethylformamide (150 ml) so that the temperature did not go over 7° C. After the addition was over, the bath was removed and the reaction was stirred at ambient temperature for 45 minutes. The ice bath was reapplied and a solution of 1-bromo-3-chloropropane (8.4 g, 53.4 mmol) in dimethylformamide (25 ml) was added dropwise. After the addition was complete, the reaction was stirred for 18 hours at ambient temperature under nitrogen. The reaction was chilled to 7° C. in an ice bath and water (200 ml) was carefully added. After stirring for 5 minutes, the aqueous mixture was extracted with ethyl acetate (5×200 ml). The ethyl acetate extract was washed with water (2×50 ml), dried with $MgSO_4$, and concentrated to yield 22.2 g of a black oily liquid. The compound was purified by prep HPLC, and combination of appropriate fractions gave 5.0 g of brown oil.

(B) 1-[4-[3-[4-(6-fluoro-1,2-benzisoxazol-3-yl)-1-piperidinyl]propoxy]-3-dimethylaminophenyl]ethanone A mixture of 1-[4-(3-chloropropoxy)-3-dimethylaminophenyl]ethanone (2.9 g, 11.3 mmol), 6-fluoro-3-(4-piperidinyl)-1,2-benzisoxazole (2.5 g, 11.3 mmol), $K_2CO_3$ (1.7 g, 12.2 mmol), KI (200 mg) and acetonitrile (125 ml) was stirred at reflux for 18 hours. The cooled reaction was poured into water and the aqueous mixture was extracted with ethyl acetate. The ethyl acetate extract was washed with water, dried with magnesium sulfate and concentrated to yield 5.3 g of an amber oil. The compound was purified by preparative HPLC (Waters Associates prep LC/System 500 utilizing 2 silica gel columns) and concentration of appropriate fractions provided 1.65 g (33%). After combining with two additional samples, the compound (3.4 g, 7.74 mmol total) was taken up in ethyl acetate and fumaric acid (0.90 g, 7.75 mmol) was added. The mixture was stirred at a mild reflux for 30 minutes and then for 1 hour at ambient temperature. The reaction was left to stand overnight and was then filtered to give 3.6 g. The compound was recrystallized twice from ethanol to provide 2.3 g and once from acetonitrile to yield 1.9 g of the compound as a fumarate salt. The compound was converted to the free base by suspending it in dilute NaOH and extracting with dichloromethane. After washing the dichloromethane extract with water and drying with $MgSO_4$, the solvent was removed in vacuo to give 1.4 g (14%) of 1-[4-[3-[4-(6-fluoro-1,2-benzisoxazol-3-yl)-1-piperidinyl] propoxy]-3-dimethylaminophenyl]ethanone as a beige solid, m.p.=94°–96° C.

Analysis: Calculated for $C_{25}H_{30}FN_3O_3$: 68.32%C, 6.88%H, 9.56%N; Found: 67.74%C, 6.74%H, 9.40%N.

EXAMPLE 63

1-[4-[3-[4-(6-Fluoro-1,2-benzisoxazol-3-yl)-1-piperidinyl]propoxy]-2-methoxyphenyl]ethanone hydrochloride A mixture of 6-fluoro-3-(4-piperidinyl)-1,2-benzisoxazole (4.4 g, 20 mmol), 1-[4-(3-chloropropoxy)-2-methoxyphenyl]ethanone (4.8 g, 20 mmol), $K_2CO_3$ (2.8 g), KI (200 mg) and acetonitrile (110 ml) was stirred and refluxed for 16 hours. The reaction was filtered and the filtrate concentrated to afford 9.0 g of a brown oil. The oil was taken up in acetone and fumaric acid (2.5 g, 22 mmol) was added. The mixture was heated to reflux and then it was stirred at ambient temperature for 1 hour. The resultant fumarate salt (7.0 g) was collected and then reversed to the free base with aqueous sodium hydroxide to afford 4.6 g of a soft solid. The solid was flash chromatographed on silica gel with dichloromethane-methanol (10%) as eluent, and after concentration of the appropriate fractions afforded 3.6 g of an off-white solid. The solid was dissolved in anhydrous ether and ethereal HCl was added to precipitate 3.3 g of the hydrochloride salt. The salt was recrystallized from ethanol to afford 3.3 g of product. Occluded alcohol was removed to yield 2.8 g (29%) of 1-[4-[3-[4-(6-fluoro-1,2-benzisoxazol-3-yl)-1-piperidinyl]propoxy]-2-methoxyphenyl]ethanone hydrochloride, m.p.=193°–195° C.

Analysis: Calculated for $C_{24}H_{28}ClFN_2O_4$: 62.27%C, 6.10%H, 6.05%N; Found: 61.88%C, 5.90%H, 5.96%N.

EXAMPLE 64

1-[4-(3-Chloropropoxy)-3-methoxyphenyl]-2,2,2-trifluoroethanone (A) 4-(3-Chloropropoxy)-3-methoxybenzoic acid To a stirred suspension under nitrogen of sodium hydride (6.4 g, 130 mmol, of about 50% oil dispersion-ether washed) in tetrahydrofuran (220 ml) was added pyrazole (4.4 g, 60 mmol) in tetrahydrofuran (60 ml), dropwise. After complete addition, the reaction was stirred for about 15 minutes, and then 4-(3-chloropropoxy)-3-methoxybenzaldehyde (24.5 g, 107 mmol) was added. The nitrogen was stopped and air was sparged into the reactor for about 3 hours. The reaction was then allowed to stir at ambient temperature open to the atmosphere for 16 hours. Water was added, the reaction was cooled in an ice bath, and concentrated hydrochloric acid (25 ml) was added dropwise. More water was added and the yellow solid that separated was collected to afford 16.2 g of product. The filtrate was then extracted with ethyl acetate to afford an additional 9.3 g. The samples were combined and recrystallized from acetonitrile to yield 12.6 g of a light, yellow solid, m.p.=154°–156° C. A 4.0 g sample was recrystallized from acetonitrile to yield 2.6 g of a yellow solid. This was combined with 0.4 g from another sample and recrystallized again from acetonitrile with charcoal treatment to afford 2.0 g of 4-(3-chloropropoxy)-3-methoxybenzoic acid as a yellow solid, m.p.=157°–159° C.

Analysis: Calculated for $C_{11}H_{13}ClO_4$: 54.00%C, 5.35%H; Found: 54.65%C, 5.34%H.

(B) 4-(3-Chloropropoxy)-3-methoxybenzoyl chloride

To a mixture of 4-(3-chloropropoxy)-3-methoxybenzoic acid (2.4 g, 10 mmol) in dichloromethane (5 ml) was added thionyl chloride (0.9 ml, 12 mmol) dissolved in dichloromethane (5 ml). The reaction was stirred and refluxed for 1 hour, and then the dichloromethane was removed in vacuo to leave a dark oil. The oil was triturated with hexane and the solid that formed while scratching with a glass rod was collected to afford 1.6 g of 4-(3-chloropropoxy)-3-methoxybenzoyl chloride, m.p.=60°–63° C.

(C) 1-[4-(3-Chloropropoxy)-3-methoxyphenyl]-2,2,2-trifluoroethanone

To a stirred mixture of 4-(3-chloropropoxy)-3-methoxybenzoyl chloride (10.0 g, 38 mmol) in methylene chloride (55 ml) cooled to −70° C., there was condensed into a reactor bromotrifluoromethane (70 g, 47 mmol). There was then added to the reactor hexamethylphosphoroustriamide (9.4 g, 41 mmol) dissolved in dichloromethane (7 ml). The first 90% was added quite rapidly, and the remainder at a slower rate. After complete addition, the reaction was stirred at −70° C. to −65° C. for an additional hour. The reaction mixture was allowed to come to room temperature. An equal volume of hexane was added and the layers were separated. The lower layer was extracted with hexane and then with diethylether. The extracts were combined and concentrated to yield 5.6 g of a thick, colorless oil. The oil was chromatographed on a Waters Prep 500 LC utilizing two silica gel columns and eluting with 20% ethyl acetate-hexane. Concentration of appropriate fractions gave 2.7 g of a light oil, which after evacuation at high vacuum solidified to a waxy, white solid (2.4 g) of 1-[4-(3-chloropropoxy)-3-methoxyphenyl]-2,2,2-trifluoroethanone.

EXAMPLE 65

4-[3-[4-(6-Fluoro-1,2-1,2-benzisoxazol-3-yl)-1-piperidinyl]propoxy]-3-hydroxy-α-methylbenzene methanol (A) 1-[4-(3-chloropropoxy)-3-hydroxyphenyl]ethanone A mixture of 1-[4-(3-chloropropoxy)-3-methoxy-phenyl]ethanone (10.0 g, 41.2 mmol) and concentrated $H_2SO_4$ (50 ml) was stirred at 65° C. for 23 hours. The cooled reaction was poured into 250 g of ice and was stirred vigorously for 10 minutes. The aqueous mixture was extracted with dichloromethane ($CH_2Cl_2$) and the resultant dichloromethane extract was washed well with 5% sodium hydroxide. The basic phases were combined and washed with dichloromethane. The aqueous mixture was cooled in an ice bath and concentrated hydrochloric acid was added until a precipitate formed. The product was isolated by filtration and dried to yield 3.1 g of a light brown solid. This was combined with an additional sample (5.0 g total) and two consecutive recrystallizations from toluene provided 3.4 g (22%) of 1-[4-(3-chloropropoxy)-3-hydroxyphenyl]ethanone as a beige solid, m.p.=101°–103° C.

Analysis: Calculated for $C_{11}H_{13}ClO_3$: 57.78%C, 5.73%H; Found: 58.17%C, 5.66%H.

(B) 4-(3-chloropropoxy)-3-hydroxy-α-methylbenzene methanol

To a flask charged with sodium borohydride (1.5 g, 39.4 mmol) under nitrogen and chilled to 10° C. was added, slowly, a solution of 1-[4-(3-chloropropoxy)-3-hydroxyphenyl]ethanone (6.0 g, 26.2 mmol) dissolved in ethanol-tetrahydrofuran (120 ml, 2:1). After total addition, the ice bath was removed and the reaction was stirred at ambient temperature for 3 hours. An additional amount of sodium borohydride (0.2 g, 5.3 mmol) was carefully added. After stirring at ambient temperature for one hour, the solvent was removed in vacuo. The resultant solid residue was diluted with water (100 ml) and left overnight. The product was isolated by vacuum filtration yielding 3.8 g. Two consecutive recrystallizations from toluene provided 3.3 g (55%) of 4-(3-chloropropoxy)-3-hydroxy-α-methylbenzene methanol as a light brown solid, m.p.=107°–109° C.

Analysis: Calculated for $C_{11}H_{15}ClO_3$: 57.27%C, 6.55%H; Found: 57.60%C, 6.43%H.

(C) 4-[3-[4-(6-fluoro-1,2-benzisoxazol-3-yl )-1-piperidinyl] propoxy ]-3-hydroxy-α-methylbenzene methanol A mixture of 6-fluoro-3-(4-piperidinyl)-1,2-benzisoxazole (4.3 g, 19.5 mmol), 4-(3-chloropropoxy)-3-hydroxy-α-methylbenzenemethanol (4.5 g, 19.5 mmol), KI (200 mg), $NaHCO_3$ (1.8 g, 21.5 mmol) and $CH_3CN$ (125 ml) was stirred at reflux under nitrogen for 24 hours. The cooled reaction was filtered and the filter cake was washed with $CH_3CN$. The filtrate was concentrated to afford an oily residue, which was partitioned between water and ethyl acetate. The ethyl acetate extract was washed with water, dried with $MgSO_4$, and concentrated to yield 8.6 g of a dark oil. The oil was purified by preparative HPLC (Waters Associates prep LC/system 500) to yield 5.0 g. The compound was recrystallized twice from ethanol to provide 3.9 g (49%) of 4-[3-[4-(6-fluoro-1,2-benzisoxazol-3-yl)-1-piperidinyl]-propoxy]-3-hydroxy-α-methyl-benzene methanol as a light beige solid, m.p.=142°–144° C.

Analysis: Calculated for $C_{23}H_{27}FN_2O_4$: 66.65%C, 6.57%H, 6.76%N; Found: 66.68%C, 6.35%H, 6.72%N.

EXAMPLE 66

2-[3-[4-(6-Fluoro-1,2-benzisoxazol-3-yl)-1-piperidinyl]propoxy]-aniline dihydrochloride (A) 2-(3-chloropropoxy)aniline To a stirred suspension of sodium hydride (11.0 g, 230 mmol of a 50% oil dispersion) in dimethylformamide (250 ml), under nitrogen, was added, dropwise, 2-aminophenol (25.0 g, 230 mmol) dissolved in dimethylformamide (125 ml). After complete addition, the reaction was stirred at ambient temperature for 1 hour, and then it was cooled to 5° C. (ice bath). 3-Chloro-1-bromopropane (36.2 g, 230 mmol) in dimethylformamide (50 ml) was added, dropwise, so that the temperature did not go above 8° C. The reaction, was stirred for 4 hours and then permitted to stand at ambient temperature for 16 hours. The reaction was poured into water and extracted with ethyl acetate. The ethyl acetate was washed (water), dried ($MgSO_4$), and the solvent concentrated to afford 25.4 g of a reddish, dark oil. About 12.0 g of the oil was chromatographed on HPLC columns. Concentration of the largest fractions gave 5.4 g of 2-(3-chloropropoxy) aniline as an oil.

(B) 2-[3-[4-(6-fluoro-1,2-benzisoxazol-3-yl)-1-piperidinyl] propoxy]aniline dihydrochloride A mixture of 6-fluoro-3-(4-piperidinyl)-1,2-benzisoxazole (4.8 g, 22 mmol), 2-(3-chloropropoxy)aniline (4.0 g, 22 mmol), $K_2CO_3$ (4.1 g, 22 mmol), KI (0.2 g), and acetonitrile (100 ml) was stirred and refluxed for 10 hours. The reaction was poured into water and the aqueous mixture was extracted with ethyl acetate. The extract was washed (water), dried ($MgSO_4$), and the solvent was concentrated to afford 9.0 g of a red solid. The solid was triturated with diethyl ether to yield 3.0 g of a beige solid. This sample was combined with a sample (1.1 g) from another run, and a hydrochloride salt was prepared by dissolving the free base in ethanol and then adding ethereal HCl. The resultant salt (3.5 g) was recrystallized twice from methanol-diethyl ether to afford 2.6 g (22%) of 2-[3-[4-(6-fluoro-1,2-benzisoxazol-3-yl)-1-piperidinyl]propoxy]aniline dihydrochloride as a brown solid, m.p.=253°–255° C.

Analysis: Calculated for $C_{21}H_{24}FN_3 \cdot 2HCl$: 57.02%C, 5.92%H, 9.50%N; Found: 56.68%C, 5.71%H, 9.35%N.

EXAMPLE 67

N-[5-Acetyl-2-[3-[4-(6-fluoro-1,2-benzisoxazol-3-yl)-1-piperidinyl]propoxy]phenyl]-acetamide (A) Preparation of 1-[3-acetylamino-4-(3-chloropropoxy) phenyl]ethanone A stirred mixture of 1-[3-acetylamino-4-hydroxyphenyl] ethanone (7.7 g, 40 mmol), $K_2CO_3$ (5.7 g), 3-chloro-1-bromopropane (8.9 g, 56 mmol) and acetone (100 ml) was refluxed for 16 hours. The reaction was allowed to cool to ambient temperature and filtered. Concentration of the filtrate yielded 8.5 g of a white solid. The solid was recrystallized from toluene and then from ethanol to afford 6.5 g of an off-white solid. A 3.3 g sample of this material was flash chromatographed on silica gel with ethyl acetate as eluent. Concentration of the appropriate fractions afforded 2.8 g of a solid. The solid was recrystallized from toluene and then from ethanol-water to yield 2.2 g (51%) of a solid, m.p.=124°–126° C.

Analysis: Calculated for $C_{13}H_{16}ClNO_3$: 57.89%C, 5.98%H, 5.19%N; Found: 57.08%C, 5.85%H, 5.13%N.

(B) N-[5-acetyl-2-[3-[4-(6-fluoro-1,2-benzisoxazol-3-yl)-1-piperidinyl]propoxy]phenyl]acetamide A mixture of 6-fluoro-3-(4-piperidinyl)-1,2-benzisoxazole (4.4 g, 20 mmol), 1-[3-acetylamino-4-(3-chloropropoxy)phenyl]ethanone (5.5 g, 20.5 mmol), $K_2CO_3$ (2.8 g), and acetonitrile (70 ml) was stirred and refluxed for 16 hours. The reaction was poured into water and the aqueous mixture was extracted with ethyl acetate. The extract was washed (water), dried ($MgSO_4$), and then it was concentrated to afford 9.5 g of a brown oil. The oil was taken up in ethyl acetate and ethereal HCl was added until the reaction was acidic. The crude, brown, hydrochloride salt was collected (8.4 g), and was immediately converted to the free base with $NH_4OH$, to afford 5.4 g of the compound as a brown oil. The oil was chromatographed on a Waters Preparative HPLC utilizing silica gel columns. Concentration of the appropriate fractions yielded 3.5 g of N-[5-acetyl-2-[3-[4-(6-fluoro-1,2-benzisoxazol-3-yl)-1-piperidinyl] propoxy]-phenyl]acetamide as a white solid, m.p.=108°–110° C.

Analysis: Calculated for $C_{25}H_{28}FN_3O_4$: 66.21%C, 6.22%H, 9.27%N; Found: 66.12%C, 6.25%H, 9.27%N.

EXAMPLE 68

3-[1-[3-(4-Ethyl-3-methoxyphenoxy)propyl]-4-piperidinyl-6-fluoro-1,2-benzisoxazole hydrochloride (A) 4-ethyl-2-methoxyphenol Acetovanillone (Aldrich, 11.0 g, 66 mmol) was dissolved in absolute ethanol (200 ml) and added to 1.5 g of 5% palladium on carbon. A few drops of concentrated hydrochloric acid were added and the mixture hydrogenated on a shaker at 42 psi. The reaction mixture was filtered through Celite, and the filtrate was concentrated to afford 10.3 g of a golden liquid. This was diluted with water, extracted with diethyl ether and the organic phase was washed with water and sodium bicarbonate. The solvent was dried ($MgSO_4$) and concentrated to afford 9.3 g of a slightly yellow liquid.

(B) 4-ethyl-2-methoxy-4-(3-chloropropoxy)benzene

A mixture of 4-ethyl-2-methoxyphenol (9.0 g, 59 mmol), 3-chloro-1-bromopropane (13.0 g, 83 mmol), $K_2CO_3$ (6.2 g) and acetone (200 ml) was stirred and refluxed for 16 hours. The reaction was allowed to cool, and then it was filtered. The filtrate was concentrated to a clear liquid. The liquid was diluted with dilute aqueous NaOH, and the basic mixture was extracted with diethyl ether. The diethyl ether was washed (water), dried ($MgSO_4$), and the solvent was concentrated to afford 11.9 g of a golden liquid. The liquid was flash chromatographed. This gave a colorless liquid, 9.9 g of 4-ethyl-2-methoxy-4-(3-chloropropoxy)benzene.

(C) 3-[1-[3-(4-ethyl-2-methoxyphenoxy)propyl]-4-piperidinyl]-6-fluoro-1,2-benzisoxazole hydrochloride A stirred mixture of 6-fluoro-3-(4-piperidinyl)-1,2-benzisoxazole (4.0 g, 18 mmol), KI (0.4 g), $K_2CO_3$ (2.5 g), 4-ethyl-2-methoxy-4-(3-chloropropoxy)benzene (4.4 g, 18 mmol) and acetonitrile was refluxed for 8 hours. The reaction was poured into water, and the aqueous suspension was extracted with ethyl acetate. The ethyl acetate extract was washed (water) dried ($MgSO_4$) and the solvent concentrated to afford 7.0 g of a brown oil. The oil was combined with 2.0 g from another sample, and the combined sample was flash chromatographed on silica gel. Concentration of the appropriate fractions yielded 4.4 g of a thick oil, which solidified on standing. The solid was dissolved in ethyl acetate and ethereal HCl was added to precipitate 4.5 g of a white hydrochloride salt. Recrystallization from acetone afforded 3.0 g (29%) of 3-[1-[3-(4-ethyl-2-methoxyphenoxy)-propyl]-4-piperidinyl]-6-fluoro-1,2-benzisoxazole hydrochloride as a white solid, m.p.=150°–152° C.

Analysis: Calculated for $C_{24}H_{29}FN_2O_3 \cdot HCl$: 64.21%C, 6.74%H, 6.24%N; Found: 64.38%C, 6.84%H, 6.14%N.

EXAMPLE 69

1-[3,5-Dimethoxy-4-[3-[4-(6-fluoro-1,2-benzisoxazol-3-yl)-1-piperidinyl]propoxy]-phenyl] ethanone (A) 3,5-dimethoxy-4-(3-bromopropoxy)acetophenone To 3,5-dimethoxy-4-hydroxyacetophenone (5.2 g) in dimethylformamide (50 ml) at 0° C. under nitrogen, was added sodium hydride (700 mg, 1.1 eq, 98%). The resulting mixture was stirred for ten minutes until evolution of gas ceased. Potassium carbonate (4 g) was added, and then 1,3-dibromopropane was added. The mixture was heated at 60° C. for one hour. When the reaction was complete, the mixture was poured into a water/ice mixture and the resulting solution was extracted with ethyl acetate (600 ml). The ethyl acetate was washed with water, brine, and then concentrated to an oil (9 g). The product was purified by chromatography on silica gel to yield 3,5-dimethoxy-4-(3-bromopropoxy)acetophenone as a light oil, 7.6 g.

(B) 1-[3,5-dimethoxy-4-[3-[4-(6-fluoro-1,2-benzisoxazol-3-yl)-1-piperidinyl]propoxy]phenyl]ethanone A stirred mixture of 6-fluoro-3-(4-piperidinyl)-1,2-benzisoxazole (3.0 g, 13.6 mmol), $K_2CO_3$ (2.1 g, 15 mmol), and 3,5-dimethoxy-4-(3-bromopropoxy)-acetophenone (4.4 g, 13.8 mmol) in acetonitrile (50 ml) was heated at reflux for 3 hours. At the end of the reaction, the mixture was diluted with dichloromethane 200 ml). The insolubles were filtered. The solution was concentrated to an oil (10 g). The purification was done by flash chromatography on a silica gel column. The product was obtained as a colorless oil (3.85 g, 61%), which crystallized from ethanol (400 ml) to give 2.94 g of 1-[3,5-dimethoxy-4-[3-[4-(6-fluoro-1,2-benzisoxazol-3-yl)-1-piperidinyl]-propoxy]phenyl]ethanone as off-white crystals, m.p.=107°–108° C.

Analysis: Calculated for $C_{25}H_{29}FN_2O_5$: 65.78%C, 6.40%H, 6.14%N; Found: 65.84%C, 6.44%H, 6.15%N.

EXAMPLE 70

N-[3-[3-[4-(6-Fluoro-1,2-benzisoxazol-3-yl)-1-piperidinyl]propoxy]-phenyl]acetamide hemifumarate (A) 3-(3-acetamidophenoxy)propyl bromide To 3-acetamidophenol (15.1 g) in dichloromethane (500 ml, dry) was added potassium carbonate (20 g) and then 1,3-dibromopropane (30 g). The resulting mixture was heated at reflux for 6 hours and then overnight at room temperature. After an additional 24 hours, the reaction was complete. Solids were filtered from the reaction mixture, and the solution was concentrated to an oil, which was purified to yield 3-(3-acetamidophenoxy)propyl bromide, 13.2 g.

(B) N-[3-[3-[4-(6-fluoro-1,2-benzisoxazol-3-yl)-1-piperidinyl]propoxy]phenyl]acetamide hemifumarate A stirred mixture of 6-fluoro-3-(4-piperidinyl)-1,2-benzisoxazole (9.25 g, 42 mmol), $K_2CO_3$ (8 g, 58 mmol) and 3-(3-acetamidophenoxy)propyl bromide (11.4 g, 42 mmol) in acetonitrile (350 ml) was heated at reflux for 3 hours. At the end of the reaction, the reaction was cooled, filtered and the solids washed with dichloromethane (100 ml). The organic solvent was removed on a rotary evaporator to leave a crude oil (18 g). Purification was by flash chromatography on a silica gel column. The product thus purified was an oil, 12.2 g, 70%. Analytically pure sample was prepared by dissolving 3 g of free base in ethanol and treating with fumaric acid solution in ethanol (850 mg:5 ml). The N-[3-[3-[4-(6-fluoro-1,2-benzisoxazol-3-yl)-1-piperidinyl]propoxy]phenyl]acetamide hemifumarate crystals obtained weighed 2.73 g, m.p.=184°–186° C.

Analysis: Calculated for $C_{23}H_{26}FN_3O_2 \cdot 0.5\ C_4H_4O_4$: 63.95%C, 6.01%H, 8.94%N; Found: 63.47%C, 5.94%H, 8.78%N.

EXAMPLE 71

3-[3-[4-(6-Fluoro-1,2-benzisoxazol-3-yl)-1-piperdinyl]propoxy]aniline

A stirred mixture of N-[3-[3-[4-(6-fluoro-1,2-benzisoxazol-3-yl)-1-piperidinyl]propoxyl]phenyl] acetamide (9.2 g, 22 mmol), prepared as described in the previous example, in 15% hydrochloric acid (110 ml) was heated at 100° C. for 2.5 hours until a homogeneous solution resulted. The reaction was cooled to 0° C. in an ice bath and basified with 50% NaOH. The product was extracted with ethyl acetate (3×200 ml). The ethyl acetate solution was washed with water, brine, then dried over $Na_2SO_4$. The solvent was removed. The crude product was purified on a flash chromatography column. The product thus obtained was a solid: 6.6 g (80%). Recrystallization from hot ethanol (50 ml) gave 3-[3-[4-(6-fluoro-1,2-benzisoxazol-3-yl)-1-piperidinyl]propoxy]-aniline as off-white crystals: 3.46 g, m.p.=115°–117° C.

Analysis: Calculated for $C_{21}H_{24}FN_3O_2$: 68.27%C, 6.55%H, 11.37%N; Found: 68.34%C, 6.53%H, 11.31%N.

EXAMPLE 72

3-[3-[4-(6-Fluoro-1,2-benzisoxazol-3-yl)-1-piperidinyl]propoxy]-4-methoxyaniline A mixture of 3-[3-[4-(6-fluoro-1,2-benzisoxazol-3-yl)-1-piperidinyl]propoxy]-4-methoxyphenylacetamide (4.2 g, 9.5 mmol), prepared as in Example 26 above, in 15% hydrochloric acid (60 ml) was heated at reflux (110° C.) for 2 hours. At the end of the reaction, the solution was cooled to 0° C. then basified with 25% NaOH to pH of 10. The product was extracted into ethyl acetate (300 ml). The ethyl acetate solution was washed with water and brine, then dried over $Na_2SO_4$. The solvent was removed at reduced pressure. The crude oil was purified by flash chromatography on a silica gel column. The product thus purified was an oil, 2.6 g. Crystallization from ethanol (5 ml) and petroleum ether (3 ml) yielded 3-[3-[4-(6-fluoro-1,2-benzisoxazol-3-yl)-1-piperidinyl]-propoxy]-4-methoxyaniline as fine crystals: 1.2 g; m.p.=94°–95° C.

Analysis: Calculated for $C_{22}H_{26}FN_3O_3$: 63.95%C, 6.01%H, 8.94%N; Found: 63.47%C, 5.94%H, 8.78%N.

EXAMPLE 73

1-[4-[3-[4-(6-Fluoro-1,2-benzisothiazol-3-yl)-1-piperidinyl]propoxy-3-methylamino-phenyl] ethanone fumarate (A) 1-[(3-N-acetyl-N-methylamino)-4-hydroxyphenyl] ethanone A solution of 2-methoxy(methylamino)benzene (26.0 g, 190 mmol) and 1,2-dichloroethane was cooled to 10°–15° C. and a solution of acetyl chloride (33.8 g, 430 mmol) dissolved in dichloroethane (50 ml) was dripped in slowly. Following this addition, an additional 100 ml dichloroethane was added. The reaction was cooled to 0° C. and aluminum chloride (72.3 g, 540 mmol) was added over the course of 45 minutes so that the temperature did not exceed 10° C. After complete addition, the reaction was heated to reflux and was stirred for 18 hours under nitrogen. The reaction was cooled and was poured into ice. The resulting aqueous phase was extracted further with dichloromethane and the combined extracts were washed with $H_2O$, dried with $MgSO_4$, and concentrated to yield 32.0 g of 1-[(3-N-acetyl-N-methylamino)-4-hydroxyphenyl]ethanone as a brown solid, m.p.=168°–171° C.

(B) 1-(4-hydroxy-3-methylaminophenyl)ethanone

A mixture of 1-[(3-N-acetyl-N-methylamino)-4-hydroxyphenyl]ethanone (15.0 g, 72.4 mmol) and concentrated HCl (150 ml) was stirred at reflux for 3 hours. The heat was terminated and the reaction stood overnight. The reaction mixture was transferred to a 1 L beaker and was chilled in an ice-salt bath. Solid sodium bicarbonate was added cautiously until the pH was about 2, and the aqueous mixture was allowed to stand overnight. The reaction mixture was continued to be made basic by the addition of solid sodium bicarbonate. After pH 8 was achieved, the reaction mixture was extracted with ethyl acetate. The ethyl acetate extract was washed with a 200 ml aliquot of water and this was then fed through a bed of Celite. After washing the cake with fresh ethyl acetate the phases were separated. The ethyl acetate extract was washed several more times with water, dried with $MgSO_4$ and concentrated to yield 10.5 g of a dark solid of 1-(4-hydroxy-3-methylaminophenyl)ethanone.

(C) 1-[4-(3-chloropropoxy)-3-methylaminophenyl] ethanone

To a stirred suspension of sodium hydride (0.87 g, 18.2 mmol of a 50% oil dispersion) in dimethylformamide (25 ml) under nitrogen and cooled to 0° in an ice-salt salt bath was added, dropwise, a solution of 1-(4-hydroxy-3-methylamino-phenyl)ethanone (3.0 g, 18.2 mmol) dissolved in dimethylformamide (55 ml) so that the temperature did not rise above 3° C. After the addition was complete, the reaction was stirred for 80 minutes at ambient temperature. The reaction was cooled to 5° C. and a solution of 1-bromo- 3-chloropropane (3.1 g, 0.0120 mol) in dimethylformamide (20 ml) was added dropwise. After this addition was complete, the ice bath was removed and the reaction was stirred at ambient temperature for 2.5 hours. Water (75 ml) was carefully added and after stirring vigorously for 5 minutes, the reaction was left to stand overnight. The aqueous mixture was extracted with ethyl acetate and the ethyl acetate extract was washed with water, dried with $MgSO_4$, and concentrated to yield 3.9 g of a dark solid. The compound was purified by preparative HPLC to afford 2.4 g of a beige solid. This was combined with an additional sample (3.8 g total) and two consecutive recrystallizations from ethanol gave 2.1 g (31%) of 1-[4-(3-chloropropoxy)-3-methyl-aminophenyl]ethanone as a fluffy, beige solid, m.p.=115°–117° C.

Analysis: Calculated for $C_{12}H_{16}ClNO_2$: 59.63%C, 6.67%H, 5.79%N; Found: 59.49%C, 6.64%H, 5.79%N.

(D) 1-[4-[3-[4-(6-fluoro-1,2-benzisothiazol-3-yl)-1-piperidinyl]propoxy-3-methylaminophenyl]ethanone fumarate A stirred mixture of 6-fluoro-3-(4-piperidinyl)-1,2-benzisothiazole (1.9 g, 79 mmol), 1-[4-(3-chloropropoxy)-3-methylaminophenyl]ethanone (1.9 g, 79 mmol), $K_2CO_3$ (1.1 g), KI (0.1 g), and acetonitrile (95 ml) was refluxed for 16 hours. The reaction was poured into water and the aqueous suspension extracted with ethyl acetate. The extract was washed (water and brine), dried ($MgSO_4$), and then the solvent was concentrated to afford 3.2 g of a thick, brown oil. The oil was chromatographed on a Waters Prep 500 LC on silica gel columns, and concentration of the appropriate fractions afforded 1.5 g of a brown oil. The oil was dissolved in acetone and fumaric acid (0.4 g, 0.003 mol) was added, and 1.9 g of a white fumarate salt was collected. The salt was recrystallized from dimethylformamide to yield 1.1 g (25%) of 1-[4-[3-[4-(6-fluoro-1,2-benzisothiazol-3-yl)-1-piperidinyl]propoxy-3-methyaminophenyl]ethanone fumarate as a white solid, m.p.=198°–200° C.

Analysis: Calculated for $C_{28}H_{32}FN_3O_6S$: 60.31%C, 5.78%H, 7.54%N; Found: 60.02%C, 5.88%H, 7.68%N.

EXAMPLE 74

N-[3-[3-[4-(6-Fluoro-1,2-benzisothiazol-3-yl)-1-piperidinyl]propoxy]-4-methoxy-phenyl]acetamide (A) N-[3-(3-chloropropoxy)-4-methoxyphenyl]acetamide To a stirred suspension, under nitrogen, of sodium hydride (1.8 g, 38 mmol) in dimethylformamide (60 ml) was added dropwise, N-(3-hydroxy-4-methoxy)acetamide (6.1 g, 34 mmol) dissolved in dimethylformamide (23 ml). After complete addition, the reaction was stirred at ambient temperature for 0.5 hour, and then 3-chloro-1-bromopropane (5.2 g, 33 mmol) in dimethylformamide (10 ml) was added, dropwise. The reaction was stirred at ambient temperature for 16 hours, and then it was poured into water, and the aqueous mixture was extracted with ethyl acetate. The extract was washed (water), dried ($MgSO_4$) and the solvent concentrated to afford a purple solid. The solid was triturated with diethyl ether and collected to afford 2:8 g of a purple solid. This sample was combined with a sample (1.2 g) from another run and was recrystallized from toluene twice to yield 2.9 g of an off-white solid. The solid was flash chromatographed on 200 g of silica gel, eluting the column with ethyl acetate, and subsequent concentration of the appropriate fractions afforded 2.4 g of a white solid. Recrystallization of the compound from toluene yielded 2.2 g (17%) of N-[3-(3-chloropropoxy-4-methoxyphenyl]acetamide, m.p.=112°–114° C.

Analysis: Calculated for $C_{12}H_{16}ClNO_3$: 55.93%C, 6.26%H, 5.44%N; Found: 56.25%C, 6.29%H, 5.44%N.

(B) N-[3-[3-[4-(6-fluoro-1,2-benzisothiazol-3-yl)-1-piperidinyl]propoxy]-4-methoxyphenyl ]acetamide A stirred mixture of 6-fluoro-3-(4-piperidinyl)-1,2-benzisothiazole (4.0 g, 17 mmol), N-[3-(3-chloropropoxy)-4-methoxyphenyl]acetamide (4.3 g, 17 mmol), $K_2CO_3$ (2.3 g), KI (0.2 g) and acetonitrile (200 ml) was refluxed for 10 hours. The cooled reaction mixture was filtered and the filtrate was concentrated to yield a dark oil. The oil was dissolved in acetone, and ethereal HCl was added to yield 5.7 g of a yellow hydrochloride salt. The salt was reversed to the free base and the resultant oil (5.2 g) was chromatographed on a Waters Associates Prep LC utilizing silica gel columns. Concentration of the appropriate fractions yielded 4.7 g of an oil, which was converted to a hydrochloride salt. The salt was converted to its free base yielding 2.8 g of a brown oil. The oil was stirred vigorously with ether to yield 1.4 g (18%) of N-[3-[3-[4-(6-fluoro-1,2-benzisothiazol-3-yl)-1-piperidinyl]propoxy]-4-methoxyphenyl]-acetamide as a white solid, 1.4 g, m.p.=109°–111° C.

Analysis: Calculated for $C_{24}H_{28}FN_3O_3S$: 63.00%C, 6.17%H, 9.18%N; Found: 62.80%C, 6.17%H, 8.86%N.

EXAMPLE 75

1-[4-[3-[4-(6-Fluoro-1,2-benzisothiazol-3-yl)-1-piperidinyl]propoxy]3-methoxy-phenyl]ethanone hydrochloride A stirred mixture of 6-fluoro-3-(4-piperidinyl)-1,2-benzisothiazole (4.0 g, 17 mmol), 1-[4-(3-chloropropoxy)-3-methoxyphenyl]ethanone (4.1 g, 17 mmol), $K_2CO_3$ (2.3 g), KI (0.2 g), and acetonitrile (100 ml) was refluxed for 9 hours. The reaction was poured into water, and the aqueous mixture was extracted with ethyl acetate. The extract was washed (water), dried ($MgSO_4$), and the solvent was concentrated to afford 8.0 g of a brown oil. The oil was chromatographed on a Waters Prep 500 HPLC on silica gel columns. Concentration of the appropriate fractions afforded a gum-like residue, which upon trituration with isopropyl ether afforded 1.9 g of a white solid. The solid was dissolved in absolute ethanol, and ethereal HCl was added to precipitate 1.7 g of a hydrochloride salt. Concentration of the isopropyl ether filtrate, and similar treatment of the residue, afforded an additional 0.5 g of the salt. The samples were combined and recrystallized from absolute ethanol to yield 1.7 g (21%) of 1-[4-[3-[4-(6-fluoro-1,2-benzisothiazol-3-yl)-1-piperidinyl]propoxy]-3-methoxyphenyl]ethanone hydrochloride as a white solid, m.p.=221°–223° C.

Analysis: Calculated for $C_{24}H_{27}FN_2O_3 \cdot HCl$: 60.18%C, 5.89%H, 5.85%N; Found: 60.01%C, 5.97%H, 5.79%N.

EXAMPLE 76

N,N-Dimethyl-4-[3-[4-(6-fluoro-1,2-benzisoxazol-3-yl)-1-piperidinyl]-propoxy]-3-methoxybenzamide (A) N,N-dimethyl-4-bromopropoxy-3-methoxybenzamide To N,N-dimethyl-4-hydroxy-3-methoxybenzamide (5.64 g, 28.7 mmol) in acetonitrile (450 ml) was added potassium carbonate (7.9 g) followed by 1,3-dibromopropane (11.6 g). The resulting reaction mixture was refluxed for 3 hours and stirred at room temperature for 12 hours. The mixture was filtered and concentrated to an oil. Following purification by column chromatography, N,N-dimethyl-4-bromopropoxy-3-methoxybenzamide as a colorless oil (7.6 g) was obtained.

(B) N,N-dimethyl-4-[3-[4-(6-fluoro-1,2-benzisoxazol-3-yl)-1-piperidinyl]propoxy]-3-methoxybenzamide A stirred mixture of 6-fluoro-3-(4-piperidinyl)-1,2-benzisoxazole (3.9 g, 17.7 mmol), N,N-dimethyl-4-bromopropoxy-3-methoxybenzamide (5.54 g, 17.5 mmol) and $K_2CO_3$ (3 g) in acetonitrile (250 ml) was heated at reflux for one hour. At the end of the reaction, the insolubles were filtered and washed with dichloromethane. The solvent was removed on a rotary evaporator. The residue was purified by flash chromatography over a silica gel column. The product thus obtained as an oil weighed 7 g. Crystallization from hot ethanol (45 ml) afforded analytically pure N,N-dimethyl-4-[3-[4-(6-fluoro-1,2-benzisoxazol-3-yl)-1-piperidinyl]propoxyl]-3-methoxybenzamide, 3.95 g, 50%, as light yellow crystals, m.p.=126°–127° C.

Analysis: Calculated for $C_{25}H_{30}FN_3O_4$: 65.92%C, 6.64%H, 9.92%N; Found: 65.76%C, 6.64%H, 9.14%N.

EXAMPLE 77

1-[4-[3-[4-(6-Fluoro-1,2-benzisoxazol-3-yl)-1-piperidinyl]propoxy]-3-methoxy-phenyl]ethanone oxime A mixture of 1-[4-[3-[4-(6-fluoro-1,2-benzisoxazol-3-yl)-1-piperidinyl]propoxy]-3-methoxyphenyl]ethanone (4.3 g, 10 mmol), prepared as in Example 3 above, hydroxylamine hydrochloride (1.3 g, 18 mmol), ammonium acetate (1.7 g, 22 mmol) and ethanol-$H_2O$ was stirred and refluxed for 16 hours. The reaction was poured into water, and the mixture was cooled in an ice bath for 2 hours. The resultant, white solid was collected, washed with water and dried to yield 4.6 g of hydrochloride salt of the oxime, m.p.=216°–218° C. The compound was dispersed in water and ammonium hydroxide was added until the suspension was decidedly basic. The basic suspension was then extracted with dichloromethane, and after washing with water, drying ($MgSO_4$), and concentrating the extract, 3.0 g of white solid melting at 168°–170° C. were harvested. The compound was recrystallized from dimethylformamide to yield 2.3 g (52%) of 1-[4-[3-[4-(6-fluoro-1,2-benzisoxazol-3-yl)-1-piperidinyl]propoxy]-3-methoxyphenyl]ethanone oxime as a white solid, m.p.=168°–170° C.

Analysis: Calculated for $C_{24}H_{28}FN_3O_4$: 65.29%C, 6.39%H, 9.52%N; Found: 65.27%C, 6.44%H, 9.46%N.

EXAMPLE 78

1-[4-3-[4-(6-Fluoro-1,2-benzisoxazol-3-yl)-1-piperidinyl]propoxy]methoxyphenyl]ethanone oxime O-methyl ether A solution of 1-[4-[3-[4-(6-fluoro-1,2-benzisoxazol-3-yl)-1-piperidinyl]propoxy]methoxyphenyl]ethanone (4.3 g, 10 mmol), prepared as in Example 3 above, methoxylamine hydrochloride (0.93 g, 10 mmol) in pyridine (75 ml)/ethanol (75 ml) was refluxed for 16 hours. Most of the solvent was evaporated under reduced pressure, and the residue was diluted with water to precipitate 1.6 g of a white solid, m.p. 200°–201° C. The aqueous filtrate upon standing deposited another crop of white crystals, which yielded 1.2 g of a pale, yellow solid with a m.p. of 70°–72° C. The initial crop of crystals was converted to its free base with aqueous NaOH. After extractive workup with ethyl acetate, 1.2 g of the free base was obtained. The two samples were combined and recrystallized from isopropyl ether to afford 2.0 g (44%) of 1-[4-[3-[4-(6-fluoro-1,2-benzisoxazol-3-yl)-1-piperidinyl]propoxy]methoxyphenyl]ethanone oxime O-methyl ether as colorless crystals, m.p.=97°–99° C.

Analysis: Calculated for $C_{25}H_{30}FN_3O_4$: 65.92%C, 6.64%H, 9.22%N; Found: 65.89%C, 6.86%H, 9.15%N.

EXAMPLE 79

1-[4-[3-[4-(6-Fluoro-1,2-benzisoxazol-3-yl)-1-piperidinyl]-propoxyl]3-methoxy-phenyl]ethanone hydrazone A stirred mixture of 1-[4-[3-[4-(6-fluoro-1,2-benzisoxazol-3-yl)-1-piperidinyl]propoxy]-3-methoxyphenyl]ethanone (4.3 g, 10 mmol), prepared as in Example 3 above, hydrazine (0.8 g, 2.5 mmol), and ethanol (40 ml) was refluxed for 16 hours. The cooled solution was concentrated to yield an oily residue. The residue was triturated with water and the resultant solid was collected to afford 4.2 g of 1-[4-[3-[4-(6-fluoro-1,2-benzisoxazol-3-yl)-1-piperidinyl]propoxy]-3-methoxyphenyl]ethanone hydrazone as a yellow solid. The compound was recrystallized from isopropanol and then from toluene to afford 1.7 g (39%), m.p.=106°–108° C.

Analysis: Calculated for $C_{24}H_{29}FN_4O_3$: 65.44%C, 6.64%H, 12.72%N; Found: 65.38%C, 6.55%H, 12.55%N.

EXAMPLE 80

6-Fluoro-3-[1-[3-[2-methoxy-4-(1-methylethenyl)phenoxy]propyl]-4-piperidinyl]-1,2-benzisoxazole hydrochloride A solution of butyllithium (4.7 ml of a 2.3M solution in hexanes, 10.7 mmol) in tetrahydrofuran (65 ml) was stirred under nitrogen and cooled to –70° C. in an isopropyl alcohol-dry ice bath. Methyltriphenylphosphonium bromide (3.8 g, 10.6 mmol) was added portionwise over the course of 10 minutes. After complete addition, the reaction was stirred at –65° C. for one hour and was then allowed to gradually warm up to ambient temperature, where it was stirred for an additional 3.5 hours. The reaction was cooled to 0° C., and a solution of 1-[4-[3-[4-(6-fluoro-1,2-benzisoxazol-3-yl)-1-piperidinyl]propoxy]-3-methoxyphenyl]ethanone prepared as in Example 3 above (4.7 g, 0.0110 mol) dissolved in tetrahydrofuran (50 ml) was added, dropwise, over the course of 30 minutes. After the addition was complete, the reaction was stirred at ambient temperature for 19 hours. The reaction was poured into water and the aqueous mixture was extracted with diethyl ether. The diethyl ether extract was washed several times with water, dried with $MgSO_4$ and concentrated to yield 7.0 g of a light orange solid. Recrystallization from toluene-hexane provided 1.4 g of triphenylphosphine oxide and concentration of the filtrate afforded 5.5 g of a glassy, beige solid. This was combined with an additional sample (6.5 g total) and purification by preparative HPLC (Water's Associates prep LC/System 500) gave 5.2 g of a beige solid, which remained contaminated by triphenylphosphine oxide. The compound was taken up in anhydrous ethanol (300 ml) and methanol (5 drops) and ethereal HCl was added to precipitate 4.0 g of a pale, white solid, m.p.=192°–194° C.

Analysis: Calculated for $C_{25}H_{30}ClFN_2O_3$: 65.14%C, 6.65%H, 6.08%N; Found: 64.95%C, 6.62%H, 6.04%N.

EXAMPLE 81

(E)-1-[4-[[4-[4-(6-Fluoro-1,2-benzisoxazol-3-yl)-1-piperidinyl]-2-butenyl]oxy]-3-methoxyphenyl]ethanone A mixture of 6-fluoro-3-(4-piperidinyl)-1,2-benzisoxazole (2.2 g, 10 mmol), $K_2CO_3$ (2 g), (E)-4-[(4- bromo-2-butenyl)oxy]-3-methoxyacetophenone (4.0 g, 1.3 eq) in acetonitrile (100 ml) was heated at reflux for 2 hours. At the end of the reaction, the solvent was removed on the rotary evaporator. The residue was extracted into dichloromethane (300 ml). The insolubles were filtered off. The dichloromethane was concentrated. The crude product was purified on a flash chromatography column. The product eluted as an oil, weight 2.87 g (64%). Recrystallization from ethanol:hexane (20 ml:5 ml) gave (E)-1-[4-[[4-[4-(6-fluoro-1,2-benzisoxazol-3-yl)-1-piperidinyl]-2-butenyl]oxy]-3-methoxy-phenyl]ethanone as off-white crystals: 2.46 g; m.p.=91°–93° C.

Analysis: Calculated for $C_{25}H_{27}FN_2O_4$: 68.48%C, 6.21%H, 6.39%N; Found: 68.28%C, 6.12%H, 6.27%N.

EXAMPLE 82

(Z)-1-[4-[(4-Chloro-2-butenyl)oxy]-3-methoxyphenyl]ethanone

A stirred mixture of 4-hydroxy-3-methoxyacetophenone (16.6 g, 10 mmole), $K_2CO_3$ (14 g, 100 mmol) and cis-1,4-dichloro-2-butene (Aldrich, 15 g, 120 mmol) in acetonitrile (250 ml) was heated at reflux for 2.5 hours. The mixture was filtered and concentrated to an oil. Purification was by flash chromatography. The fractions containing the purest product were combined and concentrated to give white crystals, 7.7 g, 30%. This was recrystallized from ether to give analytical pure (Z)-1-[4-[(4-chloro-2-butenyl)oxy]-3-methoxyphenyl] ethanone (2.72 g), m.p.=64°–66° C.

Analysis: Calculated for $C_{13}H_{15}ClO_3$: 61.30%C, 5.94%H; Found: 61.28%C, 5.94%H.

EXAMPLE 83

(Z)-1-[4-[[4-[4-(6-Fluoro-1,2-benzisoxazol-3-yl)-1-piperidinyl]-2-butenyl]oxy]-3-methoxyphenyl] ethanone A stirred mixture of 6-fluoro-3-(4-piperidinyl)-1,2-benzisoxazole (2.2 g, 10 mmol), $K_2CO_3$ (1.8 g, 13 mmol) and (Z)-1-[4-[(4-chloro-2-butenyl)oxy]-3-methoxyphenyl] ethanone (3.43 g, 9.7 mmol) in acetonitrile (100 ml) was heated at reflux for 1½ hours. At the end of the reaction, the solvent was removed and the inorganics were filtered after addition of dichloromethane (250 ml). The dichloromethane solvent was removed again. The crude oil was purified on two flash chromatography columns to give a colorless oil (2.78 g). The oil was solidified by vigorously drying on a vacuum pump. Recrystallization from ethanol (10 ml) and hexane (2 ml) gave analytically pure (Z)-1-[4-[[4-[4-(6-fluoro-1,2-benzisoxazol-3-yl)-1-piperidinyl]- 2-butenyl] oxy]-3-methoxy-phenyl]ethanone, 1.83 g,m.p.=57°–59° C.

Analysis: Calculated for $C_{25}H_{27}FN_2O_3$: 68.48%C, 6.21%H, 6.39%N; Found: 68.26%C, 6.18%H, 6.32%N.

EXAMPLE 84

(E)-1-[3-[[4-[4-(6-Fluoro-1,2-benzisoxazol-3-yl)-1-piperidinyl]-2butenyl]oxy]-4-hydroxyphenyl] ethanone hydrochloride The mixture of (E)-1-[3-[[4-[4-(6-fluoro-1,2-benzisoxazol-3-yl)-1-piperidinyl]-2-butenyl]oxy]-4-benzyloxyphenyl]ethanone (5.5 g, 10.7 mmol), acetic acid (50 ml), and hydrochloric acid (6 ml) was heated at 75° C. for 2 hours. At the end of reaction, the solvent was reduced to about 20 ml on a rotary evaporator. The solution was poured into ice water (350 ml) and extracted with dichloromethane (3×250 ml). The dichloromethane solution was washed with brine and dried over $Na_2SO_4$. A solid formed on concentration of the solvent. This was collected by filtration (3.4 g). Recrystallization from hot methanol (40 ml) gave 1.82 g of (E)-1-[3-[[4-[4-(6-fluoro-1,2-benzisoxazol-3-yl)-1-piperidinyl]-2-butenyl]oxy]-4-hydroxyphenyl]ethanone hydrochloride as white crystals, 37.5%, m.p.=208°–210° C.

Analysis: Calculated for $C_{24}H_{25}FN_2O_4 \cdot HCl$: 62.54%C, 5.69%H, 6.08%N; Found: 62.40%C, 5.60%H, 6.04%N.

EXAMPLE 85

(E)-1-[3-[[4-[4-(6-Fluoro-1,2-benzisoxazol-3-yl)-1-piperidinyl]-2-butenyl]oxy]-4-benzyloxyphenyl] ethanone (A) (E)-3-[(4'-bromo-2'-butenyl)oxy]-4-benzyloxyacetophenone To 4-benzyloxy-3-hydroxyacetophenone (17.6 g) in acetonitrile (200 ml) was added potassium carbonate (10 g), followed by the addition of (E)-1,4-dibromobutene (19 g). The resulting mixture was heated at reflux for 3 hours. The mixture was concentrated, extracted into dichloromethane, and the potassium salt was removed by filtration. Solvent was removed, and the resulting material was purified by flash chromatography to yield 20.5 g of (E)-3-[(4'-bromo-2'-butenyl)oxy]-4-benzyloxyacetophenone as white crystals.

(B) (E)-1-[3-[[4-[4-(6-fluoro-1,2-benzisoxazol-3-yl)-1-piperidinyl]-2-butenyl]oxy]-4-benzyloxyphenyl]ethanone A mixture of 6-fluoro-3-(4-piperidinyl)-1,2-benzisoxazole (5.62 g, 25.5 mmol), $K_2CO_3$ (4 g, 29 mmol), and (E)-3-[(4'-bromo-2'-butenyl)oxy]-4-benzyloxyacetophenone (10 g, 26.6 mmol) in acetonitrile (125 ml) was heated at reflux for 3.5 hours. The mixture was cooled and concentrated to a crude solid. The residue was extracted into dichloromethane (300 ml) and insolubles were filtered. The crude material from the dichloromethane solution was purified on a flash chromatography column. The product thus purified weighed 8 g as a pale white solid. Recrystallization from hot ethanol gave 7.11 g of (E)-1-[3-[[4-[4-(6-fluoro-1,2-benzisoxazol-3-yl)-1-piperidinyl]-2-butenyl]oxy]-4-benzyloxyphenyl]ethanone as off-white crystals, m.p.= 124°–125° C.

Analysis: Calculated for $C_{31}H_{31}FN_2O_4$: 72.36%C, 6.07%H, 5.44%N; Found: 72.23%C, 6.04%H, 5.04%N.

EXAMPLE 86

6-Fluoro-3-[1-[3-[(5-methoxy-1H-indol-6-yl)oxy] propyl]-4-piperidinyl]-1,2-benzisoxazole (A) 6-(3-Chloropropoxy)-5-methoxyindole To a stirred suspension of sodium hydride (0.94 g, 19.6 mmol of a 50% oil dispersion) in dimethylformamide (20 ml) under nitrogen and cooled to –5° C. was added, dropwise, 5-methoxy-6-hydroxyindole (3.2 g, 19.6 mmol) dissolved in dimethylformamide (60 ml) so that the temperature did not exceed –2° C. After complete addition, the reaction was stirred for 45 minutes at 0° C. While maintaining the reaction temperature between –5° C. and 0° C., a solution of 1-bromo-3-chloropropane (3.1 g, 19.6 mmol) dissolved in dimethylformamide (15 ml) was slowly added. The mixture was stirred at ambient temperature under nitrogen for 21 hours. The reaction was cooled in an ice bath, and water was added to destroy the excess sodium hydride, and the aqueous mixture was extracted with ethyl acetate. The ethyl acetate extract was washed with water, dried with $MgSO_4$ and concentrated to yield 5.3 g of a dark, oily liquid. This was combined with an additional sample, for a total of 10.0 g, and purification by preparative HPLC (Waters Associates prep LC/System 500) provided 5.1 g of a brown solid. A 2.5 g sample was recrystallized from isopropyl alcohol to yield 11 g (30%) of 6-(3-chloropropoxy)-5-methoxyindole as beige crystals, m.p.=73°–75° C.

Analysis: Calculated for $C_{12}H_{14}ClNO_2$: 60.13%C, 5.89%H, 5.84%N; Found: 60.26%C, 5.86%H, 5.77%N.

(B) 6-Fluoro-3-[1-[3-[(5-methoxy-1H-indol-6-yl)oxy]propyl]-4-piperidinyl]-1,2-benzisoxazole A mixture of 6-fluoro-3-(4-piperidinyl)-1,2-benzisoxazole (2.5 g, 11.5 mmol), 6-(3-chloropropoxy)-5-methoxyindole (2.5 g, 10.4 mmol), $K_2CO_3$ (1.6 g, 11.5 mmol), KI (200 mg) and acetonitrile (100 ml) was stirred at reflux under nitrogen for 40 hours. The cooled reaction was poured into water and extracted with ethyl acetate. The ethyl acetate extract was washed with water, washed with brine, dried with $MgSO_4$ and concentrated to yield 4.0 g of a solid. The compound was recrystallized from ethanol to afford 3.3 g. Another recrystallization from ethanol (utilizing a charcoal treatment) provided 2.9 g (66%) of 6-fluoro-3-[1-[3-[(5-methoxy-1H-indol-6-yl)oxy]-propyl]-4-piperidinyl]-1,2-benzisoxazole as a beige solid, m.p.=156°–158° C.

Analysis: Calculated for $C_{24}H_{26}FN_3O_3$: 68.07%C, 6.19%H, 9.92%N; Found: 67.89%C, 6.07%H, 9.91%N.

EXAMPLE 87

6-Fluoro-3-[1-[3-[(1H-indol-7-yl)oxy]propyl]-4-piperidinyl]-1,2-benzisoxazole hemifumarate (A) 7-(3-Chloropropoxy)indole To a stirred suspension of sodium hydride (0.8 g, 17 mmol of a 50% oil dispersion) in dimethylformamide (20 ml), under nitrogen, was added dropwise 7-hydroxyindole (2.1 g, 15.7 mmol) in dimethylformamide (20 ml). After complete addition, the reaction was stirred at ambient temperature for 0.5 hour and then cooled to 15° C. To this cooled solution was added, dropwise, 1-bromo-3-chloropropane (2.5 g, 15.7 mmol) in dimethylformamide (5 ml). The reaction was then stirred at ambient temperature for 16 hours. The reaction was poured into water, and the aqueous suspension extracted with ethyl acetate. The ethyl acetate was washed with water, dried ($MgSO_4$), and the solvent was concentrated to afford a dark brown oil. Following flash chromatography on silica gel, 7-(3-chloropropoxy)indole was obtained as a colorless oil, 1.0 g.

Analysis: Calculated for $C_{11}H_{12}ClNO$: 63.01%C, 5.77%H, 6.68%N; Found: 63.25%C, 5.61%H, 6.65%N.

(B) 6-Fluoro-3-[1-[3-[(1H-indol-7-yl)oxy]propyl]-4-piperidinyl]-1,2-benzisoxazole hemifumarate A stirred mixture of 7-(3-chloropropoxy)-1H-indole (3.5 g, 17 mmol), 6-fluoro-3-(4-piperidinyl)-1,2-benzisoxazole (3.5 g, 17 mmol), $K_2CO_3$ (2.3 g) and acetonitrile (60 ml) was refluxed for 11 hours. The reaction was poured into water, and the aqueous mixture was extracted with ethyl acetate. The ethyl acetate was washed with water, dried ($MgSO_4$), and the solvent was concentrated to afford a dark oil. The oil was flash chromatographed on silica gel. Upon concentration of the appropriate fractions, 3.0 g of a white, foamy substance was obtained. The substance was dissolved in ethyl acetate (75 ml) and fumaric acid (0.97 g, 83 mmol) was added. The mixture was briefly heated to reflux, and then stirred at ambient temperature for 1.5 hours. The resultant insoluble white fumarate salt was collected and afforded 4.2 g of product. Recrystallization of the salt from dimethylformamide yielded 3.1 g (36%) of 6-fluoro-3-[1-[3-[(1H-indol-7-yl)oxy]propyl]-4-piperidinyl]-1,2-benzisoxazole hemifumarate as a white solid, m.p.=213°–215° C.

Analysis: Calculated for $C_{25}H_{26}FN_3O_4$: 66.50%C, 5.80%H, 9.31%N; Found: 66.23%C, 6.14%H, 9.39%N.

EXAMPLE 88

6-Fluoro-3-[1-(3-hydroxypropyl)-4-piperidinyl]-1,2-benzisoxazole

A stirred mixture of 6-fluoro-3-(4-piperidinyl)-1,2-benzisoxazole (10.0 g, 45 mmol), $K_2CO_3$ (10.0 g), 3-bromo-1-propanol (7.3 g, 46 mmol) and acetonitrile (200 ml) was refluxed for 3 hours. The reaction was poured into $H_2O$ and 7.1 g of a beige solid was collected. The filtrate was extracted with dichloromethane, and after concentration an additional 6.7 g of crude solid was harvested. The solids were combined and triturated with refluxing ethyl acetate to afford 8.0 g of 6-fluoro-3-[1-(3-hydroxypropyl)-4-piperidinyl]-1,2-benzisoxazole as an off-white solid. A sample (4.0 g) was recrystallized from ethanol-water (with charcoal treatment) to yield 2.4 g (40%) of the alcohol as a white solid, m.p.=140°–142° C.

Analysis: Calculated for $C_{15}H_{19}FN_2O_2$: 64.73%C, 6.88%H, 10.06%N; Found: 64.79%C, 6.97%H, 10.03%N.

EXAMPLE 89

6-Fluoro-3-[1-(2-pyrimidinoxy)propyl]-4-piperidinyl]-1,2-benzisoxazole fumarate

To a stirred suspension of 6-fluoro-3-[1-(3-hydroxypropyl)-4-piperidinyl]-1,2-benzisoxazole (3.6 g, 13 mmol) in tetrahydrofuran (50 ml) was added dropwise, potassium bistrimethylsilylamide (2.6 g, 13 mmol) dissolved in tetrahydrofuran (20 ml). After complete addition, the reaction was stirred at ambient temperature for 5 min, and then 2-chloropyrimidine (1.6 g, 14 mmol) was added. The reaction was stirred at ambient temperature for 4 hours, and TLC at this time indicated an incomplete reaction. An additional quantity of the base (0.5 g) was added, and the reaction was allowed to proceed at ambient temperature for 14 additional hours. The reaction was poured into water and the aqueous mixture was extracted with dichloromethane. The extract was washed ($H_2O$), dried ($K_2CO_3$), and the solvent was concentrated to afford a wet solid. The solid was triturated with diethyl ether and the product that separated was collected to yield 1.0 g of the starting alcohol. The filtrate was then concentrated to afford 3.8 g of a waxy, yellow solid. This material was combined with 2.6 g from another run and the combined sample flash chromatographed on silica gel, eluting first with ethyl acetate and then with 8% diethylamine-ethyl acetate. Concentration of the appropriate fractions afforded 3.0 g of the desired compound as a yellow solid. The solid was converted to a fumarate salt with fumaric acid in acetone, and then reversed to its free base. It was combined with another sample and the combined sample (3.8 g) chromatographed on silica gel on HPLC (4.5% methanol-dichloromethane as eluent). Concentration of the appropriate fractions yielded 1.6 g of a yellow solid. A fumarate salt was prepared to yield 2.1 g (16%) of 6-fluoro-3-[1-[(2-pyrimidinoxy)-propyl]-4-piperidinyl]-1,2-benzisoxazole fumarate, m.p.=184°–186° C.

Analysis: Calculated for $C_{23}H_{25}FN_4O_6$: 58.47%C, 5.33%H, 11.86%N; Found: 58.52%C, 5.34%H, 11.80%N.

EXAMPLE 90

6-Aceto-2-[4-(6-fluoro-1,2-benzisoxazol-3-yl)-1-piperidinyl]methyl]-1,4-benzodioxan (A) 6-aceto-2-mesyloxymethyl-1,4-benzodioxan 6-Aceto-2-hydroxymethyl-1,4-benzodioxan (3.39 g, 16.3 mmol) was dissolved in trichloromethane (100 ml). Triethylamine (2.5 g) was added to mesylchloride (2.5 g, 1.35 eq) at 0° C. The mixture was stirred for 2 hours at room temperature. The mixture was then diluted, washed with an ice/dilute hydrochloric acid mixture (150 ml), washed with sodium bicarbonate and brine, dried over magnesium sulfate, and concentrated to yield 5.6 g. Following chromatography on a $SiO_2$ column, 3.64 g (78% yield) of 6-aceto-2-mesyloxy-methyl-1,4-benzodioxan were obtained.

(B) 6-aceto-2-[4-(6-fluoro-1,2-benzisoxazol-3-yl)-1-piperidinyl]methyl-1,4-benzodioxan A stirred mixture of 6-fluoro-3-(4-piperidinyl)-1,2-benzisoxazole (3.0 g, 13.6 mmol), $K_2CO_3$ (2 g, 14.5 mmol) and 6-aceto-2-mesyloxymethyl-1,4-benzodioxan (3.5 g, 12 mmol) in acetonitrile (100 ml) was heated at reflux for 3 hours. At the end of the reaction the solvent was removed on a rotary evaporator. The residue was extracted into dichloromethane (350 ml) and the insolubles were filtered off. The dichloromethane solution was concentrated and the crude oil was purified by flash chromatography. The product thus obtained weighed 3.38 g (59%). Recrystallization from ethanol gave 6-aceto-2-[4-(6-fluoro-1,2-benzisoxazol-3-yl)-1-piperidinyl]methyl-1,4-benzodioxan as light yellow crystals (3.2 g), m.p.=122°–123° C.

Analysis: Calculated for $C_{23}H_{23}FN_2O_4$: 67.31%C, 5.65%H, 6.83%N; Found: 67.24%C, 5.50%H, 6.75%N.

EXAMPLE 91

2-[4-(6-Fluoro-1,2-benzisoxazol-3-yl)-1-piperidinyl]methyl-1,4-benzodioxan

A stirred mixture of 6-fluoro-3-(4-piperidinyl)-1,2-benzisoxazole (3.0 g, 13.6 mmol), $K_2CO_3$ (2.45 g, 17.7 mmol), 2-methanesulfonyloxymethyl-1,4-benzodioxan (3.35 g, 13.7 mmole) in acetonitrile (100 ml) was heated at reflux for 12 hours. At the end of the reaction, the insolubles were filtered and rinsed with dichloromethane. The organic solution was concentrated. The crude oil was purified by flash chromatography on a silica gel column. The fractions containing the pure product were pooled and concentrated to a light yellow oil (3.94 g, 74%). Crystallization from ethanol and petroleum ether gave 2-[4-(6-fluoro-1,2-benzisoxazol-3-yl)-1-piperidinyl]methyl-1,4-benzodioxan as off-white crystals, 2.22 g, m.p.=86°–87° C.

Analysis: Calculated for $C_{21}H_{21}FN_2O_3$: 68.47%C, 5.75%H, 7.60%N; Found: 68.33%C, 5.75%H, 7.51%N.

EXAMPLE 92

2-[4-(6-Fluoro-1,2-benzisoxazol-3-yl)-1-piperidinyl]ethyl]-1,4-benzodioxan (A) 2-mesyloxyethyl-1,4-benzodioxan To the compound 2-hydroxyethyl-1,4-benzodioxan (11.96 g) in dichloromethane (450 ml) was added triethylamine (0.12 mol, 10 ml). Mesylchloride (9.2 g) was then added dropwise and the reaction mixture was stirred for one hour at room temperature. After completion of the reaction, the solution was washed with water, brine, and concentrated to an oil, which was purified by chromatography on silica gel to yield 2-mesyloxyethyl-1,4-benzodioxan, 17.08 g.

(B) 2-[4-(6-fluoro-1,2-benzisoxazol-3-yl)-1-piperidinyl]ethyl]-1,4-benzodioxan

A mixture of 6-fluoro-3-(4-piperidinyl)-1,2-benzisoxazole (4.7 g, 21 mmol), $K_2CO_3$ (3.5 g, 25.4 mmol) and 2-mesyloxyethyl-1,4-benzodioxan (5.5 g, 21.3 mmol) in acetonitrile (250 ml) was heated at reflux for 3.5 hours. At the end of the reaction, insolubles were filtered. The solid was washed with dichloromethane (200 ml). The solutions were combined and evaporated to an oil. This crude oil was purified by flash chromatography on a silica gel column. The material thus obtained was crystallized from ethanol. The 2-[4-(6-fluoro-1,2-benzisoxazol-3-yl)-1-piperidinyl]ethyl]-1,4-benzodioxan crystals were collected and weighed 3.8 g, 48%, m.p.=112°–113° C.

Analysis: Calculated for $C_{22}H_{23}FN_2O_3$: 69.09%C, 6.06%H, 7.32%N; Found: 69.17%C, 6.02%H, 7.31%N.

EXAMPLE 93

6-[3-[4-(6-Fluoro-1,2-benzisoxazol-3-yl)-1-piperidinyl]propoxy]-7-methoxy-1-tetralone (A) 6-(3-chloropropoxy)-7-methoxy-1-tetralone A mixture of 6-hydroxy-7-methoxy-1-tetralone (J. Org. Chem., 1985, 50, 4937) (1.5 g, 7.8 mmol), $K_2CO_3$ (1.7 g, 12.3 mmol), and acetone (30 ml) was stirred at reflux under nitrogen for 45 minutes. The reaction was cooled to ambient temperature and a solution of 1-bromo-3-chloropropane (1.9 g, 12.1 mmol) dissolved in 8 ml acetone was dripped into the mixture. After total addition, the reaction was heated to reflux and stirred under nitrogen for 21 hours. The reaction was cooled to ambient temperature and filtered. The filter cake was washed well with acetone and the filtrate was concentrated to yield 2.0 g 6-(3-chloropropoxy)-7-methoxy-1-tetralone as an amber oil.

(B) 6-[3-[4-(6-fluoro-1,2-benzisoxazol-3-yl)-1-piperidinyl]propoxy]-7-methoxy-1-tetralone A mixture of 6-fluoro-3-(4-piperidinyl)-1,2-benzisoxazole (0.78 g, 3.6 mmol), $K_2CO_3$ (0.60 g, 4.1 mmol), KI (100 mg), 6-(3-chloropropoxy)-7-methoxy-1-tetralone (0.87 g, 3.2 mmol), and acetonitrile (50 ml) was stirred at reflux under nitrogen for 17 hours. The cooled reaction was poured into 100 ml of water and the aqueous mixture was extracted with ethyl acetate. The ethyl acetate extract was washed with brine, dried with $MgSO_4$ and concentrated to yield 1.7 g of a brown oil. The oil was purified by preparative HPLC (Waters Associates Prep LC/system 500) to afford 1.0 g of a light brown solid. This was combined with an additional sample (2.3 g total) and recrystallization from ethanol yielded 1.7 g. A subsequent recrystallization from ethanol gave 1.25 g (36%) of 6-[3-[4-(6-fluoro-1,2-benzisoxazol-3-yl)-1-piperidinyl]propoxy]-7-methoxy-1-tetralone as a beige powder, m.p.=129°–131° C.

Analysis: Calculated for $C_{26}H_{29}FN_2O_4$: 69.01%C, 6.46%H, 6.19%N; Found: 68.77%C, 6.43%H, 6.16%N.

EXAMPLE 94

N-[3-[4-(6-Fluoro-1,2-benzisoxazol-3-yl)-1-piperidinyl]propyl]-6-acetyl-2-benzoxazolinone (A) N-(3-chloropropyl)-2-benzoxazolinone To a stirred suspension of sodium hydride (7.8 g, 160 mmol, ether-washed) in dimethylformamide (75 ml) was added dropwise under nitrogen, 2-benzoxazolinone (20.0 g, 150 mmol) dissolved in dimethylformamide (150 ml). After complete addition the reaction was stirred at ambient temperature for 30 min, and then it was cooled to −5° C. with an ice-acetone bath. A solution of 3-chloro-1-bromopropane (46.6 g, 300 mmol) in dimethylformamide (50 ml) was added dropwise (temperature never exceeded 0° C.). The reaction was allowed to reach ambient temperature and was stirred for 16 hours. The reaction was poured into water, and the aqueous mixture was extracted with ethyl acetate. The ethyl acetate was washed with water, dried (MgSO$_4$), and the extract concentrated to afford 21.9 g of a brown solid. The solid was recrystallized from toluene-hexane to afford N-(3-chloropropyl)-2-benzoxazolinone as large needles, 15.6 g, m.p.=264°–266° C.

(B) N-(3-chloropropyl)-6-acetyl-2-benzoxazolinone

A mixture of N-(3-chloropropyl)-2-benzoxazolinone (8.5 g, 40 mmol), polyphosphoric acid (100 g), and acetic acid (2.4 g, 2.3 ml, 40 mmol), was stirred and heated at 100° C. for 2 hours. The hot solution was poured into ice-water to deposit a yellow gum. The mixture was extracted with dichloromethane, and insolubles were filtered. The dichloromethane extract was washed with water, dried (K$_2$CO$_3$), and concentrated to afford 6.4 g of a slightly green solid. This was recrystallized from ethanol (95%) to yield N-(3-chloropropyl)-6-acetyl-2-benzoxazolinone as a brown solid, 3.5 g, m.p.=100°–103° C.

(C) N-[3-[4-(6-fluoro-1,2-benzisoxazol-3-yl)-1-piperidinyl] propyl]6-acetyl-2-benzoxazolinone A mixture of 6-fluoro-3-(4-piperidinyl)-1,2-benzisoxazole (2.0 g, 9 mmol), N-(3-chloropropyl)-6-acetyl-2-benzoxazolinone (2.4 g, 9 mmol), K$_2$CO$_3$ (3.6 g), a few crystals of KI, and acetonitrile (50 ml) was stirred and refluxed for 13 hours. The reaction was poured into water, and a dark, brown solid that separated was collected to afford 3.3 g of crude product. The solid was chromatographed on a Waters Prep 500 HPLC. Concentration of appropriate fractions afforded 2.3 g of a yellow solid, and recrystallization from ethyl acetate yielded 1.2 g (31%) of N-[3-[4-(6-fluoro-1,2-benzisoxazol-3-yl)-1-piperidinyl] propyl]-6-acetyl-2-benzoxazolinone, m.p.=152°–154° C.

Analysis: Calculated for C$_{24}$H$_{24}$FN$_3$O$_4$: 65.89%C, 5.53%H, 9.61%N; Found: 65.67%C, 5.48%H, 9.52%N.

EXAMPLE 95

N-[3-[4-(6-fluoro-1,2-benzisoxazol-3-yl)-1-piperidinyl]propyl]phthalimide

A mixture of 6-fluoro-3-(4-piperidinyl)-1,2-benzisoxazole (6.44 g, 29.1 mmole), K$_2$CO$_3$ (6.4 g, 46 mmol), N-(3-bromopropyl)phthalimide (8.4 g, 31 mmol) in acetonitrile (150 ml) was heated at reflux for 3.5 hours. The insolubles were filtered. The solvent was removed at reduced pressure and the residue was purified by silica gel column chromatography to give N-[3-[4-(6-fluoro-1,2-benzisoxazol-3-yl)-1-piperidinyl]propyl]phthalimide as a white solid. Recrystallization from ethanol yielded 9.8 g (83%) of off-white crystals, m.p.=129°–130° C.

Analysis: Calculated for C$_{23}$H$_{22}$FN$_3$O$_3$: 67.89%C, 5.44%H, 10.31%N; Found: 67.49%C, 5.38%H, 10.13%N.

EXAMPLE 96

1-(3-Aminopropyl)-4-(6-fluoro-1,2-benzisoxazol-3-yl)piperidine dihydrochloride

A mixture of N-[3-[4-(6-fluoro-1,2-benzisoxazol-3-yl)-1-piperidinyl]propyl]phthalimide (8.5 g, 21 mmol), hydrazine monohydrate (1.5 g, 30 mmol) in methanol (60 ml) was heated at reflux for 2 hours. At the end of the reaction, methanol was removed to leave a crude solid. To this was added water (60 ml), then the mixture was acidified with HCl to pH 1. The insolubles were filtered with the aid of a pad of Celite. The aqueous solution was basified with 50% NaOH, (pH 13), then extracted with dichloromethane. The combined dichloromethane solution was washed with brine, then dried to a colorless oil (4.5 g). The analytical sample (1.5 g) was prepared by treating the oil with HCl in ethanol at 0° C. The 1-(3-aminopropyl)-4-(6-fluoro-1,2-benzisoxazol-3-yl)piperidine dihydrochloride was obtained as white crystals, 2.03 g, m.p.=231°–234° C.

Analysis: Calculated for C$_{15}$H$_{20}$FN$_3$O·2HCl: 51.44%C, 6.33%H, 12.00%N; Found: 51.35%C, 6.49%H, 11.90%N.

EXAMPLE 97 cis-2-[3-[4-(6-Fluoro-1,2-benzisoxazol-3-yl)-1-piperidinyl]propyl]hexahydro-1H-isoindole-1,3-dione hydrochloride A mixture of 1-(3-aminopropyl)-4-(6-fluoro-1,2-benzisoxazol-3-yl)piperidine (3.01 g, 10.8 mmol) and cis-1,2-cyclohexane-dicarboxylic anhydride (1.9 g, 12.3 mmol) in dry pyridine (30 ml) was heated at reflux for 16 hours. The dark brown solution was concentrated to dryness on a rotary evaporator. The crude residue was purified twice by flash chromatography over a silica gel column. The pure product thus obtained weighed 2.5 g (67%). This was converted to the hydrochloride salt by treatment with HCl in ethanol (50 ml). The cis-2-[3-[4-(6-fluoro-1,2-benzisoxazol-3-yl)-1-piperidinyl]propyl]-hexahydro-1H-isoindole-1,3-dione hydrochloride crystals so obtained weighed 3.0 g, m.p.= 242°–245° C.

Analysis: Calculated for C$_{23}$H$_{28}$FN$_3$O$_3$·HCl: 61.14%C, 6.50%H, 9.34%N; Found: 61.32%C, 6.32%H, 9.27%N.

EXAMPLE 98

N-[4-[4-(6-Fluoro-1,2-benzisoxazol-3-yl)-1-piperidinyl]butyl]phthalimide

A mixture of 6-fluoro-3-(4-piperidinyl)-1,2-benzisoxazole (5.5 g, 25 mmol), 4-bromobutylphthalimide (8.0 g, 28.3 mmol, 1.13 eq), K$_2$CO$_3$ (4.55 g, 32 mmol) in acetonitrile (100 ml) was heated at reflux for 3 hours. At the end of the reaction, the mixture was filtered. The insolubles were washed with dichloromethane (200 ml). The organic solution was concentrated gradually to allow cystallization. The crude crystals (5.9 g) were collected. The mother liquor was concentrated to a solid (5.5 g). Purification was by flash chromatography over a silica gel column. The product (3.8 g) thus purified was recrystallized from ethanol (70 ml) to give 2.48 g of N-[4-[4-(6-fluoro-1,2-benzisoxazol-3-yl)-1-piperidinyl]butyl]phthalimide as white crystals, m.p.= 144°–146° C.

Analysis: Calculated for C$_{24}$H$_{24}$FN$_3$O$_3$: 68.39%C, 5.74%H, 9.97%N; Found: 68.34%C, 5.74%H, 9.84%N.

EXAMPLE 99

1-(4-Aminobutyl)-4-(6-fluoro-1,2-benzisoxazol-3-yl)piperidine dihydrochloride

A mixture of N-[4-[4-(6-fluoro-1,2-benzisoxazol-3-yl) piperidinyl]butyl]phthalimide (6.9 g, 16.4 mmol) and hydrazine monohydrate (1.64 g, 32.8 mmol) in methanol (70 ml) was heated at reflux for 3 hours. At the end of the reaction, methanol was removed to leave a crude solid. This was dissolved in water and acidified with HCl to pH 2. The insolubles were filtered. The aqueous solution was basified with 50% NaOH, and then extracted with dichloromethane. The dichloromethane solution was washed with water and brine, and then dried over $MgSO_4$. The solvent was removed to a colorless oil: 4.48 g. This oil was treated with 2.5 equivalents of HCl in ethanol. The solid was collected. Recrystallization from ethanol (65 ml) and methanol (20 ml) gave 2.0 g of 1-(4-aminobutyl)-4-(6-fluoro-1,2-benzisoxazol-3-yl)piperidine dihydrochloride as white crystals, m.p.=234°–237° C.

Analysis: Calculated for $C_{16}H_{22}FN_3O_3 \cdot 2HCl$: 52.75%C, 6.64%H, 11.53%N; Found: 52.37%C, 6.59%H, 11.07%N.

EXAMPLE 100 cis-2-[4-[4-(6-Fluoro-1,2-benzisoxazol-3-yl)-1-piperidinyl]butyl]hexahydro-1H-isoindole-1,3-dione hydrochloride A mixture of 1-(4-aminobutyl)-4-(6-fluoro-1,2-benzisoxazol-3-yl)piperidine (4.7 g, 16.1 mmol) and cis-1,2-cyclohexanedicarboxylic anhydride (3.23 g, 21 mmol) in pyridine (45 ml) was heated at reflux for 8 hours. At the end of the reaction, pyridine was removed to dryness. The crude product was purified on a silica gel column. The material thus obtained weighed 3.18 g (45%) as a clear oil. This oil was dissolved in ethanol (15 ml), then was treated with HCl in ethanol (45 ml). Crystallization took place upon cooling. The crystals were collected, 3.2 g, m.p.=229°–231° C.

Analysis: Calculated for $C_{24}H_{30}FN_3O_3 \cdot HCl$: 62.13%C, 6.73%H, 9.06%N; Found: 61.79%C, 6.68%H, 8.92%N.

EXAMPLE 101

1-[4-[3-[4-(6-Fluoro-1,2-benzisoxazol-3-yl)-1-piperidinyl]propyl]thio]-3-methoxyphenyl]ethanone (A) 1-[4-[(3-chloropropyl)thio]-3-methoxyphenyl]ethanone A mixture of 1-(4-thio-3-methoxyphenyl)ethanone (10.0 g, 54.9 mmol), potassium carbonate (9.0 g, 65.1 mmol), and acetone (100 ml) was stirred at reflux under nitrogen for 30 minutes. The reaction was cooled to ambient temperature and a solution of 1-bromo-3-chloropropane (6.5 ml, 9.5 g, 60.4 mmol) dissolved in acetone (25 ml) was dripped into the reaction. After complete addition, the reaction was heated to reflux and stirred under nitrogen for 17 hours. After the reaction was carried to substantial completion, the reaction mixture was filtered and the resulting filter cake was washed with acetone. The filtrate was concentrated to provide an amber oil. A small sample was solidified by trituration with hot cyclohexane to provide 1-[4-[(3-chloropropyl)thio]-3-methoxyphenyl]ethanone as a yellow solid, 11.7 g, m.p.=53°–55° C.

(B) 1-[4-[3-[4-(6-fluoro-1,2-benzisoxazol-3-yl)-1-piperidinyl]propyl]-thio]3-methoxyphenyl]ethanone A mixture of 6-fluoro-3-(4-piperidinyl)-1,2-benzisoxazole (3.0 g, 13.6 mmol), 1-[4-[(3-chloropropyl)-thio]-3-methoxyphenyl]ethanone (3.5 g, 13.6 mmol), $K_2CO_3$ (2.3 g, 16.6 mmol), KI (200 mg) and $CH_3CN$ (100 ml) was stirred at reflux under nitrogen for 7.5 hours and then was left at ambient temperature for 65 hours. The reaction was poured into water and the aqueous mixture was extracted with ethyl acetate. The ethyl acetate extract was washed twice with water, once with brine and dried over $MgSO_4$ The solvent was removed in vacuo to afford 6.8 g of a light brown oil. The sample was purified by flash chromatography. Concentration of appropriate fractions yielded 3.0 g. Recrystallization from ethanol provided 2.4 g (41%) of 1-[4-[3-[4-(6-fluoro-1,2-benzisoxazol-3-yl)-1-piperidinyl]propyl]thio]-3-methoxyphenyl]ethanone as a beige solid, m.p.=93°–95° C.

Analysis: Calculated for $C_{24}H_{27}FN_2O_3S$: 65.14%C, 6.15%H, 6.33%N; Found: 64.66%C, 6.17%H, 6.26%N.

EXAMPLE 102

4-(6-Fluoro-1,2-benzisoxazol-3-yl)-1-(2'-methoxyphenyl)butylpiperidine maleate (A) 2-(4-bromobutyl)anisole 2-Bromoanisole (2.0 g, 1.07 mmol) in tetrahydrofuran (20 ml) was cooled to –78° C. under nitrogen and secondary butyllithium (1.3M, 10 ml, 1.3 eq) was charged into the resulting solution for two hours. The solution was quenched with 1,4-dibromobutane (3.2 g) and allowed to stir at ambient temperature overnight. The mixture was diluted with ethyl acetate, washed with water and brine, and concentrated to an oil. Following chromatography on a $SiO_2$ column, 2.4 g of 2-(4-bromobutyl)anisole were obtained.

(B) 4-(6-fluoro-1,2-benzisoxazol-3-yl)-1-(2'-methoxyphenyl)butyl-piperidine maleate A mixture of 6-fluoro-3-(4-piperidinyl)-1,2-benzisoxazole (2.36 g, 10.7 mmole), $K_2CO_3$ (2 g, 14.5 mmol) and 2-(4-bromobutyl)anisole (2.4 g, 10 mmol) in acetonitrile (100 ml) was heated at reflux for 2.5 hours. At the end of reaction, the solvent was removed. The residue was extracted into dichloromethane (200 ml) and filtered. The dichloromethane solution was concentrated. The crude oil obtained was purified on a flash chromatography column. The material thus purified was a light yellow oil (2.73 g, 53%). This oil was dissolved in ethanol and treated with maleic acid (607 mg, 1.0 eq) in ethanol. The 4-(6-fluoro-1,2-benzisoxazol-3-yl)-1-(2'-methoxyphenyl)-butylpiperidine maleate crystals formed on concentration and subsequent cooling to 0° C. These were collected and dried to yield 2.05 g, m.p.=132°–133° C.

Analysis: Calculated for $C_{23}H_{27}FN_2O_2 \cdot C_4H_4O_4$: 65.05%C, 6.27%H, 5.62%N; Found: 65.25%C, 6.30%H, 5.70%N.

EXAMPLE 103

1-[4-(1,3-Dithian-2-yl)ethyl]phenyl-4-(6-fluoro-1,2-benzisoxazol-3-yl)butylpiperidine (A) 4-bromo-1-(1,3-dithian-2-yl)ethylbenzene To the compound p-bromoacetophenone (36.85 g, 185 mmol) in trichloro-methane (300 ml) was added 1,3-propanedithiol (25 g, 230 mmol) and boron trifluoride etherate (3 ml). The resulting mixture was stirred at room temperature for 48 hours. The mixture was diluted with dichloromethane (500 ml), washed twice with 10% sodium hydroxide (200 ml), water, and brine, and then dried ($Na_2SO_4$). The product was concentrated to an oil. A portion was stirred with ether (100 ml) and a crystalline product was formed. The crystalline product was recovered by filtration and purified by recrystallization to yield 4-bromo-1-(1,3-dithian-2-yl)ethylbenzene.

(B) 4-(4-bromobutyl)-1-(1,3-dithian-2-yl)ethylbenzene

A solution of 4-bromo-1-(1,3-dithian-2-yl)ethylbenzene (27.2 g, 94 mmol) in tetrahydrofuran (200 ml) was charged with sec-butyllithium (99 ml, 1.3M in cyclohexane, 0.13 mole) dropwise at −78° C. under nitrogen. The mixture was stirred at ambient temperature for 1.5 hours, and then quenched with 1,4-dibromobutane (42 g, 0.2 mole). After being stirred for 3 hours, the mixture was poured into ethyl acetate, and then washed with water and brine. The organic solution was then dried ($Na_2SO_4$) and concentrated to an oil. The crude product was purified by flash chromatography over a silica gel column. The 4-(4-bromobutyl)-1-(1,3-dithian-2-yl)-ethylbenzene thus purified was a light oil, 22.3 g.

Analysis: Calculated for $C_{15}H_{21}BrS_2$: 52.17%C, 6.13%H; Found: 52.60%C, 6.25%H.

(C) 1-[4-(1,3-dithian-2-yl)ethyl]phenyl-4-(6-fluoro-1,2-benzisoxazol-3-yl)butylpiperidine A mixture of 6-fluoro-3-(4-piperidinyl)-1,2-benzisoxazole (5.4 g, 24.5 mmol), $K_2CO_3$ (4.2 g, 30 mmol), 4-(4-bromobutyl)-1-(1,3-dithian-2-yl)ethylbenzene (8.5 g, 24.6 mmol) in acetonitrile (200 ml) was heated at reflux for 2.5 hours. At the end of the reaction, the mixture was filtered and the solvent was concentrated. The crude (13 g) was purified by flash chromatography over a silica gel column. The material thus purified (8.67 g; 72%) was recrystallized from ethanol (50 ml) and hexane (100 ml) to afford 6.6 g of 1-[4-(1,3-dithian-2-yl)ethyl]phenyl-4-(6-fluoro-1,2-benzisoxazol-3-yl)butylpiperidine as light yellow crystals, m.p.=108°–110° C.

Analysis: Calculated for $C_{27}H_{33}FN_2OS_2$: 66.91%C, 6.86%H, 5.78%N; Found: 66.72%C, 6.76%H, 5.71%N.

EXAMPLE 104

1-[4-(4'-Acetophenyl)butyl]-4-(6-fluoro-1,2-benzisoxazol-3-yl)piperidine

A solution of 1-[4-(1,3-dithian-2-yl)ethylphenyl]butyl-4-(6-fluoro-1,2-benzisoxazol-3-yl)piperidine (5.6 g, 11.6 mmol), water (5 ml), and methanol (30 ml), in acetone (50 ml), was treated with mercury (II) perchlorate trihydrate (5 g, 1.1 eq.) at room temperature. After 30 minutes, the reaction was completed. The solids were filtered, and the solvent was removed on a rotary evaporator. The crude product was dissolved in ethyl acetate (500 ml) and washed with water, brine, then dried over $Na_2SO_4$. The solvent was removed to give a crude oil. The purification was by flash chromatography over a silica gel column. The oil thus obtained (2.67 g, 50%) was combined with 1.1 g of oil prepared in from same fashion. Crystallization from ethanol (10 ml) and hexane (20 ml) yielded 1-[4-(4'-acetophenyl) butyl]-4-(6-fluoro-1,2-benzisoxazol-3-yl)piperidine as off-white crystals, 2.32 g, m.p.=85°–86° C.

Analysis: Calculated for $C_{24}H_{27}FN_2O_2$: 73.07%C, 6.90%H, 7.10%N; Found: 72.68%C, 7.05%H, 7.09%N.

EXAMPLE 105

1-[4-[3-[4-(6-Fluoro-1,2-benzisoxazol-3-yl)-1-piperidinyl]propylamino]-3-methoxy-phenyl]ethanone To a stirred suspension of sodium hydride (0.37 g, 7 mmol of a 50% oil dispersion) in dimethylformamide (20 ml) was added, dropwise, 1-[4-[3-[4-(6-fluoro-1,2-benzisoxazol-3-yl)-1-piperidinyl]propylamino]-3-hydroxyphenyl]ethanone (2.9 g, 7 mmol) dissolved in dimethylformamide (25 ml). The reaction was stirred at ambient temperature for 15 minutes, and then it was cooled with an ice bath to about 5° C., whereupon methyl iodide (1.0 g, 7 mmol) in dimethylformamide (1 ml) was added dropwise. The reaction was stirred at ambient temperature for 30 min, and then water was added. The resulting aqueous mixture was extracted with ethyl acetate, the extract washed with water, dried ($MgSO_4$), and the solvent was concentrated to afford 4.9 g of a brown oil, which solidified on standing. The solid was flash chromatographed on silica gel. The appropriate fractions were concentrated to yield 2.7 g of product as a yellow solid. Recrystallization from toluene-hexane yielded 2.0 g (67%) of analytically pure 1-[4-[3-[4-(6-fluoro-1,2-benzisoxazol-3-yl)-1-piperidinyl]propylamino]-3-methoxyphenyl]ethanone as a yellow solid, m.p.=96°–98° C.

Analysis: Calculated for $C_{24}H_{28}FN_3O_3$: 67.75%C, 6.63%H, 9.88%N; Found: 67.93%C, 6.72%H, 9.80%N.

EXAMPLE 106

(2,4-Difluorophenyl)-[1-(phenylmethyl)-3-pyrrolidinyl]methanone oxalate

In a 1 liter round bottom flask, a solution of ethyl-N-benzyl-3-pyrrolidine carboxylate (21.8 g, 11.7 mmol) in 140 ml of 6N HCl was heated at reflux for 2.5 hours. The solution was cooled and the solvent was removed to dryness with a vacuum pump. The residue was then treated with thionyl chloride (100 ml) for 16 hours at room temperature. After the reaction, the excess thionyl chloride was vacuum stripped to dryness (60° C., 4 hours). To the residue in the flask was added 1,3-difluorobenzene (30 g, 26 mmol) followed by aluminum chloride (25 g, 18.7 mmol) in portions at room temperature. When the mixture turned homogeneous (in about 10 minutes) it was then heated at 55° C. for 1 hour. After the reaction was complete, excess 1,3-difluorobenzene was removed under reduced pressure. The residue was partitioned between ice/water and dichloromethane (700 ml) and basified with 50% NaOH solution to pH 10. The dichloromethane solution was washed with water and brine, then dried over anhydrous $MgSO_4$. The solvent was stripped and the crude oil (31 g) was purified by flash chromatography over a silica gel column. The pure product thus obtained weighed 26 g (74%) as a yellow oil. An analytical sample was prepared by dissolving 4.2 g of the oil in ethanol and treating with an ethanol solution of oxalic acid (1.33 g, 14.8 mmol). To the mixture was added ether dropwise to cause crystallization. Recrystallization from ethanol and ether gave 2.63 g of (2,4-difluorophenyl)[1-(phenylmethyl)-3-pyrrolidinyl]methanone oxalate as white crystals, m.p.=114°–116° C.

Analysis: Calculated for $C_{20}H_{19}FNO_5$: 61.38%C, 4.89%H, 3.58%N; Found: 61.16%C, 4.80%H, 3.60%N.

EXAMPLE 107

6-Fluoro-3-[1-phenylmethyl)-3-pyrrolidinyl]-1,2-benzisoxazole fumarate (A) (2,4-difluorophenyl)[1-(phenylmethyl)-3-pyrrolidinyl]-methanone oxime To the compound (2,4-difluorophenyl)[1-(phenylmethyl)-3-pyrrolidinyl]methanone (22 g) in 95% ethanol (350 ml) and water (100 ml) was added $NH_2OH.HCl$ (10.1 g) and ammonium acetate (12.7 g, 2.1 eq). The resulting mixture was refluxed for 3.5 hours. The mixture was then allowed to stir at room temperature for 24 hours. The reaction mixture was concentrated to remove ethanol, poured into water (500 ml), and extracted with dichloromethane (500 ml). This was followed by washing with water, brine, and drying over magnesium sulfate. The product was concentrated to an oil and purified by column chromatography to yield 12 g of (2,4-difluorophenyl)[1-(phenylmethyl)-3-pyrrolidinyl] methanone oxime.

(B) 6-fluoro-3-[1-(phenylmethyl)-3-pyrrolidinyl]-1,2-benzisoxazole fumarate

A mixture of (2,4-difluorophenyl)[1-(phenylmethyl)-3-pyrrolidinyl]methanone oxime (10.8 g, 34.2 mmol), potassium hydroxide (10 g), water (100 ml), and ethanol (100 ml) was heated at reflux for 2 hours. At the end of the reaction, the solution was cooled and ethanol was removed on a rotary evaporator. The aqueous mixture was diluted with water (100 ml) then extracted with dichloromethane (500 ml). The organic solution was washed with brine and dried over anhydrous $MgSO_4$. The solution was concentrated to an oil (9.8 g). The crude product was purified by flash chromatography over a silica gel column. The product thus obtained weighed 4.46 g (44%) as a light yellow oil. The oily product was dissolved in ethanol, and then treated with a solution of fumaric acid (1.73 g, 1.0 eq) in ethanol. Crystallization took place slowly with the addition of isopropyl ether. Recrystallization from ethanol (15 ml) gave 4.6 g of 6-fluoro-3-[1-(phenylmethyl)-3-pyrrolidinyl]-1,2-benzisoxazole fumarate as white crystals, m.p.=142°–144° C.

Analysis: Calculated for $C_{22}H_{21}FN_2O_5$: 64.07%C, 5.13%H, 6.81%N; Found: 64.11%C, 5.05%H, 6.89%N.

EXAMPLE 108

(E)-1-[4-[(4-bromo-2-butenyl)oxy]-3-methoxyphenyl]ethanone

A mixture of 4-hydroxy-3-methoxyacetophenone (10 g, 59 mmol), $K_2CO_3$ (10 g, 1.2 q) and 1,4-dibromo-2-butene (>95% trans, Aldrich, 18 g, 1.2 eg) in acetone (500 ml) was heated at 55° C. for 3 hours. At the end of the reaction, the solvent was concentrated. The crude product was extracted into dichloromethane (750 ml) and the insolubles were filtered; then the solution was concentrated again to an oil. Purification on a silica gel column ($SiO_2$, 100 g, eluted with dichloromethane) yielded 7.25 g (40%) of white solid. Recrystallization from ether gave analytically pure (E)-1-[4-[(4-bromo-2-butenyl)oxy]-3-methoxyphenyl]ethanone (3.91 g), m.p.=71°–72° C.

Analysis: Calculated for $C_{13}H_{15}BrO_3$: 52.19%C, 5.50%H; Found: 52.12%C, 4.94%H.

EXAMPLE 109

4-(3-Chloropropoxy)-3-methoxybenzaldehyde

A mixture of vanillin (30.4 g, 200 mmol), $K_2CO_3$ (27.6 g) and acetone (150 ml) was stirred and refluxed for 0.5 hours. Heating was removed and 1-bromo-3-chloropropane (40.8 g, 260 mmol) in acetone was added dropwise. The reaction was stirred and refluxed for 16 hours, and then it was poured into water. The aqueous mixture was extracted with diethyl ether, the extract was dried ($MgSO_4$), and the solution was concentrated to afford an oil, which upon evacuation solidified to a white solid (50.2 g). An 8.0 g sample was flash chromatographed on silica gel with 50% ethyl acetatehexane as eluent. Concentration of appropriate fractions gave 2.7 g (37%) of 4-(3-chloropropoxy)-3-methoxybenzaldehyde as a white solid, m.p.=53°–55° C.

Analysis: Calculated for $C_{11}H_{13}ClO_3$: 57.78%C, 5.73%H; Found: 57.21%C, 5.52%H.

EXAMPLE 110

6-Fluoro-3-(3-pyrrolidinyl)-1,2-benzisoxazole hydrochloride

A mixture of 3-(6-fluoro-1,2-benzisoxazol-3-yl)-1-pyrrolidinylcarboxylic acid ethenyl ester (5.1 g, 18.4 mmol, hydrochloric acid (5 ml), and isopropyl alcohol (50 ml) was heated at reflux for 3.5 hours. At the end of the reaction, the solvent was reduced to about 30 ml on a rotary evaporator and the mixture was cooled to 0° C. for 2 hours. The crystals were collected by filtration and rinsed with cold isopropyl alcohol. The 6-fluoro-3-(3-pyrrolidinyl)-1,2-benzisoxazole hydrochloride product weighed 3.09 g (69%), m.p.= 225°–227° C.

Analysis: Calculated for $C_{11}H_{11}FN_2O \cdot HCl$: 54.44%C, 4.99%H, 11.54%N; Found: 54.35%C, 4.99%H, 11.38%N.

EXAMPLE 111

1-[4-[3-[4-(6-Fluoro-1,2-benzisoxazol-3-yl)-1-piperidinyl]propylamino]-3-hydroxy-phenyl] ethanone A mixture of N-[3-[4-(6-fluoro-1,2-benzisoxazol-3-yl)-1-piperidinyl]propyl-6-acetyl-2-benzoxazolinone (6.0 g, 14 mmol) and 10% aqueous sodium hydroxide (50 ml) was stirred and refluxed for 40 minutes. Water was added and the reaction was made acidic with 5% hydrochloric acid. Saturated $Na_2CO_3$ was added until effervescence ceased. The aqueous mixture was extracted with dichloromethane. The dichloromethane extract was washed (water), dried ($K_2CO_3$) and concentrated to afford 2.6 g of a tacky solid. The crude solid was treated with saturated $NaHCO_3$, and extracted into dichloromethane. The dichloromethane was washed (brine and then water), and dried ($MgSO_4$). The organic extract was then concentrated to yield 2.4 g of a brown solid, which was combined with another sample to yield 5.0 g. This sample was flash chromatographed on silica. A small sample (0.25 g) was recrystallized from toluene to yield 1-[4-[3-[4-(6-fluoro-1,2-benzisoxazol-3-yl)-1-piperidinyl] propylamino]-3-hydroxyphenyl]ethanone as a brownish solid, 0.15 g, m.p.=150°–152° C.

Analysis: Calculated for $C_{23}H_{26}FN_3O_3$: 67.14%C, 6.37%H, 10.21%N; Found: 67.54%C, 6.58%H, 9.95%N.

EXAMPLE 112

1-[3-Acetylamino-4-(3-chloropropoxy)phenyl] ethanone

A stirred mixture of 1-[3-acetylamino-4-hydroxyphenyl]-ethanone (7.7 g, 40 mmol), $K_2CO_3$ (5.7 g), 3-chloro-1-bromopropane (8.9 g, 56 mmol), and acetone (100 ml) was refluxed for 16 hours. The reaction was allowed to cool to ambient temperature, and filtered. Concentration of the filtrate yielded 8.5 g of a white solid. The solid was recrystallized from toluene and then from ethanol to afford 6.5 g of an off-white solid. A 3.3 g sample of this material was flash chromatographed on silica gel. Concentration of the appropriate fractions afforded 2.8 g of a white solid. The solid was recrystallized from toluene and then from ethanol-water to yield 2.2 g (51%) of 1-[3-acetylamino-4-(3-chloropropoxy)phenyl]ethanone as a white solid, m.p.= 124°–126° C.

Analysis: Calculated for $C_{13}H_{16}ClNO_3$: 57.89%C, 5.98%H, 5.19%N; Found: 57.08%C, 5.85%H, 5.13%N.

EXAMPLE 113

N-[2-(3-hydroxypropoxy) phenyl]acetamide

A stirred mixture of 2-hydroxyphenylacetamide (10.0 g, 66 mmol), $K_2CO_3$ (6.9 g), 3-bromopropanol (12.8 g, 12 mmol), and acetone (250 ml) was refluxed for 16 hours. The reaction mixture was allowed to cool, and then it was filtered. The filtrate was concentrated to yield 19.0 g of a thick, brown oil. The oil was distilled with a Kugelrohr apparatus and 11.2 g (82%) of a viscous, orange oil was collected. The oil solidified upon standing. An analytical sample was obtained by recrystallization from ethyl acetate to afford the alcohol as an off-white solid, m.p.=78°–80° C.

Analysis: Calculated for $C_{11}H_{15}NO_3$: 63.14%C, 7.23%H, 6.69%N; Found: 63.10%C, 7.32%H, 6.64%N.

EXAMPLE 114

4-[4-(6-Fluoro-1,2-benzisoxazol-3-yl)-1-piperidinyl] butyl bromide

A mixture of 6-fluoro-3-(4-piperidinyl)-1,2-benzisoxazole (12 g, 55 mmol), $K_2CO_3$ (13 g) and 1,4-dibromobutane (20 g, 9.3 mmol, 1.7 eq) in acetonitrile (300 ml) was stirred at room temperature overnight. The inorganic material was filtered. The solution was concentrated to ~80 ml, when crystals crashed out. The product was filtered to yield 14.16 g (73%), m.p.=243°–245° C.

Analysis: Calculated for $C_{16}H_{20}FN_2O$: 54.09%C, 5.67%H, 7.89%N; Found: 54.13%C, 5.52%H, 7.83%N.

EXAMPLE 115

2-[4-(6-Fluoro-1,2-benzisoxazol-3-yl)-1-piperidinyl] ethyl acetate fumarate

A mixture of 6-fluoro-3-(4-piperidinyl)-1,2-benzisoxazole (3.0 g, 13.6 mmol), $K_2CO_3$ (3.5 g, 25 mmol), 2-bromoethyl acetate (4 g, 26.5 mmol) in acetonitrile (50 ml) was heated at reflux for 4 hours. After cooling to room temperature, the inorganic salts were filtered and washed with DCM (dichloromethane 50 ml). The organic solvent was removed on a rotary evaporator to give an oil. The oily product was purified on a flash chromatography column (60 g of $SiO_2$ eluted with MeOH 2%–4% in DCM). The pure product thus obtained weighed 4.43 g. This oil was dissolved in ethanol and treated with a solution of fumaric acid (1.2 g) in ethanol. The salt crystallized out at room temperature to yield 3.44 g (57%), m.p.=154°–155° C.

Analysis: Calculated for $C_{16}H_{19}FN_2O_3 \cdot C_4H_4O_4$: 56.86%C, 5.49%H, 6.63%N; Found: 56.75%C, 5.41%H, 6.54%N.

EXAMPLE 116

N-[2-[4-(6-Fluoro-1,2-benzisoxazol-3-yl)-1-piperidinyl]ethyl]morpholine

A mixture of 6-fluoro-3-(4-piperidinyl)-1,2-benzisoxazole (3.0 g, 13.6 mmol), 2-chloroethyl morpholine hydrochloride (4.46 g, 29.7 mmol) and $K_2CO_3$ (7.3 g, 2.2 eq) in acetonitrile (60 ml) was heated at reflux for 24 hours. The crude mixture was diluted with DCM and filtered. The solvent was concentrated to an oil (~7.1 g). Purification on a silica gel column (55 g, $SiO_2$, eluted with MeOH:DCM) yielded a solid product weighing 4 g. Recrystallization from hot ethanol yielded 2.1 g (48%), m.p.=131°–132° C.

Analysis: Calculated for $C_{18}H_{24}FN_3O_2$: 64.84%C, 7.26%H, 12.60%N; Found: 64.80%C, 7.09%H, 12.77%N.

EXAMPLE 117

N-[2-[4-(6-Fluoro-1,2-benzisoxazol-3-yl)-1-piperidinyl]ethyl]phthalimide

A mixture of 6-fluoro-3-(4-piperidinyl)-1,2-benzisoxazole (5.15 g, 23.4 mmol), $K_2CO_3$ (4.2 g, 30.4 mmol) and 2-bromoethyl phthalimide (7.13 g, 28 mmol) in acetonitrile (250 ml) was heated at reflux for 3.5 hours. The solids and solvent were removed. The residue was purified by flash chromatography ($SiO_2$, 110 g, eluted with 2–4% $CH_3OH$:DCM). The product thus obtained weighed 7.8 g (84%). Part of the material was recrystallized to give 2.35 g of off white crystals, m.p.=148°–149° C.

Analysis: Calculated for $C_{22}H_{20}FN_3O_3$: 67.17%C, 5.12%H, 10.68%N; Found: 67.01%C, 5.20%H, 10.76%N.

(A) N-[2-[4-(6-Fluoro-1,2-benzisoxazol-3-yl)-1-piperidinyl]ethyl]phthalimide hydrochloride To a solution of 8.0 g of N-[2-[4-(6-fluoro-1,2-benzisoxazol-3-yl)-1-piperidinyl]ethyl]phthalimide in dichloromethane/ethanol (150 ml) was added 1M—HCl in ether. The salt crystallized out rapidly. It was filtered off, washed with ethanol and dried to afford 8.15 g with m.p.=257°–259° C., dec. Recrystallization provided 7.20 g of pure white salt, with m.p. unchanged.

Analysis: Calculated for $C_{22}H_{20}FN_3O_3 \cdot HCl$: 61.47%C, 4.92%H, 9.77%N; Found: 61.12%C, 5.21%H, 9.58%N.

EXAMPLE 118

2-[4-(6-Fluoro-1,2-benzisoxazol-3-yl)-1-piperidinyl] ethyl methyl ether fumarate A mixture of 6-fluoro-3-(4-piperidinyl)-1,2-benzisoxazole (3.75 g, 77 mmol), $K_2CO_3$ (3 g, 21.7 mmol), bromoethyl methyl ether (2.84 g, 20.4 mmol) in acetonitrile (150 ml) was heated at reflux for 3.5 hours. The reaction was cooled. The inorganics were filtered and rinsed with DCM. The organic solution was concentrated down to an oil (7 g). Purification on a flash chromatography column ($SiO_2$, 45 g; eluted with methanol/DCM) gave a light yellow oil as product (4 g, 87%). This oil was dissolved into ethanol and treated with a solution of fumaric acid (1.67 g) in ethanol (20 ml). White crystals (5.15 g) were collected, m.p.=157°–158° C.

Analysis: Calculated for $C_{15}H_{19}FN_2O_2 \cdot C_4H_4O_4$: 57.86%C, 5.88%H, 7.10%N; Found: 57.53%C, 5.94%H, 6.94%N.

EXAMPLE 119

4-[4-(6-Fluoro-1,2-benzisoxazol-3-yl)-1-piperidinyl] butyl acetate fumarate

A mixture of 6-fluoro-3-(4-piperidinyl)-1,2-benzisoxazole (9.5 g, 41 mmol), $K_2CO_3$ (7.2 g, 51 mmol), and 4-bromobutyl acetate (10 g, 51 mmol) in acetonitrile (200 ml) was heated at reflux for 3.5 hours. At the end of the reaction, the solution was cooled and filtered. The inorganic salt was washed with DCM (50 ml). The organic solvent was removed. The residue was purified on a flash chromatography column (packed with Sorbsil C30 silica gel, 100 g, eluted with DCM, 1 liter, increasing methanol from 2 to 4%, 2.5l). The material thus purified weighed 12.92 g (89%). A small sample (1.67 g) was dissolved in ethanol and treated with 1 equivalent of fumaric acid (580 mg) in ethanol to yield white crystals: 1.8 g, m.p.=142°–143° C.

Analysis: Calculated for $C_{18}H_{23}FN_2O_3 \cdot C_4H_4O_4$: 58.66%C, 6.04%H, 6.22%N; Found: 58.56%C, 6.02%H, 6.13%N.

EXAMPLE 120

4-[4-(6-Fluoro-1,2-benzisoxazol-3-yl)-1-piperidinyl] butanol fumarate

A mixture of 4-[4-(6-fluoro-1,2-benzisoxazol-3-yl)-1-piperidinyl]butyl acetate (11.5 g, 34.4 mmol), 15% NaOH (100 ml) and ethanol (100 ml) was heated at reflux for 4 hours. After cooling to room temperature, the base was neutralized with HCl to pH=7. The solution was concentrated down to a small volume (~50 ml), then extracted with DCM. The DCM solution was washed with brine and dried over MgSO$_4$. The solvent was concentrated to give~10 g of crude oil. Purification by flash chromatography (Sorbsil C-30, 100 g, eluted with MeOH:DCM, 3 liters) yielded 9.8 g of white solid. The sample for testing was prepared by treatment of the free base (2.0 g) with fumaric acid (780 mg, 1.0 eq) in ethanol. The crystals were collected and dried: 1.5 g, m.p.=131°–132° C.

Analysis: Calculated for $C_{16}H_{21}FN_2O_2 \cdot C_4H_4O_4$: 58.82%C, 6.17%H, 6.86%N; Found: 58.81%C, 6.37%H, 6.66%N.

EXAMPLE 121

4-[4-(6-Fluoro-1,2-benzisoxazol-3-yl)-1-piperidinyl] butyl decanoate fumarate

To a solution of 4-[4-(6-fluoro-1,2-benzisoxazol-3-yl)-1-piperidinyl]butanol (2.0 g, 6.84 mmol), triethylamine (1.0 g, 10 mmol) in DCM (70 ml) decanoyl chloride (1.7 g, 8.9 mmol) was added dropwise at room temperature. The mixture was stirred for 1 hour., then was concentrated to a crude solid. The solid was extracted into ethyl acetate, and the insoluble salts were filtered. The solvents were removed. The crude product was purified by flash chromatography (Sorbsil C-30, 30 g, eluted with a mixture of MeOH in DCM). The oil thus obtained (2.5 g, 81%) was converted to a fumarate salt with fumaric acid (650 mg, 1.0 eq) in ethanol. Crystals were collected: 1.48 g, m.p.=109°–110° C.

Analysis: Calculated for $C_{26}H_{39}FN_2O_3 \cdot C_4H_4O_4$: 64.04%C, 7.70%H, 4.98%N; Found: 64.30%C, 7.86%H, 4.78%N.

EXAMPLE 122

3-[4-(6-Fluoro-1,2-benzisoxazol-3-yl)-1-piperidinyl] propyl decanoate fumarate

To a solution 3-[4-(6-fluoro-1,2-benzisoxazol-3-yl)-1-piperidinyl]propanol (1.81 g, 6.5 mmol) triethylamine (0.9 g, 9.0 mmol) in DCM (45 ml) was added decanoyl chloride (1.5 g, 7.8 mmol) dropwise at room temperature. The mixture was stirred for 20 minutes, then concentrated down to a crude solid. The solid was extracted into EtOAc (20 ml), and the insoluble salts were filtered. The EtOAc was removed. The crude oil was purified by flash choursomatography (Sorbsil C-30, 30 g; eluted with MeOH:DCM). The oil thus obtained (2.54 g, 90%) was converted to a fumarate salt with fumaric acid (670 mg) in ethanol. The crystals collected weighed 1.61 g, m.p.=100°–102° C.

Analysis: Calculated for $C_{25}H_{27}FN_2O_3 \cdot C_4H_4O_4$: 63.52%C, 7.54%H, 5.11%N; Found: 63.63%C, 7.74%H, 5.03%N.

EXAMPLE 123

N,N-Diethyl-4-[4-(6-fluoro-1,2-benzisoxazol-3-yl)-1-piperidinyl]butyl carbamate fumarate To a mixture of 4-[4-(6-fluoro-1,2-benzisoxazol-3-yl)-1-piperidinyl]butanol (1.55 g, 5.3 mmol) potassium t-butoxide (750 mg, 6.7 mmol) in THF (100 ml), diethylcarbamyl chloride (900 mg, 6.63 mmol) was added dropwise at room temperature. The mixture was stirred for 2 hours, then the solvent was removed. The residue was extracted into DCM. The DCM solution was washed with brine and dried over MgSO$_4$. The solution was concentrated. The product was purified on a flash chromatography column (SiO$_2$, 14 g, eluted with 2% MeOH in DCM), to yield 1.84 g of oil. This oil was dissolved into ethanol (~5 ml) and treated with a solution of fumaric acid (850 mg, 1.0 eq) in ethanol. Crystallization was induced with a small volume of isopropyl ether to produce 2.09 g, m.p.=152°–153° C.

Analysis: Calculated for $C_{21}H_{30}FN_3O_3 \cdot C_4H_4O_4$: 59.16%C, 6.75%H, 8.28%N; Found: 59.17%C, 6.84%H, 8.16%N.

EXAMPLE 124

N-Methyl-4-[4-(6-fluoro-1,2-benzisoxazol-3-yl)-1-piperidinyl]butyl carbamate fumarate To a mixture of 4-[4-(6-fluoro-1,2-benzisoxazol-3-yl)-1-piperidinyl]butanol (1.84 g, 6.3 mmol), K$_2$CO$_3$ (850 mg) in chloroform, methyl isocyanate (448 mg, 7.7 mmol and 360 mg, 6.2 mmol) was added dropwise in two portions. The mixture was filtered and concentrated to a crude oil. Purification was done on a flash chromatography column (SiO$_2$, 11 g, eluted with 2% CH$_3$OH in DCM) to yield a light yellow oil (2.05 g, 93%.). This oil was dissolved into ethanol and treated with a solution of fumaric acid (800 mg, 1.0 eq). Crystallization was induced with drops of isopropyl ether. Weight: 1.36 g, m.p.=96°–98° C.

Analysis: Calculated for $C_{18}H_{24}FN_3O_3 \cdot C_4H_4O_4$: 56.76%C, 6.06%H, 9.02%N; Found: 56.27%C, 6.03%H, 8.86%N.

EXAMPLE 125

2-[2-[4-(6-Fluoro-1,2-benzisoxazol-3-yl)-1-piperidinyl]ethyl]-1,3-dioxane fumarate A mixture of 6-fluoro-3-(4-piperidinyl)-1,2-benzisoxazole (2.0 g, 9.1 mmol), K$_2$CO$_3$ (1.5 g, 10.9 mmol) and bromoethyl-1,3-dioxane (2.1 g, 10.7 mmol) in acetonitrile (50 ml) was heated at reflux for 3 hours. At the end, the insolubles were filtered and rinsed with DCM and the filtrate was evaporated down. The crude mixture was purified by flash chromatography over a silica gel column (Sorbsil C-30, 25 g; eluted with DCM and MeOH (1–3%) in DCM). The fractions containing the pure product were combined and concentrated to give 3.13 g of oil. The oil was treated with a fumaric acid (1.0 g) ethanol solution. The crystals were collected: 3.98 g (77%), m.p.=161°–162° C.

Analysis: Calculated for $C_{18}H_{23}FN_2O_3 \cdot C_4H_4O_4$: 58.66%C, 6.04%H, 6.22%N; Found: 58.69%C, 5.96%H, 6.20%N.

EXAMPLE 126

2-[4-(6-Fluoro-1,2-benzisoxazol-3-yl-1-piperidinyl ]ethanol hemifumarate.

(A) 2-[4-(6-Fluoro-1,2-benzisoxazol-3-yl)-1-piperidinyl] ethyl acetate

2-[4-(6-Fluoro-1,2-benzisoxazol-3-yl)-1-piperidinyl] ethyl acetate was prepared according to Example 115.

(B) 2-[4-(6-Fluoro-1,2-benzisoxazol-3-yl-1-piperidinyl] ethanol hemifumarate

2-[4-(6-Fluoro-1,2-benzisoxazol-3-yl)-1-piperidinyl] ethyl acetate (10.58 g, 34.6 mmol), 15% NaOH (100 ml) and ethanol (100 ml) was heated at reflux for 4 hours. The solution) was cooled (∞5° C.) and neutralized with HCl to pH~7. The ethanol was removed under reduced pressure. The aqueous solution was basified with NaHCO$_3$ and extracted with DCM (2×200 ml). The DCM solution was washed with brine and dried over MgSO$_4$ and evaporated to give a white solid: 6.88 g (75%). A sample (2.03 g) was dissolved in ethanol and treated with fumaric acid (660 mg, 1.0 eq). Crystallization was induced with drops of isopropyl ether to yield off-white crystals: 1.43 g, m.p.=159°–161° C.

Analysis: Calculated for C$_{14}$H$_{17}$FN$_2$O$_2$·0.5 C$_4$H$_4$O$_4$: 59.62%C, 5.94%H, 8.69%N; Found: 59.55%C, 5.95%H, 8.53%N.

EXAMPLE 127

2-[4-(6-Fluoro-1,2-benzisoxazol-3-yl)-1-piperidinyl] ethyl decanoate fumarate

A mixture of 2-[4-(6-fluoro-1,2-benzisoxazol-3-yl)-1-piperidinyl]ethyl alcohol (1.6 g, 5 mmol) and triethylamine (800 mg, 8 mmol) in chloroform (100 ml) was treated with decanoyl chloride (1.3 g, 7.2 mmol) dropwise at room temperature. The mixture was stirred for 4 hours. The solvent was removed to leave a crude solid. The solid was dissolved into a small amount of DCM (15 ml), then was filtered. The solution was concentrated.

The purification was done by flash chromatography over a silica gel column (Sorbsil C-30, 30 g; eluted with MeOH: DCM). The purified oil (2.45 g, 95%) was treated with a fumaric acid (660 mg, 1.0 eq)/ethanol solution (15 ml). Crystallization was induced by adding drops of ether; yield: 1.97 g, m.p.=109°–110° C.

Analysis: Calculated for C$_{24}$H$_{35}$FN$_2$O$_3$·C$_4$H$_4$O$_4$: 62.90%C, 7.35%H, 5.24%N; Found: 62.93%C, 7.30%H, 5.14%N.

EXAMPLE 128

N,N-Diethyl-2-[4-(6-fluoro-1,2-benzisoxazol-3-yl)-1-piperidinyl]-ethyl carbamate fumarate To a mixture of 2-[4-(6-fluoro-1,2-benzisoxazol-3-yl)-1-piperidinyl]ethanol (1.6 g, 6 mmol) and potassium t-butoxide (850 mg, 7.6 mmol) in THF (100 ml) diethyl carbamyl chloride (1.03 g, 7.5 mmol) was added dropwise at room temperature. The mixture was stirred for 4 hours. The reaction mixture was concentrated to a crude solid. The solid was dissolved in DCM and purified on a flash chromatography column (Sorbsil C-30,27 g; eluted with a MeOH: DCM mixture). The product thus purified as a light oil (2.2 g, 91%) was dissolved into ethanol and treated with a fumaric acid (690 mg, 1.0 eq)/ethanol solution (15 ml). Crystallization on cooling yielded 2.15 g of white crystals, m.p.=133°–135° C.

Analysis: Calculated for C$_{19}$H$_{26}$FN$_3$O$_3$·C$_4$H$_4$O$_4$: 57.61%C, 6.31%H, 8.76%N; Found: 57.49%C, 6.25%H, 8.54%N.

EXAMPLE 129

2-[4-[(6-Fluoro-1,2-benzisoxazol-3-yl)-1-piperidinyl]ethyl]amine hemifumarate (A) N-[4-(6-fluoro-1,2-benzisoxazol-3-yl)-1-piperidinyl] ethyl phthalimide N-[4-(6-fluoro-1,2-benzisoxazol-3-yl)-1-piperidinyl] ethyl phthalimide was prepared according to Example 117.

(B) 2-[4-[(6-Fluoro-1,2-benzisoxazol-3-yl)-1-piperidinyl] ethyl]amine hemifumarate A mixture of 2-[4-(6-fluoro-1,2-benzisoxazol-3-yl)-1-piperidinyl]ethyl phthalimide (4.6 g, 11.7 mmol) and hydrazine monohydrate (1.17 g, 23.4 mmol) in methanol (50 ml) was heated at reflux overnight. At the end of the reaction, methanol was removed to leave a crude solid. This was stirred with water (150 ml) and acidified with HCl to pH=2. The insolubles were filtered. The aqueous solution was basified with 50% NaOH then extracted with DCM (2×250 ml). The DCM solution was washed with brine and dried over MgSO$_4$. The solvent was removed to produce a colorless oil: 2.12 g. This oil was treated with a solution of fumaric acid (935 mg, 1.0 eq) in ethanol. The salt crystallized out: 0.99 g, m.p.=203°–205° C. A second crop of 0.73 g (m.p.=198°–200° C) was collected later.

Analysis: Calculated for C$_{14}$H$_{18}$FN$_3$O$_3$·0.5C$_4$H$_4$O$_4$: 59.80%C, 6.27%H, 13.07%N; Found: 59.51%C, 6.35%H, 13.31%N.

EXAMPLE 130

2-[4-(6-Fluoro-1,2-benzisoxazol-3-yl)-1-piperidinyl] ethyl decanamide fumarate

To a mixture of 2-[4-(6-fluoro-1,2-benzisoxazol-3-yl)-1-piperidinyl]ethylamine (1.49 g, 5.5 mmol) and triethylamine (1.0 g, 10 mmol) in chloroform (50 ml) decanoyl chloride (1.26 g, 6.6 mmol) was added at room temperature. The mixture was stirred for 3 hours at room temperature. The solvent was stripped down to a crude mixture. This crude mixture was purified by flash chromatography over a silica gel column (SiO$_2$, 20 g; eluted with a solution of MeOH (0–3%) in DCM). The fractions containing the pure product were pooled and concentrated to give 2.3 g of oil. This oil was converted to a fumarate salt by treatment with fumaric acid (655 mg) in ethanol. The ethanol was concentrated down to a small volume and 3 volumes of isopropyl ether was added. This mixture was stirred overnight to cause crystallization. The solids were collected, weighed: 1.83 g (60.5%), m.p.=108°–110° C.

Analysis: Calculated for C$_{24}$H$_{36}$FN$_3$O$_2$·C$_4$H$_4$O$_4$: 63.02%C, 7.56%H, 7.87%N; Found: 62.42%C, 7.58%H, 7.66%N.

EXAMPLE 131

2-[4-(6-Fluoro-1,2-benzisoxazol-3-yl)-1-piperidinyl] ethyl acetamide fumarate

A mixture of 2-[4-(6-fluoro-1,2-benzisoxazol-3-yl)-1-piperidinyl]ethylamine (2.56 g, 9.7 mmol) and triethylamine (1.45 g, 14.5 mmol) in DCM (50 ml) was treated with dropwise addition of acetyl chloride (1.0 g, 12.7 mmol) at room temperature. The mixture was stirred for 4 hours at room temperature. The reaction mixture was diluted with DCM and washed with brine. The organic solution was dried over MgSO$_4$ and concentrated to a crude oil. The crude oil was purified by flash chromatography over a silica gel column (SiO$_2$, 20 g; eluted with (0–2%) CH$_3$OH in DCM). The pure product thus obtained weighed 1.36 g (46%). It was converted to a fumarate salt by treatment with fumaric acid (517 mg) in ethanol Recrystallization from ethanol gave white crystals; weight: 1.53 g, m.p.=132°–133° C.

Analysis: Calculated for C$_{16}$H$_{20}$FN$_3$O$_2$·C$_4$H$_4$O$_4$: 57.00%C, 5.74%H, 9.97%N; Found: 57.05%C, 5.85%H, 9.95%N.

EXAMPLE 132

2-[[2-[4-(6-Fluoro-1,2-benzisoxazol-3-yl)-1-piperidinyl]ethyl]amino]ethyl acetate fumarate A mixture of 2-[4-[(6-fluoro-1,2-benzisoxazol-3-yl)-1-piperidinyl]ethyl]amine (2.0 g, 7.6 mmol), K$_2$CO$_3$ (1.38 g, 10 mmol) and bromoethyl acetate (1.40 g, 8.3 mmol) in acetonitrile (50 ml) was heated at reflux for 4 hours. At the end, the insolubles were filtered off and rinsed with DCM. The solvent was evaporated down. The crude mixture was purified by flash chromatography over a silica gel column (Sorbsil C-30, 30 g; eluted with 2% CH$_3$OH in DCM, 800 ml). The oil (1.15 g) thus obtained was treated with a solution of fumaric acid (358 mg) in ethanol. Crystallization was induced by adding drops of ethyl ether, yield: 1.09 g, m.p.=116°–118° C.

Analysis: Calculated for C$_{18}$H$_{24}$FN$_3$O$_3$·C$_4$H$_4$O$_4$: 56.77%C, 6.06%H, 9.03%N; Found: 56.32%C, 5.97%H, 8.94%N.

EXAMPLE 133

Methyl 2-[4-[(6-fluoro-1,2-benzisoxazol-3-yl)-1-piperidinyl]ethyl carbamate fumarate A mixture of 2-[4-[(6-fluoro-1,2-benzisoxazol-3-yl)-1-piperidinyl]ethyl]amine (2.0 g, 7.6 mmol) and triethylamine (1.0 g, 10 mmol) in DCM (50 ml) was treated with methyl chloroform ate (860 mg, 9.12 mmol) dropwise at room temperature. The mixture was stirred for 1 hour. The reaction mixture was diluted with DCM and washed with brine. The organic solution was dried over MgSO$_4$ and concentrated to a crude oil. The purification was done by flash chromatography over a silica gel column (28 g of Sorbsil C-30, eluted with DCM and MeOH/DCM). The pure oil thus obtained weighed 2.34 g. It was converted to a fumarate salt by treatment with fumaric acid (840 mg, 1.0 eq) in ethanol. Crystallization was induced by adding drops of isopropyl ether, yield: 2.31 g, m.p.=163°–165° C.

Analysis: Calculated for C$_{16}$H$_{20}$FN$_3$O$_3$·C$_4$H$_4$O$_4$: 54.92%C, 5.53%H, 9.61%N; Found: 54.49%C, 5.45%H, 9.24%N.

EXAMPLE 134

Z-2-[2-[4-(6-Fluoro-1,2-benzisoxazol-3-yl)-1-piperidinyl]ethyl]hexahydro-1H-isoindole-1,3-dione fumarate A mixture of 1-(2-aminoethyl)-4-(6-fluoro-1,2-benzisoxazol-3-yl)piperidine (3.77 g, 14.3 mmol) and cis-1,2-cyclohexane-dicarboxylic anhydride (2.82 g, 18.2 mmol, 1.25 eq) in dry pyridine (50 ml) was heated at 65° C. for 48 hours. The dark brown solution was concentrated to dryness on a rotary evaporator. The crude residue was purified twice by flash chromatography over a silica gel column (SiO$_2$, 45 g and 50 g, eluted with DCM and 1% CH$_3$OH in DCM). The pure product thus obtained 2.35 g (41%), was converted to the fumarate salt by treatment with fumaric acid (660 mg) in ethanol. The crystals after two recrystallizations weighed 1.37 g, m.p.=172°–173° C.

Analysis: Calculated for C$_{22}$H$_{26}$FN$_3$O$_3$·C$_4$H$_4$O$_4$: 60.57%C, 5.87%H, 8.15%N; Found: 60.40%C, 5.55%H, 7.82%N.

EXAMPLE 135

(S)-(+)-3-[4-(6-Fluoro-1,2-benzisoxazol-3-yl)-1-piperidinyl]-2-methyl-1-propanol fumarate A mixture of 4-(6-fluoro-1,2-benzisoxazol-3-yl) piperidine (7.2 g, 32.7 mmol), (S)-(+)-3-bromo-2-methyl-1-propanol (5.0 g, 32.6 mmol), K$_2$CO$_3$ (7.19 g, 52 mmol) in acetonitrile (250 ml) was heated at reflux overnight. The insolubles were filtered off. The solvent was removed at reduced pressure and the crude residue was purified by silica gel chromatography (SiO$_2$, 84 g, eluted with 21 of 1% CH$_3$OH in DCM) to give the target compound as an off-white solid (8.83 g, 94%). A sample of 1.7 g was converted to the fumarate salt by treatment with fumaric acid (710 mg) in ethanol. Recrystallization from ethanol yielded 1.74 g of white crystals, m.p.=119°–121° C.

Analysis: Calculated for C$_{20}$H$_{25}$FN$_2$O$_6$: 58.82%C, 6.17%H, 6.86%N; Found: 58.81%C, 6.24%H, 6.76%N.

EXAMPLE 136

4-(6-Fluoro-1,2-benzisoxazol-3-yl)-1-[3-(1-piperidinyl)propyl]piperidine difumarate A mixture of 4-(6-fluoro-1,2-benzisoxazol-3-yl) piperidine (3.0 g, 13.6 mmol), N-(3-chloropropyl)piperidine hydrochloride (4.05 g, 20.4 mmol), K$_2$CO$_3$ (6 g, 43.4 mmol), tetrabutylammonium hydrogen sulfate (phase transfer catalyst, 2.3 g) in acetonitrile (100 ml) and water (15 ml) was heated at reflux for 16 hours. The mixture was washed with brine and the layers were separated. The organic solution was concentrated. The crude product (6.4 g) was purified by flash chromatography over a silica gel column (55 g, sorbsil C-30; eluted with 2% CH$_3$OH:0.5% DEA in DCM, 1.4 l). The oil thus purified (4.5 g) was treated with fumaric acid (1.6 g) in ethanol. The solid was collected: weight 3.1 g, m.p.178°–181° C. Recrystallization from ethanol yielded 2.28 g of white crystals, m.p.=190°–192° C.

Analysis: Calculated for C$_{20}$H$_{24}$FN$_3$O$_2$·C$_4$H$_4$O$_4$: 58.22%C, 6.28%H, 7.27%N; Found: 58.39%C, 6.36%H, 7.34%N.

EXAMPLE 137

1-(3-Dimethylaminopropyl)-4-(6-fluoro-1,2-benzisoxazol-3-yl)piperidine difumarate A mixture of 6-fluoro-3-(4-piperidinyl)-1,2-benzisoxazole (3.05 g, 13.8 mmol), 3-dimethylaminopropyl chloride hydrochloride (3.4 g, 21 mmol), K$_2$CO$_3$ (6.2 g, 45 mmol), tetrabutylammonium hydrogen sulfate (phase transfer catalyst, 1.5 g) in acetonitrile (100 ml) and water (50 ml) was heated at 60° C. overnight. The aqueous phase was separated, and acetonitrile was removed at reduced pressure. The residue was extracted into DCM. The organic solution was washed with H$_2$O and brine, then dried with MgSO$_4$. The solvent was removed and the crude product (4.3 g) was treated with fumaric acid (1.58 g, 1.0 eq) in dilute ethanol. The crystals were collected (2.53 g), m.p.=192°–194° C. Recrystallization from ethanol yielded 2.08 g of white crystals, mp=194°–195° C.

Analysis: Calculated for C$_{17}$H$_{24}$FN$_3$O$_2$·C$_4$H$_4$O$_4$: 55.86%C, 6.00%H, 7.82%N; Found: 56.11%C, 5.94%H, 7.86%N.

EXAMPLE 138

(R)-(−)-3-[4-(6-Fluoro-1,2-benzisoxazol-3-yl)-1-piperidinyl]-2-methyl-1-propanol fumarate A mixture of 4-(6-fluoro-1,2-benzisoxazol-3-yl) piperidine (14.5 g, 65 mmol), K$_2$CO$_3$ (10 g, 72 mmol), (R)-(−)-3-bromo-2-methyl-1-propanol (10 g, 65.3 mmol), tetrabutylammonium hydrogen sulfate (1.27 g, phase transfer catalyst) in acetonitrile (300 ml) and H$_2$O (5 ml) was heated at reflux for 6 hours. The mixture was cooled and the solvent was removed on rotary evaporator. The residue was extracted into methylene chloride (DCM), and the insolubles were filtered. After concentration of the extract, the crude product was purified by flash chromatography over a silica gel column (SiO$_2$, 150 g; eluted with DCM, 1 l; 2% CH$_3$OH in DCM, 1.6 l). The material thus purified weighed 17 g (89%). The sample for testing was prepared by treatment of a sample (2.28 g) with fumaric acid (953 mg) in ethanol. The crystals formed slowly upon addition of isopropyl ether. These were collected and dried: weight 1.84 g, m.p.= 114°–115° C.

Analysis: Calculated for C$_{16}$H$_{21}$FN$_2$O$_2$·C$_4$H$_4$O$_4$: 58.82%C, 6.17%H, 6.86%N; Found: 58.48%C, 6.08%H, 6.57%N.

EXAMPLE 139

3-[1-[3-[4-(1-Methoxyethyl)-2-hydroxyphenoxyl] propyl]-4-piperidinyl]-6-fluoro-1,2-benzisoxazole A mixture of 6-fluoro-3-(4-piperidinyl)-1,2-benzisoxazole (5.7 g, 26.0 mmol), 4-(3-chloropropoxy)-3-hydroxy-α-methylbenzenemethanol (6.0 g, 26.0 mmol), NaHCO$_3$ (2.4 g, 28.6 mmol), KI(200 mg) and CH$_3$CN (150 ml) was stirred at reflux under N$_2$ for 17 hours. A TLC showed a trace of the alkylating side chain, therefore additional 6-fluoro-3-(4-piperidinyl)-1,2-benzisoxazole (0.6 g, 2.7 mmol) and NaHCO$_3$ (0.22 g, 2.6 mmol) was added and the reaction was refluxed 3 hours longer. The cooled reaction was concentrated and the residue was partitioned between EtOAc and H$_2$O. The EtOAc extract was washed with H$_2$O then brine and after drying with MgSO$_4$ the extract was concentrated to yield 11.9 g of a beige oil. The sample was purified by preparative HPLC (Water's Associates Prep LC/System 500 utilizing 2 silica gel columns and eluting with 5% MeOH—CH$_2$Cl$_2$). Concentration of later fractions afforded 4.2 g of 4-[3-[4-(6-fluoro-1,2-benzisoxazol-3-yl)-1-piperidinyl]propoxy]-3-hydroxy-,α-methylbenzenemethanol. Concentration of earlier fractions gave 4.0 g of a mixture of 4-[3-[4-(6-fluoro-1,2-benzisoxazol-3-yl)-1-piperidinyl]propoxy]-3-hydroxy-α-methylbenzenemethanol and 3-[1-[3-[4-(1-methoxyethyl)-2-hydroxy-phenoxy]-propyl]-4-piperidinyl]-6-fluoro-1,2-benzisoxazole (the latter was apparently formed by the reaction of the former with MeOH on silica gel). The mixture was dissolved in anhydrous Et$_2$O (330 ml) and anhydrous MeOH (100 ml) and ethereal HCl was added. After stirring 1.5 hours, anhydrous Et$_2$O was added and the resultant solid was collected and dried to yield 2.9 g of a mixture of the respective HCl salts. The solid was suspended in H$_2$O and was basified with NH$_4$OH. The aqueous mixture was extracted with CH$_2$Cl$_2$ and the extract was washed with H$_2$O, dried with MgSO$_4$ and concentrated to yield 2.7 g of a light beige oil. The oil was purified by preparative HPLC (Water's Associates Prep LC/System 500 using 2 silica gel columns and 3% MeOH—CH$_2$Cl$_2$ as eluent). Concentration of later fractions yielded 0.5 g of 4-[3-[4-(6-fluoro-1,2-benzisoxazol-3-yl)-1-piperidinyl]-propoxy]-3-hydroxy-α-methylbenzenemethanol. Concentration of earlier fractions gave an oil that solidified upon standing. The product was triturated with heptane and filtered to yield 1.2 g of a white powder. The compound was recrystallized from EtOH to provide 1.1 g (10%) of 3-[1-[3-[4-(1-methoxyethyl)-2-hydroxyphenoxy]propyl]-4-piperidinyl]-6-fluoro-1,2-benzisoxazole as clean white crystals m.p.=98°–100° C.

Analysis: Calculated for C$_{24}$H$_{29}$FN$_2$O$_4$: 67.27%C, 6.82%H, 6.54%N; Found: 67.18%C, 6.84%H, 6.54%N.

EXAMPLE 140

6-Fluoro-3-[1-[3-[(1H-indol-5-yl)oxy]propyl]-4-piperidinyl]-1,2-benzisoxazole

A mixture of 6-fluoro-3-(4-piperidinyl)-1,2-benzisoxazole (2.6 g, 11.8 mmol), K$_2$CO$_3$ (1.6 g, 11.6 mmol), KI (200 mg), 5-(3-chloropropoxy)indole (2.2 g, 10.5 mmol) and CH$_3$CN (100 ml) was stirred at reflux under N$_2$ for 18 hours. The cooled reaction was poured into H$_2$O and the aqueous mixture was extracted with EtOAc. The EtOAc extract was washed 2 times with H$_2$O, 2 times with brine and after drying with MgSO$_4$ the solvent was removed in vacuo to yield 5.1 g of a dark oil. The oil was purified by preparative HPLC (Water's Associates Prep LC/System 500, using 2 silica gel columns and 4% MeOH—CH$_2$Cl$_2$ as eluent) to afford 2.65 g (65%) of a beige solid. Recrystallization from ethanol gave 2.2 g (54%) of a beige powder, m.p.=118°–121° C.

Analysis: Calculated for C$_{23}$H$_{24}$FN$_3$O$_2$: 70.21%C, 6.15%H, 10.68%N; Found: 69.80%C, 6.21%H, 10.78%N.

EXAMPLE 141

6-Fluoro-3-[1-3-(isoquinol-5-yl) oxy]propyl]-4-piperidinyl]-1,2-benzisoxazole sesquifumarate A stirred mixture of 6-fluoro-3-(4-piperidinyl)-1,2-benzisoxazole (2.8 g, 13 mmol), 5-(3-chloropropoxy) isoquinoline (2.8 g, 13 mmol), K$_2$CO$_3$ (1.7 g) and CH$_3$CN (50 ml) was refluxed for 16 hours. The reaction was filtered and the filtrate was concentrated to an oil. The filter cake was treated with H$_2$O, and the aqueous suspension was extracted with CH$_2$Cl$_2$. The filtrate was also extracted with CH$_2$Cl$_2$, and the extracts were combined, washed (H$_2$O), dried (K$_2$CO$_3$) and concentrated to yield 5.4 g of a brown oil. The oil was purified by HPLC on silica gel columns, eluting with CH$_2$Cl$_2$/MeOH (5%), to afford 2.3 g of a yellow oil. The oil was dissolved in EtOAc and fumaric acid (0.66 g, 1 eq) was added. The mixture was refluxed briefly, and then stirred at ambient temperature for 16 hours. The resulting white solid was collected to afford 2.2 g of the fumarate salt. The compound was recrystallized from DMF to yield 1.4 g (18.6%) of the isoquinoline as a sesquifumarate m.p.= 213°–215° C.

Analysis: Calculated for C$_{30}$H$_{30}$FN$_3$O$_8$: 62.17%C, 5.22%H, 7.25%N; Found: 62.01%C, 5.11%H, 7.28%N.

EXAMPLE 142

6-Fluoro-3-[1-[3-[(1-H-indol-4-yl)oxy]propyl]-4-piperidinyl]-1,2-benzisoxazole

A mixture of 6-fluoro-3-(4-piperidinyl)-1,2-benzisoxazole (3.5 g, 16 mmol), K$_2$CO$_3$ (2.2 g, 16 mmol), KI (200 mg), 4-(3-chloropropoxy)indole (3.0 g, 14 mmol) and CH$_3$CN (100 ml) was stirred at reflux under N$_2$ for 7 hours and then at ambient temperature for 68 hours. Reflux was resumed for an additional 6 hours whereupon a TLC revealed incomplete reaction. K$_2$CO$_3$ (0.5 g, 4 mmol) was added and the reaction was stirred at reflux for 17 hours. The cooled reaction was poured into H$_2$O and the aqueous mixture was extracted with EtOAc. The organic extract was washed with H$_2$O and saturated NaCl and after drying over MgSO$_4$ the solvent was removed to afford 5.7 g of a beige solid. The product was purified by preparative HPLC (Water's Associates Prep LC/System 500 using 2 silica gel columns and 4% MeOH—CH$_2$Cl$_2$ as eluent) to yield 3.4 g (61%) of a beige solid. Two consecutive recrystallizations from EtOH provided 2.3 g (41%) of a white powder, m.p.=129°–131° C.

Analysis: Calculated for C$_{23}$H$_{24}$FN$_3$O$_2$: 70.21%C, 6.15%H, 10.68%N; Found: 69.90%C, 6.15%H, 10.65%N.

EXAMPLE 143

6-Fluoro-3-[1-[3-[(6-methoxy-1H-indol-5-yl)oxy] propyl]-4-piperidinyl]-1,2-benzisoxazole hemifumarate A mixture of 6-fluoro-3-(4-piperidinyl)-1,2-benzisoxazole (3.0 g, 14 mmol), 5-(3-chloropropoxy)-6- methoxyindole (3.0 g, 13 mmol), K$_2$CO$_3$ (2.1 g, 14 mmol), KI (200 mg) and CH$_3$CN (150 ml) was stirred at reflux under N$_2$ for 48 hours. The cooled reaction was poured into H$_2$O and the aqueous mixture was extracted with EtOAc. The EtOAc extract was washed with H$_2$O and brine and was dried with MgSO$_4$. Removal of the solvent in vacuo gave 5.6 g of a dark oil. The oil was purified by preparative HPLC (Water's Associates Prep LC/System 500 using 2 silica gel columns and 2% Et$_2$NH-EtOAC as eluent) to yield 2.5 g (47%) of a beige solid. Recrystallization from EtOH afforded 2.0 g of an off white powder. A 1.8 g (4 mmol) sample was dissolved in warm EtOAc and fumaric acid (0.5 g, 4 mmol) was added. The reaction was stirred at ca 40° C. for 30 minutes and was then allowed to gradually cool to ambient temperature. The resultant hemifumarate salt was collected and dried to yield 2.0 g. The product was recrystallized from EtOH to provide 1.5 g (25%) of a light beige powder m.p.=186°–188° C.

Analysis: Calculated for C$_{26}$H$_{28}$FN$_3$O$_5$: 64.84%C, 5.87%H, 8.73%N; Found: 64.22%C, 5.85%H, 8.55%N.

EXAMPLE 144

1-[4-[3-[4-(6-Fluoro-1,2-benzisothiazol-3-yl)-1-piperidinyl]propoxy]-3-hydroxyphenyl]ethanone A mixture of 6-fluoro-3-(4-piperidinyl)-1,2-benzisothiazole (2.4 g, 10.1 mmol), 1-[4-(3-chloropropoxy)-3-hydroxyphenyl]ethanone (2.5 g, 11.1 mmol), NaHCO$_3$, (0.94 g, 11.1 mmol), KI (100 mg) and CH$_3$CN (100 ml) was stirred at reflux under N$_2$ for 65 hours. The cooled reaction was poured into H$_2$O and the aqueous mixture was extracted with EtOAc. The EtOAc extract was washed with H$_2$O (1×) and brine (3×) and after drying with MgSO$_4$ the solvent was evaporated to give 4.2 g of a dark solid. Three consecutive recrystallizations from EtOH provided 2.1 g (48%) of glittery beige crystals m.p.=135°–137° C.

Analysis: Calculated for C$_{23}$H$_{25}$FN$_2$O$_3$S: 64.47%C, 5.88%H, 6.54%N; Found: 64.44%C, 5.69%H, 6.29%N.

EXAMPLE 145

4-[3-[4-(6-Fluoro-1,2-benzisothiazol-3-yl)-1-piperidinyl]propoxy]-3-methoxy-α-methylbenzenemethanol To a stirred solution of 1-[4-[3-[4-(6-fluoro-1,2-benzisothiazol-3-yl)-1-piperidinyl]propoxy]-3-methoxyphenyl]ethanone (4.1 g, 9.3 mmol) in 60 ml MeOH-THF (1:1) under N$_2$ at ambient temperature, NaBH$_4$ (0.386 g, 10.2 mmol) was added portionwise. After complete addition, the reaction was stirred for 3.5 hours and was concentrated to yield a white gum. This was triturated with H$_2$O (2×) and the aqueous fraction was decanted away. Residual water was removed under high vacuum to afford 5.0 g of a white powder. The compound was taken up in boiling toluene and the insolubles were filtered away. Concentration of the toluene filtrate afforded 3.8 g of a beige solid. Purification via preparative HPLC (Water's Associates prep LC/System 500, using 2 silica gel columns and 2% Et$_2$NH-EtOAc) provided 2.7 g of a light beige solid. The product was recrystallized from EtOAc to afford 1.7 g (42%) of a pure white powder, m.p.=113°–115° C.

Analysis: Calculated for C$_{24}$H$_{29}$FN$_2$O$_3$S: 64.84%C, 6.58%H, 6.30%N; Found: 64.85%C, 6.44%H, 6.19%N.

EXAMPLE 146

(R)-(–)-3-[4-(6-Fluoro-1,2-benzisoxazol-3-yl)-1-piperidinyl]-2-methyl-1-propyl acetate fumarate To a mixture of (R)-(–)-3-[4-(6-fluoro-1,2-benzisoxazol-3-yl)-1-piperdinyl]-2-methyl-1-propanol (3.2 g, 11 mmol), triethylamine (3.2 g, 11 mmol) in DCM (100 ml), acetyl chloride (890 mg, 11.3 mmol) was added dropwise at 0° C. The mixture was stirred at room temperature for 4.5 hours. The solvent was removed on a rotary evaporator. The triethylamine HCl salt was filtered off using a small amount of DCM. The crude product was dissolved in DCM was purified by flash chromatography over a silica gel column (SiO$_2$, 30 g; eluted with DCM and 1% CH$_3$OH in DCM). The oil, thus purified, weighed 2.11 g (58%). This oil was treated with a solution of fumaric acid (695 mg, 1.0 eq.) in ethanol to give the fumarate salt. Recrystallization from ethanol and isopropyl ether again yielded white crystals, 2.09 g. m.p.=118°–120° C.

Analysis: Calculated for C$_{18}$H$_{23}$FN$_2$O$_3$·C$_4$H$_4$O$_4$: 58.66%C, 6.04%H, 6.22%N; Found: 58.53%C, 5.76%H, 8.91%N.

EXAMPLE 147

1-(R)-(–)-[4-[3-(6-Fluoro-1,2-benzisoxazol-3-yl)-1-piperidinyl]-2-methyl-1-propoxyl-3-methoxyphenyl]ethanone fumarate (A) (R)-(–)-3-[4-(6-fluoro-1,2-benzisoxazol-3-yl)-1-piperidinyl]-2-methyl-1-propyl methanesulfonate To a mixture of (R)-(–)-3-[4-(6-fluoro-1,2-benzisoxazol-3-yl)-1-piperidinyl]-2-methyl-1-propanol (7.26 g, 24.8 mmol), triethylamine (3 ml, 30 mmol) in methylene chloride (DCM, 120 ml), methanesulfonyl chloride (3.13 g, 27.3 mmol) was added dropwise at 0° C. The mixture was stirred at room temperature for 1 hour., then concentrated down to a crude mixture. Triethylamine hydrochloride salt was removed by filtration with DCM/ether as solvent. The crude oily mixture was purified with a flash chromatography column (SiO$_2$, 90 g; eluted with DCM). The colorless oil, which is the methanesulfonate ester, weighed 6.48 g (70%), and was used directly in the following step.

(B) 1-(R)-(–)-[4-[3-[4-(6-fluoro-1,2-benzisoxazol-3-yl)-1-piperidinyl]-2-methylproproxy]-3-methoxyphenyl] ethanone fumarate A solution of the above methanesulfonate (6.48 g, 175 mmol) in DMF (5 ml) was added in one portion to an aged (hour) cold mixture of acetovanillone (4.13 g, 24.9 mmol) and sodium hydride (670 mg, 26.5 mmol) in DMF (40 ml) at 0° C. The resulting mixture was warmed to ~50° C. briefly and stirred at room temperature for 16 hours. The mixture was extracted into DCM (500 ml) and washed twice with water, then brine. The organic solution was dried over MgSO$_4$ and concentrated to an oil. This crude mixture was purified twice by flash chromatography over a silica gel column. The material thus purified weighed 5.37 g. The fumarate salt was prepared by treatment of purified oil with fumaric acid (1.0 eq.) in ethanol and ether. Slightly off-white crystals were collected: 3.76 g (38%), m.p.=141°–142° C.

Analysis: Calculated for C$_{25}$H$_{29}$FN$_2$O$_4$·C$_4$H$_4$O$_4$: 62.58%C, 5.98%H, 5.03%N; Found: 62.52%C, 5.75%H, 4.96%N.

EXAMPLE 148

3-[4-(6-Fluoro-1,2-benzisoxazol-3-yl)-1-piperidinyl]-2,2-dimethyl-1-propanol fumarate A mixture of 4-(6-fluoro-1,2-benzisoxazol-3-yl) piperidine (3.0 g, 13.6 mmol), K$_2$CO$_3$ (12.5 g, 17.5 mmol), 3-bromo-2,2-dimethyl-1-propanol (3 g, 21 mmol, 1.5 eq.), tetra-butylammonium hydrogen sulfate (1 g, phase transfer catalyst) in water (5 ml) and acetonitrile (150 ml) was heated at reflux for 43 days. TLC showed a small spot for the expected product. The mixture was diluted with EtOAc (400 ml) and washed with brine. The organic solution was dried and concentrated to a dark brown mixture. The crude mixture was purified carefully by flash chromatography (SiO$_2$, 95 g to afford the dried pure product; 260 mg, (6%) as an oil. This oil was converted to the fumarate salt by treatment with fumaric acid (98.5 mg, 1.0 eg.) in ethanol. Recrystallization from ethanol:ether yielded 210 mg of white crystals, m.p.=144°–145°

EXAMPLE 149

1-(S)-(+)-[4-[3-[4-(6-Fluoro-1,2-benzisoxazol-3-yl)-1-piperidinyl]-2-methyl-1-propoxy]-3-methoxyphenyl]ethanone fumarate (A) (S)-(+)-3-[4-(6-fluoro-1,2-benzisoxazol-3-yl)-1-piperidinyl]-2-methyl-1-propyl methanesulfonate To a mixture of (S)-(+)-3-[4-(6-fluoro-1,2-benzisoxazol-3-yl)-1-piperidinyl]-2-methyl-1-propanol (8.8 g, 30 mmol), triethylamine (3.2 g, 32 mmol) in dichloromethane (DCM, 150 ml), methanesulfonyl chloride (4 g, 35 mmol) was added dropwise at 0° C. over 10 minutes. The mixture was stirred at room temperature for 1 hour, then concentrated. Triethylamine HCl salt was filtered off with a little DCM as solvent. The crude oil was purified with a flash chromatography column (SiO$_2$, 90 g; eluted with DCM). The colorless oil thus purified weighed 5.28 g (47%) was used immediately in the following step.

(B) 1-(S)-(+)-[4-[3-[4-(6-fluoro-1,2-benzisoxazol-3-yl)-1-piperidinyl]-2-methyl-propoxy]-3-methoxyphenyl]ethanone fumarate A solution of (S)-(+)-3-[4-(6-fluoro-1,2-benzisoxazol-3-yl)-1-piperidinyl]-2-methyl-1-propyl methanesulfonate (5.28 g, 14.27 mmol) in dimethylformamide (DMF, 10 ml) was added in one portion to an aged (1 hour) cold mixture of acetovanillone (3.55 g, 33.1 mmol) and sodium hydride (530 mg, 22 mmol) in DMF (35 ml) at 0° C. under N$_2$. The reaction was stirred overnight (16 hours.) at room temperature. The mixture was diluted with EtOAc and washed with H$_2$O (2 times) and brine. The organic solution was dried and concentrated to an oil (9.4 The crude oil mixture was purified by flash chromatography (SiO$_2$, 60 g). The oil purified weighed 4.3 g, (68%) and was converted to the fumarate salt (fumaric acid, 1.13 g) in ethanol. Recrystallization from ethanol gave 1.36 g of white crystals, m.p.=163°–165° C.

Analysis: Calculated for C$_{25}$H$_{29}$FN$_2$O$_4$·C$_4$H$_4$O$_4$: 62.58%C, 5.98%H, 5.03%N; Found: 62.40%C, 5.84%H, 4.92%N.

EXAMPLE 150

2-[4-(6-Fluoro-1,2-benzisoxazol-3-yl)—piperidinyl] ethyl thioacetate fumarate

To a stirred solution of 0° C. of triphenlyphosphine (13.3 g, 50 mmol) in THF (150 ml), diisopropylazodicarboxylate (10.2 ml, 50 mmol) was added dropwise. After stirring at 0° C. for 0.5 hour, a solution of 6-fluoro-3-[1-(2-hydroxyethyl)-4-piperidinyl]-1,2-benzisoxazole (8.5 g, 32 mmol) and thioacetic acid (10.2 ml, 0.14 mol) in DMF (35 ml) was added dropwise. The reaction was then stirred at ambient temperature for 16 h, and then it was concentrated at 60° C., under vacuum, to yield a red oil. The oil was triturated with H$_2$O, and then it was flash chromatographed on silica gel, eluting first with CH$_2$Cl$_2$ and then with 10% MeOH-CH$_2$Cl$_2$. The appropriate fractions were concentrated to yield 16.5 g of an oil. The oil was triturated with Et$_2$O and the solid (reaction by-products) that formed was removed by filtration. The filtrate was treated with fumaric acid (4.3 g), and 7.2 g of the fumarate salt of the desired product was obtained as an off white solid. The salt was recrystallized from EtOAc and then twice from EtOH to afford 1.0 g (7.0%) of the thioacetate as an off white solid, m.p.=118°–120° C.

EXAMPLE 151

N-[2-[4-(6-Fluoro-1,2-benzisoxazol-3-yl)-1-piperidinyl]ethyl]-4,5-dichlorophthalimide A mixture of 2-[4-[(6-fluoro-1,2-benzisoxazol-3-yl)-1-piperidinyl]ethyl]amine (2.83 g, 10.7 mmol) and 4,5-dichlorophthalic anhydride (2.56 g, 11.93 mmol, 1.1 eq) in methylene chloride (100 ml, DCM) was stirred for 2 h, white solids precipitated and the TLC showed disappearance of the starting material. The solvent was removed, and the crude solid was loaded onto a flash chromatography column (28 g, SiO$_2$, sorbsil C-30, eluted with 1% MeOH in DCM; 0.5% of NH$_4$OH was added towards the end of elution). The material thus purified weighed 2.26 g as white crystals. Recrystallization twice from a large volume of hot ethanol (400 ml) yielded 1.57 g of white shining crystals, m.p.=132°–134° C.

Analysis: Calculated for C$_{22}$H$_{18}$FN$_3$O$_3$: 57.16%C, 3.92%H, 9.09%N; Found: 57.13%C, 3.63%H, 8.93%N.

EXAMPLE 152

N-[2-[4-(6-Fluoro-1,2-benzisothiazol-3-yl)-1-piperidinyl]ethyl]phthalimide hydrochloride.

A mixture of 6-fluoro-3-(4-piperidinyl)-1,2-benzisothiazole (3.3 g, 14 mmol), 2-bromoethylphthalimide (3.7 g, 14.7 mmol), K$_2$CO$_3$ (2.0 g) and CH$_3$CN (85 ml) was stirred and refluxed for 2.5 hours. The reaction was poured into H$_2$O and a white precipitate resulted, which was collected to afford 2.0 g of product. The aqueous filtrate was extracted with CHCl$_3$, the extract washed (H$_2$O), dried (MgSO$_4$) and was concentrated to afford 3.5 g of an off-white solid. Upon trituration of this solid with acetone, an additional 2.0 g of product was realized. The two samples were combined and suspended in MeOH (50 ml), and ethereal HCl was added until the reaction mixture was acidic. After stirring for 1 hour at ambient temperature, Et$_2$O (50 ml) was added to afford 3.7 g of the hydrochloride salt. The salt was recrystallized from MeOH-Et$_2$O to yield 2.3 g (37%) of the compound as a white solid, m.p=271°–273° C.

Analysis: Calculated for C$_{22}$H$_{20}$FN$_3$O$_2$S·HCl: 59.25%C, 4.75%H, 9.42%N; Found: 58.99%C, 4.60%H, 9.33%N.

EXAMPLE 153

N-[2-[4-(6-Fluoro-1,2-benzisoxazol-3-yl)-1-piperidinyl]ethyl]-3,6-dichlorophthalimide A mixture of 2-[4-[(6-fluoro-1,2-benzisoxazol-3-yl)-1-piperidinyl]ethyl]amine (2.44 g, 9.24 mmol) and 3,6-dichlorophthalic anhydride (2.01 g; 9.27 mmol) in dichloromethane (DCM,50 ml) was stirred at room temperature for 1 hour. White precipitates formed and the TLC of the reaction mixture showed that there was no starting amine remaining. The solvent was stripped down and the white solids which were poorly soluble in DCM were loaded onto a flash chromatography column, (SiO$_2$; 30 g) and the column was eluted with a solution of 1% CH$_3$OH in DCM. The desired product thus obtained weighed 2.29 g (54%). Recrystallization from hot ethanol yielded 2.15 g of white crystals, m.p.=163°–164° C.

Analysis: Calculated for $C_{22}H_{18}Cl_2FN_3O_3$: 57.16%C, 3.92%H, 9.09%N; Found: 57.16%C, 3.64%H, 9.13%N.

EXAMPLE 154

N-[2-[4-(6-Fluoro-1,2-benzisoxazol-3-yl)-1-piperidinyl]ethyl]-4-chlorophthalimide A mixture of 2-[4-[(6-fluoro-1,2-benzisoxazol-3-yl)-1-piperdinyl]ethyl]amine (2.13 g, 8.07 mmol), 4-chlorophthalic acid monosodium salt (2.2 g, 10 mmol) and dicyclohexylcarbodiimide (DCC, 4.25 g, 20.6 mmol) in acetonitrile (150 ml) was stirred at room temperature for 24 hours. The cloudy mixture was filtered, then the solvent was stripped down. The residue was partitioned between water and dichloromethane (DCM). The DCM solution was washed with brine and dried over $MgSO_4$. The solvent was removed. The crude product was purified on a flash chromatography column ($SiO_2$, 35 g; eluted with DCM, and 1% $CH_3OH$ in DCM). The desired product thus obtained weighed 1.3 g. Recrystallization from ethanol yielded 590 mg as white crystals, m.p.=170°–171° C.

Analysis: Calculated for $C_{22}H_{19}FN_3O_3$: 61.76%C, 4.48%H, 9.82%N; Found: 61.87%C, 4.93%H, 9.89%N.

EXAMPLE 155

N-[2-[4-(6-Fluoro-1,2-benzisoxazol-3-yl)-1-piperidinyl]ethyl]-3-fluorophthalimide A mixture of 2-[4-[(6-fluoro-1,2-benzisoxazol-3-yl)-1-piperidinyl]ethyl]amine (2.37 g, 8.98 mmol), 3-fluorophthalic acid (1.82 g, 9.9 mmol) and dicyclohexylcarbodiimide (DCC, 5.5 g, 26.7 mmol, 2.6 eq) in dichloromethane (DCM, 250 ml) was stirred at room temperature for 18 hours. The solids were filtered off. The organic solution was concentrated down. The residue was purified on a flash chromatography column ($SiO_2$, 50 g; eluted with 1.4 liter; 2–6% $CH_3OH$:DCM, 1 liter). The desired product thus obtained weighed 2.64 g (71%) as an off-white solid. Recrystallization from hot ethanol gave 1.41 g of white crystals, m.p.=142°–143° C.

Analysis: Calculated for $C_{22}H_{19}F_2N_3O_3$: 64.22%C, 4.66%H, 10.21%N; Found: 64.11%C, 4.70%H, 10.14%N.

EXAMPLE 136

N-[2-[4-(6-Fluoro-1,2-benzisoxazol-3-yl)-1-piperidinyl]ethyl]-4-fluorophthalimide A mixture of 2-[4-[(6-fluoro-1,2-benzisoxazol-3-yl)-1-piperidinyl]ethyl]amine (3.2 g, 12 mmol), 4-fluorophthalic anhydride (freshly prepared according to the procedure of Markezich, U.S. Pat. No. 3,956,321, 1976; 2.0 g, 12 mmol) and dicyclohexylcarbodiimide (DCC, 2.48 g, 12 mmol) in chloroform (100 ml) was stirred at room temperature for 18 hours. The insolubles were filtered off. The solution was loaded onto a flash chromatography column ($SiO_2$, 45 g) then was eluted with a solution of 2% methanol in methylene chloride. The fractions containing the desired product were pooled and concentrated to yield 2.9 g of white solid. The material was converted to a hydrochloride salt by treatment with a solution of hydrochloride in ethanol. Recrystallization from ethanol gave the pure sample, 1.01 g, m.p. 253°–255° C.

Analysis: Calculated for $C_{22}H_{19}FN_3O_3 \cdot HCl$: 59.00%C, 4.50%H, 9.38%N; Found: 58.81%C, 4.38%H, 9.48%N.

EXAMPLE 157

N-[2-[4-(6-Fluoro-1,2-benzisoxazol-3-yl)-1-piperidinyl]ethyl]-4-methylphthalimide A mixture of 2-[4-([6-fluoro-1,2-benzisoxazol-3-yl)-1-piperidinyl]ethyl]amine (2.44 g, 9.24 mmol), 4-methylphthalic anhydride (1.76 g, 10.8 mmol) and dicyclohexylcarbodiimide (2.1 g, 1.0 mmol) in dichloromethane (DCM, 100 ml) was stirred at room temperature for 2 hours. The insolubles were filtered off. The DCM solution was concentrated to a crude solid. This was purified on a flash chromatography column (35 g, $SiO_2$, Sorbsil-C-30; eluted with 1% $CH_3OH$ in 99% DCM). The material thus purified weighed 1.0 g (26%) as a white solid. Recrystallization from hot ethanol gave 665 mg of crystals, m.p.=138°–140° C.

Analysis: Calculated for $C_{23}H_{22}FN_3O_3$: 67.80%C, 5.44%H, 10.31%N; Found: 67.67%C, 5.48%H, 10.30%N.

EXAMPLE 158

N-[2-[4-(6-Fluoro-1,2-benzisoxazol-3-yl)-1-piperidinyl]ethyl]-4-methoxyphthalimide A stirred mixture of 2-[4-[(6-fluoro-1,2-benzisoxazol-3-yl)-1-piperidinyl]ethyl]amine (2.63 g, 10 mmol) and 4-methoxyphthalic anhydride (1.78 g, 10 mmol) in dichloromethane (100 ml) is stirred at room temperature for 3 hours. The solvent is then removed under reduced pressure and the residual material is purified by flash chromatography. The product is purified further by recrystallization to give N-[2-[4-(6-fluoro-1,2-benzisoxazol-3-yl)-1-piperidinyl]ethyl]-4-methoxy-phthalimide.

EXAMPLE 159

N-[2-[4-(6-Fluoro-1,2-benzisoxazol-3-yl)-1-piperidinyl]ethyl]-4-nitrophthalimide hydrochloride A mixture of 2-[4-[(6-fluoro-1,2-benzisoxazol-3-yl)-1-piperidinyl]ethyl]amine (2.9 g, 11 mmol), 4-nitrophthalic anhydride (2.33 g, 12.1 mmol) and dicyclohexylcarbodiimide (2.25 g, 11 mmol) in dichloromethane (DCM, 150 ml) was stirred at room temperature for 16 hours. The mixture was filtered. The brownish solution was loaded onto a flash chromatography column, ($SiO_2$, 35 g; eluted with DCM, then 2% $CH_3OH$ in DCM). The desired product thus obtained weighed 2.35 g (49%) as a pale white solid, m.p. 191°–193° C. This solid was converted to the hydrochloride salt by treatment with an HCl solution in ethanol to yield 1.54 g, m.p.=250°–253° C. dec.

Analysis: Calculated for $C_{22}H_{19}FN_4O_5 \cdot HCl$: 55.64%C, 4.25%H, 11.90%N; Found: 55.81%C, 4.08%H, 11.67%N.

EXAMPLE 160

4-[4-(6-Fluoro-1,2-benzisoxazol-3-yl)-1-piperidinyl]-2-methyl-2-hydroxybutane fumarate, To a solution of ethyl 3-[4-(6-fluoro-1,2-benzisoxazol-3-yl)-1-piperidinyl]propionate (3.21 g, 10 mmol) in tetrahydrofuran (THF, 100 ml), was added methylmagnesium bromide (10 ml, 30 mmol, 3M solution in ether) dropwise over 15 minutes at room temperature under $N_2$. The resulting mixture was stirred for 16 hours. The mixture was slowly hydrolyzed with aqueous $NH_4Cl$ solution. The THF solution was diluted with EtOAc (300 ml), then was washed with water and brine. The organic solution was separated and dried over $MgSO_4$. After removal of solvent, the crude product was purified by flash chromatography (25 g, SiO$_2$; eluted with 1 CH$_3$OH:99 DCM). The material thus purified weighed 2.36 g (77%) as white crystals. This was converted to the fumarate salt by treatment with fumaric acid (895 mg) in ethanol. Recrystallization from ethanol yielded white crystals, 2.47 g, m.p.=156°–158° C.

Analysis: Calculated for C$_{17}$H$_{23}$FN$_2$O$_2$·C$_4$H$_4$O$_4$: 59.70%C, 6.44%H, 6.63%N; Found: 59.40%C, 6.27%H, 6.28%N.

EXAMPLE 161

Ethyl 3-[4-(6-fluoro-1,2-benzisoxazol-3-yl)-1-piperidinyl]propionate fumarate

A mixture of 4-(6-fluoro-1,2-benzisoxazol-3-yl) piperidine (5 g, 22.7 mmol), K$_2$CO$_3$ (3.8 g, 27.5 mmol) and ethyl bromopropionate (5 g, 27.6 mmol, 1.2 eq) in acetonitrile (200 ml) was heated at reflux for 16 hours. The mixture was cooled and filtered. The solvent was removed, and the residue was purified on a flash chromatography column (60 g, SiO$_2$, eluted with DCM). The material thus purified weighed 7.27 g (83%). The fumarate salt was prepared by treatment of the free base (2.17 g) with fumaric acid (820 mg, 1.0 eq) in ethanol. Recrystallization from ethanol yielded 2.49 g of white crystals, m.p.=135°–136° C.

Analysis: Calculated for C$_{17}$H$_{21}$FN$_2$O$_3$·C$_4$H$_4$O$_4$: 57.79%C, 5.77%H, 6.42%N; Found: 57.86%C, 5.67%H, 6.30%N.

EXAMPLE 162

2,3-dihydro-2-[2-[4-(6-Fluoro-1,2-benzisoxazol-3-yl)-1-piperidinyl]ethyl]-3-hydroxy-1H-isoindol-1-one To a suspension of N-[2-[4-(6-fluoro-1,2-benzisoxazol-3-yl)-1-piperidinyl-ethyl]phthalimide (7.8 g, 19.8 mmol) in methanol (250 ml) and DCM (30 ml) was added NaBH$_4$ (1.7 g, 45.5 mmol) at room temperature under nitrogen. After stirring for 0.5 hours the homogeneous reaction mixture was concentrated. The remaining solid was purified on a flash chromatography column (SiO$_2$, 1:1 EtOAc/DCM, increased to 10% MeOH) to give 7.0 g (90%) of the desired product as a solid which was recrystallized from EtOAc, m.p.=172°–173° C.

Analysis: Calculated for C$_{22}$H$_{22}$FN$_3$O$_3$: 66.82%C, 5.61%H, 10.63%N; Found: 66.63%C, 5.52%H, 10.51%N.

EXAMPLE 163

2,3-dihydro-2-[2-[4-(6-Fluoro-1,2-benzisoxazol-3-yl)-1-piperidinyl]ethyl]-1H-isoindol-1-one To 2-[2-[4-(6-fluoro-1,2-benzisoxazol-3-yl)-1-piperidinyl]ethyl]-2,3-dihydro-3-hydroxy-1H-isoindol-1-one (2.2 g, 5.6 mmol) was added a solution of trifluoroacetic acid (11.0 ml) in dichloromethane (30 ml) at room temperature, under nitrogen. Triethylsilane (1.5 ml) was then added and the reaction mixture was allowed to stir for 18 hours at which time it was poured into a NaHCO$_3$ (sat.). The layers were separated and the aqueous phase was extracted with DCM (3×). The combined organics were washed with brine and dried (Na$_2$SO$_4$). Filtration and concentration gave the crude product as a solid which was recrystallized from EtOAc. to give 1.6 g (79%) of the desired product as a white solid, m.p.=166°–168° C.

Analysis: Calculated for C$_{22}$H$_{22}$FN$_3$O$_2$: 69.64%C, 5.84%H, 11.07%N; Found: 69.37%C, 5.70%H, 11.00%N.

EXAMPLE 164

(S)-3-[4-(6-Fluoro-1,2-benzisoxazol-3-yl)-1-piperidinyl]-2-methylpropyl-methyl carbamate To a solution of 2-[2-[4-(6-fluoro-1,2-benzisoxazol-3-yl)-1-piperidinyl]ethyl]-2,3-dihydro-3-hydroxy-1H-isoindol-1-one (3.1 g, 10.6 mmol) in dry THF (120 ml) was added methyl isocyanate (0.66 ml, 11.1 mmol) followed by milled K$_2$CO$_3$ (2.2 g, 15.9 mmol) at room temperature, under nitrogen. The reaction mixture was stirred for 3 days at which time it was filtered through a pad of Celite and the solids washed with EtOAc. The combined filtrates were concentrated to give the crude product which was purified via flash column chromatography (silica gel, 2% Et$_3$N/EtOAc). The product containing fractions were concentrated to give 2.7 g (73%) of the desired product as an oil which solidified on standing. Recrystallization from EtOAc/pet.ether gave the product as a solid, m.p.=72°–74° C.

Analysis: Calculated for C$_{18}$H$_{24}$FN$_3$O$_3$: 61.88%C, 6.92%H, 12.03%N; Found: 61.82%C, 7.02%H, 11.77%N.

EXAMPLE 165

(S)-3-[4-(6-Fluoro-1,2-benzisoxazol-3-yl)-1-piperidinyl]-2-methylpropyl decanoate fumarate To a solution of 2-[2-[4-(6-fluoro-1,2-benzisoxazol-3-yl)-1-piperidinyl]ethyl]-2,3-dihydro-3-hydroxy-1H-isoindol-1-one (3.2 g, 10.9 mmol) in DCM (110 ml) was added decanoyl chloride (2.3 ml, 10.9 mmol) at 0° C., under nitrogen. The reaction mixture was stirred for 1.25 hours (0° C.) at which time it was poured into NaHCO$_3$ (sat.). The layers were separated and the aqueous phase was extracted with DCM (2×). The combined organics were dried, filtered and concentrated to give the crude product which was purified via flash column chromatography (silica gel, 30% EtOAc/DCM). The product containing fractions were concentrated to give 3.4 g (70%) of the desired product as a yellow oil. The fumarate salt was prepared in ethanol with fumaric acid (1.05 eq.). The white salt was filtered and washed with isopropyl ether, m.p. 110°–112° C.

Analysis: Calculated for C$_{26}$H$_{39}$FN$_2$O$_3$·C$_4$H$_4$O$_4$: 64.04%C, 7.70%H, 4.98%N; Found: 64.07%C, 7.75%H, 4.90%N.

EXAMPLE 166

(S)-6-Fluoro-3-[1-(3-methoxyphenyl-2-methylpropyl)-4-piperidinyl]-1,2-benzisoxazole To a solution of 2-[2-[4-(6-fluoro-1,2-benzisoxazol-3-yl)-1-piperidinyl]ethyl]-2,3-dihydro-3-hydroxy-1H-isoindol-1-one (3.3 g, 11.3 mmol) in dry THF (120 ml) was added potassium tert-butoxide (1.9 g, 16.9 mmol) followed by dimethyl sulfate (1.2 ml, 11.9 mmol) at room temperature, under nitrogen. The reaction mixture was stirred for 21 hours at which time it was filtered through a pad of Celite and the solids washed with EtOAc. The combined filtrates were concentrated to give the crude product. Purification via flash column chromatography (silica gel, 0–20% acetone/DCM) afforded 1.6 g (46%) of the desired product as a solid, m.p.=40°–42° C.

Analysis: Calculated for C$_{17}$H$_{23}$FN$_2$O$_2$: 66.65%C, 7.57%H, 9.14%N; Found: 66.49%C, 7.48%H, 9.12%N.

EXAMPLE 167

(±)-6-Fluoro-3-[1-(3-hydroxybutyl)-4-piperidinyl]-1,2-benzisoxazole

Racemic 3-hydroxybutyl tosylate was prepared in a manner described by Ferreira et al., Tetrahedron, 46, pp.

6311–6318, (1990). To a solution of the racemic tosylate (9.2 g, 37.7 mmol) in acetonitrile (190 ml) was added 6-fluoro-3-(4-piperidinyl)-1,2-benzisoxazole (8.3 g, 37.7 retool) followed by milled potassium carbonate (7.8 g, 56.6 mmol) at room temperature under nitrogen. The reaction mixture was warmed to reflux for 4.5 hours and allowed to cool to room temperature. The solids were removed via filtration through a pad of Celite and were washed with EtOAc. The combined filtrates were concentrated to give the crude product. Purification via preparative HPLC (silica gel, 10% MeOH/EtOAc) afforded 6.3 g (57%), m.p.=100°–102° C.

Analysis: Calculated for $C_{16}H_{21}FN_2O_2$: 65.73%C, 7.24%H, 9.58%N; Found: 65.59%C, 7.30%H, 9.52%N.

EXAMPLE 168

(S)-6-Fluoro-3-[1-(3-hydroxy-2-methylpropyl)-4-piperidinyl]-1,2-benzisothiazole fumarate A mixture of 6-fluoro-3-(4-piperidinyl)-1,2-benzisothiazole (4.6 g, 20 mmol), (R)-(–)-3-bromo-2-methyl-1-propanol (3.0 g, 20 mmol), $K_2CO_3$ (2.7 g, 20 mmol), tetrabutylammonium sulfate (0.058 g), $CH_3CN$ (95 ml) and $H_2O$ (19 ml) was stirred and refluxed for 4.5 hours. After standing at ambient temperature for 16 hours, the reaction was poured into $H_2O$, and subsequent extractive workup of the aqueous with EtOAc yielded 6.8 g of a partially solidified oil. The product was purified by flash chromatography on silica gel, eluting the column with $CH_2Cl_2$, then 2% MeOH—$CH_2Cl_2$ and finally 5% MeOH—$CH_2Cl_2$. Concentration of the appropriate fractions yielded 5.2 g of a waxy solid. The solid was dissolved in acetone and fumaric acid (1.9 g, 1.0 eq) was added and the reaction briefly heated at reflux. The resultant fumarate salt precipitated from solution yielding 4.8 g of white solid. The compound was recrystallized from acetonitrile to yield 3.1 g (36%) of the alcohol as a white solid, m.p.=151°–153° C.

Analysis: Calculated for $C_{16}H_{21}FN_2OS \cdot C_4H_4O_4$: 56.59%C, 5.94%H, 6.60%N; Found: 56.31%C, 5.96%H, 6.48%N.

EXAMPLE 169

N-[2-[4-(6-Fluoro-1,2-benzisoxazol-3-yl)-1-piperidinyl]ethyl]-3,6-difluorophthalimide A mixture of 2-[4-[(6-fluoro-1,2-benzisoxazol-3-yl)-1-piperidinyl]ethyl]amine (1.53 g, 5.8 mmol), 3,6-difluorophthalic anhydride (1.0 g, 5.43 mmol) and dicyclohexylcarbodiimide (DCC, 1.84 g, 8.9 mmol) in methylene chloride (DCM, 100 ml) was stirred for 6 hours, and then left standing overnight at room temperature The solids were filtered off. The solution was loaded onto a silica gel column (35 g, Sorbsil C-30), then eluted with a mixture of methanol and DCM (1%–2%). The fractions containing the desired product were pooled and concentrated to give 1.23 g of white solid. Recrystallization from DCM and hot ethanol yielded 1.03 g (44.5%) of white crystals, m.p.=144°–145° C.

Analysis: Calculated for $C_{22}H_{18}F_3N_3O_3$: 61.54%C, 4.23%H, 9.79%N; Found: 61.63%C, 3.83%H, 9.77%N.

EXAMPLE 170

N-[2-[4-(6-Fluoro-1,2-benzisoxazol-3-yl)-1-piperidinyl]ethyl]-1,2,3,4-tetrahydro-isoquinoline-1,3-dione A mixture of 2-[4-[(6-fluoro-1,2-benzisoxazol-3-yl)-1-piperidinyl]ethyl]amine (2.45 g, 9.28 mmol), homophthalic anhydride (1.78 g, 10.9 mmol) and DCC (2.2 g, 10.7 mmol) in $CHCl_3$ (100 ml) was stirred at room temperature for 3.5 hours. The insolubles were filtered off. The solution was loaded onto a flash chromatography column (Sorbsil C-30, 40 g), eluted with DCM (1.5 l), 2% $CH_3OH$ in DCM (1 l), then washed with 20% $CH_3OH$ in DCM. The fractions containing the front spot were pooled and concentrated to give 500 mg of yellow solid. This solid was recrystallized again from ethanol to provide 340 mg (10.7%) of crystals, m.p.=148°–150° C.

Analysis: Calculated for $C_{23}H_{22}FN_3O_3$: 67.80%C, 5.44%H, 10.31%N; Found: 67.54%C, 5.31%H, 10.17%N.

EXAMPLE 171

2-[4-[(6-Fluoro-1,2-benzisothiazol-3-yl)-1-piperidinyl]ethyl]amine sesquifumarate To a stirred solution of N-[2-[4-(6-fluoro-1,2-benzisothiazol-3-yl)-1-piperidinyl]ethyl]phthalimide (17.0 g, 42 mmol) and MeOH (200 ml) under $N_2$ was added, dropwise, hydrazine monohydrate (4.2 g, 83 mmol). After complete addition, the reaction was stirred at reflux for 17 hours. The reaction mixture was concentrated and the resultant residue was dissolved in $H_2O$. The aqueous solution was acidified to pH=2 with concentrated HCl and the precipitate was filtered. The filtrate was basified with 50% NaOH and the product was extracted into $CH_2Cl_2$. The $CH_2Cl_2$ extract was washed with $H_2O$, dried with $MgSO_4$ and concentrated to yield 6.0 g (52%) of a beige oil. A 5.8 g sample of the oil (21 mmol) was warmed in EtOH (100 ml) and fumaric acid (2.7 g, 23 mmol) was added. The solution was refluxed gently for 15 minutes and was stirred at ambient temperature for 1.5 hours Anhydrous $Et_2O$ (400 ml) was added and the product collected to yield 7.1 g of an off-white powder. A portion (3.0 g) was recrystallized from MeOH-$Et_2O$ to provide 1.7 g (22%) of the sesquifumarate salt as a white powder m.p.=169°–171° C.

Analysis: Calculated for $C_{14}H_{18}FN_3S \cdot 1.5C_4H_4O_4$: 52.97%C, 5.35%H, 9.27%N; Found: 52.96%C, 5.44%H, 9.39%N.

EXAMPLE 172

(S)-6-Fluoro-3-[1-(3-hydroxybutyl)-4-piperidinyl]-1,2-benzisoxazole (S)-Hydroxybutyl tosylate was prepared in a manner described by Ferreira et al., Tetrahedron, 46, pp. 6311–6318, (1990). To a solution of the tosylate (6.8 g, 28.0 mmol) in acetonitrile (150 ml) was added 6-fluoro-3-(4-piperidinyl)-1,2-benzisoxazole (6.2 g, 28.0 mmol) followed by milled potassium carbonate (5.8 g, 42.0 mmol) at room temperature under nitrogen. The reaction mixture was warmed to reflux for 3 hours and allowed to cool to room temperature. The solids were removed via filtration through a pad of Celite and were washed with EtOAc. The combined filtrates were concentrated to give the crude product. Purification via flash column chromatography (silica gel, 0–10% MeOH/EtOAc) afforded 5.5 g (67%) of the desired product as an oil which solidified on standing, m.p.=84°–86° C.

Analysis: Calculated for $C_{16}H_{21}FN_2O_2$: 65.73%C, 7.24%H, 9.58%N; Found: 65.58%C, 6.83%H, 9.50%N.

EXAMPLE 173

(R)-6-Fluoro-3-[1-(3-hydroxybutyl)4-piperidinyl]-1,2-benzisoxazole (R)-Hydroxybutyl tosylate was prepared in a manner described by Ferreira et al., Tetrahedron, 46, pp. 6311–6318, (1990). To a solution of the tosylate (8.4 g, 34.2 mmol) in acetonitrile (120 ml) was added 6-fluoro-3-(4-piperidinyl)-1,2-benzisoxazole (7.5 g, 34.2 mmol) followed by milled potassium carbonate (7.1 g, 51.3 mmol) at room temperature under nitrogen. The reaction mixture was warmed to reflux for 2 hours and allowed to cool to room temperature. The solids were removed via filtration through a pad of Celite and were washed with EtOAc. The combined filtrates were concentrated to give the crude product. Purification via flash column chromatography (silica gel, 10% MeOH/EtOAc) afforded 6.0 g (60%) of the desired product as an oil which solidified on standing, m.p.=82°–84° C.

Analysis: Calculated for $C_{16}H_{21}FN_2O_2$: 65.73%C, 7.24%H, 9.58%N; Found: 65.66%C, 7.13%H, 9.53%N.

EXAMPLE 174

N-[2-[4-(6-Fluoro-1H-indazol-3-yl)-1-piperazinyl]ethyl]phthalimide

A mixture of 6-fluoro-3-(4-piperazinyl)-1H-indazole (4.0 g, 18 mmol), $K_2CO_3$ (2.7 g, 20 mmole), N-(2-bromoethyl)phthalimide (4.8 g, 19 mmole) and $CH_3CN$ (100 ml) was stirred at reflux under $N_2$ for 4 hours. After standing at ambient temperature for 65 hours, the reaction was poured into $H_2O$. The resultant solid was collected to yield 4.0 g of a yellow powder. The product was recrystallized twice from ethanol to yield 3.5 g (50%) of a beige powder m.p.= 220°–223° C.

Analysis: Calculated for $C_{21}H_{20}FN_5O_2$: 64.11%C, 5.12%H, 17.80%N; Found: 64.16%C, 5.04%H, 17.82%N.

(A) N-[2-[4-(6-Fluoro-1H-indazol-3-yl)-1-piperazinyl]ethyl]phthalimide hydrochloride A 5.0 g sample of N-[2-[4-(6-fluoro-1H-indazol-3-yl)-1-piperazinyl]ethyl]phthalimide was suspended in methanol (130 ml) and was made acidic with ethereal-HCl. After stirring for 1 hour, anhydrous ether (100 ml) was added and the suspension was stirred for an additional 30 minutes. The solid was collected and dried to afford 4.5 g of an off-white powder. This was combined with an additional sample (7.3 g total) and recrystallization from MeOH gave 4.3 g of the salt as an off-white powder, mp=265°–268° C.

Analysis: Calculated for $C_{21}H_{20}FN_5O_2$·HCl: 58.62%C, 4.92%H, 16.29%N; Found: 58.60%C, 4.83%H, 16.19%N.

EXAMPLE 175

Ethyl 3-[4-(6-Fluoro-1,2-benzisothiazol-3-yl)-1-piperidinyl]propionate hydrochloride.

A mixture of 6-fluoro-3-(4-piperidinyl)-1,2-benzisothiazole (6.0 g, 25 mmol), ethyl 3-bromopropionate (4.5 g, 25 mmol), $K_2CO_3$ (3.5 g) and $CH_3CN$ (100 ml) was stirred and refluxed for 16 hours. The reaction was poured into $H_2O$, and after extractive workup with EtOAc, 6.0 g of an orange oil was realized. The oil was dissolved in $Et_2O$ and ethereal HCl was added to precipitate 6.3 g of a white hydrochloride salt. The salt was recrystallized from $CH_3CN$ to yield 6.0 g (64%) of the desired compound. An analytical sample was obtained by recrystallization of a 1.0 g sample from EtOH-$Et_2O$ to yield 0.8 g of a white solid, m.p.= 197°–199° C.

Analysis: Calculated for $C_{17}H_{21}FN_2O_2S$·HCl: 54.76%C, 5.95%H, 7.51%N; Found: 54.77%C, 5.99%H, 7.28%N.

EXAMPLE 176

4-[4-(6-Fluoro-1,2-benzisothiazol-3-yl)-1-piperidinyl]-2-methyl-2-hydroxybutane hemifumarate To a stirred solution, under $N_2$, of ethyl 3-[4-(6-fluoro-1,2-benzisothiazol-3-yl)-1-piperidinyl ]propionate (3.1 g, 9 mmol), in THF (100 ml) was added, dropwise, methylmagnesium bromide (9.0 ml, 27 mmol of a 3M solution in ether). The reaction was stirred at ambient temperature for 16 hours and then a saturated solution $NH_4Cl$ was added dropwise, with cooling. The reaction was further diluted with $H_2O$, and after extractive workup of the aqueous mixture with EtOAc, 2.8 g of a waxy solid resulted. The solid was dissolved in EtOAc and 3.0 g of fumaric acid was added, and 5.0 g of a fumarate salt was collected, which was contaminated with unreacted fumaric acid. The crude salt was recrystallized from MeOH-$Et_2O$, and then from DMF to afford 1.6 g (45.7%) of the desired compound as a hemifumarate, m.p.= 237°–239° C.

Analysis: Calculated for $C_{17}H_{23}FN_2OS·C_4H_4O_4$: 59.98%C, 6.64%H, 7.36%N; Found: 59.75%C, 6.65%H, 7.39%N.

EXAMPLE 177

N-[2-[4-(6-Fluoro-1,2-benzisoxazol-3-yl)-1-piperidinyl]ethyl]-3-hydroxyphthalimide hydrochloride A mixture of 2-[4-[(6-fluoro-1,2-benzisoxazol-3-yl)-1-piperidinyl]ethyl]amine (2.48 g, 9.3 mmol), 3-hydroxyphthalic anhydride (1.8 g, 10.9 mmol) and dicyclohexylcarbodiimide (2.2 g, 10.7 mmol) in chloroform (100 ml) was stirred at room temperature for 48 hours. The mixture was filtered. The yellow solution was loaded onto a flash chromatography column ($SiO_2$, 40 g; eluted with DCM, 1 l; and 2% $CH_3OH$ in DCM, 1 l). The desired product thus obtained as a light yellow solid weighed 2.12 g (55%), m.p.=156°–157° C. This material was converted to the hydrochloride salt by treatment with a solution of hydrochloric acid in ethanol. The off-white crystals were collected: 1.97 g, m.p.=270°–272° C. dec.

Analysis: Calculated for $C_{22}H_{20}FN_3O_4$·HCl: 59.26%C, 4.75%H, 9.42%N; Found: 59.34%C, 4.70%H, 9.19%N.

EXAMPLE 178

N-[2-[4-(6-Fluoro-1,2-benzisoxazol-3-yl)-1-piperidinyl]ethyl]-4-fluorophthalimide A solution of 2-[4-[(6-fluoro-1,2-benzisothiazol-3-yl)-1-piperidinyl]ethyl]amine (2.7 g, 10 mmol), 4-fluorophthalic anhydride (1.6 g, 10 mmol) and DMF (50 ml) was stirred under $N_2$ at ambient temperature for 1 hour and then at 70° for 2 hours. Most of the DMF was removed in vacuo to afford 4.6 g of a damp, beige solid. The compound was dissolved in anhydrous $Et_2O$ (100 ml) and MeOH (75 ml) and the insolubles were filtered off. The filtrate was made acidic with ethereal HCl to precipitate the HCl salt. Additional anhydrous $Et_2O$ (500 ml) was added and the salt was collected to give 3.5 g of a beige solid. Recrystallization from EtOH provided 2.0 g (44%) of an off-white powder, m.p.=269°–271° C.

Analysis: Calculated for $C_{22}H_{19}F_2N_3O_2S$·HCl: 56.96%C, 4.35%H, 9.06%N; Found: 57.33%C, 4.33%H, 9.11%N.

EXAMPLE 179

6-Fluoro-3-[1-(3-hydroxy-3-ethylpentyl)-4-piperidinyl]-1,2-benzisoxazole

To a solution of ethyl 3-[4-(6-fluoro-1,2-benzisoxazol-3-yl)-1-piperidinyl]propionate (3.9 g, 12.0 mmol) in THF (100 ml) was added ethylmagnesium bromide (12.0 ml, 36.0 mmol, 3.0M in ether) at room temperature under nitrogen (mild exotherm). The reaction mixture was stirred for 17 hours at which time it was carefully quenched with NH$_4$Cl (sat., 20 ml). The precipitated salts were dissolved into water (25 ml) and the layers were separated. The aqueous phase was extracted with EtOAc (2X) and the combined organics were washed with brine and dried (Na$_2$SO$_4$). Filtration and concentration gave the crude product which was purified via flash column chromatography (silica gel, 1% MeOH/DCM) to give 2.4 g (61%) of the desired product as an oil which solidified on standing, m.p.=50°–53° C.

Analysis: Calculated for C$_{19}$H$_{27}$FN$_2$O$_2$: 68.24%C, 8.14%H, 8.38%N; Found: 67.99%C, 8.11%H, 8.48%N.

EXAMPLE 180

Decanoic acid 2-[2-[4-(6-Fluoro-1,2-benzisoxazol-3-yl)-1-piperidinyl]ethyl]-3-oxo-2,3-dihydro-1H-isoindol-1-yl ester To a solution of 2-[2-[4-(6-fluoro-1,2-benzisoxazol-3-yl)-1-piperidinyl]ethyl-2,3-dihydro-3-hydroxy-1H-isoindol-1-one (1.4 g, 3.5 mmol) in DCM (30 ml) was added Et$_3$N (1.2 ml, 8.8 mmol) followed by decanoyl chloride at 0° C. under nitrogen. After stirring for 1h in the cooling bath, the solvent was removed using a stream of nitrogen. The remaining residue was diluted with EtOAc and the precipitated triethylamine hydrochloride was filtered off. The filtrate was concentrated and the remaining oil was flushed through alumina with ether to give 1.6 g (83%) of the desired product as a yellow oil.

Analysis: Calculated for C$_{32}$H$_{40}$FN$_3$O$_4$: 69.92%C, 7.33%H, 7.64%N; Found: 69.70%C, 7.39%H, 7.56%N.

EXAMPLE 181

6-Chloro-2-[2-[4-(6-fluoro-1,2-benzisoxazol-3-yl)-1-piperidinyl]ethyl]-1H-benz[de]isoquinoline-1,3(2H)-dione A mixture of 2-[4-[(6-fluoro-1,2-benzisoxazol-3-yl)-1-piperidinyl]ethyl]amine (2.32 g, 8.8 mmol) and 4-chloro-1,8-naphthalic anhydride (2.45 g, 10.5 mmol, 1.25 eq) in chloroform (120 ml) was stirred at room temperature overnight. To the mixture was added 5 ml of methanol and the solution was concentrated down to 20 ml. The resulting mixture was loaded onto a flash chromatography column (SiO$_2$, 50 g ; eluted with dichloromethane, DCM, 1 l, and 2% CH$_3$OH in DCM, 1 l). The product thus obtained as a light yellow solid weighed 2.61 g. Recrystallization from CH$_2$Cl$_2$/ethanol gave 2.5 g of pale white crystals, m.p.= 207°–209° C.

Analysis: Calculated for C$_{26}$H$_{21}$ClFN$_3$O$_3$: 65.34%C, 4.43%H, 8.79%N; Found: 64.87%C, 4.32%H, 8.67%N.

EXAMPLE 182

N-[2-[4-(6-Fluoro-1,2-benzisoxazol-3-yl)-1-piperidinyl]ethyl]-4-tert-butylphthalimide fumarate A mixture of 2-[4-[(6-fluoro-1,2-benzisoxazol-3-yl)-1-piperidinyl]ethyl]amine (2.0 g, 7.57 mmol) and 4-(t-butyl) phthalic anhydride (1.62 g, 7.94 mmol) in dimethylformamide (DMF, 20 ml) was heated at 135° C. for 3 hours. The solvent was removed on a rotary evaporator under vacuum, and further dried on a vacuum pump. The residue was purified by flash chromatography over a silica gel column (SiO$_2$, 35 g; eluted with DCM, and 1–2% of methanol in DCM). The product thus obtained as an oil was triturated with isopropyl ether and dried to a waxy solid. This solid was converted to the fumarate salt by treatment with a solution of fumaric acid (778 mg) in ethanol. The crystals were collected and weighed: 3.03 g; m.p.=198°–199° C.

Analysis: Calculated for C$_{26}$H$_{28}$FN$_3$O$_3$·C$_4$H$_4$O$_4$: 63.71%C, 5.70%H, 7.43%N; Found: 63.46%C, 6.05%H, 7.27%N.

EXAMPLE 183

N-[2-[4-(6-Fluoro-1H-indazol-3-yl)-1-piperidinyl] ethyl]phthalimide hydrochloride A mixture of 6-fluoro-3-(4-piperidinyl)-1H-indazole (2.5 g, 11 mmol), 2-bromoethylphthalimide (3.0 g, 10 mmol), NaHCO3 (1.0 g) and DMF (30 ml) was stirred and heated at 60° C. for 2.5 hours. The reaction was poured into H$_2$O, and after extractive workup with EtOAc there remained 4.0 g of a golden oil. The oil was dissolved in EtOAc and ethereal HCl was added to yield 1.9 g of the hydrochloride salt as a white solid. The solid was recrystallized from MeOH-Et$_2$O and then from DMF to afford 0.54 g (11%) of the compound as a white solid, m.p.=270°–272° C.

Analysis: Calculated for C$_{22}$H$_{21}$FN$_4$O$_2$·HCl: 61.61%C, 5.17%H, 13.06%N; Found: 61.50%C, 5.05%H, 12.86%N.

EXAMPLE 184

2-[2-[4-(6-Fluoro-1,2-benzisothiazol-3-yl)-1-piperidinyl]-2,3-dihydro-3-hydroxy-1H-isoindol-1-one hydrochloride To a stirred solution of the N-[2-[4-(6-fluoro-1,2-benzisothiazol-3-yl)-piperidinyl]ethyl]phthalimide (2.5 g, 6 mmol) in MeOH (50 ml)—CH$_2$Cl$_2$ (20 ml) was added NaBH$_4$ (0.8 g, 21 mmol). The reaction was stirred at ambient temperature for 2 hours, and then the solvent was evaporated. The residue was diluted with H$_2$O, and extractive workup of the aqueous with CH$_2$Cl$_2$ afforded 2.2 g of a beige solid. The solid was combined with a sample from a prior run, and the combined sample (3.2 g) was chromatographed on a Waters Prep 500 LC, eluting with EtOAc-Et$_2$NH (5%). Concentration of the appropriate fractions afforded 2.2 g of a white solid. The solid was dissolved in EtOAc and ethereal HCl was added to yield 2.0 g of a hydrochloride salt. The salt was recrystallized first from EtOH and then from DMF to yield 1.2 g (31%) of a white solid, m.p.=210°–212° C.

Analysis: Calculated for C$_{22}$H$_{22}$FN$_3$O$_2$S·HCl: 58.99%C, 5.18%H, 9.38%N; Found: 58.89%C, 5.23%H, 9.16%N.

EXAMPLE 185

N-[2-[4-(6-Fluoro-1,2-benzisothiazol-3-yl)-1-piperidinyl]-4-methylphthalimide hydrochloride A mixture of 2-[4-[(6-fluoro-1,2-benzisothiazol-3-yl)-1-piperidinyl]ethyl]amine (3.4 g, 12 mmol), 4-methylphthalic anhydride (2.0 g, 12 mmol) and DMF (75 ml) was stirred at 70° C. under N$_2$ for 3.5 hours. Most of the DMF was removed in vacuo, and the oily residue was diluted with H$_2$O. EtOAc was added to the aqueous mixture and the biphase was filtered through Celite to remove an insoluble yellow solid. The solid was scraped away from the Celite and was dissolved in CH$_2$Cl$_2$. The solution was filtered through the original Celite cake, and the CH$_2$Cl$_2$ filtrate was washed with H$_2$O, dried with MgSO$_4$ and concentrated to yield 0.5 g (10%) of an off-white solid. The phases of the EtOAc/H$_2$O filtrate were separated and the aqueous was further extracted with EtOAc. The EtOAc extract was washed with H$_2$O, dried with MgSO$_4$ and concentrated to afford 3.5 g (69%) of an off-white solid.

The two samples were combined and recrystallized from EtOH to give 2.2 g of a white powder. The product was dissolved in anhydrous ether (200 ml) and methanol (100 ml) and the solution was made acidic with ethereal HCl. After ca. 30 minutes of stirring the salt began to precipitate. Additional anhydrous ether (400 ml) was added over 2 hours and the resultant white solid was collected to yield 2.2 g. Recrystallization from MeOH-ether provided 1.7 g (30%) of a white powder, m.p.=268°–271° C.

Analysis: Calculated for C$_{23}$H$_{22}$FN$_3$O$_2$S·HCl: 60.06%C, 5.04%H, 9.14%N; Found: 60.01%C, 5.00%H, 9.12%N.

EXAMPLE 186

6-Fluoro-3-[1-(3-hydroxy-3-piperidinyl)-4-piperidinyl]-1,2-benzisoxazole hydrochloride To a solution of ethyl 3-[4-(6-fluoro-1,2-benzisoxazol-3-yl)-1-piperidinyl]propionate (4.5 g, 14.0 mmol) in THF (120 ml) was added propylmagnesium chloride (21.1 ml, 42.0 mmol, 2.0M in ether) at room temperature under nitrogen (mild exotherm). The reaction mixture was stirred for 17 hours at which time it was carefully quenched with NH$_2$Cl (sat., 30 ml). The layers were separated and the aqueous phase was extracted with EtOAc (2X). The combined organics were washed with brine and dried (Na$_2$SO$_4$). Filtration and concentration gave the crude product which was purified via flash column chromatography (silica gel, 2% Et$_3$N/ether). After flushing the product through alumina with ether, the hydrochloride salt was prepared in ether/EtOAc (1:1, 40 ml, 1 drop IPA) with ethereal HCl to give 2.5 g (45%) of the desired product as a white solid, m.p.= 163°–164° C.

Analysis: Calculated for C$_{21}$H$_{31}$FN$_2$O$_2$·HCl: 63.22%C, 8.08%H, 7.02%N; Found: 62.97%C, 7.95%H, 7.01%N.

EXAMPLE 187

N-[2-[4-(6-Fluoro-1,2-benzisoxazol-3-yl)-1-piperidinyl]ethyl]-3-nitrophthalimide fumarate A mixture of 2-[4-[(6-fluoro-1,2-benzisoxazol-3-yl)-1-piperidinyl]ethyl]amine (2.09 g, 7.9 mmol) and 3-nitrophthalic anhydride (1.6 g, 8.3 mmol, 1.05 eq) in dimethylformamide (DMF, 20 ml) was heated at 135° C. for 3 hours. The solvent was removed on a rotary evaporator under vacuum and further dried on a vacuum pump. The residue was purified by flash chromatography over a silica gel column (SiO$_2$, 35 g; eluted with dichloromethane, 300 ml, and 3% CH$_3$OH in DCM, 300 ml). The product thus obtained, 2.01 g, was dissolved into DCM (15 ml) and ethanol (5 ml) and was treated with a solution of fumaric acid (530 mg, 1.0 eq) in ethanol (15 ml). The crystals were collected and weighed: 2.03 g, m.p.=237°–239° C. carefully quenched with Nh$_2$Cl (sat., 30 ml). The layers were separated and the aqueous phase was extracted with EtOAc (2 ml). The combined organics were washed with brine and dried (Na$_2$S)$_4$). Filteration and concentration gave the crude product which was purified via flash column chromatography (silicia gel, 2% Et$_3$N/ether). after flushing the product through alumina with ether, the hydrochloride salt was prepared in ether/EtOAc (1:1, 40 ml, 1 drop IPA) with ethereal HCl to give 2.5 g (45% ) of the desired product as a white solid, m.p.=163°–160° C.

Analysis: Calculated for C$_{22}$H$_{19}$FN$_4$O$_5$·C$_4$H$_4$O$_4$: 56.32%C, 4.18%H, 10.10%N; Found: 55.94%C, 4.23%H, 9.87%N.

EXAMPLE 188

N-[2-[4-(6-Fluoro-1,2-benzisoxazol-3-yl)-1-piperidinyl]ethyl]-4-hydroxyphthalimide hydrochloride A mixture of 2-[4-(6-fluoro-1,2-benzisoxazol-3-yl)-1-piperidinyl]ethyl]amine (5 g, 18.9 mmol), 4-hydroxyphthalic acid (4.14 g, 1.2 eq), and dicyclohexylcarbodiimide (DCC, 8.61 g, 4.18 mmol) in dimethylformamide (50 ml, DMF) was stirred and heated at 75° C. for 18 hours. The mixture was cooled, and the solids (DCU) were filtered and rinsed with dichloromethane (DCM). The solution was concentrated down to dryness. The residue was dissolved into dichloromethane (100 ml) and the insolubles, which contained the product also, were filtered and collected. The solution was concentrated down to 50 ml and loaded onto a flash chromatography column (SiO$_2$, 50 g ; eluted with DCM, and methanol:DCM mixture). The desired product was collected as a pinkish solid, 1.71 g. This solid was converted to the hydrochloride salt in ethanol with an HCl in ether solution (1M, 5 ml). The crystals were collected and dried; weight: 1.2 g; m.p.=272°–275° C. dec.

Analysis: Calculated for C$_{22}$H$_{20}$FN$_3$O$_4$·HCl: 59.26%C, 4.75%H, 9.42%N; Found: 59.08%C, 4.60%H, 9.34%N.

EXAMPLE 189

(±)-6-Fluoro-3-[1-(3-hydroxybutyl)-4-piperidinyl]-1,2-benzisothiazole hydrochloride A mixture of 6-fluoro-3-(4-piperidinyl)-1,2-benzisothiazole (3.9 g, 17 mmol), K$_2$CO$_3$ (2.3 g, 17 mmol, (±)-3-hydroxybutyl tosylate (4.0 g, 16 mmol) and CH$_3$CN (100 ml) was stirred at reflux under N$_2$ for 5 hours. The cooled reaction was filtered through Celite and the cake was rinsed with EtOAc. The filtrate was concentrated to afford 6.7 g of a red oil. Purification via preparative HPLC. (Water's Associates Prep LC/System 500, using 2 silica gel columns and 10% MeOH—CH$_2$Cl$_2$) provided 2.5 g of a beige solid. The product was dissolved in of MeOH and the solution amount of MeOH and the solution was acidified with ethereal HCl. Additional Et$_2$O was added to precipitate 1.9 g of the HCl salt. Recrystallization from MeOH-Et$_2$O gave 1.7 g and a second recrystallization from CH$_3$CN yielded 1.0 g (18%) of a light beige powder, m.p.= 182°–184° C.

Analysis: Calculated for C$_{16}$H$_{21}$FN$_2$OS·HCl: 55.72%C, 6.43%H, 8.12%N; Found: 55.83%C, 6.54%H, 8.19%N.

EXAMPLE 190

Decanoic acid 1,1-diethyl-3-[4-(6-fluoro-1,2-benzisoxazol-3-yl)-1-piperidinyl]-propyl ester hydrochloride To a solution of 6-fluoro-3-[1-(3-hydroxy-3-ethylpentyl)-4-piperidinyl]-1,2-benzisoxazole (2.5 g, 7.48 mmol) in DCM (100 ml) was added decanoyl chloride (1.5 ml, 7.48 mmol) at 0° C., under nitrogen. The reaction mixture was stirred for 4 days at which time it was poured into NaHCO$_3$ (sat., 50 ml). The layers were separated and the aqueous phase was extracted with DCM (2X). The combined organics were dried, filtered and concentrated to give the crude product which was purified via flash column chromatography (silica gel, 20–40% EtOAc/DCM). The product containing fractions were concentrated to give 3.0 g (81%) of the desired product as a yellow oil. The hydrochloride salt was prepared in anhydrous ether (60 ml) and isopropanol (1 ml) with ethereal HCl. The white salt was filtered and washed with anhydrous ether, m.p.=159°–161° C.

Analysis: Calculated for $C_{29}H_{45}FN_2O_3 \cdot HCl$: 66.33%C, 8.83%H, 5.33%N; Found: 66.45%C, 9.01%H, 5.31%N.

EXAMPLE 191

N-[2-[4-(6-Fluoro-1,2-benzisoxazol-3-yl)-1-piperidinyl]ethyl]-2,3-naphthalimide

A mixture of 2-[4-(6-fluoro-1,2-benzisoxazol-3-yl)-1-piperidinyl]ethylamine (2.0 g, 7.58 mmol), and 2,3-naphthalenedicarboxylic anhydride (1.58 g, 7.95 mmol) in dimethylformamide (20 ml, DMF) was heated at 150° C. for 2 hours. At the end, the mixture was cooled and the solvent was removed to dryness. The residue was purified by flash chromatography over silica gel column (60 g of $SiO_2$, eluted with dichloromethane (DCM), and 1.5% $CH_3OH$ in DCM). The product crystallized out on concentration; weight: 1.6 g (47%). Recrystallization from chloroform:ethanol gave 1.38 g of off-white crystals, m.p.=192°–193° C.

Analysis: Calculated for $C_{26}H_{22}FN_3O_3$: 70.42%C, 5.00%H, 9.48%N; Found: 69.85%C, 4.59%H, 9.27%N.

EXAMPLE 192

2,3-Dihydro-2-[2-[4-(6-fluoro-1,2-benzisoxazol-3-yl)-1-piperidinyl]ethyl]-3-hydroxy-3-methyl-1H-isoindol-1-one fumarate To the solution of N-[2-[4-(6-fluoro-1,2-benzisoxazol-3-yl)-1-piperidinyl]ethyl]phthalimide (6.2 g, 15.87 mmol) in tetrahydrofuran (THF, 80 ml) was added dropwise a solution of methylmagnesium bromide (3M, 6.5 ml, 1.2 eq) in ether at room temperature under $N_2$. The mixture was stirred at 55° C. for 16 hours. The reaction mixture was treated with $NH_4Cl$ solution (10 ml) and partitioned between brine and ethyl acetate. The EtOAc solution was washed with brine and dried. Filtration and concentration gave a crude product (3.9 g). This crude product was purified on a flash chromatography column (40 g, $SiO_2$; eluted with 0.5% $CH_3OH$ in DCM). The pure product (1.75 g, 27%) thus obtained was treated with fumaric acid (500 m, 1.0 eq) in ethanol to yield 1.8 g, m.p.=167°–168° C.

Analysis: Calculated for $C_{23}H_{24}FN_3O_3 \cdot C_4H_4O_4$: 61.71%C, 5.37%H, 8.00%N; Found: 61.47%C, 5.67%H, 7.82%N.

EXAMPLE 193

2,3-Dihydro-2-[2-[4-(6-fluoro-1,2-benzisoxazol-3-yl)-1-piperidinyl]ethyl]-3-methylene-1H-isoindol-1-one hydrochloride To the solution of 2,3-dihydro-2-[2-[4-(6-fluoro-1,2-benzisoxazol-3-yl)-1-piperidinyl]ethyl]-3-hydroxy-3-methyl-1H-isoindol-1-one (4.88 g, 11.9 mmol) in chloroform (50 ml) was added HCl·ether (1M, 20 ml) solution. A precipitate formed. This mixture was stirred for 18 hours at room temperature. The mixture was basified with triethylamine and washed with brine. The organic solution was dried and concentrated to a crude material. The purification was done by flash chromatography over silica gel column ($SiO_2$, 60 g; eluted with DCM). The pure product thus obtained weighed 3.28 g (70%). Treatment with HCl—ether solution in ethanol gave 1.52 g of white crystals, m.p.=261°–263° C.

Analysis: Calculated for $C_{23}H_{20}FN_3O \cdot HCl$: 64.56%C, 5.42%H, 9.82%N; Found: 64.47%C, 5.51%H, 9.72%N.

EXAMPLE 194

1-[2-[4-(6-Fluoro-1,2-benzisoxazol-3-yl)-1-piperidinyl]ethyl]cyclohexanol hydrochloride To pentamethylene bis(magnesium bromide) (35.0 ml, 17.5 mmol, 0.5M in THF) was added a solution of ethyl 3-[4-(6-fluoro-1,2-benzisoxazol-3-yl)-1-piperidinyl]propionate (5.6 g, 17.5 mmol) in THF (100 ml) at 0° C., under nitrogen-mild exotherm. The reaction mixture was warmed to room temperature and stirred for 17 hours at which time it was carefully quenched with $NH_4Cl$ (sat., 50 ml). The precipitated salts were dissolved into water (25 ml) and the layers were separated. The aqueous phase was extracted with EtOAc (2X) and the combined organics were then dried ($Na_2SO_4$). Filtration and concentration gave the crude product which was purified via flash column chromatography (silica gel, 50% EtOAc/DCM then 100% EtOAc) to give 2.8 g (46%) of the desired product as a white solid. The hydrochloride salt was prepared in anhydrous ether (125 ml) and methanol (15 ml) with ethereal HCl, m.p.=210° C. (dec.).

Analysis: Calculated for $C_{20}H_{27}FN_2O_2 \cdot HCl$: 62.74%C, 7.37%H, 7.32%N; Found: 62.85%C, 7.53%H, 7.14%N.

EXAMPLE 195

5-[4-(6-Fluoro-1,2-benzisothiazol-3-yl)-1-piperidinyl]-3-ethyl-3-hydroxypentane hydrochloride To a stirred solution, under $N_2$, of ethyl 3-[4-(6-fluoro-1,2-benzisothiazol-3-yl)-1-piperidinyl]propionate (5.3 g, 16 mmol) in THF (200 ml), was added dropwise, ethyl magnesium bromide (15.7 ml of a 3.0M solution in $Et_2O$). The reaction was stirred at ambient temperature for 16 hours and then following cooling in an ice bath, a saturated solution of $NH_4Cl$ was added dropwise. The aqueous mixture was extracted with EtOAc, and the extract was washed ($H_2O$), dried ($MgSO_4$) and the solvent was concentrated to afford 5.8 g of a yellow oil. The oil was chromatographed on a preparative HPLC, upon a silica gel column, eluting with 6% $MeOH/CH_2Cl_2$. Concentration of the appropriate fractions yielded 3.7 g of a yellow oil. The oil was dissolved in $Et_2O$ and ethereal HCl was added to precipitate 4.0 g of a white salt. The salt was recrystallized twice from EtOH-$Et_2O$) to afford 1.4 g (22%) of the alcohol as a white solid, m.p.=207°–209° C.

Analysis: Calculated for $C_{19}H_{27}FN_2OS \cdot HCl$: 58.98%C, 7.29%H, 7.24%N; Found: 58.95%C, 7.63%H, 7.11%N.

EXAMPLE 196

Ethyl 3-[4-(6-fluoro-1H-indazol-3-yl)-1-piperazinyl]propionate hydrochloride

To a stirred suspension of 6-fluoro-3-(4-piperazinyl)-1H-indazole (9.9 g, 45 mmol), $K_2CO_3$ (6.8 g, 49 mmol) and $CH_3CN$ (210 ml) under $N_2$ was added, dropwise, ethyl 3-bromopropionate (8.1 g, 45 mmol) in $CH_3CN$ (20 ml). After complete addition, the reaction was stirred at reflux for 16.5 hours. A TLC. revealed remaining starting indazole; therefore, triethylamine (1.5 g, 14 mmol) was added dropwise to the cool reaction mixture. The reaction was stirred at reflux for 1 hour longer with no additional change by TLC. The reaction was cooled, filtered, and the filtrate concentrated to yield 14.6 g of an off-white solid. The material was purified by preparative HPLC. (Water's Associates Prep LC/System 500A using 2 silica gel columns and 6.5%

MeOH—CH$_2$Cl$_2$ as eluent). Concentration of appropriate fractions gave 8.1 g (51%) of a grey-white solid. A 1.5 g sample was dissolved in MeOH (45 ml) and was acidified with ethereal HCl. The solution was stirred for 5 minutes and anhydrous ether (50 ml) was added. Within one minute the HCl salt precipitated. More anhydrous ether (100 ml) was added and the salt was collected and dried to yield 1.5 g of a white solid. Recrystallization from ethanol provided 1.2 g (37%) of fluffy white crystals, m.p.=224°–226° C.

Analysis: Calculated for C$_{16}$H$_{21}$FN$_4$O$_2$·HCl: 53.86%C, 6.21%H, 15.70%N; Found: 53.81%C, 5.88%H, 15.37%N.

EXAMPLE 197

4-[4-(6-Fluoro-1,2-benzisoxazol-3-yl)-1-piperidinyl]-2-methylbutyl decanoate fumarate To a mixture of 4-[4-(6-fluoro-1,2-benzisoxazol-3-yl)-1-piperidinyl]-2-methyl-2-butanol (4.68 g, 15.3 mmol) and triethylamine (2.23 g, 22.3 mmol) in chloroform (20 ml) was added decanoyl chloride (3.5 g, 18.4 mmol, 1.2 eq) dropwise at 0° C. The reaction was stirred at ambient temperature for 4 hours. The solvent was removed. The residue was purified by flash chromatography over a silica gel column (SiO$_2$, 65 g, eluted with DCM, 1 l, 1% CH$_3$OH in DCM, 1 l). The product thus purified weighed 5.7 g (80%) as an oil. This oily product was converted to the fumarate salt in ethanol with fumaric acid (1.51 g, 1.0 eq) to yield 3.34 g, m.p.=133°–134° C.

Analysis: Calculated for C$_{27}$H$_{41}$FN$_2$O$_3$·C$_4$H$_4$O$_4$: 64.56%C, 7.87%H, 4.86%N; Found: 64.42%C, 7.74%H, 4.78%N.

EXAMPLE 198

2-[2-[4-(6-Fluoro-1,2-benzisoxazol-3-yl)-1-piperidinyl]ethyl]-2,3-dihydro-3-methyl-1H-isoindol-1-one hydrochloride A mixture of 2-[2-[4-(6-fluoro-1,2-benzisoxazol-3-yl)-1-piperidinyl]ethyl]-2,3-dihydro-3-hydroxy-3-methyl-1H-isoindol-1-one (3.96 g, 9.7 mmol) and lithium aluminum hydride (1.1 g, 50% in oil, 1.5 eq) in tetrahydrofuran (50 ml) was stirred at room temperature for 16 hours. The mixture was quenched carefully with a small amount of ice, then was diluted with ethyl acetate (200 ml). The mixture was stirred for 20 minutes. The insolubles were filtered. The organic solution was dried over MgSO$_4$ and concentrated down to a yellow oil (4.5 g). This oil was purified by flash chromatography over silica gel column (SiO$_2$, 58 g; eluted with DCM, 1 l, and 1% CH$_3$OH in DCM). Only 1.91 g of desired product was obtained. This material was treated with HCl (1M HCl in ether, 6 ml) in ethanol followed by isopropyl ether to yield 1.48 g (36%), m.p.=213°–215° C.

Analysis: Calculated for C$_{23}$H$_{24}$FN$_3$O$_2$·HCl: 64.25%C, 5.86%H, 9.77%N; Found: 63.88%C, 5.74%H, 9.44%N.

EXAMPLE 199

1-[2-[4-(6-fluoro-1,2-benzisoxazol-3-yl)-1-piperidinyl]ethyl]cyclopentanol hydrochloride In a flame-dried 500 ml round-bottom flask, equipped with addition funnel and condenser, was placed magnesium metal (3.4 g, 140 mmol) and anhydrous ether (20 ml). A solution of 1,4-dibromobutane (4.4 ml, 36.5 mmol) in anhydrous ether (10 ml) was then syringed into the addition funnel and added dropwise to the magnesium metal. Initially no reaction took place, but with the addition of a few crystals of iodine and gentle heating the Grignard reagent began to form. The rate of addition was such that a gentle reflux was maintained. Upon complete addition, the Grignard was stirred for 0.5 hours. A solution of 3-[4-(6-fluoro-1,2-benzisoxazol-3-yl)-1-piperidinyl]propionate (9.0 g, 28.1 mmol) in THF (75 ml) was then added (dropwise, exothermic) at room temperature and stirred for 21.5 hours. The reaction mixture was carefully quenched with NH$_4$Cl (sat., 100 ml) and the precipitated magnesium salts were dissolved into water (50 ml). The layers were separated and the aqueous phase was extracted with EtOAc (2x). The combined organics were dried (Na$_2$SO$_4$), filtered and concentrated to give the crude product. Purification via flash column chromatography (silica gel, .50% EtOAc/DCM) gave 6.2 g (67%) of the desired product as a white solid. The hydrochloride salt was prepared in EtOAc (50 ml), ether (40 ml), and methanol (5 ml) with ethereal HCl, m.p.=185°–188° C.

Analysis: Calculated for C$_{19}$H$_{25}$FN$_2$O$_2$·HCl: 61.87%C, 7.10%H, 7.59%N; Found: 61.79%C, 7.09%H, 7.53%N.

EXAMPLE 200

4-[4-(6-Fluoro-1H-indazol-3-yl)-1-piperazinyl]-2-hydroxy-2-methylbutane hydrochloride To a stirred solution of ethyl 3-[4-(6-fluoro-1H-indazol-3-yl)-1-piperazinyl]propionate (5.0 g, 16 mmol) in THF (120 ml) under N$_2$ was added, dropwise, methylmagnesium bromide (15.6 ml of a 3.0M solution in Et$_2$O; 0.047 mol). The temperature was maintained below 30° C. during the addition by using a water bath. After complete addition, the reaction was stirred at ambient temperature for 5 hours The reaction was cooled in an ice bath and saturated NH$_4$Cl (25 ml) was added. The mixture was extracted with EtOAc, and the EtOAc extract was washed with H$_2$O, dried with Na$_2$SO$_4$ and concentrated to yield 5.0 g of a white solid. The product was recrystallized from EtOAc to yield 3.8 g of white crystalline flakes. The compound was dissolved in anhydrous Et$_2$O (200 ml) and MeOH (20 ml) and the insolubles were filtered away. The filtrate was acidified with ethereal HCl to precipitate the salt. Additional anhydrous Et$_2$O (200 ml) was added and the suspension was stirred 15 minutes. The solid was collected to yield 4.5 g of a white powder. Two recrystallizations from MeOH gave 2.2 g. The concentrated mother liquor from the MeOH recrystallizations (2.0 g) was recrystallized from DMF to afford 1.2 g. The two samples were combined and a final recrystallization from MeOH provided 3.0 g (57%) of a white powder m.p.= 254°–256° C.

Analysis: Calculated for C$_{16}$H$_{23}$FN$_4$O·HCl: 56.05%C, 7.06%H, 16.34%N; Found: 55.99%C, 6.99%H, 16.27%N.

EXAMPLE 201

N-[2-[4-(6-Fluoro-1,2-benzisoxazol-3-yl)-1-piperidinyl]ethyl]-4-aminophthalimide fumarate A solution containing 2-[4-[(6-fluoro-1,2-benzisoxazol-3-yl)-1-piperidinyl]ethyl]amine (6.8 g, 25.7 mmol), dicyclohexyl carbodiimide (DCC, 8.2 g, 39 mmol) and 4-aminophthalic acid (4.57 g, 25.2 mmol) in dimethylformamide (DMF, 100 ml) was heated at 110° C. for 5 hours and kept at 65° C. for 18 hours. At the end of the reaction, the solids (DCU) were filtered and the solvent was removed on a rotary evaporator using a vacuum pump. The resulting crude product was purified by flash chromatography (SiO$_2$, 130 g) and provided 7.5 g (83%) of the desired product. It was converted to the fumarate salt which was recrystallized from ethanol and isopropyl ether: 7.1 g, m.p.=229°–230° C.

Analysis: Calculated for $C_{22}H_{21}FN_4O_3 \cdot C_4H_4O_4$: 59.54%C, 4.80%H, 10.68%N; Found: 58.99%C, 4.79%H, 10.37%N.

EXAMPLE 202

N-[2-[4-(6-Fluoro-1,2-benzisoxazol-3-yl)-1-piperidinyl]ethyl]-6-pyrrolo-3,4-6]pyridine-5,7-dione fumarate A solution of 2-[4-(6-fluoro-1,2-benzisoxazol-3-yl)-1-piperidinyl]ethylamine (4.14 g, 15.7 mmole) and 3,4-pyridinedicarboxylic anhydride (2.64 g, 17.7 mmol) in dimethylformamide (DMF, 100 ml) was heated at 130° C. for 18 hours. The solvent was removed on the rotary evaporator with a vacuum pump. The residue was dissolved into ethanol (250 ml) and the insolubles were filtered. To the ethanol solution was added fumaric acid (1.82 g, 1.0 eq), then the solution was concentrated to 120 ml. Isopropyl ether (120 ml) was added and the mixture was stirred overnight. The white crystals (3.1 g, 48%), m.p.=203°–206° C., were collected and recrystallized again from ethanol to give 2.34 g of pure product, m.p. =208°–209° C.

Analysis: Calculated for $C_{21}H_{19}N_4O_3 \cdot C_4H_4O_4$: 58.82%C, 4.54%H, 10.98%N; Found: 58.59%C, 4.67%H, 10.71%N.

EXAMPLE 203

N-[2,3-Epoxypropyl)-4-(6-fluoro-1,2-benzisoxazol-3-yl)piperidine fumarate

A mixture of 4-(6-fluoro-1,2-benzisoxazol-3-yl)piperidine (11 g, 50 mmol), $K_2CO_3$ (7.5 g, 54 mmol) and epibromohydrin (9 g, 54 mmol) in acetonitrile (150 ml) was heated at reflux for 16 hours. The mixture was filtered and concentrated to dryness. The crude product was purified by flash chromatography ($SiO_2$, 180 g, eluted with methylene chloride (DCM), and 1–2% $CH_3OH$ in DCM). The material thus purified as off-white solids weighed 8.7 g (63%). This material (3 g) was converted to fumarate salt in ethanol and isopropyl ether to give 3.27 g of white crystals, m.p.=145°–147° C.

Analysis: Calculated for $C_{15}H_{17}FN_2O_2 \cdot C_4H_4O_4$: 58.16%C, 5.39%H, 7.14%N; Found: 57.93%C, 5.35%H, 7.02%N.

EXAMPLE 204

4-[3-[4-(6-Fluoro-1,2-benzisoxazol-3-yl)-1-piperidinyl]-2-hydroxy-1-propoxy]phenyl methyl ether A mixture of 4-(6-fluoro-1,2-benzisoxazol-3-yl)piperidine (4.4 g, 20 mmol) and 2,3-epoxypropyl-4-methoxyphenyl ether (3.7 g, 20.5 mmol) in isopropyl alcohol (80 ml) was heated to reflux for 2 hours. The mixture was cooled and the crystals were collected to yield 6.81 g (85%), m.p.=134°–135° C.

Analysis: Calculated for $C_{22}H_{25}FN_2O_4$: 65.99%C, 6.29%H, 7.00%N; Found: 66.11%C, 6.31%H, 6.94%N.

EXAMPLE 205

3-[4-(6-Fluoro-2-benzisoxazol-3-yl)-1-piperidinyl]-2-hydroxy-1-propylphthalimide A mixture of 4-(6-fluoro-1,2-benzisoxazol-3-yl)piperidine (5.5 g, 25 mmol) and N-(2,3-epoxypropyl)phthalimide (5.1 g, 25.5 mmol) in isopropanol (100 ml) was heated at reflux for 4 hours and stirred at 65° C. for 18 hours. The reaction was cooled and the solvent was removed on a rotary evaporator. The white solids were dissolved in methylene chloride and purified on a silica gel column (110 g, eluted with 1% $CH_3OH$ in DCM, 1.5 l). The pure product thus obtained weighed 7.91 g, 75%. Recrystallization from DCM and isopropyl ether yielded 4.0 g, m.p.=162°–163° C.

Analysis: Calculated for $C_{23}H_{22}FN_3O_4$: 65.24%C, 5.24%H, 9.92%N; Found: 65.00%C, 5.05%H, 9.77%N.

EXAMPLE 206

1-[4-(6-Fluoro-1,2-benzisoxazol-3-yl)-1-piperidinyl]-3-phthalimido-2-propyl decanoate fumarate To a solution of 3-[4-(6-fluoro-1,2-benzisoxazol-3-yl)-1-piperidinyl]-2-hydroxy-1-propylphthalimide (6.26 g, 14.5 mmol), triethylamine (2.0 g, 20 mmol) in chloroform (200 ml) was charged with decanoyl chloride (3.6 g, 18.9 mmol, 1.26 equivalent) dropwise at room temperature. The mixture was stirred overnight. The mixture was concentrated and the crude product was purified on a flash chromatography column. The product thus obtained as an oil (4.96 g, 59%). This oil was converted to fumarate salt in a dilute ethanol solution to yield 2.0 g, m.p.=138°–140° C.

Analysis: Calculated for $C_{33}H_{40}FN_3O_5 \cdot C_4H_4O_4$: 64.06%C, 6.39%H, 6.06%N; Found: 63.90%C, 6.39%H, 5.88%N.

EXAMPLE 207

N-[2-[4-(6-Fluoro-1H-indazol-3-yl)-1-piperazinyl]ethyl]-4-methylphthalimide dihydrochloride A solution of 2-[4-[(6-fluoro-1H-indazol-3-yl)-1-piperazinyl]ethyl]amine (1.9 g, 7.2 mmol), 4-methylphthalic anhydride (1.2 g, 7.4 mmol) and DMF (50 ml) was stirred at 75° C. for 5 hours. Most of the DMF was removed in vacuo and the resultant red oil was triturated with $H_2O$ to produce a brown solid. The product was dissolved in $CH_2Cl_2$ and the organic extract was washed with $H_2O$, dried with $MgSO_4$ and concentrated to afford 2.8 g of a foam. The compound was suspended in MeOH (50 ml) and made acidic with ethereal HCl and the resultant solution was stirred for 1 hour. Anhydrous $Et_2O$ was added to precipitate 2.5 g of an off-white powder. This was combined with an additional sample (4.3 g total), and two recrystallizations from MeOH-$Et_2O$ provided 3.0 g (56%) of an off-white powder, m.p.=238°–241° C.

Analysis: Calculated for $C_{22}H_{22}Cl_2FN_5O_2 \cdot 2HCl$: 55.01%C, 5.04%H, 14.58%N; Found: 55.35%C, 5.09%H, 14.56%N.

EXAMPLE 208

N-[2-[4-(6-Fluoro-1H-indazol-3-yl)-1-piperazinyl]ethyl]-4-fluorophthalimide hydrochloride A solution of 2-[4-[(6-fluoro-1H-indazol-3-yl)-1-piperazinyl]ethyl]amine (4.0 g, 15 mmol), 4-fluorophthalic anhydride (2.5 g, 15 mmol) and DMF (75 ml) was stirred at 75° C. under $N_2$ for 4 hours. The reaction was concentrated to yield 6.7 g of a brown solid. The product was suspended in MeOH (150 ml) and was acidified with ethereal HCl. After stirring for 30 minutes, anhydrous $Et_2O$ was added and the resultant beige solid was collected to yield 5.1 g. The compound was recrystallized from MeOH-ether to give 3.8 g (56%) of an off-white powder, m.p.=282°–285° C.

Analysis: Calculated for $C_{21}H_{19}F_2N_5O_2 \cdot HCl$: 56.32%C, 4.50%H, 15.64%N; Found: 56.07%C, 4.35%H, 15.63%N.

EXAMPLE 209

N-[2-[4-(6-Fluoro-1,2-benzisoxazol-3-yl)-1-piperidinyl]ethyl]4-(1-decanoyl) aminophthalimide To a solution of 2-[4-(6-fluoro-1,2-benzisoxazol-3-yl)-1-piperidinyl]ethyl]-4-aminophthalimide (1.5 g, 3.67 mmol), triethylamine (0.46 mg, 4.6 mmol) in chloroform (30 ml) was charged with decanoyl chloride (0.8 mg, 4.2 mmol) dropwise at room temperature. The mixture was stirred for 1 hour. An additional portion of decanoyl chloride (0.1 mg, 0.52 mmol) was added to complete the reaction. The mixture was concentrated down, and the crude product was purified on a flash chromatography column (30 g of silica gel; eluted with dichloromethane (DCM) and 1% $CH_3OH$ in DCM). The oily product was dissolved in ethanol and treated with ether to yield white crystals 1.04 g (47.5%), m.p.= 159°–160° C.

Analysis: Calculated for $C_{32}H_{39}N_4O_4$: 68.31%C, 6.99%H, 9.96%N; Found: 68.47%C, 7.27%H, 9.95%N.

EXAMPLE 210

N-[2-[4-(6-Fluoro-1,2-benzisoxazol-3-yl)-1-piperidinyl]ethyl]-4-(1-decanoyl) oxyphthalimide fumarate To a mixture of 2-[4-(6-fluoro-1,2-benzisoxazol-3-yl)-1-piperidinyl]ethyl]-4-hydroxyphthalimide (5.1 g, 12.5 mmol), triethylamine (2.09 g, 1.67 equiv) in chloroform (150 ml) was charged decanoyl chloride (3.8 g, 20 mmol) dropwise at room temperature. The mixture was stirred at room temperature overnight (16 hours). The solution was diluted with methylene chloride (DCM, 150 ml) and washed with brine. The organic solution was dried and concentrated to a crude mixture. Purification on a flash chromatography column ($SiO_2$, 100 g, eluted with DCM and 1% $CH_3OH$ in DCM) yielded a colorless oil (5.0 g, 71%). This product was treated with fumaric acid (1.0 g) in ethanol (30 ml) and isopropyl ether (15 ml) to give 3.1 g of white crystals, m.p.=108°–110° C.

Analysis: Calculated for $C_{32}H_{38}FN_3O_5 \cdot C_4H_4O_4$: 63.61%C, 6.23%H, 6.18%N; Found: 63.71%C, 6.30%H, 6.25%N.

EXAMPLE 211

2-[2-[4-(6-Fluoro-1H-indazol-3-yl)-1-piperazinyl] ethyl-2,3-dihydro-3-hydroxy-1H-isoindol-1-one hemifumarate To a stirred suspension of N2-[2-[4-(6-fluoro-1H-indazol-3-yl)-1-piperazinyl]ethyl]-phthalimide (4.0 g, 10 mmol) in MeOH (125 ml) and $CH_2Cl_2$ (15 ml) under $N_2$, was added $NaBH_4$ (0.89 g, 23 mmol) in one portion. The reaction was stirred at ambient temperature for 45 minutes and was concentrated to yield a damp white solid. Flash chromatography using silica gel and 5% MeOH—$CH_2Cl_2$ increasing to 10% MeOH—$CH_2Cl_2$ as eluent, provided 4.5 g of a beige liquid. The liquid was dissolved in MeOH (50 ml), and the solution was acidified with ethereal HCl. Anhydrous $Et_2O$ was added to precipitate 2.9 g of a white solid. This was combined with an additional sample (4.6 g total) and was suspended in $H_2O$ (100 ml). $NaHCO_3$ was added to attain pH ~7 and the gummy mixture was extracted with $CH_2Cl_2$. The $CH_2Cl_2$ extract was dried with $MgSO_4$ and concentrated to yield 4.1 g of a white foam. The compound was purified by preparative HPLC. (Water's Associates Prep LC/System 500, using 2 silica gel columns and 5% $Et_2NH$-EtOAc as eluent). Concentration of appropriate fractions gave 2.1 g (5.3 mmol) of a beige foam. The compound was dissolved in EtOAc (50 ml) and the insolubles were filtered away. The filtrate was gently warmed and fumaric acid (0.70 g, 6.0 mmol) was added. After stirring at mild reflux for 30 minutes and at ambient temperature for 1 hour, the mixture was diluted with anhydrous $Et_2O$ (50 ml).

The resultant solid was collected and dried to yield 2.2 g. Recrystallization from ethanol-ether provided 1.1 g (16%) of the hemi-fumarate salt as a slightly off-white solid m.p.= 165°–168° C.

Analysis: Calculated for $C_{21}H_{22}FN_5O_2 \cdot 0.5C_4H_4O_4$: 60.91%C, 5.35%H, 15.45%N; Found: 60.41%C, 5.15%H, 15.22%N.

EXAMPLE 212

4-[3-[4-(6-Fluoro-1,2-benzisoxazol-3-yl)-1-piperidinyl ]-2-hydroxy-1-propoxy]-3-methoxyphenyl methanone A stirred mixture of 4-(2,3-epoxypropoxy)-3-methoxyphenyl methanone (4.5 g, 22.5 mmol) and 4-(6-fluoro-1,2-benzisoxazol-3-yl)piperidine (5.36 g, 24.3 mmol) in isopropyl alcohol (150 ml) was heated at 55° C. for 16 hours. The mixture was cooled and the solvent flash removed on a rotary evaporator. The residue was purified by flash chromatography over a silica gel column ($SiO_2$, 80 g; eluted with dichloromethane, DCM, and 1% $CH_3OH$ in DCM). The oil thus obtained solidified quickly, weight: 9.47 g. Recrystallization from ethanol and isopropyl ether, then toluene provided 8.6 g (86%) of white crystals, m.p.= 107°–108° C.

Analysis: Calculated for $C_{24}H_{27}FN_2O_5$: 65.15%C, 6.15%H, 6.33%N; Found: 65.35%C, 6.04%H, 6.05%N.

EXAMPLE 213

1-[4-(6-Fluoro-1,2-benzisoxazol-3-yl)-1-piperidinyl]-2-propanone hydrochloride

A mixture of 4-(6-fluoro-1,2-benzisoxazol-3-yl) piperidine (7.45 g, 33.4 mmol), $K_2CO_3$ (5.5 g) and bromo-2,2-dimethoxypropane (6.84 g, 37.6 mmol) in acetonitrile (200 ml) was heated and stirred at reflux for 4 hours. An additional charge of bromo-2,2-dimethoxypropane (5.1 g, 28 mmol) was added and the mixture was refluxed overnight. After being cooled to room temperature, the mixture was filtered, and the solvent was removed on a rotary evaporator. The residue was purified by flash chromatography over a silica gel column ($SiO_2$, 100 g; eluted with dichloromethane, DCM, and 1% $CH_3OH$ in DCM). The oil product thus obtained weighed 2.2 g (24%). The oil product was dissolved into ethanol (10 ml) then was treated with HCl in ether solution (1M, 9 ml) at room temperature. The crystals were collected, 2.08 g, m.p.=220°–223° C. dec.

Analysis: Calculated for $C_{15}H_{17}FN_2O_2 \cdot HCl$: 57.60%C, 5.80%H, 8.96%N; Found: 57.49%C, 5.97%H, 8.67%N.

EXAMPLE 214

1-[(4-Aceto-2-methoxy)phenoxy]-3-[4-(6-fluoro-1,2-benzisoxazol-3-yl)-1-piperidinyl]-2-propyl decanoate fumarate To a stirred mixture of 4-[3-[4-(6-fluoro-1,2-benzisoxazol-3-yl)-1-piperidinyl ]-2-hydroxy-1-propoxy]-

3-methoxyphenyl methanone (3.64 g, 8.23 mmol), triethylamine (1.6 g, 16 mmol) in chloroform (150 ml) was added decanoyl chloride (2.35 g, 12.4 mmole, 1.5 eq) dropwise at room temperature. The mixture was then heated at reflux for 1 hour The mixture was cooled and diluted with methylene chloride (DCM) and washed with water and brine. The organic solution was dried and concentrated to a crude mixture. Purification on a flash chromatography column (SiO$_2$, 65 g; eluted with DCM, 0.4 l and 1% CH$_3$OH in DCM, 0.6 l) yielded a colorless oil: 3.29 g (67%). This product was treated with fumaric acid (623 mg) in ethanol (10 ml) and isopropyl ether (50 ml) to give 2.64 g of a white solid, m.p.=109°–110° C.

Analysis: Calculated for C$_{34}$H$_{45}$FN$_2$O$_6$·C$_4$H$_4$O$_4$: 64.03%C, 6.93%H, 3.93%N; Found: 63.86%C, 6.88%H, 3.74%N.

EXAMPLE 215

N-[2-[4-(6-Fluoro-1,2-benzisoxazol-3-yl)-1-piperidinyl]ethyl]thiaphthalimide

A mixture of N-[2-[4-(6-fluoro-1,2-benzisoxazol-3-yl)-1-piperidinyl]ethyl]phthalimide (3.93 g, 10 mmol) and 2,4-bis(4-methoxyphenyl)-1,3, 2,4-dithiadephosphetane-2,4-disulfide (2.02 g, 5 mmol, 1 equiv. Lawesson's Reagent) is stirred and heated in anhydrous tetrahydrofuran for 3 hours at 60° C. The reaction mixture is evaporated on silica gel and purified by chromatography on a silica gel column. The product is further purified by recrystallization to afford N-[2-[4-(6-fluoro-1,2-benzisoxazol-3-yl)-1-piperidinyl]ethyl]thiaphthalimide.

EXAMPLE 216

By using substantially the same procedure as described in Example 215 except that 10 mmol (2 equiv.) of Lawesson's Reagent is used and the reaction time at 60° C. is extended to 5 hours there is obtained N-[2-[4-(6-fluoro-1,2-benzisoxazol-3-yl)-1-piperidinyl]ethyl-1,3-bis-thiaphthalimide.

EXAMPLE 217

N-2-[4-(6-Fluoro-1-decanoyl-1H-indazol-3-yl)-1-piperazinyl ]-ethyl]phthalimide maleate To a stirred suspension of NaH (0.50 g of a 50% oil dispersion, 12.5 mmol) in DMF (10 ml) under N$_2$ and cooled to −15° C., was added dropwise, N-[2-[4-(6-fluoro-1H-indazol-3-yl)-1-piperazinyl]ethyl]phthalimide (4.0 g, 10.2 mmol) dissolved in DMF (45 ml) over 45 minutes so that the temperature did not exceed −8° C. The reaction was stirred for 1 hour allowing the temperature to warm to 0° C. The reaction was cooled to −12° C. and a solution of decanoyl chloride (2.9 g, 15.3 mmole) in DMF (13 ml) was added dropwise so that the temperature remained below −5° C. After complete addition, the reaction was stirred at ambient temperature for 18 hours. The reaction was poured into ice-cold H$_2$O (125 ml) and the aqueous mixture was extracted with EtOAc. The EtOAc extract was washed with H$_2$O/Brine (3×), dried with MgSO$_4$ and concentrated to yield 5.7 g of a beige oil that readily crystallized. This was combined with another sample (6.4 g total) and purification via flash chromatography, over silica gel using 3% MeOH/CH$_2$Cl$_2$ as eluent, afforded 4.9 g (78%) of a white solid. Another previously purified sample was combined with this (6.3 g, 11.5 mmol total) and the product was dissolved in hot absolute ethanol (100 ml). Maleic acid (1.4 g, 12.1 mmole) was added and the solution was stirred at a mild reflux for 30 minutes. The reaction was concentrated to a white slush that was diluted with petroleum ether (100 ml) and stirred for ca 2 hours. The resultant solid was collected to yield 5.5 g of shiny white crystals. The salt was recrystallized twice from absolute ethanol to afford 4.3 g and a third recrystallization from CH$_3$CN gave 3.8 g (39%) of the analytically pure maleate salt as a white solid, m.p.=154°–156° C.

Analysis: Calculated for C$_{31}$H$_{38}$FN$_5$O$_3$·C$_4$H$_4$O$_4$: 63.34%C, 6.38%H, 10.55%N; Found: 63.46%C, 6.33%H, 10.60%N.

EXAMPLE 218

2-[4-[6-Fluoro-1,2-benzisoxazol-3-yl)-1-piperidinyl] propyl]amine dihydrochloride hemihydrate (A) 2-[4-[6-Fluoro-1,2-benzisoxazol-3-yl)-1-piperidinyl] propionitrile A mixture of 4-(6-fluoro-1,2-benzisoxazol-3-yl)-1-piperidine (10 g, 45.4 mmol); 2-chloropropionitril (10 g, 112 mmol), K$_2$CO$_3$ (9.4 g, 1.5 eq) in acetonitrile (100 ml) was stirred and heated at 80° C. for 16 hours. The mixture was filtered and concentrated to dryness. The crude solids were purified by flash chromatography (SiO$_2$, 160 g; eluted with methylene chloride, (DCM) 1.5 l; and 1% CH$_3$OH in DCM, 1 l). The white solid material thus obtained weighed 10.1 g and was recrystallized from ethanol and isopropyl ether to yield 5.1 g, m.p.-133°–134° C.

Analysis: Calculated for C$_{15}$H$_{16}$FN$_3$O: 65.92%C, 5.90%H, 15.37%N; Found: 65.92%C, 5.85%H, 15.52%N.

(B) 2-[4-(6-Fluoro-1,2-benzisoxazol-3-yl)-1-piperidinyl] propyl]amine dihydrochloride hemihydrate To a solution of 2-[4-(6-fluoro-1,2-benzisoxazol-3-yl)-1-piperidinyl]propionitrile (6.7 g, 24.5 mmol) in THF (200 ml) was added lithium aluminum hydride (3.6 g, 50% in oil, 2 eq) in portions under N$_2$ at room temperature for 3.5 hours. At the end of the reaction, the excess of LAH was carefully hydrolyzed with ice-chips (7 ml) under N$_2$. A solution of 15% NaOH (2 ml) was added, then the mixture was stirred for 30 minutes. The insolubles were filtered and the organic solution was concentrated down to a pale oil (7.6 g) which partially solidified. A sample (1.5 g) of this mixture was dissolved into ethanol and was treated with HCl (6 ml, 1M in ether). The white solid which precipitated was collected and recrystallized from ethanol to give 708 mg, m.p. 215°–217° C. of the dihydrochloride hemihydrate.

Analysis: Calculated for C$_{15}$H$_{20}$FN$_3$O·2HCl·0.5H$_2$O: 50.14%C, 6.45%H, 11.69%N, 2.50%H$_2$O; Found: 49.94%C, 6.17%H, 11.11%N, 2.12%H$_2$O.

EXAMPLES 219

N-[2-[4-(6-Fluoro-1,2-benzisoxazol-3-yl)-1-piperidinyl]propyl]phthalimide hydrochloride To a stirred mixture of 2-[4-(6-fluoro-1,2-benzisoxazol-3-yl)-1-piperidinyl]-propyl]amine 2.56 g, 9.2 mmol) and triethylamine (1.35 g, 13.5 mmol) in chloroform (150 ml) was added phthalic anhydride (1.61 g, 10.9 mmol). The mixture was stirred at room temperature for 4 hours. At the end of the reaction the solvent was evaporated on a rotary evaporator and the crude residue was dried in vacuo. The purification was done by flash chromatography over a silica gel column (40 g, SiO$_2$, eluted with methylene chloride, then increase the MeOH concentration to 2%). The pure product thus obtained (2.18 g) was combined with another batch of same quality material (1.53 g) and then was converted to the hydrochloride salt with HCl in ether solution. The white solid was recrystallized from methanol to give 3.12 g, m.p.=275°–277° C.

Analysis: Calculated for $C_{23}H_{22}FN_3O_3 \cdot HCl$: 62.23%C, 5.22%H, 9.47%N; Found: 61.93%C, 5.32%H, 9.46%N.

EXAMPLE 220

N-[2-[4-(1-Decanoxycarbonyl-6-fluoro-1H-indazol-3-yl)-1-piperazinyl]ethyl]-phthalimide hydrochloride A mixture of decanyl chloroformate, (2.4 g, 11 mmol), and N-[2-[4-(6-fluoro-1H-indazol-3-yl)-1-piperazinyl]ethyl]phthalimide (3.9 g, 10 mmol) was warmed on the steam bath for 15 minutes. The reaction was allowed to cool to ambient temperature, and then ether was added to the residue. The resulting solid was filtered to afford N-[2-[4-(1-decanoxy-6-fluoro-1H-indazol-3-yl)-1-piperazinyl]ethyl]phthalimide hydrochloride.

EXAMPLE 221

N-[2-[4-(6-Fluoro-1,2-benzisoxazol-3-yl)-1-piperidinyl]ethyl]-3-methoxyphthalimide hydrochloride A mixture of 2-[4-(6-fluoro-1,2-benzisoxazol-3-yl)-1-piperidinyl]ethyl]-3-hydroxyphthalimide hydrochloride (4.36 g, 10.33 mmol) and $K_2CO_3$ (3.6 g, 26 mmol) in methanol was stirred for 15 minutes. Then dimethylsulfate (4.0 g, 3.17 mmol) was added, followed by potassium t-butoxide (1.1 g, 10 mmol) and the mixture was stirred at room temperature for 4 hours. The reaction mixture was concentrated and the residue was extracted with DCM (400 ml). The organic layer was filtered and concentrated and the resulting residue was chromatographed on silical gel (47 g $SiO_2$), eluting with DCM and MeOH:DCM mixture. The resulting product (1.4 g) was converted to the hydrochloride salt in ethanol with 1N-HCl in ether. The resulting white solid was recrystallized from methanol to give 1.12 g, mp=247°–250° C.

Analysis: Calculated for $C_{23}H_{22}FN_3O_4 \cdot HCl$: 60.07%C, 5.04%H, 9.14%N; Found: 59.79%C, 5.05%H, 8.98%N.

EXAMPLE 222

6-Fluoro-3-[1-[3-(2,5-dimethoxyphenoxy)propyl]-4-piperidinyl]-1,2-benzisoxazole hydrochloride (A) 2-(3-Chloropropoxy)-1,4-dimethoxybenzene A mixture of 2,5-dimethoxyphenol (29 g, 0.19 mol), $K_2CO_3$ (35 g), 3-chlorobromopropane (38.5 g, 0.25 mol) and acetone (250 ml) was stirred and refluxed for 6 hours, and then stirred at ambient temperature for 16 hours. The reaction was filtered, and the filtrate was concentrated to an orange liquid. The liquid was taken up into $Et_2O$, and the organic layer washed with 1N NaOH, $H_2O$, dried ($MgSO_4$) and was concentrated to yield 37.8 g of an orange solid. An 11.7 g sample of this solid was flash chromatographed on silica gel (180 g) with 5% EtOAc/$CH_2Cl_2$ as eluent. Concentration of similar fractions gave 7.2 g of white, waxy solid, which was recrystallized from petroleum ether to afford a white solid, m.p. 48°–50° C.

Analysis: Calculated for $C_{11}H_{15}ClO_3$: 57.27%C, 6.55%H; Found: 57.19%C, 6.52%H.

(B) 6-Fluoro-3-[1-[3-(2,5-dimethoxyphenoxy)propyl]-4-piperidinyl]-1,2-benzisoxazole Hydrochloride A mixture of 6-fluoro-3-(4-piperidinyl)-1,2-benzisoxazole (3.0 g, 14.0 mmol), 2-(3-chloropropoxy)-1,4-dimethoxybenzene, $K_2CO_3$ (2.1 g) and acetonitrile (50 mL) was stirred and refluxed for 24 hours. The reaction was filtered and the filtrate was concentrated to 5.0 g of an oil. The oil was chromatographed on a preparative HPLC on a silica gel column with 5% MeOH—$CH_3Cl_2$ as eluent. Concentration of the appropriate fractions afforded 4.6 g of an oil, which, with ethereal HCl, was converted to 4.0 g of a white hydrochloride salt. The salt was recrystallized twice from EtOH to yield 2.9 g of product as a white solid, m.p. 186°–188° C.

Analysis: Calculated for $C_{23}H_{27}FN_2O_4 \cdot HCl$: 61.26%C, 6.26%H, 6.21%N; Found: 61.14%C, 6.38%H, 6.15%N.

EXAMPLE 223

4-[3-[4-(6-Fluoro-1,2-benzisoxazol-3-yl)-1-piperidinyl]propoxyl-2-hydroxy-5-methoxy-alpha-methylbenzenemethanol (A) 1-[4-(3-Chloropropoxy)-2-hydroxy-5-methoxyphenyl]ethanone A mixture of 2,4-dihydroxy-5-methoxyacetophenone (1.4 g, 7.7 mmol), $K_2CO_3$ (1.4 g, 10.0 mmol), 3-chlorobromopropane (1.6 g, 10.0 mmol) and acetone (25 mL) was stirred and refluxed under $N_2$ for 16 hours. The reaction was poured into $H_2O$, and the aqueous suspension was extracted with ethyl acetate. The extract was washed ($H_2O$, brine) dried ($MgSO_4$) and concentrated to yield 1.4 g of an off-white solid. Recrystallization twice from ethanol afforded 0.4 g of the alkylated phenol as a solid, m.p. 99°–101° C.

Analysis: Calculated for $C_{12}H_{15}ClO_4$: 55.71%C, 5.84%H; Found: 55.61%C, 5.92%H.

(B) 1-[4-[3-[4-(6-Fluoro-1,2-benzisoxazol-3-yl)-1-piperidinyl]propoxy]-2-hydroxy-5-methoxyphenyl]ethanone A mixture of 6-fluoro-3-(4-piperidinyl)-1,2-benzisoxazole (4.2 g, 19 mmol), 1-[4-(3-chloropropoxy)-2-hydroxy-5-methoxyphenyl]ethanone (5.0 g, 19 mmol), $NaHCO_3$ (1.8 g, 20 mmol) and acetonitrile (120 mL) was stirred and refluxed for 16 hours. The reaction was filtered and the filtrate was concentrated to a dark oil. The oil was taken up in anhydrous ether and ethereal HCl was added to precipitate 8.7 g of an off-white hydrochloride salt. A 2.0 g sample of the salt was converted to its free base and chromatographed by preparative HPLC (silica gel with 5% MeOH/$CH_2Cl_2$ as eluent). Concentration of the desired fractions gave 1.1 g of a white solid, which was recrystallized from EtOH to yield 0.85 g of the product, m.p. 122°–124° C.

Analysis: Calculated for $C_{24}H_{27}FN_2O_5$: 65.15%C, 6.15%H, 6.33%N; Found: 64.93%C, 6.23%H, 6.20%N.

(C) 4-[3-[4-(6-Fluoro-1,2-benzisoxazol-3-yl)-1-piperidinyl]propoxy]-2-hydroxy-5-methoxy-alpha-methylbenzenemethanol To a stirred solution of 4-[3-[4-(6-fluoro-1,2-benzisoxazol-3-yl)-1-piperidinyl]-2-hydroxy-5-methoxyphenyl]ethanone (3.0 g, 6.8 mmol) in tetrahydrofuran/ethanol (70 ml, 4:3) was added sodium borohydride (0.26 g, 6.8 mmol). The reaction was stirred at ambient temperature for 0.75 hours, and then concentrated to afford a thick oil. The oil was triturated with $H_2O$ and the aqueous suspension was extracted with $CH_2Cl_2$. The extract was washed with $H_2O$, dried ($MgSO_4$) and concentrated to afford 3.4 g of a white solid. The solid was recrystallized from MeOH and then from EtOH to yield 0.80 g of solid, m.p. 156°–158° C.

Analysis: Calculated for $C_{24}H_{29}FN_2O_5$: 64.85%C, 6.58%H, 6.30%N; Found: 64.73%C, 6.58%H, 6.13%N.

EXAMPLE 224

N-[2-[4-(6-Fluoro-1,2-benzisoxazol-3-yl)-1-piperidinyl]ethyl]phthalimide fumarate A solution of fumaric acid (448 mg, 3.86 mmol) in ethanol was added to a hot solution of 2-[4-(6-fluoro-1,2-benzisoxazol-3-yl)-1-piperidinyl]ethyl]phthalimide (1.52 g, 3.86 mmol) in ethanol. The solution was cooled and the crystals were collected to yield 1.9 g. Recrystallization once from ethanol yielded 1.15 g of the fumarate salt, m.p. 231°–232° C.

Analysis: Calculated for $C_{22}H_{20}FN_3O_3 \cdot C_4H_4O_4$: 61.29%C, 4.75%H, 8.25%N; Found: 61.03%C, 4.68%H, 8.38%N.

EXAMPLE 225

N-[2-[4-(6-Fluoro-1,2-benzisoxazol-3-yl)-1-piperidinyl]butyl]phthalimide (A) 1-[4-(6-Fluoro-1,2-benzisoxazol-3-yl)-1-piperidinyl]-2-hydroxybutane A stirred mixture of 4-(6-fluoro-1,2-benzisoxazol-3-yl)piperidine (5.5 g, 25 mmol) and 1,2-expoxybutane (1.89 g, 26.3 mmol) in isopropyl alcohol (100 ml) was heated at 65° C. for 2 days. This mixture was cooled and the solvent was removed to leave a brown oil which was purified by flash chromatography over a silica gel column ($SiO_2$, 70 g; eluted with DCM, 1 l and MeOH:DCM 2%: 98%) to give an off-white solid weighing 6.3 g. Recrystallization from hot ethanol yielded 1.96 g of fine crystals, m.p. 87°–88° C.

Analysis: Calculated for $C_{16}H_{21}FN_2O_2$: 65.73%C, 7.24%H, 9.58%N; Found: 65.83%C, 7.12%H, 9.54%N.

(B) N-[2-[4-(6-Fluoro-1,2-benzisoxazol-3-yl)-1-piperidinyl]butyl]phthalimide

A solution of diethyl azodicarboxylate (DEAD, 4.9 g, 28.3 mmol) in THF (50 ml) was added dropwise to a solution of 2-[4-(6-fluoro-1,2-benzisoxazol-3-yl)-1-piperidinyl]butanol (6.9 g, 23.6 mmol), phthalimide (4.16 g, 1.2 eq), and triphenylphosphine (7.4 g, 28.3 mmol) in THF (200 ml) at room temperature. The solution was stirred at room temperature for 24 hours. After the reaction, the solvent was stripped to dryness. The residue was stirred in ether (200 ml) and the insolubles were removed by filtration. The oily residue from concentration of the ether solution was purified by two flash chromatography ($SiO_2$, 75 g, eluted with dichloromethane, DCM, and 1–2% $CH_3OH$ in DCM) and (100 g of $SiO_2$; eluted with DCM, 1 l, and 1% $CH_3OH$ in DCM, 1.2 l). Two close compounds were separated and the top compound on TLC (1.6 g) was recrystallized from isopropyl ether to yield 0.76 g of white crystals, m.p. 86°–88° C.

Analysis: Calculated for $C_{24}H_{24}FN_3O_3$: 68.39%C, 5.74%H, 9.97%N; Found: 68.47%C, 5.67%H, 9.97%N.

EXAMPLE 226

N-[3-[4-(6-Fluoro-1,2-benzisoxazol-3-yl)-1-piperidinyl]butyl]phthalimide hydrochloride A solution of diethyl azodicarboxylate (DEAD, 4.9 g, 28.3 mmol) in THF (50 ml) was added dropwise to a solution of 2-[4-(6-fluoro-1,2-benzisoxazol-3-yl)-1-piperidinyl]-butanol (6.9 g, 23.6 mmol), phthalimide (4.16 gm, 1.2 eq), and triphenylphosphine (7.4 g, 28.3 mmol) in THF (200 ml) at room temperature. The solution was stirred at room temperature for 24 hours. After the reaction, the solvent was stripped and the residue was stirred in ether (200 ml). The insolubles were removed by filtration. The oily residue from concentration of the ether solution was purified by two flash chromatography ($SiO_2$, 75 g; eluted with dichloromethane, DCM, and 1–2% $CH_3OH$ in DCM) and $SiO_2$, 100 g; eluted with DCM, 1 l; and 1% $CH_3OH$ in DCM, 1.2 l). Two close compounds were separated. The lower compound on TLC 3.66 g) was treated with HCl/ether in ethanol, and the solid salt was precipitated with hexane. Recrystallization from ethanol and isopropyl ether yielded white crystals 3.26 g, m.p. 210°–214° C. dec.

Analysis: Calculated for $C_{24}H_{24}FN_3O_3HCl$: 62.95%C, 5.50%H, 9.18%N; Found: 62.70%C, 5.58%H, 9.13%N.

EXAMPLE 227

4-Fluoro-N-[2-[4-(6-fluoro-1H-indazol-3-yl)-1-piperidinyl]ethyl]phthalimide maleate (A) 1-Benzoyl-6-fluoro-3-(1-phenoxycarbonyl-4-piperidinyl)-1H-indazole To a solution of 1-benzoyl-6-fluoro-3-(1-methyl-4-piperidinyl)-1H-indazole (2.0 g, 5.93 mmol) in dichloromethane (100 ml) was added phenyl chloroformate (3.9 ml, 29.65 mmol) at room temperature. The reaction mixture was stirred at room temperature for 24 hours, refluxed for an additional 0.5 hours and subsequently concentrated. The remaining residue was dissolved into dichloromethane and washed with 10% HCl (aq.). The organic phase was dried ($MgSO_4O$, filtered, and concentrated to give an oil which was purified via flash column chromatography (silica gel, 20% DCM/EtOAc). Concentration of the product-containing fractions gave an oil which solidified on standing. The white solid was washed with EtOAc, leaving 0.47 g of the desired product, m.p. 137°–139° C.

Analysis: Calculated for $C_{26}H_{22}FN_3O_3$: 70.42%C, 5.00%H, 9.48%N; Found: 70.38%C, 4.81%H, 9.42%N.

(B) [4-(6-Fluoro-1H-indazol-3-yl)-1-piperidinyl]acetonitrile

To a suspension of 1-benzoyl-6-fluoro-3-(1-phenoxycarbonyl-4-piperidinyl)-1H-indazole (31.6 g, 71.3 mmol) in ethanol (500 ml) was added, 50% KOH(aq.) (100 g of KOH in 100 g $H_2O$) at room temperature. The reaction mixture was warmed to reflux for 4 hours and cooled to room temperature. After adjusting the pH to about one (to litmus) using HCl (con., 110 ml), the volatiles were removed under reduced pressure. The remaining wet solid was diluted with water and collected via filtration. The solid material was dissolved into hot water to which 50% NaOH(aq.) was added (pH was about 10, to litmus). The precipitated 4-(6-fluoro-1H-indazol-3-yl)piperidine (10.7 g) was filtered and used without further purification.

To a stirred suspension of 4-(6-fluoro-1H-indazol-3-yl)piperidine (4.95 g, 22.6 mmol) and $NaHCO_3$ (2.1 g, 24.9 mmol) in dry acetonitrile (110 ml) was added chloroacetonitrile (1.6 ml, 24.9 mmol) at room temperature, under nitrogen. The suspension was warmed to reflux for 22.5 hours, cooled to room temperature, and subsequently filtered. The remaining solids were washed with DCM and the combined filtrates were concentrated. The resulting brown oil was dissolved into EtOAc and washed with water. The organic phase was dried ($MgSO_4O$, filtered and concentrated to give a brown solid which was re-dissolved into DCM/EtOAc and flushed through alumina with DCM. The eluent was concentrated to give 5.2 g of the desired product as a solid, m.p. 149°–151° C.

Analysis: Calculated for $C_{14}H_{15}FN_4$: 65.10%C, 5.85%H, 21.69%N; Found: 64.84%C, 5.90%H, 21.74%N.

(C). 2-[4-(6-Fluoro-1H-indazol-3-yl)-1-piperidinyl] ethylamine

To a solution of [4-(6-fluoro-1H-indazol-3-yl)-1-piperidinyl]-acetonitrile (6.1 g, 23.6 mmol) in dry THF (235 ml) was added (dropwise) lithium aluminum hydride (LAH) (28.4 mmol, 1.0M in THF) at room temperature, under nitrogen. Upon complete addition, the reaction mixture was warmed to reflux for 3 hours. After cooling to 0° C. in an ice bath, the reaction was carefully quenched with water (4.0 ml). The solids were removed via filtration and washed with THF. The combined filtrates were concentrated to give 5.6 g of the desired product. This material was suspended in DCM and filtered to give the product as an off-white solid, m.p. 125°–128° C.

Analysis: Calculated for $C_{16}H_{21}FN_2O_2$: 65.73%C, 7.24%H, 9.58%N; Found: 65.83%C, 7.12%H, 9.54%N.

Analysis: Calculated for $C_{14}H_{19}FN_4$: 64.10%C, 7.30%H, 21.36%N; Found: 63.60%C, 7.10%H, 21.03%N.

(D). 4-Fluoro-N-[2-[4-(6-fluoro-1H-indazol-3-yl)-1-piperidinyl]]ethyl]-phthalimide maleate To a solution of 2-[4-(6-fluoro-1H-3-indazolyl)-1-piperidinyl]ethylamine (6.1 g, 23.3 mmol) in DMF (230 ml) was added 4-fluorophthalic anhydride (4.2 g, 25.5 mmol) at room temperature under nitrogen. The reaction mixture was warmed to 80° C. for 2.5 hours at which time it was allowed to cool to room temperature. The DMF was removed under reduced pressure to give a brown oil which was dissolved into DCM/MeOH. Purification via flash column chromatography (silica gel, 2% MeOH/DCM) afforded 3.6 g of the desired product as a white solid. The maleate salt was prepared in methanol (75 ml) using maleic acid (2.1 eq.). The precipitated salt was collected via filtration and recrystallized from acetonitrile to give a white solid, m.p. 193°–195° C.

Analysis: Calculated for $C_{22}H_{20}F_2N_4O_2 \cdot C_4H_4O_4$: 59.31%C, 4.59%H, 10.64%N; Found: 59.13%C, 4.80%H, 10.80%N.

EXAMPLE 228

N-[2-[4-(6-Fluoro-1H-indazol-3-yl)-1-piperazinyl] ethyl]-methylphthalimide hydrochloride A solution of 2-[4-[(6-fluoro-1H-indazol-3-yl)-1-piperazinyl]ethylamine (5.9 g, 22.4 mmol), 3-methyphthalic anhydride (3.7 g, 22.5 mmol) and DMF (120 ml) was stirred at 85° C. for 22 hours under $N_2$. Most of the DMF was distilled off to afford 12.5 g of a dark oil. The oil was purified by preparative HPLC (Waters Associates Prep 500 using 2 silica gel columns and 4% MeOH—$CH_3Cl_2$ as eluent) to yield 6.4 g of a yellow foam. A 1.0 g sample was suspended in MeOH (25 ml) and the made acids made acidic with ethereal HCl. After about 20 minutes the resultant solution was filtered and the filtrate was diluted with anhydrous $Et_2O$ to precipitate the salt. The light yellow solid was collected to give 0.90 g which was triturated with boiling $CH_3CN$ (40 ml) and after cooling the product was collected to provide 0.75 g of a white solid, m.p. 266°–269° C.

Analysis: Calculated for $C_{22}H_{22}FN_5O_2 \cdot HCl$: 59.53%C, 5.22%H, 15.78%N; Found: 59.31%C, 4.98%H, 15.77%N.

EXAMPLE 229

N-[2-[4-(6-Fluoro-1H-indazol-3-yl)-1-piperazinyl] propyl]phthalimide hydrochloride A mixture of 6-fluoro-3-(4-piperazinyl)-1H-indazole (7.0 g, 31.8 mmol), $NaHCO_3$ (2.9 g, 34.5 mmol), N-(3-bromopropyl)phthalimide (8.5 g, 31.8 mmol) and acetonitrile (200 ml) was stirred at reflux under $N_2$ for 21 hours. Most of the acetonitrile was removed in vacuo and the resultant yellow residue was triturated with $H_2O$ to afford a solid. The product was isolated by filtration and dried to yield 12.7 g. Recrystallization from EtOH gave 7.8 g of a yellow solid. A 2.0 g sample was suspended in MeOH (25 ml) and the pH was adjusted to pH-1 with ethereal-HCl. After 30 minutes of stirring at ambient temperature, the thick suspension was diluted with isopropyl ether (10 ml) and $Et_2O$ (50 ml) and the salt collected to yield 1.9 g. Recrystallization from EtOH provided 1.4 g (38%) of a light yellow solid, m.p. 261°–264° C.

Analysis: Calculated for $C_{22}H_{22}FN_5O_2 \cdot HCl$: 59.53%C, 5.22%H, 15.78%N; Found: 59.48%C, 5.25%H, 15.56%N.

EXAMPLE 230

4-Fluoro-N-[2-[4-(1H-indazol-3-yl)-1-piperazinyl] ethyl]phthalimide maleate (A) 1-Benzenesulfonyl-3-(1-phenoxycarbonyl-4-piperazinyl)-1H-indazole To a solution of 1-benzenesulfonyl-3-(1-methyl-4-piperazinyl)-1H-indazole (2.1 g, 5.89 mmol) in dichloromethane (100 ml) was added phenyl chloroformate (3.8 ml, 29.45 mmol) at room temperature. The reaction mixture was warmed to reflux for 2 hours, cooled to room temperature, and concentrated. The residue was diluted with ethyl acetate, filtered and purified via flash column chromatography (silica gel, ethyl acetate). Concentration of the product containing fractions gave an oil which solidified on standing. The product was washed well with heptane to give 1.5 g of a white solid, m.p. 112°–114° C.

Analysis: Calculated for $C_{24}H_{22}N_4O_4S$: 62.32%C, 4.79%H, 12.11%N; Found: 62.28%C, 4.73%H, 12.15%N.

(B) [4-(1H-Indazol-3-yl)-1piperazinyl]acetonitrile

To a suspension of 1-benzenesulfonyl-3-(1-phenoxycarbonyl-4-piperazinyl)-1H-indazole (31.3 g, 67.7 mmol) in ethanol (500 ml) was added, 50% KOH (aq.) (100 g of KOH in 100 g $H_2O$) at room temperature. The reaction mixture was warmed to reflux for 6.5 hours and cooled to room temperature. After adjusting the pH to about two using HCl (con., 120 ml), the volatiles were removed under reduced pressure. The remaining residue was diluted with water and removed via filtration. The aqueous filtrate was washed with EtOAc and basified to pH=8 using 50% NaOH (aq.). The product was extracted into 10:1 dichloromethane/isopropylalcohol. The combined organics were dried ($MgSO_4$), filtered, and concentrated to give 13.0 g of desired 3-piperazin-1-yl-1H-indazole as a brown solid which was used without further purification.

To a stirred suspension of 3-piperazin-1-yl-1H-indazole (6.0 g, 29.7 mmol) and $NaHCO_3$ (2.7 g, 32.7 mmol) in dry acetonitrile (125 ml) was added chloroacetonitrile (2.1 ml, 31.2 mmol) at room temperature, under nitrogen. The suspension was warmed to reflux for 17.5 hours, cooled to room temperature, and subsequently filtered. The remaining solids were washed with dichloromethane and the combined filtrates were concentrated. The resulting brown oil was purified via flash column chromatography (silica gel, 0–50% EtOAc/DCM) to give 4.0 g of product as an off-white solid, m.p. 121°–123° C.

Analysis: Calculated for $C_{13}H_{15}N_5$: 64.71%C, 6.27%H, 29.02%N; Found: 64.47%C, 6.23%H, 28.82%N.

(C) 4-Fluoro-N-[2-[4-(1H-indazol-3-yl)-1-piperazinyl] ethyl]phthalimide maleate

133

To a solution consisting of [4-(1H-indazol-3-yl)-1-piperazinyl]acetonitrile (8.7 g, 36.1 mmol) in tetrahydrofuran (360 ml) was added lithium aluminum hydride (dropwise, 43.3 ml of a 1.0M solution in tetrahydrofuran, 43.3 mmol) at room temperature, under nitrogen. The reaction mixture was warmed to reflux for 3 hours at which time it was allowed to cool to room temperature. The reaction was carefully quenched with water (3.5 ml) and the precipitated salts were removed via filtration and washed with EtOAc. The combined filtrates were concentrated to give a solid. This material was suspended in ether (4 days) and collected via filtration to give 4.7 g of 2-[4-(1-indazol-3-yl)-1-piperazinyl]ethylamine which was used without further purification.

A solution of intermediate 2-[4-(1-indazol-3-yl)-1-piperazinyl]ethylamine (1.0 g, 4.1 mmol) and 4-fluorophthalic anhydride (0.75 g, 4.5 mmol) in dimethylformamide (40 ml) was warmed to 80° C. for 4 hours. After cooling to room temperature, the dimethylformamide was removed in vacuo (<0.5 mmHg, 55° C.) to give a brown oil which solidified on standing. The solid material was suspended in EtOAc and warmed to reflux for 3 hours. The desired product remained as a yellow solid (0.86 g) and was collected via filtration and dried under high vacuum. The maleate salt was prepared in refluxing methanol using maleic acid (0.53 g, 4.6 mmol). The off-white solid was collected via filtration and washed with methanol, m.p. 211°–215° C.

Analysis: Calculated for $C_{21}H_{20}FN_5O_2 \cdot C_4H_4O_4$: 58.94%C, 4.75%H, 13.75%N; Found: 58.69%C, 4.91%H, 13.77%N.

EXAMPLE 231

N-[2-[4-(1-Decanoyl-6-fluoro-1H-indazol-3-yl)-1-piperazinyl]ethyl]phthalimide maleate To a stirred suspension of NaH (0.50 g of a 60% oil dispersion, 12.5 mmol) in dimethylformamide(DMF) (10 ml) under $N_2$ and cooled to −15° C., was added dropwise, 2-[2-[4-(6-fluoro-1H-indazol-3-yl)-1-piperazinyl]ethyl]-1H-isoindol-1,3-(2H)dione (4.0 g, 10.2 mmol) dissolved in DMF (45 ml) over 45 minutes so that the temperature did not exceed −8° C. The reaction was stirred for 1 hour allowing the temperature to warm to 0° C. The reaction was cooled to −12° C. and a solution of decanoyl chloride (2.9 g, 15.3 mmol) in DMF (13 ml) was added dropwise so that the temperature remained below −5° C. After complete addition, the reaction was stirred at ambient temperature for 18 hours. The reaction was poured into ice-cold $H_2O$ (125 ml) and the aqueous mixture was extracted with EtOAc. The EtOAc extract was washed with $H_2O$/brine, dried with $MgSO_4$ and concentrated to yield 5.7 g of a beige oil that readily crystallized. This was combined with another sample (6.4 g total) and purification via flash chromatography, over silica gel using 3% MeOH—$CH_3Cl_2$ as eluent, afforded 4.9 g of a white solid. Another previously purified sample was combined with this (6.3 g, 11.5 mmol total) and the product was dissolved in hot absolute ethanol (100 ml). Maleic acid (1.4 g, 12.1 mmol) was added and the solution was stirred at a mild reflux for 30 minutes. The reaction was concentrated to a white slush that was diluted with petroleum ether (100 ml) and stirred for 2 hours. The resultant solid was collected to yield 5.5 g of shiny white crystals. The salt was recrystallized twice from absolute ethanol to afford 4.3 g and a third recrystallization from $CH_3CN$ gave 3.8 g of the maleate salt as a white solid, m.p. 154° 156° C.

Analysis: Calculated for $C_{31}H_{38}FN_5O_3 \cdot C_4H_4O_4$: 63.34%C, 6.38%H, 10.55%N; Found: 63.46%C, 6.33%H, 10.60%N.

134

EXAMPLE 232

N-2-[4-(1-Benzoyl-6-fluoro-1H-indazol-3-yl)-1-piperazinyl]ethyl]-phthalimide hydrochloride A mixture of 2-[2-[4-(6-fluoro-1H-indazol-3-yl)-1-piperazinyl]ethyl]-1H-isoindol-1,3-(2H)-dione (6.0 g, 15 mmol) and benzoyl chloride (25 ml) was stirred at 175° C. under N for 2.0 hours. The reaction was cooled and diluted with anhydrous $Et_2O$ and the resultant hydrochloride salt was collected to yield 7.2 g. The compound was stirred in boiling absolute ethanol (300 ml) for 1 hour and then at ambient temperature overnight. The solid was collected and dried to afford 6.9 g. Recrystallization from MeOH gave 3.9 g of a light grey solid, m.p. 257°–260° C.

Analysis: Calculated for $C_{28}H_{24}FN_5O_3 \cdot HCl$: 62.98%C, 4.72%H, 13.12%N; Found: 62.92%C, 4.70%H, 13.22%N.

EXAMPLE 233

N-1,2-[4-(1-Ethoxycarbonyl-6-fluoro-1H-indazol-3-yl)-1-piperazinyl]-ethyilphthalimide maleate A mixture of N-[2-[4-(6-fluoro-1H-indazol-3-yl)-1-piperazinyl]ethyl]phthalimide (1.8 g, 4.6 mmol) and ethyl chloroformate (5.7 g, 52.3 mmol) was heated on a steam bath for 10 minutes. The reaction was cooled and an additional 2.3 g (20.9 mmol) ethyl chloroformate was added. The reaction was returned to the steam bath for 10 minutes longer and then cooled. The resultant solid was triturated with anhydrous $Et_2O$ and collected to yield 2.0 g. The solid was suspended in $H_2O$ (100 ml) and $NaHCO_3$ was added to make the pH=8. The aqueous mixture was extracted with $CH_2Cl_2$ and the $CH_2Cl_2$ extract was washed with $H_2O$, dried with $Na_2SO_4$ and concentrated to afford 2.0 g of a yellow oil that crystallized readily. The product was flashed over 80 g silica gel using 2% $Et_2NH$-EtOAc as eluent to afford 130 g (2.36 mmol) of an off-white solid. The compound was dissolved in hot absolute ethanol (55 ml) and maleic acid (0.28 g, 2.36 mmol) was added. The solution was refluxed gently for 10 minutes and then cooled. Most of the ethanol was removed in vacuo and the resultant white suspension was diluted with anhydrous $Et_2O$ (50 ml). The solid that was produced was collected to yield 1.35 g. Recrystallization from $CH_3CN$ gave 1.15 g of the maleate salt as a white powder, m.p. 214°–216° C.

Analysis: Calculated for $C_{24}H_{24}FN_5O_4 \cdot C_4H_4O_4$: 57.83%C, 4.85%H, 12.04%N; Found: 57.87%C, 4.96%H, 11.98%N.

EXAMPLE 234

3-[2-[4-(6-Fluoro-1,2-benzisoxazol-3-yl)-1-piperidinyl]ethyl]-2-methyl-3H-quinazolin-4-one A stirred mixture of 3-(4-piperidinyl)-6-fluorobenzisoxazole (4 g, 18.2 mmol), $K_2CO_3$ (3.76 g, 27.2 mmol) and 3-(2-chloroethyl)-2-methyl-3H-4-quinazolinone (6.0 g, 27 mmol) in acetonitrile (300 ml) was heated at reflux for 16 hours. The reaction was complete as judged by TLC. The solids were filtered and the solvent was evaporated. The residue was purified over a flash chromatography column (SiO$_2$, 75 gm, eluted with dichloromethane and MeOH in dichloromethane). The pure product thus obtained weighed 6.5 gm. Recrystallization from ethanol yielded white crystals, 3.94 gm (53%), m.p. 164°–165° C. This material appeared pure by TLC over silica gel plates.

Analysis: Calculated for $C_{23}H_{23}FN_4O_2$: 67.97%C, 5.70%H, 13.78%N; Found: 67.66%C, 5.66%H, 13.60%N.

EXAMPLE 235

4-(6-Fluoro-1,2-benzisoxazol-3-yl)-1-[3-(2,3-dihydro-1H-isoindol-2-yl)propyl]piperidine difumarate A stirred mixture of 3-[4-(6-fluoro-1,2-benzisoxazol-3-yl)-1-piperidinyl]propyl amine (3.46 g, 12.5 mmol), $K_2CO_3$ (4 g, 29 mmol) and α,α'-dibromo-o-xylene (3.3 g, 12.5 mmol) in acetonitrile (300 ml) was heated at reflux for 3.5 hours. The mixture was cooled and the insolubles were filtered. The dark red solution was concentrated down to a dark oil. This oil was purified by flash chromatography over a silica gel column ($SiO_2$, 45 g; eluted with dichloromethane and MeOH in dichloromethane). The product thus obtained weighed 1.95 g as an oil. This oil was dissolved in ethanol and was treated with a solution of fumaric acid (600 mg) in ethanol. The resulting crystals were collected as an off white solid and weighed 1.44 gm, m.p. 206°–209° C.

Analysis: Calculated for $C_{23}H_{26}FN_3O \cdot 2C_4H_4O_4$: 60.88%C, 5.60%H, 6.87%N; Found: 60.47%C, 5.81%H, 6.84%N.

EXAMPLE 236

4-(6-Fluoro-1,2-benzisoxazol-3-yl)-1-1,2-(2,3-dihydro-1H-isoindol-2-yl)ethyl]piperidine dihydrochloride A mixture of 2-[4-(6-fluoro-1,2-benzisoxazol-3-yl)-1-piperidinyl]ethylamine (2.67 g, 10.1 mmol), α,α'-dibromo-o-xylene (2.76 g, 10.4 mmol) and $K_2CO_3$ (3.2 g, 23 mmol) in acetonitrile (300 ml) was heated at reflux for 1 hour. The mixture turned pinkish and reaction was complete. The mixture was cooled, then filtered. The solution was concentrated down to a foam. Extraction with ether yielded 1.13 g of off-white solids. This material was dissolved into methanol with another batch (1.15 g), prepared in a similar way, and was treated with ethereal HCl-ether (15 mi, 1M). The crystals which formed weighed 2.35 g, with m.p.= 259°–262° C.

Analysis: Calculated for $C_{22}H_{24}FN_3O_2 \cdot 2HCl$: 60.28%C, 5.98%H, 9.59%N; Found: 59.98%C, 5.83%H, 9.48%N.

EXAMPLE 237

4-(6-Fluoro-1,2-benzisoxazol-3-yl)-1-[2-(5-fluoro-2,3-dihydro-1H-isoindol-2-yl)ethyl]piperidine difumarate.

To a solution of 2-[4-(6-fluoro-1,2-benzisoxazol-3-yl)-1-piperidinyl]ethyl-4-fluorophthalimide (4.5 g, 10.9 mmol) in tetrahydrofuran (120 ml) was charged with a solution of lithium aluminum hydride (35 ml, 35 mmol, 1M in ether) dropwise under $N_2$ at room temperature. The mixture was stirred at room temperature for 24 hours. The excess of hydride was quenched carefully with ice chips and 5 ml of 20% NaOH. The mixture was stirred for 1 hour, diluted with EtOAc (200 ml) then filtered. The organic solution was concentrated to dryness. The residue was purified by flash chromatography over a silica gel column ($SiO_2$, 70 gm; eluted with 1% $CH_3OH$: 99% dichloromethane). The product thus obtained (weighed 3.0 g) was dissolved into ethanol and treated with a solution of fumaric acid (918 mg) in ethanol. The crystals formed were collected to yield 2.25 g of white crystals, m.p. 228°–229° C.

Analysis: Calculated for $C_{22}H_{23}F_2N_3O \cdot 2C_4H_4O_4$: 58.53%C, 5.08%H, 6.83%N; Found: 58.48%C, 4.98%H, 6.78%N.

EXAMPLE 238

4-(6-Fluoro-1,2-benzisoxazol-yl)-1-[2-(2,3-dihydro-1H-isoindol-2-yl)propyl]piperidine fumarate A stirred mixture of 2-[4-(6-fluoro-1,2-benzisoxazol-3-yl)-piperidinyl]propylamine (2.92 g, 10.5 mmol), α,α'-dibromo-o-xylene (3.0 g, 11.03 mmol) and $K_2CO_3$ (3.5 g, 25.3 mmol) in aceotnitrile (150 ml) was heated at reflux for 6 hours. The insolubles were filtered off. The solvent was removed on a rotary evaporator. The residue was purified twice by flash chromatography over a silica gel column (40 g and 45 g of silica gel). The product after purification weighed 1.15 g. This oil was treated with a solution of fumaric acid (490 mg) in ethanol. The off white crystals were collected to yield 680 mg, m.p. 164°–165° C.

Analysis: Calculated for $C_{23}H_{26}FN_3O \cdot C_4H_4O_4$: 65.44%C, 6.10%H, 8.48%N; Found: 64.83%C, 6.01%H, 8.08%N.

EXAMPLE 239

N-[3-[4-(6-Fluoro-1,2-benzisoxazol-3-yl)-1-piperidinyl]-2-hydroxy-1-propyl]-2,3-dihydro-1H-isoindole dihydrochloride To a stirred mixture of 1-(3-amino-2-hydroxypropyl-4-(6-fluoro-1,2-benzisoxazol-3-yl)piperidine (2.24 g, 7.6 mmol), $K_2CO_3$ (1.61 g, 11.7 mmol) in acetonitrile (100 ml) was added α,α'-dibromo-o-xylene (1.54 g, 6.1 mmol). The mixture was heated at reflux for 4 hours then cooled. The insolubles were filtered. The dark red solution was concentrated down. The residue was purified by flash chromatography over s silica gel column ($SiO_2$, 30 g; eluted with 1% $CH_3OH$ in dichloromethane). The product so obtained weighed 940 mg as an oil. This oil was dissolved in ethanol and was treated with a solution of HCl in ethanol (188 mg of AcCl in ethanol). The dark solids were collected and recrystallized again in ethanol to yield off-white crystals (1.01 g), m.p. 240°–243° C.

Analysis: Calculated for $C_{23}H_{26}FN_3O_2 \cdot 2HCl$: 58.98%C, 6.03%H, 8.97%N; Found: 58.72%C, 6.16%H, 8.94%N.

EXAMPLE 240

N-[2-[4-(6-Fluoro-1,2-benzisoxazol-3-yl)-1-piperidinyl]ethyl]-2,3-dihydro-5-(triisopropylsilyl)oxy-1H-isoindole difumarate A mixture of 2-[4-(6-fluoro-1,2-benzisoxazol-3-yl)-1-piperidinyl]ethylamine (1.52 g, 5.73 mmol), 1,2-dibromo-4-(triisopropylsilyl)oxy-xylene (2.4 g,(1.8 g, 13 mmol) $K_2CO_3$ (1.8 g, 13 mmol) in acetonitrile (300 ml) was stirred overnight (18 hours) at room temperature. The mixture was filtered and the solvent was stripped. The residue was purified by flash chromatography over a silica gel column (7 gm of $SiO_2$; eluted with 1–3% $CH_3OH$ in dichloromethane. The product thus purified (weight: 900 mg) was converted to the fumarate salt by treatment with fumaric acid (194 mg) in hot ethanol. The crystals were collected and weighed 590 mg, m.p. 208°–210° C.

Analysis: Calculated for $C_{31}H_{44}FN_3O_2Si \cdot 2C_4H_4O_4$: 60.84%C, 6.81%H, 5.46%N; Found: 60.41%C, 6.87%H, 5.35%N.

EXAMPLE 241

N-[2-[4-(6-Fluoro-1,2-benzisoxazol-3-yl)-1-piperidinyl]-ethyl]-2,3-dihydro-5-hydroxy-1H-isoindole fumarate hydrate To a stirred solution of N-[2-[4-(6-fluoro-1,2-benzisoxazol-3-yl)-1piperidinyl]ethyl]-2,3-dihydro-5-(triisopropylsilyl)oxy-1H-isoindole (11.5 g, 21.5 mmol) in tetrahydrofuran (50 ml) was added a solution of tetrabutyl ammonium fluoride (1M in tetrahydrofuran, 24 ml, 24 mmol) in portions at room temperature. The mixture was stirred for 2 hours, then diluted with methylene chloride (200 ml). The organics was washed with $H_2O$ and brine, dried with anhydrous $MgSO_4$. The solvents were removed and the residue was purified by flash chromatography over a silica gel column (90 g of $SiO_2$; eluted with 1–4% of $CH_3OH$ in methylene chloride). The desired fractions were combined and concentrated to give 1.5 g of free base. This solid was recrystallized from ethanol to yield 570 mg of off white crystals. The crystals were converted to fumarate salt in hot ethanol and water to give pinkish crystals, 560 mg, m.p. 191°–193° C.

Analysis: Calculated for $C_{22}H_{24}FN_3O_2 \cdot C_4H_4O_4 \cdot H_2O$: 60.57%C, 5.87%H, 8.15%N; Found: 60.20%C, 6.73%H, 8.04%N.

EXAMPLE 242

4-(6-Fluoro-1H-indazol-3-yl)-1-[2-(2,3-dihydro-1H-isoindol-2-yl)ethyl]piperidine dimaleate To a solution of N-[2-[4-(6-fluoro-1H-indazol-3-yl)-1-piperidinyl]ethyl]phthalimide hydrochloride (Example 183) (3.1 g, 7.91 mmol) in THF (100 ml) was added lithium aluminum hydride (16.6 ml of a 1.0M solution in THF, 16.6 mmol) at room temperature, under nitrogen. The reaction mixture was warmed to reflux for 6.5 hours and cooled to room temperature. The reaction was quenched with water (1.5 ml, dropwise) and the precipitated salts were removed via filtration. The solids were washed with DCM and the combined filtrates concentrated to give 2.5 g of the crude product as a solid. The dimaleate salt was prepared in methanol using 3.5 g (>4.0 e.q.) of maleic acid. The light green precipitate was collected via filtration and washed with methanol. Recrystallization from methanol gave 2.1 g of the desired product as an off-white solid, m.p. 196°–199° C.

Analysis: Calculated for $C_{22}H_{25}FN_4 \cdot 2C_4H_4O_4$: 60.40%C, 5.58%H, 9.39%N; Found: 60.33%C, 5.42%H, 9.42%N.

EXAMPLE 243

2-[4-(6Fluoro-1,2-benzisoxazol-3-yl)-1-piperidinyl]-1-(2,3-dihydro-1H-isoindol-2-yl)-ethanone (A) 2-[4-(6-fluoro-1,2-benzisoxazol-3-yl)-1-piperidinyl]acetamide The mixture of 4-(6-fluoro-1,2-benzisoxazol-3-yl)piperidine (6.77 g, 30.7 mmol), $K_2CO_3$ (5 g, 36.2 mmol) and 2-bromoacetamide (4.46 g, 32.3 mmol) in acetonitrile (250 ml) was heated to reflux for 4 hours. The insolubles were filtered and rinsed with dichloromethane (DCM). The solvents were removed. The residual solid was dissolved in DCM and upon concentration of this solution, 2.3 g of product crystallized out and was collected when the volume was reduced to about 50 ml. The rest of the product in DCM was purified by flash chromatography over a silica gel column (80 gm, $SiO_2$; eluted with DCM and 1% $CH_3OH$ in DCM). The total product (4.2 g) thus purified was recrystallized from ethanol to yield 2.82 g of white crystals, m.p. 170°–172° C. dec.

Analysis: Calculated for $C_{14}H_{16}FN_3O_2$: 60.64%C, 5.82%H, 15.15%N; Found: 60.66%C, 5.87%H, 15.10%N.

(B) 2-[4-(6-Fluoro-1,2-benzisoxazol-3-yl)-1-piperidinyl]-1-(2,3-dihydro-1H-isoindol-2-yl)-ethanone To a mixture of 2-[4-(6-fluoro-1,2-benzisoxazol-3-yl)-1-piperidinyl]acetamide (2.56 g, 9.2 mmol) in DMF (40 ml) was chipped in sodium hydride (770 mg, 60% in oil, 20.1 mmol) at room temperature under $N_2$. The mixture was heated to 65° C. for 3 hours. α,α'-dibromoxylene (2.43 g, 9.2 mmol) was added and the resulting mixture was heated at 70° C. for 4 hours, then left standing overnight for 16 hours. The DMF mixture was poured into $H_2O$ (400 ml) and the organics were extracted into ethyl acetate (250 ml). The ethyl acetate solution was washed with brine and dried over $MgSO_4$. The solvent was removed and the residue was purified by flash chromatography over a silica gel column ($SiO_2$, 45 gm; eluted with 1% $CH_3OH$: 99% DCM). The product thus purified as a white solid weighed 1.73 g. Recrystallization from a small amount of ethanol yielded white crystals: 1.65 g, m.p. 184°–85° C.

Analysis: Calculated for $C_{22}H_{22}FN_3O_2$: 69.64%C, 5.84%H, 11.07%N; Found: 69.48%C, 5.67%H, 11.05%N.

EXAMPLE 244

2-[4-(6Fluoro-1,2-benzisoxazol)-1-piperidinyl]-1-(2,3-dihydro-1H-isoindol-2-yl)ethanone fumarate Free base (1 g, Example 243B) of 2-[4-(6-fluoro-1,2-benzisoxazol-3-yl)-1-piperidinyl]-1-(2,3-dihydro-1H-isoindol-2-yl)ethanone dissolved in hot ethanol (~10 ml) was treated with a solution of fumaric acid (306 mg) in hot ethanol. The mixture was cooled and the product collected, 1.2 gm, m.p. 223°–225° C.

Analysis: Calculated for $C_{22}H_{22}FN_3O_2 \cdot C_4H_4O_4$: 63.02%C, 5.29%H, 8.48%N; Found: 62.86%C, 5.03%H, 8.39%N.

EXAMPLE 245

4-(6-Fluoro-1H-indazol-3-yl)-1-[2-(5-fluoro-2,3-dihydro-1H-isoindol-2-yl)ethyl]piperazine dimaleate To a solution consisting of 2-[4-(6-fluoro-1H-indazol-3-yl)-1-piperidinyl]ethylamine (6.1 g, 23.2 mmol) in DMF (230 ml) was added 4-fluorophthalic anhydride (4.2 g, 25.5 mmol) at room temperature, under nitrogen. The reaction mixture was warmed to 80° C. for 2.5 hours at which time it was allowed to cool to room temperature. The DMF was removed under reduced pressure (<0.5 mmHg, 55° C.) to give a brown oil which was dissolved into DCM/MeOH. Purification via flash column chromatography (silica gel, 2% MeOH/DCM) afforded 3.6 g of 4-fluoro-N-[2-[4-(6-fluoro-1H-indazol-3-yl)-1-piperidinyl]ethyl]phthalimide. To a solution of the latter compound (3.6 g 8.8 mmol) in anhydrous THF (1130 ml) was added LAH (18.4 ml of a 1.0M solution in THF, 18.4 mmol) at room temperature, under nitrogen. The reaction mixture was warmed to reflux for 4 hours. Upon cooling to room temperature, the reaction was quenched with water (1.5 ml, dropwise). The precipitated salts were removed via filtration and washed with DCM. The combined filtrates were concentrated to give a solid which was purified via flash column chromatography (silica gel, 0–8% MeOH/DCM). The product containing fractions were concentrated to give 2.4 g product as an off-white solid. The dimaleate salt was prepared in methanol using 2.4 g. of maleic acid. The white precipitate was collected via filtration and washed with methanol, m.p. 186°–188° C.

Analysis: Calculated for $C_{22}H_{24}F_2N_4 \cdot 2C_4H_4O_4$: 58.63%C, 5.25%H, 9.12%N; Found: 58.45%C, 5.29%H, 9.07%N.

EXAMPLE 246

4-(1H-Indazol-3-yl)-1-[2-(2,3-dihydro-5-fluoro-1H-isoindol-2-yl)ethyl]-piperazine dimaleate To a suspension consisting of 4-fluoro-2-[2-[4-(1H-indazol-3-yl)-1piperazinyl]ethyl]phthalimide (4.8 g, 12.1 mmol) in THF (120 ml) was added LAH (dropwise, 25.5 ml of a 1.0M solution in THF, 25.5 mmol) at room temperature, under nitrogen. The reaction mixture was warmed to reflux for 4 hours during which time it became homogeneous. Upon cooling to room temperature, the reaction was carefully quenched with water (11.5 ml) and the precipitated salts were removed via filtration and washed with DCM. The combined filtrates were concentrated to give the crude product. This material was dissolved into DCM/MeOH (minimal) and purified via preparative HPLC (single column of silica gel, 5% MeOH/DCM, 4 L, then increased to 10% MeOH/DCM, 3 L) to give 2.9 g of the desired product. The dimaleate salt was prepared in methanol (200 ml) using maleic acid (2.2 eq., 2.0 g, 17.5 mmol). The resulting salt was collected via filtration and washed with methanol to give an off-white solid, m.p. 182°–184° C.

Analysis: Calculated for $C_{21}H_{24}FN_5 \cdot 2C_4H_4O_4$: 58.29%C, 5.40%H, 11.72%N; Found: 57.96%C, 5.39%H, 11.65%N.

EXAMPLE 247

4-(6-Fluoro-1H-indazol-3-yl)-1-[2-(2,3-dihydro-4-methyl-1H-isoindol-2-yl)ethyl]piperazine difumarate To a stirred solution of 2-[2-[4-(6-fluoro-1H-indazol-3-yl)-1-piperazinyl]ethyl]-3-methylphthalimide (5.4 g, 13.3 mmol) in THF (200 ml) under $N_2$ was added, dropwise, LAH (30.0 ml of a 1.0M LAH/THF solution). After complete addition, the reaction was stirred at reflux for 4.5 hours. The reaction was cooled in an ice bath and $H_2O$ (2 ml) was carefully added followed by 1.0M NaOH (3 ml). The mixture was filtered and the filtrate was concentrated to yield 5.0 g of a brown oil. Trituration of the oil with $Et_2O$ produced a white solid that was isolated by filtration to give 2.1 g of a white solid. The compound was purified via preparative HPLC (Water's Associates Prep LC/500 using 2 silica gel columns and eluting initially with 10% MeOH—$CH_2Cl_2$ changing to 15% MeOH—$CH_2Cl_2$). Concentration of appropriate fractions yielded 1.5 g (4.0 mmol) of a beige solid. The compound was dissolved in EtOAc (125 ml) and MeOH (4 ml) and the solution was warmed and filtered. The filtrate was stirred near reflux and a solution of fumaric acid (0.92 g, 8.0 mmol) in hot MeOH-EtOAc (1:1, 8 ml) was added. The mixture was allowed to cool and the resultant product was collected to give 2.1 g of an off-white solid, m.p. 212°–215° C.

Analysis: Calculated for $C_{22}H_{26}FN_5 \cdot 2C_4H_4O_4$: 58.91%C, 5.60%H, 11.45%N; Found: 58.88%C, 5.66%H, 11.62%N.

EXAMPLE 248

4-(6-Fluoro-1H-indazol-3-yl)-1-[2-(2,3-dihydro-5-methyl-1H-isoindol-2-yl)ethyl]piperazine difumarate To a stirred solution of 2-[2-[4-(6-fluoro-1H-indazol-3-yl)-1-piperazinyl]ethyl]-4-methylphthalimide (5.46, 13.3 mmol) in THF (200 ml) under $N_2$ was added, dropwise, LAH (30.0 ml of a 1.0M LAH/THF solution). After complete addition, the reaction was stirred at reflux for 4.5 hours. The reaction mixture was cooled in an ice bath and $H_2O$ (2 ml) was carefully added followed by 1.0M NaOH (3 ml). The mixture was filtered and the filtrate was concentrated to yield 4.7 g of a brown solid. The compound was triturated with $Et_2O$ and filtered to give 2.4 g of a white solid. The compound was purified by preparative HPLC (Water's Associates Prep 500 using 2 silica gel columns and eluting initially with 10% MeOH—$CH_3Cl_2$ switching to 15% MeOH—$CH_3Cl_2O$. Concentration of appropriate fractions gave 1.7 g (4.5 mmol) of a beige solid. The solid was dissolved in EtOAc (130 ml) and MeOH (4 ml) and filtered. The filtrate was stirred near reflux and was treated with a solution of fumaric acid (1.04 g, 9.0 mmol) dissolved in hot MeOH (6 ml) and EtOAc (6 ml). The mixture was cooled to ambient temperature and the salt was isolated by filtration to provide 2.4 g of an off-white solid, m.p. 212°–215° C.

Analysis: Calculated for $C_{22}H_{26}FN_5 \cdot 2C_4H_4O_4$: 58.91%C, 5.60%H, 11.45%N; Found: 58.63%C, 5.35%H, 11.41%N.

EXAMPLE 249

4-(6-Fluoro-1H-indazol-3-yl)-1-1,2-(5-fluoro-2,3-dihydro-1H-isoindol-2-yl)ethyl]piperazine dimaleate To a stirred solution of 2-[2-[4-(6-fluoro-1H-indazol-3-yl)-1-piperazinyl]ethyl]-4-fluorophthalimide (2.9 g, 7.1 mmol) in THF (100 ml) under $N_2$ was added, dropwise, LAH (16.0 ml of a 1.0M LAH/THF solution) over 30 minutes. The reaction was stirred at ambient temperature for 1 hour, reflux for 3.5 hours and then at ambient for 18 hours. The reaction was cooled in an ice bath and $H_2O$ (2 ml) was carefully added followed by 1.0M NaOH (2 ml). The mixture was filtered and the filter cake was rinsed with 10% MeOH—EtOAc. The filtrate was concentrated to yield 2.5 g of a beige solid. The compound was purified by preparative HPLC (Waters Associates Prep 500 using 2 silica gel columns and eluting initially with 8% MeOH—$CH_2Cl_2$ increasing the polarity to 12% MeOH—$CH_3Cl_2O$ to yield 1.7 g (4.3 mmol) of a grey solid. The compound was dissolved in warm EtOAc (75 ml) and MeOH (7 ml) and filtered. The filtrate was warmed and stirred and maleic acid (1.0 g, 8.6 mmol) was added. The reaction was stirred at gentle reflux for 15 minutes and then at ambient temperature for 45 minutes. Anhydrous $Et_2O$ (100 ml) was added and the solid was collected to give 2.5 g. Recrystallization from $CH_3CN$ provided 1.7 g of the dimaleate salt as a light grey solid, m.p. 196°–199° C.

Analysis: Calculated for $C_{21}H_{23}F_2N_5 \cdot 2C_4H_4O_4$: 56.58%C, 5.08%H, 11.38%N; Found: 56.38%C, 5.01%H, 11.38%N.

EXAMPLE 250

4-(1H-Indazol-3-yl)-1-[2-(2,3-dihydro-1H-isoindol-2-yl)ethyl]piperazine dimaleate A suspension of 4-(1H-indazol-3-yl)piperazine (1.6 g, 7.9 mmol), N-(2-bromoethyl)phthalimide (2.1 g, 7.9 mmol), and sodium bicarbonate (0.7 g, 8.3 mmol) in acetonitrile (160 ml) was warmed to reflux for 24 hours. Upon cooling to room temperature, the reaction mixture was filtered through a pad of celite and the solids were washed with DCM. The combined filtrates were concentrated to give the N-[2-[4-(1H-indazol-3-yl)-1-piperazinyl]ethyl]phthalimide which was used without further purification.

To a suspension consisting of N-[2-[4-(1H-indazol-3-yl)-1-piperazinyl]ethyl]phthalimide 2.9 g, 7.9 mmol) in THF (100 ml) was added LAH (dropwise, 19.0 ml of a 1.0M solution in THF, 19.0 mmol) at room temperature, under nitrogen. The reaction mixture was warmed to reflux for 4 hours during which time it became homogeneous. Upon cooling to room temperature, the reaction was carefully quenched with water (1.5 ml) and the precipitated salts were removed via filtration and washed with DCM. The combined filtrates were concentrated to give the crude product as an oil. Purification via flash column chromatography (silica gel, 5% MeOH/DCM) afforded 0.77 g of the desired product. The dimaleate salt was prepared in methanol using maleic acid (2.1 eq., 0.54 g). The resulting salt was collected via filtration and washed with methanol to give a greenish solid, m.p. 178°–183° C.

Analysis: Calculated for $C_{21}H_{25}N_5 \cdot 2C_4H_4O_4$: 60.10%C, 5.74%H, 12.08%N; Found: 59.82%C, 5.65%H, 12.10%N.

EXAMPLE 251

4-(6-Fluoro-1H-indazol-3-yl)-1-[2-(2,3-dihydro-1H-isoindol-2-yl)ethyl]piperazine dimaleate To a stirred solution of N-[2-[4-(6-fluoro-1H-indazol-3-yl)-1-piperazinyl]ethyl]phthalimide (5.5 g, 14.0 mmol) in THF (125 ml) under $N_2$ at ambient temperature was added, dropwise, LAH (33.0 ml of a 1.0M LAH/THF solution) over 30 minutes. After complete addition the reaction was stirred at ambient temperature for 45 minutes, and then at reflux for 4.5 hours. After stirring at ambient temperature for 64 hours, the reaction was cooled in an ice bath and $H_2O$ (5.0 ml) was carefully added followed by 1M NaOH (2 ml). The reaction was filtered and the oily filter cake was rinsed with THF and 10% MeOH-EtOAc. The combined organic filtrate was concentrated to afford 5.5 g of a sticky white substance. This was combined with an additional sample (7.5 g total) and purification via preparative HPLC (Water's Associates Prep LC/500 using 2 silica gel columns and 10% MeOH—$CH_2Cl_2$ as eluent) provided 6.0 g (16.4 mmol) of a beige solid. The product was dissolved in warm EtOAc (150 ml) and treated with Darco-G60 for 20 minutes. The decolonizing carbon was removed by filtration through a bed of celite and the warm filtrate was treated with a solution of maleic acid (3.8 g, 32.8 mmol) in hot EtOH (17 ml). A white solid precipitated and the mixture was stirred 1.5 hours at ambient temperature. The compound was isolated by filtration to afford 8.9 g of a light grey solid. Recrystallization from MeOH gave 5.2 g of the dimaleate salt, m.p. 205°–207° C. Calculated Analysis: Calculated for $C_{21}H_{24}FN_5 \cdot 2C_4H_4O_4$: 58.29%C, 5.40%H, 11.72%N; Found: 58.27%C, 5.31%H, 11.69%N.

EXAMPLE 252

6-Fluoro-3-[4-[2-(2,3-dihydro-1H-isoindol-2-yl)ethyl]-1-piperazinyl]-N-phenyl-1H-indazol-1-carboxamide dimaleate To a stirred suspension of NaH (0.40 g of 60% oil dispersion; 10.0 mmol) in DMF (10 ml) under $N_2$ and cooled to −3° C., was added, dropwise, a solution of 4-(6-fluoro-1H-indazol-3-yl)-1-[2,3-dihydro-1H-isoindol-2-yl)ethyl] piperazine (3.3 g, 9.0 mmol) in DMF (45 ml) over 60 minutes, maintaining the temperature below 0° C. The mixture was stirred for 60 minutes at 0° C. and then a solution of phenyl isocyanate (1.2 g, 10.0 mmol) in DMF (5 ml) was added dropwise at −2° C. After complete addition the reaction was stirred at ambient temperature for 20 hours. The reaction was poured into $H_2O$, and the aqueous mixture was extracted with ethyl acetate. The ethyl acetate extract was washed with $H_2O$, washed with brine, dried with $MgSO_4$, and concentrated to afford 5.6 g of a dark oil. The oil was purified by preparative HPLC (Waters Associates Prep 500 using 2 silica gel columns and 4% MeOH—$CH_2Cl_2$ as eluent) to yield 2.9 g of a dark oil. A 2.7 g (5.6 mmol) sample was dissolved in warm EtOAc (100 ml) and MeOH (5 ml) and the particulate matter was filtered away. The filtrate was warmed and stirred and a solution of maleic acid (1.3 g, 11.2 mmol) in hot MeOH (5 ml) was added. The reaction was refluxed mildly for 15 minutes and then was stirred at ambient temperature for 2 hours. The resultant suspension was diluted with petroleum ether (150 ml) and the dark solid collected to yield 3.2 g. The compound was recrystallized from $CH_3CN$ (utilizing Darco G-60 decolonizing carbon) to afford 1.6 g of a grey solid, m.p. 189°191° C.

Analysis: Calculated for $C_{28}H_{29}FN_6O \cdot 2C_4H_4O_4$: 60.33%C, 5.20%H, 11.73%N; Found: 60.36%C, 4.86%H, 11.85%N.

EXAMPLE 253

4-(1-Decanoyl-6-fluoro-1H-indazol-3-yl)-1-[2-(2,3-dihydro-1H-isoindol-2-yl)ethyl]piperazine dimaleate To a stirred suspension of NaH (0.40 g of 60% oil dispersion, 10.0 mmol) in DMF (10 ml) under $N_2$ and cooled to −3° C. was added, dropwise, a solution of 4-(6-fluoro-1H-indazol-3-yl)-1-[2-(2,3-dihydro-1H-isoindol-2-yl)ethyl] piperazine (3.3 g, 9.0 mmol) in DMF (45 ml) over 65 minutes so that the temperature was maintained below 0° C. The reaction was stirred for 1 hour and was cooled to −2° C. A solution of decanoyl chloride (1.9 g, 10.0 mmol) in DMF (5 ml) was added dropwise over 10 minutes. After complete addition the reaction was stirred at ambient temperature for 20 hours. The reaction was poured into $H_2O$ (75 ml) and the aqueous mixture was extracted with EtOAc. The EtOAc extract was washed with $H_2O$, washed with brine, dried with $MgSO_4$ and concentrated to afford 5.1 g of a dark oil. The oil was purified by preparative HPLC (Water's Prep 2000 utilizing 1 silica gel column and 4% MeOH—$CH_2Cl_2$ as eluent) to yield 3.1 g (66%) of a dark oil. The oil (2.75 g, 5.3 mmol) was dissolved in warm EtOAc (100 ml) was treated with maleic acid (1.26 g, 10.9 mmol). After warming for 30 minutes the grey suspension was stirred at ambient temperature for 60 minutes. The reaction was diluted with anhydrous $Et_2O$ (30 ml) and petroleum ether (200 ml) and the resultant dark grey solid was collected to yield 3.77 g. The salt was recrystallized from $CH_3CN$ (using Darco G-60) to yield 2.6 g of a light grey solid, m.p. 191°–194° C.

EXAMPLE 254

4-(6-Fluoro-1H-indazol-3-yl)-1-[3-(2,3-dihydro-1H-isoindol-2-yl)propyl]piperazin dimaleate To a stirred solution of 2-[3-[4-(6-fluoro-1H-indazol-3-yl)-1-piperazinyl]propyl]phthalimide (5.3 g, 13.0 mmol) in THF (200 ml) under $N_2$ was added, dropwise, LAH (27.0 ml of a 1.0M LAH/THF solution). After complete addition, the reaction was stirred at reflux for 4.5 hours. The reaction was cooled in an ice bath and $H_2O$ (2 ml) was carefully added, followed by 1.0M NaOH (3 ml). The mixture was filtered and the filtrate was concentrated to afford 4.8 g of a white 4 solid. The compound was purified by preparative HPLC (Water's Associates Prep 500, utilizing 2 silica gel columns and 5% Et$_2$NH—EtOAc as eluent) to give 3.0 g of a beige solid. Recrystallization from EtOAc provided 1.1 g (2.9 mmol) of an off white solid. The compound was dissolved in hot EtOAc (200 ml) and MeOH (10 ml) and maleic acid (0.68 g, 5.8 mmol) was added. The reaction was warmed for 15 minutes and after stirring at ambient temperature for 30 minutes and standing at about 4° C. for 1.5 hours, the dimaleate salt was collected to yield 1.7 g of an off-white solid, m.p. 183°–186° C.

Analysis: Calculated for $C_{31}H_{42}FN_5O\cdot 2C_4H_4O_4$: 62.30%C, 6.70%H, 9.31%N; Found: 62.34%C, 6.74%H, 9.23%N.

EXAMPLE 255

2-[4-(6-Fluoro-1,2-benzisoxazol-3-yl)-1-piperidinyl]-1-(2,3-dihydroindol-1-yl)ethanone fumarate A stirred mixture of 4-(6-fluoro-1,2-benzisoxazol-3-yl)piperidine (10 g, 45.4 mmol), K$_2$CO$_3$ (7.2 g, 52.5 mmol) and N-(2-bromoacetyl)indoline (12 g, 50 mmol) in acetonitrile (300 ml) was heated at reflux for 4 hours. The mixture was cooled and filtered. The solution was concentrated down until solid appeared. The crystals were collected: weight 12.68 g. The mother liquor was concentrated to dryness. The residues were purified further by flash chromatography to yield an additional 1.35 g. Total yield was 14.03 g. A 2 g sample was dissolved in ethanol/methylene chloride and was treated with a solution of fumaric acid (612 mg) in ethanol to yield 2.58 g, m.p. 226°–227° C.

Analysis: Calculated for $C_{22}H_{22}FN_3O_2\cdot C_4H_4O_4$: 63.02%C, 5.29%H, 8.48%N; Found: 62.79%C, 5.30%H, 8.40%N.

EXAMPLE 256

1-(1,2,3,4-Tetrahydro-1H-isoquinoline-2-yl)-2-[4-(6-fluoro-1,2-benzisoxazol-3-yl)-1-piperidinyl]-ethanone hydrochloride ethanolate A mixture of 4-(6-fluoro-1,2-benzisoxazol-3-yl)piperidine (4.33 g, 19.7 mmol), K$_2$CO$_3$ (3.45 g, 25 mmol, 1.25 eq) and 2-bromoacetyl-1,2,3,4-tetrahydroisoquinoline (5 g, 20 mmol) in acetonitrile (200 ml) was heated at reflux for 2 hours. The reaction was cooled and the insolubles were filtered. The solvent was removed and the crude oil was purified by flash chromatography over a silica gel column (90 g of SiO$_2$; eluted with DCM and 1% CH$_3$OH in DCM). The oil thus purified weighed 6.41 g. A 3 g sample was dissolved into ethanol (20 ml) and was treated with 1M-HCl-ether solution (10 ml). The crystals were collected and recrystallized twice from ethanol to yield 2.43 g of white crystals as the hydrochloride ethanolate, m.p. 206°–208° C.

Analysis: Calculated for $C_{23}H_{24}FNO_2\cdot HCl\cdot C_2H_6O$: 63.08%C, 6.56%H, 8.83%N; Found: 63.24%C, 6.62%H, 8.89%N.

EXAMPLE 257

N-[2-[4-(6-Fluoro-1,2-benzisoxazol-3-yl)-1-piperidinyl]ethyl-1,2,3,4-tetrahydroisoquinoline difumarate To a solution of 2-[4-(6-fluoro-1,2-benzisoxazol-3-yl)-1-piperidinyl]-1-(1,2,3,4-tetrahydro-1H-isoquinoline-2-yl)ethanone (2.36 g, 6 mmol) in THF (40 ml) was charged lithium aluminum hydride (15 ml, 1M in ether) dropwise under N$_2$ at room temperature. The mixture was stirred for 3 hours at room temperature. At the end, the excess of hydride was quenched with ice chips and 2 ml of 20% NaOH. The mixture was diluted with EtOAc and filtered. The solvents were removed to dryness. The residue was purified by flash chromatography over a silica gel column (SiO$_2$, 18 g; eluted with 1% CH$_3$OH in DCM). The product thus obtained weighed 1.62 g. This material was dissolved into hot ethanol and was treated with a solution of fumaric acid (490 mg) in ethanol. The mixture was cooled and the crystals were collected to yield 1.15 g, m.p. 218°–220° C.

Analysis: Calculated for $C_{23}H_{26}FN_3O\cdot 2C_4H_4O_4$: 60.88%C, 5.60%H, 6.87%N; Found: 61.00%C, 5.50%H, 6.64%N.

EXAMPLE 258

2-(1,2,3,4-Tetrahydro-1H-isoquinoline-2-yl)-1-[4-(6-fluoro-1,2-benzisoxazol-3-yl)-1-piperidinyl]ethanone fumarate (A) 1-(2-Chloroacetyl)-4-(6-fluoro-1,2-benzisoxazol-3-yl)piperidine A solution of 4-(6-fluoro-1,2-benzisoxazol-3-yl)piperidine (4.4 g, 20 mmol), triethylamine (2.1 g, 21 mmol) in chloroform (50 ml) was added to a solution of chloroacetyl chloride (2.5 g, 22 mmol) in chloroform (100 ml) dropwise at room temperature. The mixture was stirred for 2 hours. The solution was diluted with dichloromethane (DCM, 100 ml) and then washed with H$_2$O and brine. The solvent was removed and the oily product was purified by flash chromatography (SiO$_2$, 50 g; eluted with DCM and 1% CH$_3$OH in DCM). The pure product was obtained as an oil, 4.2 g. Crystallization from ethanol yielded 2.2 g of white crystals, m.p. 101°–102° C.

Analysis: Calculated for $C_{14}H_{14}ClFN_2O_2$: 56.67%C, 4.76%H, 9.44%N; Found: 56.70%C, 4.75%H, 9.46%N.

(B) 2-(1,2,3,4-Tetrahydro-1H-isoquinoline-2-yl)-1-[4-(6-fluoro-1,2-benzisoxazol-3-yl)-1-piperidinyl]ethanone fumarate A mixture of 4-(6-fluoro-1,2-benzisoxazol-3-yl)-1-piperidinyl-2-chloroacetamide (3.0 g, 10.8 mmol), K$_2$CO$_3$ (1.5 gm, 10.8 mmol) and 1,2,3,4-tetrahydroisoquinoline (1.4 g, 10.5 mmol) in acetonitrile (90 ml) was heated at reflux for 4 hours. The reaction was cooled and filtered. The solvent was removed, and the residue was purified by flash chromatography over a silica gel column (50 g of SiO$_2$; eluted with DCM and 1% CH$_3$OH in DCM). The light yellow oil (3.28 g) thus obtained was dissolved in ethanol and treated with a solution of fumaric acid (968 mg) in ethanol. The solid crystals were collected and recrystallized again to give 3.18 g of off-white crystals, m.p. 188°–189° C.

Analysis: Calculated for $C_{23}H_{24}FN_3O_2\cdot C_4H_4O_4$: 63.65%C, 5.54%H, 8.25%N; Found: 63.42%C, 5.33%H, 8.16%N.

EXAMPLE 259

N-[3-[4-(6-Fluoro-1,2-benzisoxazol-3-yl)-1-piperidinyl]-2-hydroxy-1-propyl]-1,2,3,4-tetrahydroisoquinoline difumarate A mixture of N-[3-(2,3-epoxy)propyl]-4-(6-fluoro-1,2-benzisoxaz-3-yl)piperidine (3.56 g, 12.9 mmol) and 1,2,3,4-tetrahydroisoquinoline (2.06 g, 15.4 mmol) in isopropyl alcohol (150 ml) was heated at reflux for 4 hours. At the end of the reaction, the solvent was removed. The residual oil was purified by flash chromatography over a silica gel column (SiO$_2$, 45 g, eluted with 1% CH$_3$OH: 99% methylene chloride). The product thus purified as a light oil, weighed 4.15 g. The oil was treated with a solution of fumaric acid (1.98 gm, 17 mmol) in ethanol. The white crystals so obtained were recrystallized in a large volume of hot ethanol (~150 ml). The recrystallized crystals weighed 2.75 g, m.p. 179°–181° C.

Analysis: Calculated for $C_{24}H_{28}FN_3O_2 \cdot 2C_4H_4O_4$: 59.90%C, 5.66%H, 6.55%N; Found: 60.06%C, 5.77%H, 6.36%N.

EXAMPLE 260

6,7-Dimethoxy-2-[3-[4-(6-fluoro-1,2-benzisoxazol-3-yl)-1-piperidinyl]2-hydroxy-1-propyl]-1,2,3,4-tetrahydroisoquinoline A stirred mixture of 1-(2,3-epoxypropyl)-4-(6-fluoro-1,2-benzisoxazol-3-yl)piperidine (3.2 g, 11.6 mmol), $K_2CO_3$ (2 gm, 1.25 eq) and 6,7-dimethoxy-1,2,3,4-tetrahydroisoquinoline hydrochloride (3.3 g, 1.25 eq) in isopropyl alcohol (200 ml) was heated at reflux for 6 hours. The mixture was cooled and filtered. The solvent was removed to about 50 ml and the solution was allowed to stand overnight. Crystals (0.6 g) formed and were collected. The mother liquor was concentrated to a white solid. Recrystallization twice from ethanol yielded the product (1.95 g, m.p. 153°–154° C.

Analysis: Calculated for $C_{26}H_{32}FN_3O_4$: 66.51%C, 6.87%H, 8.95%N; Found: 66.51%C, 7.05%H, 8.83%N.

EXAMPLE 261

N-[2-[4-(6-Fluoro-1H-indazol-3-yl)-1-piperidinyl]ethyl]-1,2,3,4-tetrahydroisoquinoline dimaleate To a solution of 4-(6-fluoro-1H-indazol-3-yl)piperidine (4.8 g, 18.9 mmol) in $CH_3CN$ (200 ml) was added 2-bromo-1-(1,2,3,4-tetrahydroisoquinoline-2-yl)ethanone (4.8 g, 18.9 mmol) and sodium bicarbonate (1.9 g, 22.7 mmol) at room temperature. The reaction mixture was warmed to reflux (4 hours), cooled to room temperature and filtered through a pad of celite. The solids were washed with DCM and the combined filtrates were concentrated. The remaining residue was purified via preparative HPLC (silica gel, 5–10% MeOH/DCM) to give 4.1 g of 1-(1,2,3,4-tetrahydroisoquinoline-2-yl)-2-[4-(6-fluoro-1H-indazol-3-yl)-1-piperidinyl]ethanone which was used without further purification. To a suspension of the latter (3.7 g, 9.4 mmol) in THF (100 ml) was added (dropwise) lithium aluminum hydride (11.3 ml of 1.0M solution in THF, 11.3 mmol) at room temperature, under nitrogen. The reaction mixture was warmed to reflux (5 hours), cooled to room temperature and carefully quenched with water (10 ml). The precipitated salts were removed via filtration and washed with 1:1 EtOAc/DCM. The combined filtrates were concentrated and the remaining oil was purified via flash column chromatography (silica gel, 10% MeOH/DCM) to give 2.2 g of the product. The dimaleate salt was prepared in methanol (30 ml) with maleic acid (3.0 eq.), m.p. 185°–187° C.

Analysis: Calculated for $C_{23}H_{27}FN_4 \cdot 2C_4H_4O_4$: 60.98%C, 5.78%H, 9.18%N; Found: 60.85%C, 5.75%H, 9.09%N.

EXAMPLE 262

2-[4-(6-Fluoro-1H-indazol-3-yl)-1-piperazinyl]-1-(1,2,3,4-tetrahydro-1H-inoquinolin-2-yl)ethanone difumarate A mixture of 6-fluoro-3-(4-piperazinyl)-1H-indazole (3.1 g, 14 mmol), 2-bromoacetyl-1,2,3,4-tetrahydroisoquinoline (3.6 g, 14 mmol), $NaHCO_3$ (1.4 g, 17 mmol) and $CH_3CN$ (150 ml) was stirred at reflux under $N_2$ for 6 hours. The cooled reaction was filtered and the filtrate was concentrated to yield 6.1 g of an off-white foam. The compound was purified by preparative HPLC (Water's Associates prep 500 using 2 silica gel columns and 5% MeOH—$CH_3Cl_2$ as eluent). Concentration of appropriate fractions gave 4.1 g of an off-white solid. A 0.8 g (2.0 mmol) sample was dissolved in warm EtOAc (30 ml) and MeOH (4 ml) and filtered. The filtrate was heated to reflux and was treated with a solution of fumaric acid (0.47 g, 4.0 mmol) in MeOH/EtOAc (1:1, 8 ml). The mixture was cooled and the resultant white solid was collected to yield 0.88 g. This was combined with another small sample (1.0 g total) and recrystallization from ethanol provided 0.75 g of a white solid, m.p. 235°–238° C.

Analysis: Calculated for $C_{22}H_{24}FN_5O \cdot 2C_4H_4O_4$: 57.60%C, 5.16%H, 11.19%N; Found: 57.68%C, 5.26%H, 11.31%N.

EXAMPLE 263

N-1,2-[4-(6-Fluoro-1H-indazol-3-yl)-1-piperazinyl]ethyl]-1,2,3,4-tetrahydroisoquinoline difumarate To a stirred solution of 2-[4-(6-fluoro-1H-indazole-3-yl)-1-piperazinyl]-1-(1,2,3,4-tetrahydro-1H-isoquinoline-2-yl)ethanone (3.2 g, 8.1 mmol) in THF (75 ml) under N, was added dropwise, LAH (20.0 ml of a 1.0M LAH/THF solution). After complete addition, the reaction was stirred at ambient temperature for 20 hours. The reaction was cooled in an ice bath and cold $H_2O$ was added followed by 1 ml of 1.0M NaOH. The mixture was filtered and the filter cake was washed with EtOAc. The filtrate was concentrated to yield 2.5 g of a white solid. The compound was purified by preparatige HPLC (Water's Associates Prep 500, using 1 silica gel column and 10% MeOH—$CH_2Cl_2$ as eluent) to yield 2.0 g of a white solid. A 1.8 g (4.7 mmol) sample was stirred as a solution in warm EtOAc (100 ml) and was treated with a solution of fumaric acid (1.1 g, 9.5 mmol) in boiling MeOH (12 ml). The reaction was warmed for 5 minutes and after stirring at ambient temperature for 1.5 hours the resultant white solid was collected to yield 2.7 g of the difumarate salt, m.p. 210°–213° C.

Analysis: Calculated for $C_{22}H_{26}FN_5 \cdot C_4H_4O_4$: 58.91%C, 5.60%H, 11.45%N; Found: 58.77%C, 5.42%H, 11.22%N.

EXAMPLE 264

1-(1,2,3,4-Tetrahydro-1H-guinolin-1-yl)-2-[4-(6-fluoro-1,2-benzisoxazol-3-yl)-1-piperidinyl]ethanone furmarate A stirred mixture of 4-(6-fluoro-1,2-benzisoxazol-3-yl)piperidine (4.7 g, 21.4 mmol), $K_2CO_3$ (3.6 g, 25.6 mmol) and N-(2-bromoacetyl(6 g, 23.6 tetrahydroquinoline (6 g, 23.6 mmol) in acetonitrile (200 ml) was heated at reflux for 1.5 hours. The mixture was cooled and the solids were filtered off. The solvent was stripped to dryness. The residue was purified by flash chromatography ($SiO_2$, 100 gm; eluted with methylene chloride (DCM) and 1% $CH_3OH$ in DCM). The product thus purified weighed 7.75 g. A sample of 1.88 g in ethanol was treated with a solution of fumaric acid (550 mg, 1.0 eq) in ethanol to yield the fumaric salt, 2.15 g, m.p. 162°–163° C.

Analysis: Calculated for $C_{23}H_{24}FN_3O_2 \cdot C_4H_4O_4$: 63.65%C, 5.54%H, 8.25%N; Found: 63.52%C, 5.46%H, 8.17%N.

EXAMPLE 265

N-[2-[4-(6-Fluoro-1,2-benzisoxazol-3-yl)-1-piperidinyl]ethyl]-1,2,3,4-tetrahydroquinoline fumarate To a stirred solution of 2-[4-(6-fluoro-1,2-benzisoxazol-3-yl)-1-piperidinyl]-1-(1,2,3,4-tetrahydroquinolin-1-yl)

ethanone (5.5 g, 14 mmol) in THF (0.50 ml) was charged with lithium aluminum hydride (17 ml, 17 mmol, 1M in ether) dropwise under N at room temperature. The mixture was stirred for 8 hours at room temperature. At the end of this period the excess of hydride was quenched with ice chips and 3 ml of 20% NaOH. The mixture was diluted with EtOAc (150 ml) and stirred for 1 hour. The EtOAc was dried with $MgSO_4$ and filtered. The solvent was removed to dryness. The residue was purified by flash chromatography over a silica gel column ($SiO_2$, 55 g; eluted with 1–3% $CH_3OH$:DCM). The product thus obtained weighed 1.83 g. This material was dissolved into hot ethanol and was treated with a solution of fumaric acid (700 mg) in ethanol. The crystals were collected and weighed 1.85 g, m.p. 192°–193° C.

Analysis: Calculated for $C_{23}H_{26}FN_3O \cdot C_4H_4O_4$: 65.44%C, 6.10%H, 8.48%N; Found: 65.20%C, 6.19%H, 8.32%N.

EXAMPLE 266

N-[3-[4-(6-Fluoro-1,2-benzisoxazol-3-yl)-1-piperidinyl)-2-hydroxy-1-propyl]-1,2,3,4-tetrahydroquinoline hemifumarate A stirred mixture of N-(2,3-epoxypropyl)-4-(6-fluoro-1,2-benzisoxazol-3,4-yl)piperidine (2.41 g, 8.73 mmol), 1,2,3,4-tetrahydroquinoline (1.33 g, 10 mmol, in isopropyl alcohol (50 ml) was heated at reflux for 6 hours. The solution was cooled and the solvent was removed on a rotary evaporator. The crude solid was purified by flash chromatography over a silica gel column ($SiO_2$, 40 g, eluted with methylene chloride DCM, and 1–3% MeOH in DCM). The product thus purified weighed 2.0 g. This material was dissolved in ethanol and was treated with a solution of fumaric acid (567 mg, 1.0 eq) in ethanol. The solids collected were recrystallized again from ethanol (543 ml) to yield 1.0 g of white crystals, as a hemifumarate, m.p. 170°–171° C.

Analysis: Calculated for $C_{24}H_{28}FN_3O_2 \cdot 0.5 \cdot C_4H_4O_4$: 66.79%C, 6.47%H, 8.99%N; Found: 66.27%C, 6.54%H, 8.86%N.

EXAMPLE 267

N-[2-[4-(6-Fluoro-1,2-benzisoxazol-3-yl)-1-piperidinyl]acetyl]10,11-dihydro-5H-dibenz[b,f]azepine fumarate A stirred mixture of 2-chloroacetyl-10,11-dihydro-5H-dibenz[b,f]azepine (6.6 g, 24.3 mmol), 4-(6-fluoro-1,2-benzisoxazol-3-yl)piperidine (5 g, 22.7 mmol) and $K_2CO_3$ (3.5 g, 40 mmol) in acetonitrile (300 ml) was heated at reflux for 4 hours. The insolubles were filtered, and the solvent was removed on a rotary evaporator. The crude product was purified by flash chromatography over a silica gel column (100 g of $SiO_2$; eluted with dichloromethane (DCM) and 1–2% $CH_3OH$ in DCM). The product thus obtained weighed 8.7 g as a yellow oil. A sample (1.5 g) of this material was dissolved in ethanol and was treated with a solution of fumaric acid in ethanol (360 mg/3 ml). The solids collected were recrystallized from acetonitrile to yield 890 mg of white crystals, m.p. 182°–183° C.

Analysis: Calculated for $C_{28}H_{26}FN_3O_2 \cdot C_4H_4O_4$: 67.24%C, 5.29%H, 7.35%N; Found: 66.66%C, 5.17%H, 7.33%N.

EXAMPLE 268

N-[2-[4-(6-Fluoro-1,2-benzisoxazol-3-yl)-1-piperidinyl]ethoxyphthalimide hemihydrate A mixture of 3-(4-piperidinyl)-6-fluorobenzisoxazole (3.42 g, 15 mmol), N-(2-bromoethoxy)-phthalimide (4.3 g, 16 mmol) and $K_2CO_3$ (26 g, 18 mmol) in acetonitrile (150 ml) was heated at reflux for 2 hours. The solids were removed and the solvent was evaporated. The residue was purified over a flash chromatography column (packed with $SiO_2$, 60 g; eluted with dichloromethane (DCM) and 1% $CH_3OH$ in DCM). The pure product thus obtained, weighing 6.8 g was crystallized from DCM:ethanol. Recrystallization from ethanol and i-propyl ether yielded white crystals (2.4 g, m.p. 125°–127° C. ) as the hemihydrate.

Analysis: Calculated for $C_{22}H_{20}FN_3O_4 \cdot 0.5 \cdot H_2O$: 63.15%C, 5.05%H, 10.04%N, 2.15%$H_2O$; Found: 63.20%C, 5.16%H, 9.80%N, 2.32%$H_2O$.

EXAMPLE 269

3-[4-(6-Fluoro-1,2-benzisoxazol-3-yl)-1-piperidinyl]-2-hydroxy-1-propylamine hydrochloride hydrate A stirred mixture of 3-[4-(6-fluoro-1,2-benzisoxazol-3-yl)-1-piperidinyl]-2-hydroxy-1-propylphthalimide (6.2 g, 14.6 mmol) and hydrazine hydrate (1.4 g, 28 mmol) in methanol (300 ml) was heated at reflux for 4 hours, then at 65° C. for 16 hours. The mixture was cooled and the solvent was stripped to dryness. The white residue was stirred with $H_2O$ (40 ml) and acidified with HCl to pH=3. The milky white solids were filtered with the aid of Celite. The light yellow solution was basified with NaOH to pH=9, then extracted with methylene chloride (DCM, 3×180 ml). The DCM solution was washed with brine, dried and stripped to give an oil (2.93 g) which solidified slowly. A 1 gm sample of this solid was treated with a HCl/MeOH solution to precipitate out a hydrochloride salt. This salt was recrystallized from ethanol =$H_2O$ to yield 0.52 g of white crystals, m.p. =150°–152° C.

Analysis: Calculated for $C_{15}H_{20}FN_3O_2 \cdot HCl \cdot H_2O$: 51.80%C, 6.67%H, 12.08%N; Found: 51.74%C, 6.32%H, 12.05%N.

EXAMPLE 270

N-[2-[4-(6-Fluoro-1,2-benzisoxazol-3-yl)-1-piperidinyl]ethyl]-3-pyridinecarboxamide dihydrochoride hydrate To a mixture of 2-[4-(6-fluoro-1,2-benzisoxazol-3-yl)-1-piperidinyl]ethylamine (1.17 g, 4.34 mmol) and triethylamine (1.08 g, 10.8 mmol) in chloroform (30 ml) was added nicotinoyl chloride hydrochloride (0.96 g, 5.4 mmol) in one portion. The mixture was stirred for 1 hour at room temperature. The solution was diluted with methylene chloride (DCM) and washed with brine and dried over anhydrous $MgSO_2$. The solution was concentrated and the crude product was purified by flash chromatography over a silica gel column ($SiO_2$, 25 g; eluted with DCM and 1–3% MeOH in DCM). The free base thus purified weighed 1.7 g. This product was treated with 1M•HCl in ethanol and recrystallized twice from methanol:isiproply ether to yield white crystals, 1.19 g, m.p. 243°–245° C. as a dihydrochloride hydrate.

Analysis: Calculated for $C_{20}H_{21}FN_4O_2 \cdot 2HCl \cdot H_2O$: 52.30%C, 5.49%H, 12.20%N, 3.92%$H_2O$; Found: 52.34%C, 5.39%H, 12.11%N, 3.68%$H_2O$.

EXAMPLE 271

N-[2-[4-(6-Fluoro-1H-indazol-3-yl)-1-piperazinyl]ethyl]-3-phenyl-2-quinoxalinamine dihydrochloride A mixture of 2-[4-[(6-fluoro-1H-indazol-3-yl)-1-piperazinyl]ethylamine (4.3 g, 16.3 mmol) and 2-chloro-3- phenylquinoxaline (4.7 g, 19.5 mmol) was heated at 160° C. for 5 hours in an autoclave. After standing at ambient temperature for 2 days, the residue was partitioned between $CH_2Cl_2$ and $H_2O$. The $CH_3Cl_2$ extract was washed with $H_2O$, dried with $MgSO_4$ and concentrated to yield 7.5 g of a brown solid. The solid was purified by preparative HPLC (Water's Associates Prep LC System 500, using 2 silica gel columns and 4.5% MeOH—$CH_3Cl_2$ as eluent). Concentration of later fractions afforded 2.3 g of the desired product as a yellow foam. A 1.4 g sample was suspended in MeOH (30 ml) and $Et_2O$-HCl (6.0 ml of a 1.0 m $Et_2O$-HCl solution) was added. Initially a yellow solution formed and about 20 minutes later a precipitate began to form. The suspension was stirred for 30 minutes longer and anhydrous $Et_2O$ (100 ml) was added. The resultant light yellow solid was collected to give 1.5 g. The product was stirred in boiling $CH_3CN$ (100 ml) for 1.0 hour and after cooling the solid was isolated by filtration to afford 1.2 g of a light yellow solid, m.p. 244°–246° C.

Analysis: Calculated for $C_{27}H_{26}FN_7 \cdot 2HCl$: 60.00%C, 5.22%H, 18.14%N; Found: 59.79%C, 5.27%H, 18.34%N.

EXAMPLE 272

1,2-bis-[4-(6-Fluoro-1,2-benzisoxazol-3-yl)-1-piperidinyl]ethane difumarate

To a stirred mixture of 4-(6-fluoro-1,2-benzisoxazol-3-yl)piperidine (2.2 g, 10 mmol) and $K_2CO_3$ (1.47 g, 11 mmol) in acetonitrile (50 ml) was added 1,2-dibromoethane (1 g, 5.4 mmol) dropwise at room temperature. The mixture was stirred at room temperature for 16 hours. The reaction mixture was filtered and the solvent was removed on a rotary evaporator. The crude solid was purified by flash chromatography ($SiO_2$, 30 g; eluted with methylene chloride, DCM, and MeOH in DCM). The product thus purified, weighed 513 mg. This solid was treated with fumaric acid (270 mg, 2 eq) in ethanol. The crystals collected were recrystallized from ethanol:$H_2O$ to yield 630 mg of white crystals, m.p. =246°–247° C.

Analysis: Calculated for $C_{26}H_{28}F_2N_4O_2$: 58.45%C, 5.19%H, 8.02%N; Found: 58.36%C, 5.22%H, 7.92%N.

EXAMPLE 273

1,3-Bis-[4-(6-fluoro-1,2-benzisoxazol-3-yl)-1-piperidinyl]-2-hydroxypropane dihydrochloride A stirred mixture of 1-(2,3-epoxypropyl)-4-(6-fluoro-1,2-benzisoxazol-3-yl)piperidine (1.19 g, 4.3 mmol) and 4-(6-fluoro-1,2-benzisoxazol-3-yl)piperidine (0.95 g, 4.3 mmol) in isopropyl alcohol (50 ml) was heated at reflux for 1 hour, then stirred at 65° C. for 16 hours. The solvent was removed on a rotary evaporator. The solid residues were purified by flash chromatography over a silica gel column ($SiO_2$, 35 g; eluted with methylene chloride, DCM, and $CH_3OH$ in DCM). The product thus obtained, weighed 2.55 g. This material was dissolved in ethanol and was treated with a solution of HCl (1M in ether). The salt collected weighed 2.35 g, m.p. >270° C. dec.

Analysis: Calculated for $C_{27}H_{30}F_2N_4O_3 \cdot 2HCl$: 56.95%C, 5.66%H, 9.84%N; Found: 56.55%C, 5.68%H, 9.51%N.

EXAMPLE 274

2-[2-[4-(6-Fluoro-1,2-bezisoxazol-3-yl)-1-piperidinyl]ethyl]-2-phenyl-3-indandione A mixture of 4-(6-fluoro-1,2-benzisoxazol-3-yl)piperidine (2.2 g, 10 mmol), $K_2CO_3$ (1.6 g, 11.6 mmol) and 2-toluenesulfonyl-2-phenyl-1,3-indandione (4.2 g, 10 mmol) in acetonitrile (50 ml) was heated at reflux for 3 hours. The mixture was cooled and the insolubles were filtered. The solvent was removed on a rotary evaporator. The residue was purified twice using a flash chromatography column ($SiO_2$, 45 g and 40 g; eluted with DCM). The product thus purified was recrystallized from ethanol (30 ml) and isopropyl ether, yield: 2.8 g, m.p. 149°–150° C.

Analysis: Calculated for $C_{29}H_{25}FN_2O_3$: 74.34%C, 5.38%H, 5.98%N; Found: 74.24%C, 5.50%H, 6.87%N.

EXAMPLE 275

2-[4-(6-Fluoro-1,2-benzisoxazol-3-yl)-1-piperidinyl] acetonitrile

A mixture of 4-(6-fluoro-1,2-benzisoxazol-3-yl)piperidine (11 g, 50 mmol), $K_2CO_3$ (8.5 g, 61.6 mmol) and 2-chloroacetonitrile (5.5 g, 73 mmol) in acetonitrile (250 ml) was heated at reflux for 24 hours. The insolubles were filtered off and rinsed with methylene chloride (DCM). During concentration of the solvents on the rotary evaporator, crystals appeared. The crystals were collected and weighed 5.79 g. The product in the mother liquor was further purified by flash chromatography over a silica gel column ($SiO_2$, 70 g; eluted with DCM, and 1% $CH_3OH$ in DCM). The second crop of product thus obtained weighed 5.2 g. The total yield was 10.9 g. The sample was recrystallized once more form ethanol, m.p. 130°–132° C.

Analysis: Calculated for $C_{14}H_{14}FN_3O$: 64.85%C, 5.44%H, 16.21%N; Found: 64.68%C, 5.32%H, 16.26%N.

EXAMPLE 276

3-[4-(6-Fluoro-1,2-benzisoxazol-3-yl)-1-piperidinyl] propionitrile

A mixture of 4-(6-fluoro-1,2-benzisoxazol-3-yl)piperidine (11 g, 50 mmol), $K_2CO_3$ (8.5 g, 74 mmol) and 3-bromopropionitrile (8.2 g, 1.2 eq) in acetonitrile (300 ml) was heated at reflux for 24 hours. The mixture was cooled and the insolubles were filtered. The solvent was removed on a rotary evaporator and the crude product was purified by flash chromatography over a silica gel column ($SiO_2$, 120 g). The product thus purified weighed 8.94 g. Recrystallization from ethanol yielded the nitrile as white crystals 4.3 g, m.p. 100°–101° C.

Analysis: Calculated for $C_{15}H_{16}FN_3O$: 65.92%C, 5.90%H, 15.37%N; Found: 65.87%C, 5.87%H, 15.37%N.

EXAMPLE 277

1-Phenoxycarbonyl-3-(1-phenoxycarbonyl-4-piperidinyl)-1H-indazole

To a suspension of 3-(1-methyl-4-piperidinyl)-1H-indazole (5.0 g, 23.2 mmol) in DCM (100 ml) was added potassium carbonate (8.0 g, 58.0 mmol) followed by the dropwise addition of phenyl chloroformate (6.9 ml, 51.0 mmol) at room temperature. After stirring for five days, the reaction was filtered through a pad of celite and the solids were washed with DCM. The combined filtrates were concentrated and the remaining solid was purified via flash column chromatography (silica gel, 10% methanol/DCM) to give 6.7 g of the 1-phenoxycarbonyl-3-(1-methyl-4-piperidinyl)-1H-indazole as the hydrochloride salt. The free amine of the latter compound was prepared in $Na_2CO_3$ (sat.) and extracted into EtOAc. Concentration of the organic layer afforded 4.7 g of the free amine which was used without further purification.

To a solution of 1-phenoxycarbonyl-3-(1-methyl-4-piperidinyl)-1H-indazole) (4.7 g, 14.0 mmol) in DCM (100 ml) was added potassium carbonate (0.85 g, 6.2 mmol) followed by phenyl chloroformate (2.1 ml, 15.4 mmol) at room temperature, under nitrogen. After stirring for 2 days, the reaction mixture was filtered through a pad of celite and the solids were washed with DCM. The remaining oil was purified via flash column chromatography (silica gel, DCM) to give another oil which solidified from EtOAc/pet. ether. The white solid (4.2 g) was collected via filtration and washed with pet ether, m.p. 113°–116° C.

Analysis: Calculated for $C_{26}H_{23}N_3O_4$: 70.74%C, 5.25%H, 9.52%N; Found: 70.47%C, 5.17%H, 9.38%N.

EXAMPLE 278

[4-(6-Fluoro-1H-indazol-3-yl)-1-piperazinyl]acetonitrile

A mixture of 6-fluoro-3-(4-piperazinyl)-1H-indazole (6.0 g, 2.7 mmol), $NaHCO_3$ (2.5 g, 3.0 mmol) chloroacetonitrile (2.5 g, 3.3 mmol) and $CH_3CN$ (150 mol) was stirred at reflux under $N_2$ for 18 hours. The cooled reaction was poured into $H_2O$ and the aqueous solution was extracted with EtOAc. The EtOAc extract was washed with $H_2O$, washed with brine, dried with $MgSO_4$ and concentrated to yield 7.0 g of a tan solid. A 1.3 g sample was recrystallized from EtOAc to yield 0.65 g of a beige solid, m.p. 154°–156° C.

Analysis: Calculated for $C_{13}H_{14}FN_5$: 60.22%C, 5.44%H, 27.01%N; Found: 59.97%C, 5.55%H, 26.91%N.

EXAMPLE 279

1-[4-(3-Chloropropoxy)-3-methoxyphenyl]-2-hydroxyethanone

A solution of 1-[4-(3-chloropropoxy)-3-methoxyphenyl] ethanone (4.3 g, 17.7 mmol), [bis(trifluoroacetoxy)iodo]benzene (15.6 g, 36.2 mmol), $H_2O$ (18 ml), $CF_3CO_2H$ (2.8 ml) and $CH_3CN$ (90 ml) was refluxed for 3 hours. The $CH_3CN$ was removed under reduced pressure and the resulting yellow liquid was partitioned between H and $CH_3Cl_2$. The biphasic mixture was filtered, the organic phase collected, washed with saturated NaHCO solution and concentrated to afford 1.5 g of an amorphous brown solid. The solid was flash chromatographed on silica gel, eluting the column with 5% EtOAc/$CH_3Cl_2$. Concentration of similar fractions afforded 0.7 g of the compound as a pale yellow solid, m.p. 99°–101° C.

EXAMPLE 280

1-[4-[3-[4-(6-Fluoro-1,2-benzisoxazol-3-yl)-1-piperidinyl]propoxy]-3-methoxyphenyl]-2-hydroxyethanone A mixture of 3-(4-piperidinyl)-6-fluoro-1,2-benzisoxazole (1.3 g, 5.8 mmol), 1-[4-(3-chloropropoxy)-3-methoxyphenyl]-2-hydroxyethanone (1.5 g, 5.8 mmol), $NaHCO_3$ (1.5 g) and 1-methyl-2-pyrrolidinone (50 ml) was stirred under $N_2$ at 100° C. for 6 hours. The reaction was poured into $H_2O$, and the aqueous suspension was extracted with EtOAc. The extract was washed ($H_2O$), dried ($MgSO_4O$ and concentrated to afford the product.

This invention thus provides a group of chemical compounds that are capable of producing antipsychotic effects and may be capable of affecting negative symptoms of schizophrenia in a beneficial manner. In addition, many of the compounds may also have reduced tendencies to produce extrapyramidal side effects in mammals.

We claim:
1. A compound of the formula:

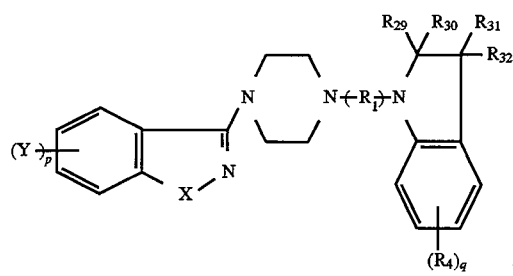

wherein

X is —O—, —S—, —NH—, or —N($R_2$);

$R_2$ is selected from the group consisting of lower alkyl, aryl lower alkyl, aryl, cycloalkyl, aroyl, alkanoyl, and phenylsulfonyl groups;

aryl is as defined hereinafter;

p is 1 or 2;

Y is hydrogen, lower alkyl, hydroxy, chlorine, fluorine, bromine, iodine, lower alkoxy, trifluoromethyl, nitro, or amino; $R_1$ is —$CR_{24}R_{27}$—($CR_{23}R_{24}$)$_n$—$CR_{24}R_{27}$— where n is 0,1,2 or 3; or —$CHR_{24}CH=CH—CHR_{24}$—,
—$CHR_{24}$—C≡C—$CHR_{24}$—,
—$CHR_{24}$—CH=CH—$CR_{23}R_{24}CHR_{24}$—,
—$CHR_{24}$—$CR_{23}R_{24}$—CH=CH—$CHR_{24}$—,
—$CHR_{24}$—C≡C—$CR_{23}R_{24}$—$CHR_{24}$—, or
—$CHR_{24}$—$CR_{23}R_{24}$—C≡C—$CHR_{24}$—, the —CH=CH— bond being cis or trans;

$R_{23}$ is hydrogen, ($C_1$–$C_{18}$) linear alkyl, phenyl, hydroxy, ($C_1$–$C_{18}$) alkoxy, aryloxy, aryl ($C_1$–$C_{18}$) alkyloxy, ($C_1$–$C_{18}$) alkanoyloxy, hydroxy ($C_1$–$C_6$) alkyl, ($C_1$–$C_{18}$) alkoxy ($C_1$–$C_6$) alkyl, phenyl ($C_1$–$C_6$) alkyloxy, aryl ($C_1$–$C_{18}$) alkyloxy ($C_1$–$C_6$) alkyl, ($C_1$–$C_{18}$) alkanoyloxy ($C_1$–$C_6$) alkyl or

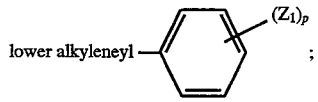

where $Z_1$ is lower alkyl, —OH, lower alkoxy, —$CF_3$, —$NO_2$, —$NH_2$, or halogen, p is as previously defined, and aryl is as defined hereinafter;

$R_{24}$ is hydrogen, ($C_1$–$C_{18}$) linear alkyl, phenyl, hydroxy (C—$C_6$)alkyl, ($C_1$–$C_{18}$)alkoxy($C_1$–$C_6$)alkyl, phenyl ($C_1$–$C_6$)alkyloxy, aryl($C_1$–$C_{18}$)alkyoxy($C_1$–$C_6$)alkyl, ($C_1$–$C_{18}$)alkanoyloxy ($C_1$–$C_6$)alkyl or

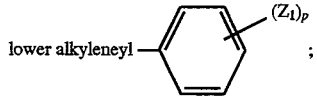

where $Z_1$ and p are as previously defined, and aryl is as defined hereinafter;

$R_{27}$ is hydrogen or $R_{24}$ and $R_{27}$ taken together with the carbon to which they are attached form C=O or C=S;

$R_4$ is hydrogen, lower alkyl, lower alkoxy, hydroxy, tri($C_1$–$C_6$)alkylsilyloxy, hydroxy lower alkyl, alkanoyloxy lower alkyl, amino, mono- or dialkylamino, ($C_1$–$C_{18}$)acyl amino, ($C_1$–$C_{18}$)alkanoyl, trifluoromethyl, chlorine, fluorine, bromine, nitro —O—C(=O)—(C$_1$-C$_{18}$straight or branched chain) alkyl or —C(=O)—aryl, wherein aryl is as defined hereinafter;

R$_{29}$ and R$_{30}$ are hydrogen, (C$_1$-C$_{18}$)alkyl, aryl(C$_1$-C$_6$) alkyl, or aryl, wherein aryl is as defined hereinafter;

R$_{31}$ and R$_{32}$ are hydrogen, hydroxy, (C$_1$-C$_6$)alkyl, aryl (C$_1$-C$_6$)alkyl, aryl, hydroxymethyl, or CHOR$_{33}$ where R$_{33}$ is (C$_1$-C$_{18}$)alkanoyl, wherein aryl is as defined hereinafter; or either R$_{29}$ and R$_{30}$ taken together or R$_{31}$ and R$_{32}$ taken together with the carbon group to which they are attached form a C=O or C=S group;

in which aryl is phenyl or

where R$_5$ is hydrogen, lower alkyl, lower alkoxy, hydroxy, chlorine, fluorine, bromine, iodine, lower monoalkylamino, lower dialkylamino, nitro, cyano, trifluoromethyl, or trifluoromethoxy;

q is 1,2,3, or 4;

and, any hydroxyl group attached to an aliphatic or aromatic carbon atom, or any primary or secondary nitrogen atom may be acylated with a (C$_4$-C$_{18}$) carboxylic group, in addition, any nitrogen atom may alternatively be acylated with a (C$_4$-C$_{18}$) alkoxycarbonyl group;

all geometric, optical, and stereoisomers thereof, or a pharmaceutically acceptable acid addition salt thereof.

2. The compound of claim 1, wherein X is —N(R$_2$)—.

3. The compound of claim 2, wherein R$_2$ is (C$_1$-C$_{18}$) alkanoyl or (C$_1$-C$_{18}$)alkoxycarbonyl.

4. An antipsychotic composition, which comprises the compound of claim 1 in an amount sufficient to produce an antipsychotic effect, and a pharmaceutically acceptable carrier therefor.

5. A method of treating psychoses, which comprises administering to a mammal a psychoses-treating effective amount of the compound of claim 1.

6. An analgesic composition, which comprises the compound of claim 1 in an amount sufficient to produce a pain-relieving effect, and a pharmaceutically acceptable carrier therefor.

7. A method of alleviating pain, which comprises administering to a mammal a pain-relieving effective amount of the compound of claim 1.

8. A depot pharmaceutical composition, which comprises a pharmaceutically acceptable carrier and a therapeutically effective amount of the compound of claim 1, wherein the compound contains an acylated hydroxy group, or an acylated amino group.

9. The depot pharmaceutical composition of claim 8, wherein the hydroxy group is acylated, or the amino group is acylated with (C$_4$-C$_{18}$)alkanoyl group or a (C$_4$-C$_{18}$) alkoxycarbonyl group.

10. The composition of claim 8, which contains a pharmaceutically acceptable oil.

11. The composition of claim 10, wherein the oil is selected from the group consisting of coconut oil, peanut oil, sesame oil, cotton seed oil, corn oil, soybean oil, olive oil, and synthetic esters of fatty acids and polyfunctional alcohols.

12. The composition of claim 9, which contains a pharmaceutically acceptable oil.

13. The composition of claim 12, wherein the oil is selected from the group consisting of coconut oil, peanut oil, sesame oil, cotton seed oil, corn oil, soybean oil, olive oil, and synthetic esters of fatty acids and polyfunctional alcohols.

14. A method for providing a long acting antipsychotic effect, which comprises injecting into a mammal an amount of the composition of claim 8 sufficient to produce a long acting antipsychotic effect.

15. A method for providing a long acting antipsychotic effect, which comprises injecting into a mammal an amount of the composition of claim 9 sufficient to produce a long acting antipsychotic effect.

16. A method for providing a long acting antipsychotic effect, which comprises injecting into a mammal an amount of the composition of claim 13 sufficient to produce a long acting antipsychotic effect.

* * * * *

UNITED STATES PATENT AND TRADEMARK OFFICE
CERTIFICATE OF CORRECTION

PATENT NO. : 5,652,241
DATED : July 29, 1997
INVENTOR(S) : Glamkowski et al.

It is certified that error appears in the above-identified patent and that said Letters Patent is hereby corrected as shown below:

Title page, item [54], lines 1 and 2 of Title, change "4-(HETEROARYL)-1-[(2,3-DIHYDRO-1-INDOL-1-YL)ALKYL]PIPERADINES AND" to -- 4-(HETEROARYL)-1-[(2,3-DIHYDRO-1H-INDOL-1-YL)ALKYL]PIPERAZINES AND--;

Title page, item [57], Abstract, line 2, change "the" to --The--;

Claim 1, col. 152, line 16, change "-N($R_2$);" to -- -N($R_2$)-; --;
 line 18, after "alkanoyl," insert --alkoxycarbonyl,--;
 line 48, after "halogen" please delete the comma (",") and insert therefor a semicolon (";");
 line 28, change "-$CHR_{24}$-C=C-$CHR_{24}$-," to -- -$CHR_{24}$-C≡C-$CHR_{24}$-, --;
 line 29, change "-$CHR_{24}$-CH=CH-$CR_{23}R_{24}CHR_{24}$-," to
  -- -$CHR_{24}$-CH=CH-$CR_{23}R_{24}$-$CHR_{24}$-, --;
 line 31, change "-$CHR_{24}$-C=C-$CR_{23}R_{24}$-$CHR_{24}$-," to
  -- -$CHR_{24}$-C≡C-$CR_{23}R_{24}$-$CHR_{24}$-, --;
 line 31, change "-$CHR_{24}$-$CR_{23}R_{24}$-C=C-$CHR_{24}$-," to
  -- -$CHR_{24}$-$CR_{23}R_{24}$-C≡C-$CHR_{24}$-, --;
 line 51, change "(C-$C_6$)alkyl," to --($C_1$-$C_6$)alkyl,--;

UNITED STATES PATENT AND TRADEMARK OFFICE
CERTIFICATE OF CORRECTION

PATENT NO. : 5,652,241
DATED : July 29, 1997
INVENTOR(S) : Glamkowski et al.

It is certified that error appears in the above-identified patent and that said Letters Patent is hereby corrected as shown below:

Claim 1, col. 153, line 1, after "nitro" insert a comma (",");
                line 12, delete "group";
                line 13, delete "a";
                line 13, delete "group";
                line 29, change "carboxylic" to --alkanoyl--.

Signed and Sealed this

Seventh Day of December, 1999

Attest:

Q. TODD DICKINSON

*Attesting Officer*      *Acting Commissioner of Patents and Trademarks*